(12) United States Patent
Lau et al.

(10) Patent No.: US 6,881,746 B2
(45) Date of Patent: Apr. 19, 2005

(54) GLUCAGON ANTAGONISTS/INVERSE AGONISTS

(75) Inventors: Jesper Lau, Farum (DK); Inge Thoger Christensen, Lyngby (DK); Peter Madsen, Bagsvaerd (DK); Paw Bloch, Taastrup (DK); Carsten Behrens, Kobenhavn (DK); Janos Tibor Kodra, Kobenhavn (DK); Poul Enrico Nielsen, Borup (DK)

(73) Assignee: Novo Nordick A/S, Bagsvaerd (DK)

( * ) Notice: Subject to any disclaimer, the term of this patent is extended or adjusted under 35 U.S.C. 154(b) by 0 days.

(21) Appl. No.: 10/448,529

(22) Filed: May 30, 2003

(65) Prior Publication Data

US 2004/0014789 A1 Jan. 22, 2004

Related U.S. Application Data

(60) Provisional application No. 60/394,145, filed on Jul. 3, 2002, and provisional application No. 60/434,255, filed on Dec. 18, 2002.

(30) Foreign Application Priority Data

| Dec. 3, 2001 | (DK) | ....................................... 2001 01789 |
| Jun. 27, 2002 | (DK) | ....................................... 2002 01006 |
| Dec. 17, 2002 | (DK) | ....................................... 2002 01927 |

(51) Int. Cl.$^7$ .................... A61K 31/425; C07D 277/04; A61P 3/00
(52) U.S. Cl. ...................... 514/365; 548/190; 548/202
(58) Field of Search ................ 548/190, 202; 514/365

(56) References Cited

U.S. PATENT DOCUMENTS

| 4,359,474 A | 11/1982 | Anderson et al. | ......... 424/273 P |
| 4,374,130 A | 2/1983 | Barcza | ....................... 424/184 |
| 5,776,954 A | 7/1998 | de Laszlo et al. | .......... 514/340 |
| 5,837,719 A | 11/1998 | de Laszlo et al. | .......... 514/343 |
| 5,880,139 A | 3/1999 | Chang | ....................... 514/326 |
| 6,639,077 B1 * | 10/2003 | Cote et al. | ............... 546/269.7 |

FOREIGN PATENT DOCUMENTS

| WO | WO 94/14426 A1 | 7/1994 |
| WO | WO 97/16442 A1 | 5/1997 |
| WO | WO 98/04528 A2 | 2/1998 |
| WO | WO 98/21957 A1 | 5/1998 |
| WO | WO 98/22108 A1 | 5/1998 |
| WO | WO 98/22109 A1 | 5/1998 |
| WO | WO 98/24780 A3 | 6/1998 |
| WO | WO 98/24780 A2 | 6/1998 |
| WO | WO 98/24782 A2 | 6/1998 |
| WO | WO 99/01423 A1 | 1/1999 |
| WO | WO 99/32448 A1 | 7/1999 |
| WO | WO 00/39088 A1 | 7/2000 |
| WO | WO 00/69810 A1 | 11/2000 |
| WO | WO 02/00612 A1 | 1/2002 |
| WO | WO 02/40444 A1 | 5/2002 |
| WO | WO 02/40445 A1 | 5/2002 |
| WO | WO 02/40446 A1 | 5/2002 |

OTHER PUBLICATIONS

Azizeh et al., Bioorganic & Medicinal Chemistry Letters, vol. 2, No. 16, pp. 1849–1852 (1995).
Collins et al., Bioorganic & Medicinal Chemistry Letters, vol. 2, No. 9, pp. 915–918 (1992).
Madsen et al., J. Med. Chem., vol. 41, pp. 5150–5157 (1998).
Post et al., Proc. Natl. Acad. Sci. USA, vol. 90, pp. 1662–1666 (1993).
Unson et al., Peptides, vol. 10, pp. 1171–1177 (1989).
Unson et al., The Journal of Biological Chemistry, vol. 269, No. 17, pp. 12548–12551 (1994).

* cited by examiner

*Primary Examiner*—Rita Desai
*Assistant Examiner*—Robert Shiao
(74) *Attorney, Agent, or Firm*—Rosemarie R. Wilk-Orescar; Reza Green; Richard W. Bosk

(57) ABSTRACT

Novel compounds that act to antagonize the action of the glucagon peptide hormone on the glucagon receptor. More particularly, it relates to glucagon antagonists or inverse agonists.

32 Claims, No Drawings under 35 U.S.C. 119 of
GLUCAGON ANTAGONISTS/INVERSE AGONISTS

CROSS-REFERENCE TO RELATED APPLICATIONS

This application claims priority under 35 U.S.C. 119 of Danish application no. PA 2001 01789 filed Dec. 3, 2001, Danish application no. PA 2002 01006 filed on Jun. 27, 2002 and Danish application no. PA 2002 01927 filed on Dec. 17, 2002 and U.S. application No. 60/394,145 filed on Jul. 3, 2002 and U.S. provisional application No. 60/434,255 filed on Dec. 18, 2002, the contents of which are fully incorporated herein by reference.

FIELD OF THE INVENTION

The present invention relates to agents that act to antagonize the action of the glucagon peptide hormone on the glucagon receptor. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones.

Glucagon is produced in the alpha islet cells of the pancreas and insulin in the beta islet cells. Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, ie substances that inhibit or prevent glucagon-induced responses. The antagonist can be peptidic or non-peptidic in nature.

Native glucagon is a 29 amino acid peptide having the sequence:
His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH Glucagon exerts its action by binding to and activating its receptor, which is part of the Glucagon-Secretin branch of the 7-transmembrane G-protein coupled receptor family. The receptor functions by activating the adenylyl cyclase second messenger system and the result is an increase in cAMP levels.

Several publications disclose peptides that are stated to act as glucagon antagonists. Probably, the most thoroughly characterized antagonist is DesHis[1][Glu[9]]-glucagon amide (Unson et al., Peptides 10, 1171 (1989); Post et al., Proc. Natl. Acad. Sci. USA 90, 1662 (1993)). Other antagonists are DesHis[1],Phe[6][Glu[9]]-glucagon amide (Azizh et al., Bioorganic & Medicinal Chem. Lett. 16, 1849 (1995)) and NLeu[9],Ala[11,16]-glucagon amide (Unson et al., J. Biol. Chem. 269 (17), 12548 (1994)).

Peptide antagonists of peptide hormones are often quite potent. However, they are generally known not to be orally available because of degradation by physiological enzymes, and poor distribution in vivo. Therefore, orally available non-peptide antagonists of peptide hormones are generally preferred. Among the non-peptide glucagon antagonists, a quinoxaline derivative, (2-styryl-3-[3-(dimethylamino) propylmethylamino]-6,7-dichloroquinoxaline was found to displace glucagon from the rat liver receptor (Collins, J. L. et al., Bioorganic and Medicinal Chemistry Letters 2(9) :915–918 (1992)). WO 94/14426 (The Wellcome Foundation Limited) discloses use of skyrin, a natural product comprising a pair of linked 9,10-anthracenedione groups, and its synthetic analogues, as glucagon antagonists. U.S. Pat. No. 4,359,474 (Sandoz) discloses the glucagon inhibiting properties of 1-phenyl pyrazole derivatives. U.S. Pat. No. 4,374,130 (Sandoz) discloses substituted disilacyclohexanes as glucagon inhibiting agents. WO 98/04528 (Bayer Corporation) discloses substituted pyridines and biphenyls as glucagon antagonists. U.S. Pat. No. 5,776,954 (Merck & Co., Inc.) discloses substituted pyridyl pyrroles as glucagon antagonists and WO 98/21957, WO 98/22108, WO 98/22109 and U.S. Pat. No. 5,880,139 (Merck & Co., Inc.) disclose 2,4-diaryl-5-pyridylimidazoles as glucagon antagonists. Furthermore, WO 97/16442 and U.S. Pat. No. 5,837,719 (Merck & Co., Inc.) disclose 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to possess glucagon antagonistic activity. Madsen et al. (J. Med. Chem. 41, 5151–7 (1998)) discloses a series of 2-(benzimidazol-2-ylthio)-1-(3,4-dihydroxyphenyl)-1-ethanones as competitive human glucagon receptor antagonists. WO 99/01423 and WO 00/39088 (Novo Nordisk A/S) disclose different series of alkylidene hydrazides as glucagon antagonists/inverse agonists. WO 00/69810, WO 02/00612, WO 02/40444, WO 02/40445 and WO 02/40446 (Novo Nordisk A/S) disclose further classes of glucagon antagonists.

These known glucagon antagonists differ structurally from the present compounds.

SUMMARY OF THE INVENTION

Definitions

The following is a detailed definition of the terms used to describe the compounds of the invention:

"Halogen" designates an atom selected from the group consisting of F, Cl, Br and I.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

In the same way "$C_{1-10}$-alkyl" denotes a saturated, branched or straight hydrocarbon group having from 1 to 10 carbon atoms.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

In the same way "$C_{2-10}$-alkenyl" denotes a saturated, branched or straight hydrocarbon group having from 2 to 10 carbon atoms.

The term "$C_{1-6}$-alkoxy" as used herein refers to the radical —O—$C_{1-6}$-alkyl, wherein $C_{1-6}$-alkyl is as defined above. Representative examples are methoxy, ethoxy, n-propoxy, iso-propoxy, butoxy, sec-butoxy, tert-butoxy, pentoxy, isopentoxy, hexoxy, isohexoxy and the like.

The term "$C_{1-6}$-alkylthio" as used herein refers to the radical —S—$C_{1-6}$-alkyl, wherein $C_{1-6}$-alkyl is as defined above. Representative examples include, but are not limited to, methylthio, ethylthio, n-propylthio, isopropylthio, butylthio, isobutylthio, sec-butylthio, tert-butylthio, n-pentylthio, isopentylthio, neopentylthio, tert-pentylthio, n-hexylthio, isohexylthio and the like.

The term "$C_{3-10}$-cycloalkyl" as used herein represents a saturated, carbocyclic group having from 3 to 10 carbon atoms. Representative examples are cyclopropyl, cyclobutyl, cyclopentyl, cyclohexyl, cycloheptyl, cyclooctyl, cyclononyl, cyclodecyl and the like.

The term "$C_{7-10}$-bicycloalkyl" as used herein represents a bicyclic, saturated, carbocyclic group having from 7 to 10 carbon atoms. Representative examples are bicyclo[3.1.0]hexyl, bicyclo[4.1.0]heptyl, bicyclo[3.1.1]heptyl, bicyclo[2.2.1]heptyl and the like.

The term "$C_{3-10}$-cycloalkenyl" as used herein represents a non-aromatic, carbocyclic group having from 3 to 10 carbon atoms containing one or two double bonds. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl, 1-cyclononenyl, 2-cyclononenyl, 1-cyclodocenyl, 2-cyclodocenyl, and the like.

The term "aryl" as used herein is intended to include carbocyclic, aromatic ring systems such as 6 membered monocyclic and 9 to 14 membered bi- and tricyclic, carbocyclic, aromatic ring systems. Representative examples are phenyl, biphenylyl, naphthyl, anthracenyl, phenanthrenyl, fluorenyl, indenyl, azulenyl and the like. Aryl is also intended to include the partially hydrogenated derivatives of the ring systems enumerated above. Non-limiting examples of such partially hydrogenated derivatives are 1,2,3,4-tetrahydronaphthyl, 1,4-dihydronaphthyl, indanyl and the like.

The term "aryloxy" as used herein denotes a group —O-aryl, wherein aryl is as defined above.

The term "arylthio" as used herein denotes a group —S-aryl, wherein aryl is as defined above.

The term "heteroaryl" as used herein is intended to include aromatic, heterocyclic ring systems containing one or more heteroatoms selected from nitrogen, oxygen and sulfur such as 5 to 7 membered monocyclic and 8 to 14 membered bi- and tricyclic aromatic, heterocyclic ring systems containing one or more heteroatoms selected from nitrogen, oxygen and sulfur. Representative examples are furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the ring systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

"Aryl-$C_{1-6}$alkyl", "heteroaryl-$C_{1-6}$alkyl", "aryl-$C_{2-6}$-alkenyl" etc. mean $C_{1-6}$alkyl or $C_{2-6}$-alkenyl as defined above, substituted by an aryl or heteroaryl as defined above, for example:

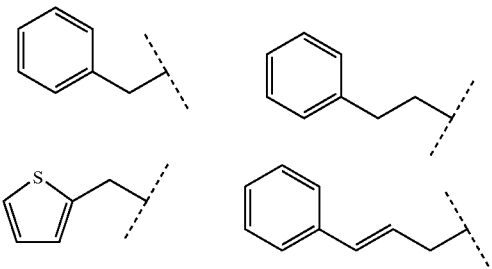

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

The term "reatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DESCRIPTION OF THE INVENTION

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, butyl-, tetramethylammonium salts and the like.

Also intended as pharmaceutically acceptable acid addition salts are the hydrates, which the present compounds, are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into the required compound. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment of disorders and diseases in which such an antagonism is beneficial.

The compounds according to the invention preferably have an $IC_{50}$ value of no greater than 5 µM as determined by the Glucagon Binding Assay (I) or Glucagon Binding Assay (II) disclosed herein.

More preferably, the compounds according to the invention have an $IC_{50}$ value of less than 1 µM, preferably of less than 500 nM and even more preferred of less than 100 nM as determined by the Glucagon Binding Assay (I) or Glucagon Binding Assay (II) disclosed herein.

Furthermore, the compounds according to the invention preferably have a higher binding affinity to the glucagon receptor than to the GIP receptor. Accordingly, the present compounds may be applicable for the treatment of hyperglycemia, hyper insulinemia, beta-cell rest, improved beta-cell function by restoring first phase response, prandial hyperglycemia, preventing apoptosis, IFG, metabolic syndrome, hypoglycemia, hyper-/hypokalemia, normalising glucagon levels, improved LDL/HDL ratio, reducing snacking, eating disorders, weight loss, PCOS, obesity as a consequence of diabetes, LADA, insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction (male & female), glaucoma, post surgical stress, ameliorating organ tissue injury caused by reperfusion of blood flow after ischaemia, ischemic heart damage, heart insufficiency, congestional heart failure, stroke, myocardial infarction, arrythmia, premature death, anti-apoptosis, wound healing, IGT (impaired glucose tolerance), insulin resistance syndromes, syndrome X, type 1 diabetes, type 2 diabetes, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

Furthermore, they may be applicable as diagnostic agents for identifying patients having a defect in the glucagon receptor, as a therapy to increase gastric acid secretions and to reverse intestinal hypomobility due to glucagon administration.

They may also be useful as tool or reference molecules in labelled form in binding assays to identify new glucagon antagonists.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form, comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound of the general formula (I) as well as any diastereomer or enantiomer or tautomeric form thereof including mixtures of these or a pharmaceutically acceptable salt thereof for the preparation of a medicament for the treatment of disorders or diseases, wherein a glucagon antagonistic action is beneficial.

The invention also relates to a method for the treatment of disorders or diseases, wherein a glucagon antagonistic action is beneficial the method comprising administering to a subject in need thereof an effective amount of a compound according to the invention.

In one embodiment of the invention the present compounds are used for the preparation of a medicament for the treatment of any glucagon-mediated conditions and diseases.

In another embodiment of the invention the present compounds are used for the preparation of a medicament for the treatment of hyperglycemia.

In yet another embodiment of the invention the present compounds are used for the preparation of a medicament for lowering blood glucose in a mammal. The present compounds are effective in lowering the blood glucose, both in the fasting and the postprandial stage.

In still another embodiment of the invention the present compounds are used for the preparation of a pharmaceutical composition for the treatment of IGT.

In a further embodiment of the invention the present compounds are used for the preparation of a pharmaceutical composition for the treatment of type 2 diabetes.

In yet a further embodiment of the invention the present compounds are used for the preparation of a pharmaceutical composition for the delaying or prevention of the progression from IGT to type 2 diabetes.

In yet another embodiment of the invention the present compounds are used for the preparation of a pharmaceutical composition for the delaying or prevention of the progression from non-insulin requiring type 2 diabetes to insulin requiring type 2 diabetes.

In a further embodiment of the invention the present compounds are used for the preparation of a pharmaceutical composition for the treatment of type 1 diabetes. Such treatment is normally accompanied by insulin therapy.

In yet a further embodiment of the invention the present compounds are used for the preparation of a pharmaceutical composition for the treatment of obesity.

In still a further embodiment of the invention the present compounds are used for the preparation of a pharmaceutical composition for the treatment of disorders of the lipid metabolism.

In still another embodiment of the invention the present compounds are used for the preparation of a pharmaceutical composition for the treatment of an appetite regulation or energy expenditure disorder.

In a further embodiment of the invention, treatment of a patient with the present compounds is combined with diet and/or exercise.

In a further aspect of the invention the present compounds are administered in combination with one or more further active substances in any suitable ratios. Such further active substances may eg be selected from antidiabetics, antiobesity agents, antihypertensive agents, agents for the treatment of complications resulting from or associated with diabetes and agents for the treatment of complications and disorders resulting from or associated with obesity.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), eg $N^{\epsilon B29}$-tetradecanoyl des (B30) human insulin, EP 214 826 and EP 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, EP 368 187 (Aventis), eg Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulpho-meglitinides, nylureas, biguamides, oxadiazolidinediones, thiazolidinediones, insulin sensitizers, insulin secretagogues, such as glimepiride, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In one embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguamide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the α-cells eg tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent eg cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds eg in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further embodiment of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant).

In another embodiment the antiobesity agent is dexamphetamine or amphetamine.

In another embodiment the antiobesity agent is leptin.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitore, imidazolines, 11-β-hydroxysteroid dehydrogenase inhibitors, lipoprotein lipase activatore, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typical doses are in the order of about half the dose employed for oral administration.

The compounds of this invention are generally utilized as the free substance or as a pharmaceutically acceptable salt thereof. One example is a base addition salt of a compound having the utility of a free acid. When a compound of the formula (I) contains a free acid such salts are prepared in a conventional manner by treating a solution or suspension of a free acid of the formula (I) with a chemical equivalent of a pharmaceutically acceptable base. Representative examples are mentioned above.

For parenteral administration, solutions of the novel compounds of the formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
| --- | --- |
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of the glucagon antagonists of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Some of the NMR data shown in the following examples are only selected data.

In the examples the following terms are intended to have the following, general meanings:

Alloc: allyloxycarbonyl
DCM: dichloromethane, methylenechloride
DIC: diisopropylcarbodiimide
DIPEA: N,N-diisopropylethylamine
DMF: N,N-dimethylformamide
DMSO: dimethyl sulphoxide
Fmoc: 9-fluorenylmethyloxycarbonyl
HOBt: 1-hydroxybenzotriazole MeOH: methanol
NMP: N-methyl-2-pyrrolidinone
THF: tetrahydrofuran
TFA: trifluoroacetic acid HPLC-MS (Method A)

The following instrumentation was used:
Sciex API 150 Single Quadropole mass spectrometer
Hewlett Packard Series 1100 G1312A Bin pump
Gilson 215 micro injector
Hewlett Packard Series 1100 G1315A DAD diode array detector
Sedex 55 evaporative light scattering detector
A Valco column switch with a Valco actuator controlled by timed events from the pump.
The Sciex Sample control software running on a Macintosh Power G3 computer was used for the instrument control and data acquisition.

The HPLC pump was connected to two eluent reservoirs containing:

| A: | Acetonitrile containing 0.05% TFA |
| B: | Water containing 0.05% TFA |

The requirements for the samples are that they contain approximately 500 µg/ml of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 µl of the sample solution on the column, which was eluted with a gradient of acetonitrile in 0.05% TFA The eluate from the column was passed through a flow splitting T-connector, which passed approximately 20 µl/min through approx. 1 m 75µ fused silica capillary to the API interface of API 150 spectrometer.

The remaining 1.48 ml/min was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following table.

| Column | Waters X-terra C18 5 µ 3 mm × 50 mm id | |
|---|---|---|
| Gradient | 5%–90% acetonitrile in 0.05% TFA linearly during 7.5 min at 1.5 ml/min | |
| Detection | UV: 214 nm | ELS: 40° C. |
| MS | Experiment: Start: 100 amu | Stop: 800 amu |
| | | Step: 0.2 amu |
| | Dwell: 0.571 msec | |
| | Method: Scan 284 times = 9.5 min | |

HPLC-MS (Method B)

The following instrumentation was used:
Hewlett Packard series 1100 G1312A Bin Pump
Hewlett Packard series 1100 Column compartment
Hewlett Packard series 1100 G1315A DAD diode array detector
Hewlett Packard series 1100 MSD The instrument was controlled by HP Chemstation software.

The HPLC pump was connected to two eluent reservoirs containing:

| A: | 0.01% TFA in water |
| B: | 0.01% TFA in acetonitrile |

The analysis was performed at 40° C. by injecting an appropriate volume of the sample (preferably 1 µL) onto the column, which was eluted with a gradient of acetonitrile.

The HPLC conditions, detector settings and mass spectrometer settings used are given in the following table.

| Column | Waters Xterra MS C-18 X 3 mm id |
|---|---|
| Gradient | 10%–100% acetonitrile lineary during 7.5 min at 1.0 ml/min |
| Detection | UV: 210 nm (analog output from DAD) |
| MS | Ionisation mode: API-ES |
| | Scan 100–1000 amu step 0.1 amu |

General Procedure (A)

General procedure (A) may be used for solid phase preparation of compounds of general formula ($I_a$):

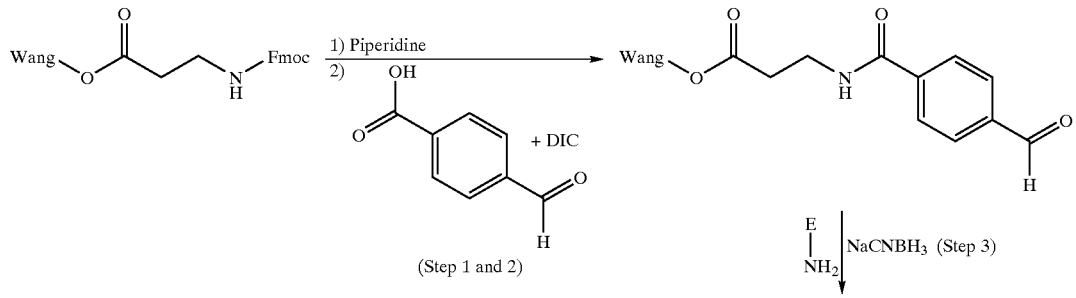

-continued

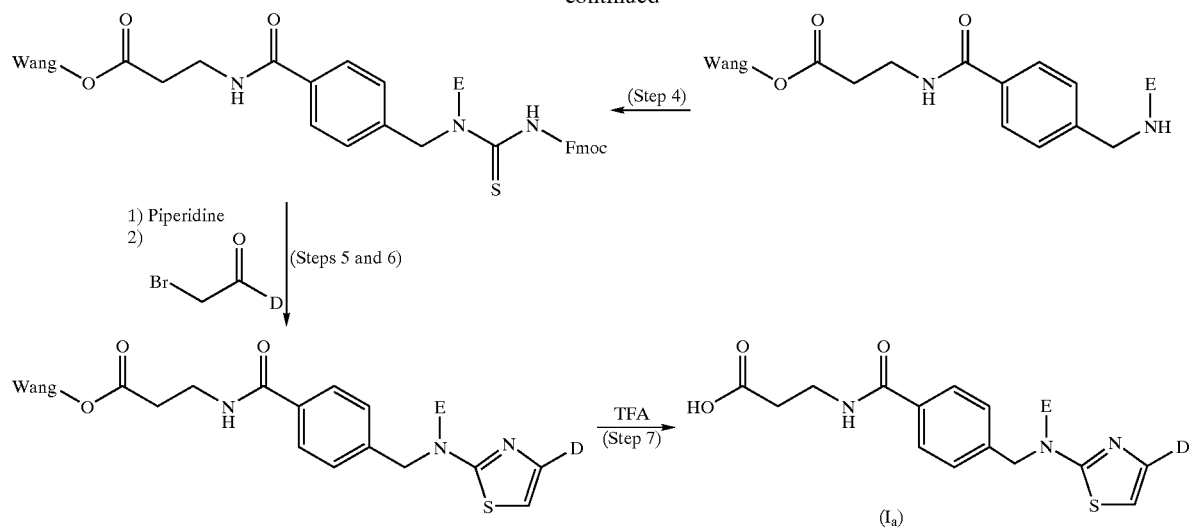

Steps 1 to 3:

These steps are analogous to the corresponding steps described in WO 00/69810 and WO 02/00612.

Steps 4 and 5: Thiourea Formation

The formation of 1,1-disubstituted thioureas on solid phase from resin-bound secondary amines is a known reaction and have been described with Fmoc-isothiocyanate (P. C. Kearney et al., *J. Org Chem.*, 1998, 63, 196–200) and Alloc-isothiocyanate (D. Dodd et al., *Tetrahedron Lett.*, 1998, 39, 5701–4) as synthetic equivalents of H-NCS. The present methodology utilises Fmoc-isothiocyanate followed by deprotection of the Fmoc-protected thiourea with piperidine.

Step 6: Thiazole Formation

The reaction generally is known (P. C. Kearney et al., *J. Org Chem.*, 1998, 63, 196–200 and J. Stadlwieser et al., *Angew. Chem. Int. Ed. Engl.*, 1998, 37, 1402–4) and is performed by reacting a resin-bound thiourea with a α-haloketone under basic or acidic conditions. The reaction is normally performed at ambient temperature or at elevated temperature, up to the temperature of the boiling point of the solvent(s). The solvent can be one (or a mixture of two or more) of the following: dioxane, THF, DCM, 1,2-dichloropropane, acetonitrile, DMF, N-methylpyrrolidone, DMSO, toluene and ethyl acetate.

Step 7: Cleavage from Resin

This step is analogous to the corresponding transformations described in WO 00/69810 and WO 02/00612.

The general procedure (A) is further illustrated in the following example:

Example 1

General Procedure (A)

3-(4-{[(4-Cyclohex-1-enylphenyl)-(4-phenylthiazol-2-yl)amino]methyl}benzoylamino)propionic acid

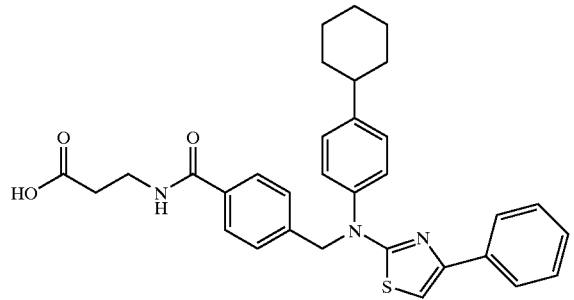

Reaction scheme:

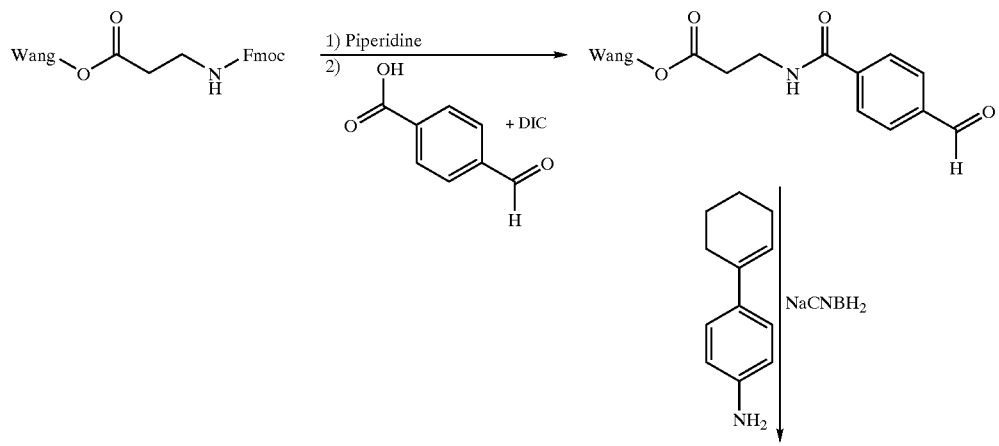

-continued

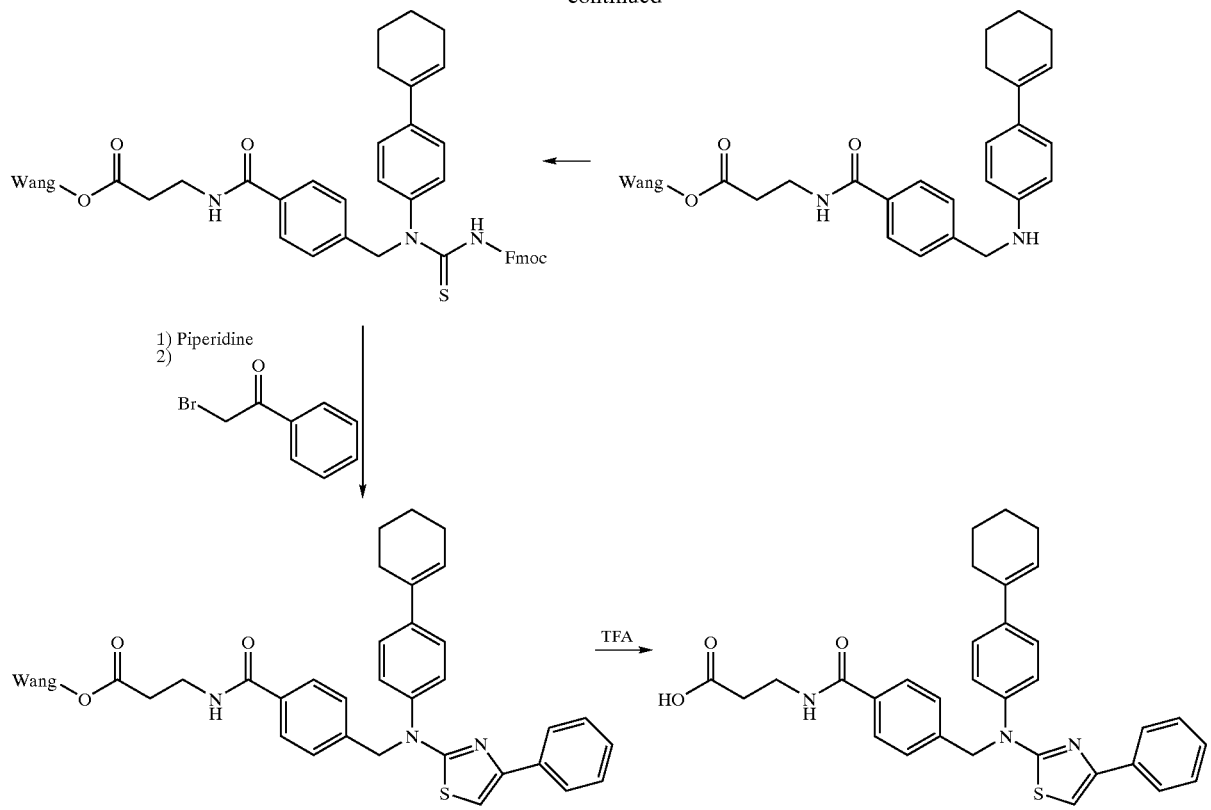

Fmoc-β-Ala-Wang resin (0.57 mmol/g, 50 μmol) was treated with piperidine (20% in NMP, 1000 μL) for 10 min and the resin was drained. This was repeated once. The resin was washed with NMP (6×1000 μL). 4-Carboxybenzaldehyde (0.5 M in NMP, 500 μL), HOBt (0.5 M in NMP, 500 μL) and DIC (0.5 M in toluene, 500 μL) were added and the resulting mixture was shaken for 15 hours at room temperature. The resin was drained and washed with DMF (3×1000 uL). The resulting resin-bound aldehyde was added the appropriate amine, in this case 4-(cyclohex-1-enyl)aniline, prepared as described in WO 00/69810 (1.0 M in NMP, 600 μL), NaCNBH₃ (1.0 M in NMP: methanol (7:3), 600 μL) and acetic acid (140 μL). The resulting mixture was shaken for 9 hours at room temperature, drained and washed with MeOH (1000 μL) for 1 hour, followed by washing with with 5% DIPEA in methanol (1×) and NMP (2×) (1000 μl each). The resulting resin-bound amine was treated with Fmoc-isothiocyanate (0.55 M in DCP, 1000 μL) and the mixture was shaken for 10 hours at room temperature and washed with NMP (2×1000 μL) and DCM (1000 μL). The resin was treated with piperidine (20% in NMP, 1000 μL) for 10 min and the resin was drained. This was repeated once. The resin was washed with NMP (6×1000 μL). The appropriate bromoethanone, in this case 2'-bromoacetophenone (0.75 M in NMP, 1000 μL) and acetic acid (100 μL) were added to the resin and the mixture was shaken for 13 hours at room temperature and washed with NMP (2×1000 μL). The product was cleaved from the resin by treatment with 50% TFA in DCM for 1 hour. Concentration in vacuo afforded the title compound.

HPLC-MS (Method (A)): m/z: 538 (M+1); Rt: 7.85 min.

The compounds of the invention may be further purified by methods known to those skilled in the art, eg by flash chromatography or HPLC. The compounds in the following examples 2–249 were similarly prepared and all found to be hits when screening at 1.4 μM (a "hit" is defined as a compound at the given concentration that is able to displace >40% of labelled glucagon from the human glucagon receptor).

Example 2

General Procedure (A)

3-(4-{[(4-Cyclohexylphenyl)-(4-phenylthiazol-2-yl)amino]methyl}benzoylamino)propionic acid

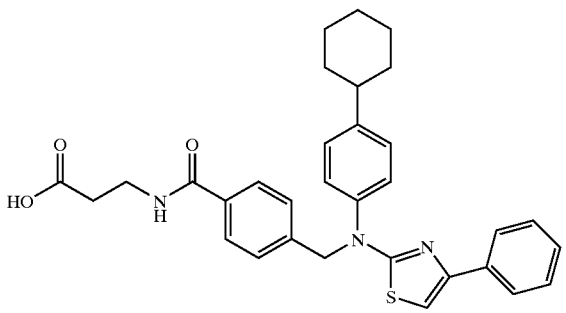

Example 3

General Procedure (A)

3-(4-{[(4-Cyclohexylphenyl)-(5-methyl-4-phenylthiazol-2-yl)amino]methyl}benzoylamino)propionic acid

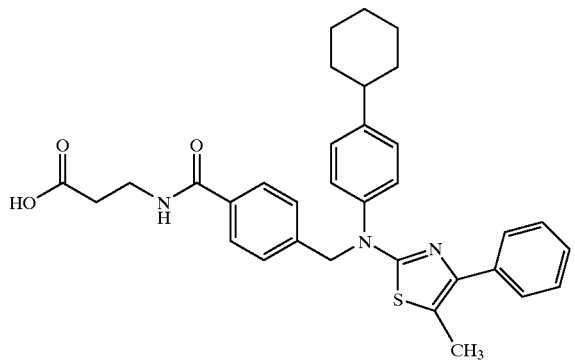

Example 4

General Procedure (A)

3-(4-{[[4-(4-Chlorophenyl)thiazol-2-yl]-(4-cyclohexylphenyl)amino]methyl}benzoylamino)propionic acid

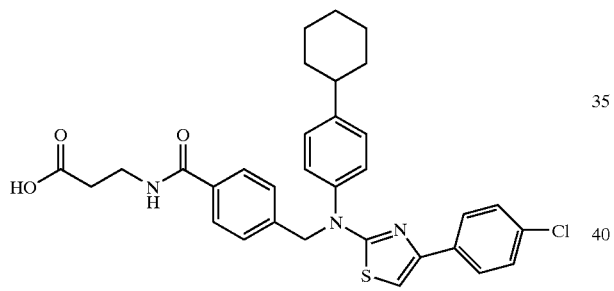

Example 5

General Procedure (A)

3-[4-({(4-Cyclohexylphenyl)-[4-(4-trifluoromethoxyphenyl)thiazol-2-yl]amino}methyl)benzoylamino]propionic acid

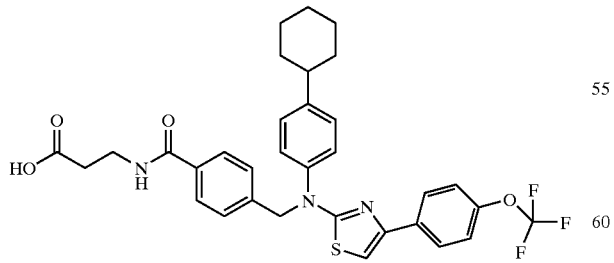

$^1$H NMR (DMSO-d$_6$): 1.23–1.39 (m, 4H); 1.68–1.79 (m, 4H); 3.43 (q, 2H); 5.28 (s, 2H); 7.24 (s, 1H); 7.29 (d, 2H); 7.37 (d, 4H); 7.43 (d, 2H); 7.75 (d, 2H); 7.94 (d, 2H); 8.41 (t, 1H).

Example 6

General Procedure (A)

3-(4-{[(4-Biphenyl-4-ylthiazol-2-y)-(4-cyclohexylphenyl)amino]methyl}benzoylamino)propionic acid

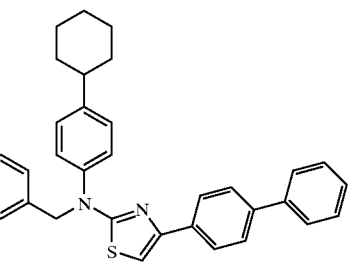

$^1$H NMR (DMSO-d$_6$): 1.23–1.40 (m, 4H); 1.68–1.79 (m, 4H); 3.43 (q, 2H); 5.31 (s, 2H); 7.22 (s, 1H); 7.30 (d, 2H); 7.36–7.38 (m, 3H); 7.44–7.48 (m, 4H); 7.69 (d, 4H); 7.76 (d, 2H); 7.93 (d, 2H); 8.42 (t, 1H).

Example 7

General Procedure (A)

3-(4-{[(4-Cyclohexylphenyl)-(4-naphthalen-2-ylthiazol-2-yl)amino]methyl}benzoylamino)propionic acid

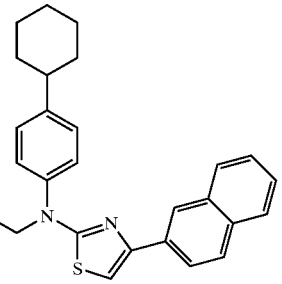

$^1$H NMR (DMSO-d$_6$): 1.31–1.40 (m, 4H); 1.68–1.80 (m, 4H); 3.43 (q, 2H); 5.36 (s, 2H); 7.28 (s, 1H); 7.29 (d, 2H); 7.39 (d, 2H); 7.47–7.54 (m, 4H); 7.75 (d, 2H); 7.88–7.96 (m, 2H); 7.98 (d, 2H); 8.36 (s 1H); 8.42 (t, 1H).

Example 8

General Procedure (A)

3-[4-({(4-Cyclohexylphenyl)-[4-(4-trifluoromethylphenyl)thiazol-2-yl]amino}methyl)benzoylamino]propionic acid

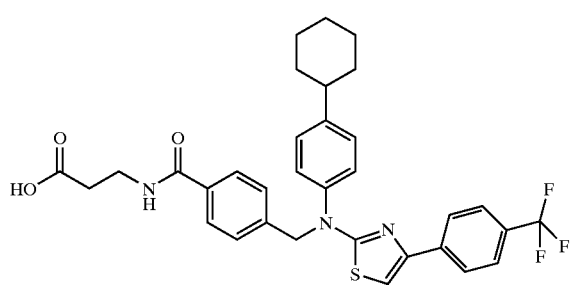

$^1$H NMR (DMSO-$d_6$): 1.34–1.39 (m, 4H); 1.67–1.79 (m, 4H); 3.43 (q, 2H); 5.30 (s, 2H); 7.29 (d, 2H); 7.36 (s, 1H); 7.40 (d, 2H); 7.43 (d, 2H); 7.74 (dd, 4H); 8.04 (d, 2H); 8.42 (t, 1H).

Example 9

General Procedure (A)

3-(4-{[(4-Cyclohex-1-enylphenyl)-(5-methyl-4-phenylthiazol-2-yl)amino]methyl}benzoylamino)propionic acid

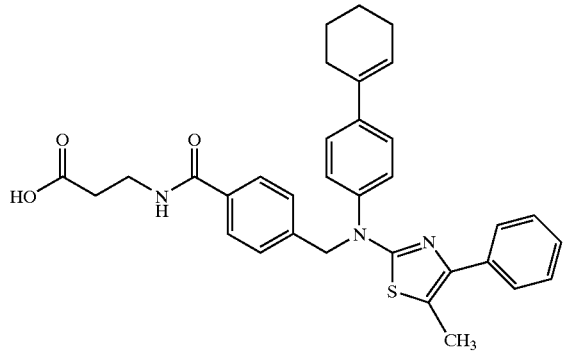

Example 10

General Procedure (A)

3-(4-{[[4-(4-Chlorophenyl)-thiazol-2-yl]-(4-cyclohex-1-enylphenyl)amino]methyl}benzoylamino)propionic acid

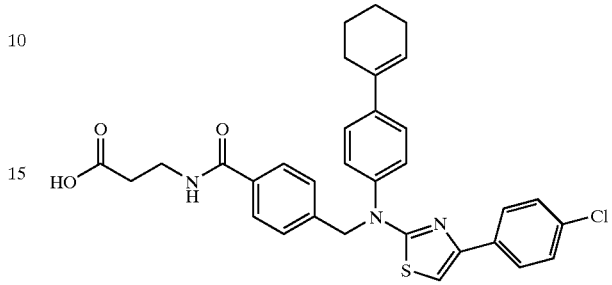

Example 11

General Procedure (A)

3-[4-({(4-Cyclohex-1-enylphenyl)-[4-(4-trifluoromethoxyphenyl)thiazol-2-yl]amino}methyl)benzoylamino]propionic acid

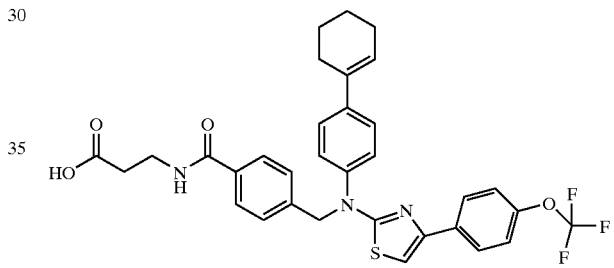

HPLC-MS (Method (A)): m/z: 622 (M+1); Rt: 8.45 min.

Example 12

General Procedure (A)

3-[4-({(4-Cyclohex-1-enylphenyl)-[4-(4-nitrophenyl)thiazol-2-yl]amino}methyl)benzoylamino]propionic acid

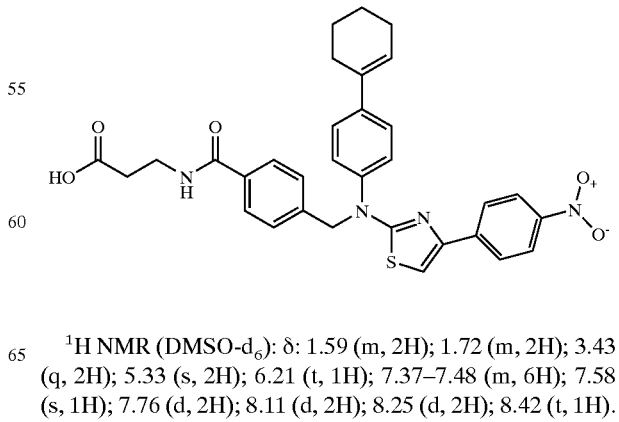

$^1$H NMR (DMSO-$d_6$): δ: 1.59 (m, 2H); 1.72 (m, 2H); 3.43 (q, 2H); 5.33 (s, 2H); 6.21 (t, 1H); 7.37–7.48 (m, 6H); 7.58 (s, 1H); 7.76 (d, 2H); 8.11 (d, 2H); 8.25 (d, 2H); 8.42 (t, 1H).

Example 13

General Procedure (A)

3-(4-{[(4-Biphenyl-4-ylthiazol-2-yl)-(4-cyclohex-1-enylphenyl)amino]methyl}benzoylamino)propionic acid

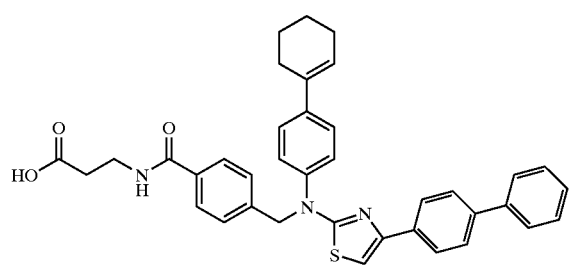

Example 14

General Procedure (A)

3-(4-{[(4-Cyclohex-1-enylphenyl)-(4-naphthalen-2-ylthiazol-2-yl)amino]methyl}benzoylamino) propionic acid

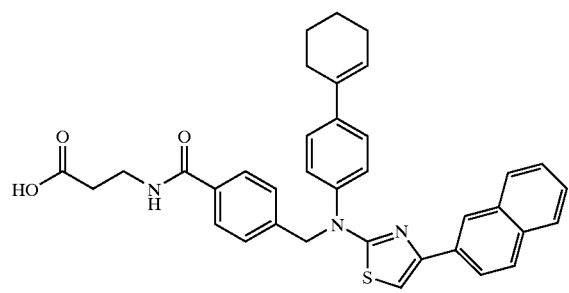

$^1$H NMR (DMSO-$d_6$): 1.60 (m, 2H); 1.72 (m, 2H); 3.43 (q, 2H); 5.38 (s, 2H); 6.21 (t, 1H); 7.35 (s, 1H); 7.43–7.53 (m, 8H); 7.77 (d, 2H); 7.91 (m, 4H); 7.99 (d, 2H); 8.39 (s, 1H); 8.42 (t, 1H).

Example 15

General Procedure (A)

3-[4-({(4-Cyclohex-1-enylphenyl)-[4-(4-trifluoromethylphenyl)thiazol-2-yl]amino}methyl)benzoylamino]propionic acid

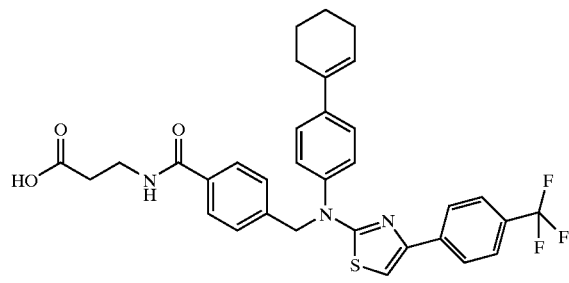

HPLC-MS (Method (A)): m/z: 606 (M+1); Rt: 8.28 min.

Example 16

General Procedure (A)

3-(4-{[(4-tert-Butylcyclohexyl)-(4-phenylthiazol-2-yl)amino]methyl}benzoylamino)propionic acid

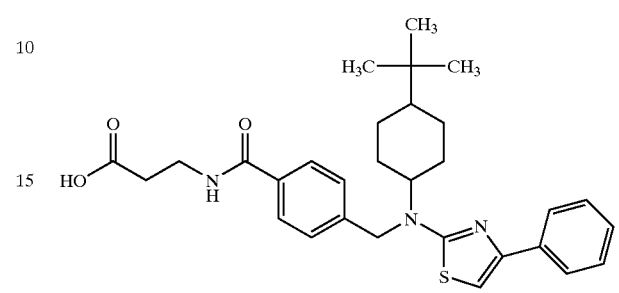

Example 17

General Procedure (A)

3-(4-{[(4-tert-Butylcyclohexyl)-(5-methyl-4-phenylthiazol-2-yl)amino]methyl}benzoylamino) propionic acid

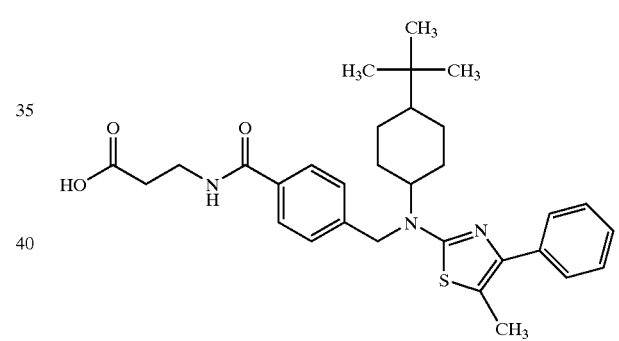

Example 18

General Procedure (A)

3-[4-({(4-tert-Butylcyclohexyl)-[4-(4-chlorophenyl)thiazol-2-yl]amino}methyl)benzoylamino]propionic acid

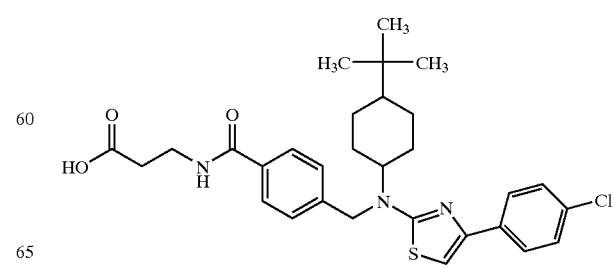

Example 19

General Procedure (A)

3-[4-({(4-tert-Butylcyclohexyl)-[4-(4-trifluoromethoxyphenyl)thiazol-2-yl]amino}methyl)benzoylamino]propionic acid

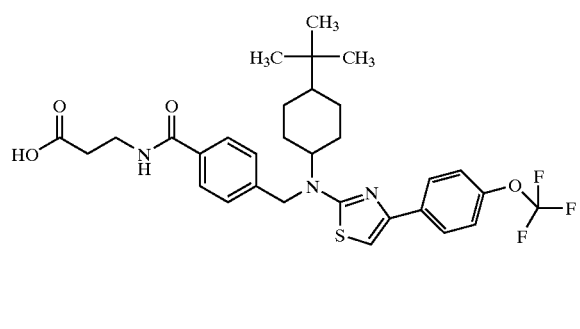

Example 20

General Procedure (A)

3-(4-{[(4-Biphenyl-4-ylthiazol-2-yl)-(4-tert-butylcyclohexyl)amino]methyl}benzoylamino)propionic acid

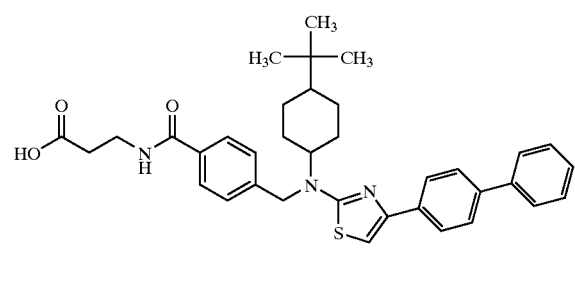

Example 21

General Procedure (A)

3-(4-{[(4-tert-Butylcyclohexyl)-(4-naphthalen-2-ylthiazol-2-yl)amino]methyl}benzoylamino)propionic acid

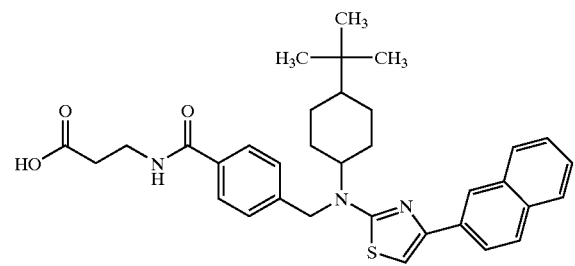

Example 22

General Procedure (A)

3-[4-({(4-tert-Butylcyclohexyl)-[4-(4-trifluoromethylphenyl)thiazol-2-yl]amino}methyl)benzoylamino]propionic acid

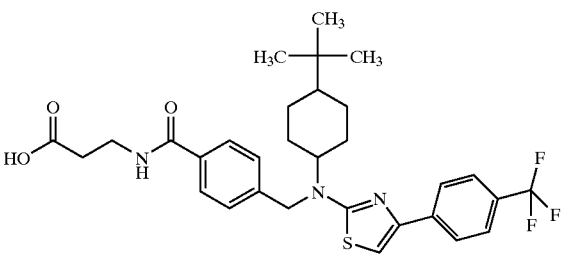

Example 23

General Procedure (A)

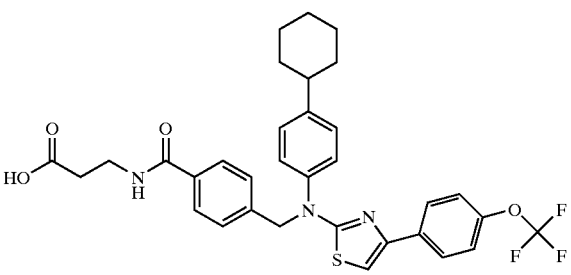

Example 24

General Procedure (A)

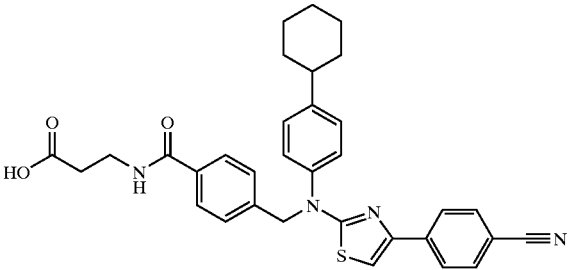

Example 25
General Procedure (A)
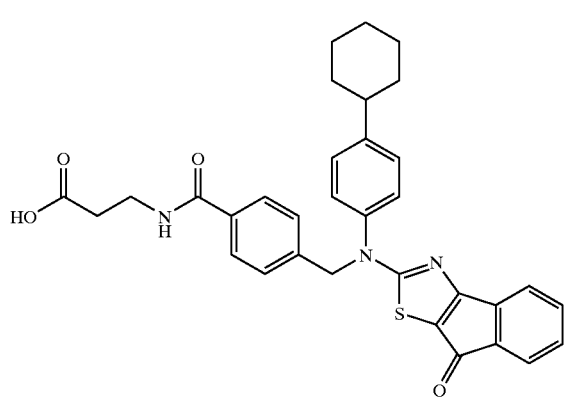
Example 26
General Procedure (A)
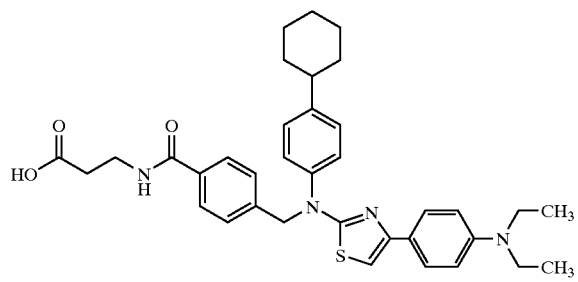
Example 27
General Procedure (A)
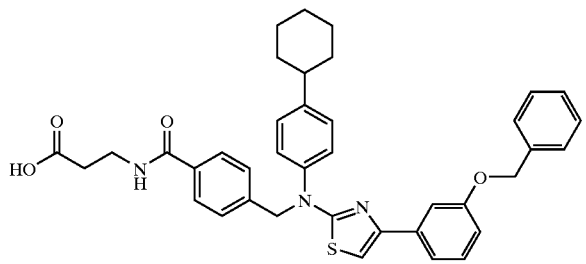
Example 28
General Procedure (A)
3-(4-{[[4-(3,5-Bis-trifluoromethylphenyl)thiazol-2-yl]-(4-cyclohexylphenyl)amino]methyl}benzoylamino)propionic acid
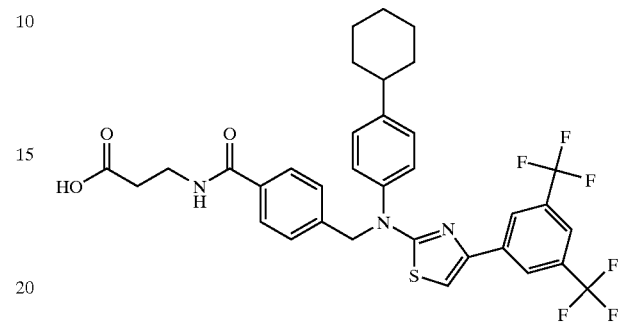
$^1$H NMR (DMSO-d$_6$): δ: 1.31–1.36 (m, 4H); 1.64–1.76 (m, 4H); 5.24 (s, 2H); 7.27 (d, 2H); 7.34 (d, 2H); 7.41 (d, 2H); 7.62 (s, 1H); 7.71 (d, 2H); 7.93 (s, 1H); 8.39 (s, 2H); 8.42 (t, 1H).
Example 29
General Procedure (A)
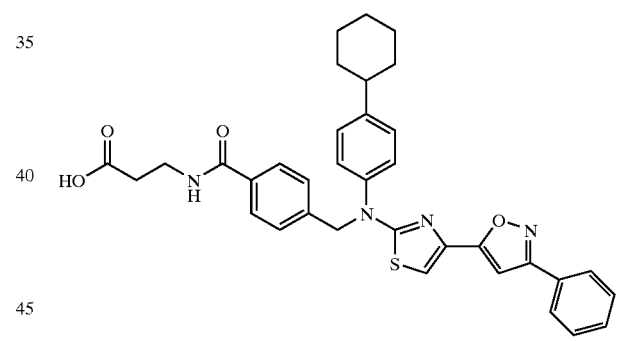
Example 30
General Procedure (A)
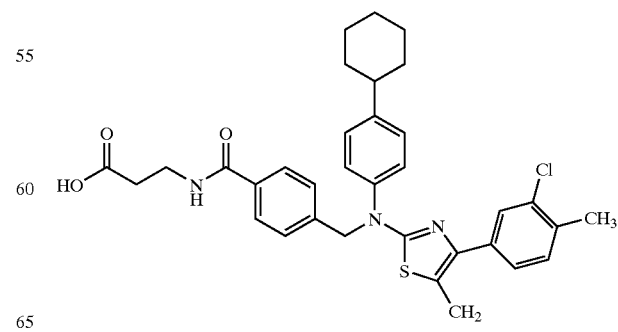

Example 31
General Procedure (A)
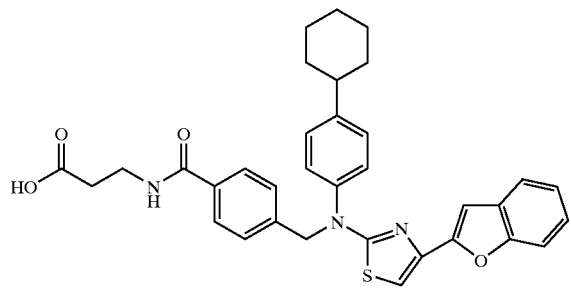
Example 34
General Procedure (A)
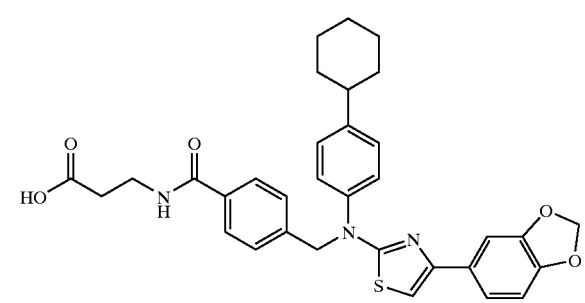
Example 32
General Procedure (A)
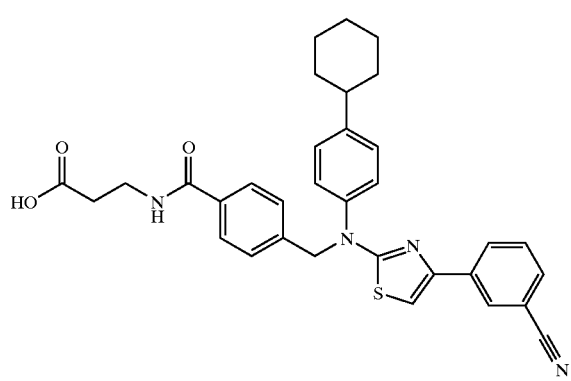
Example 35
General Procedure (A)
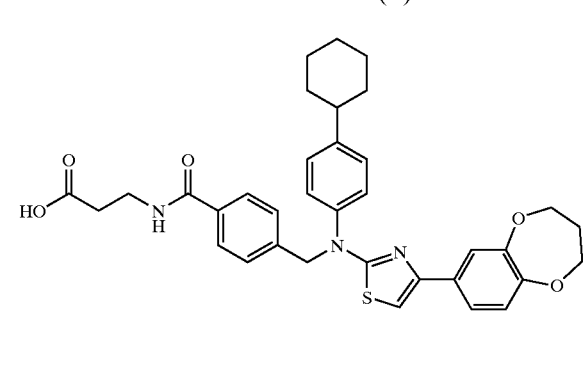
Example 33
General Procedure (A)
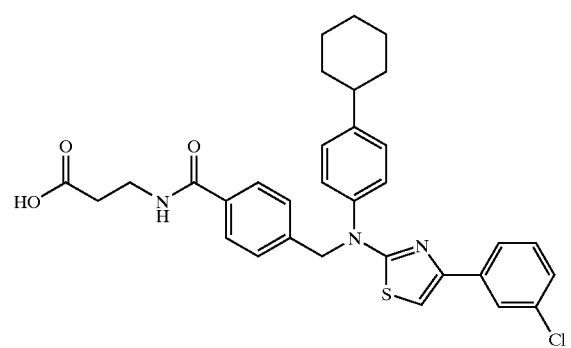
Example 36
General Procedure (A)
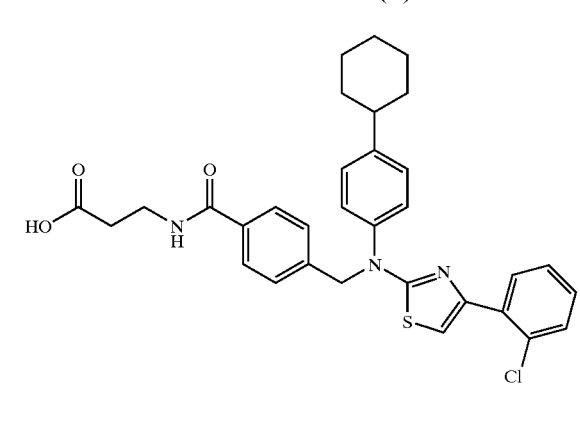

Example 37
General Procedure (A)
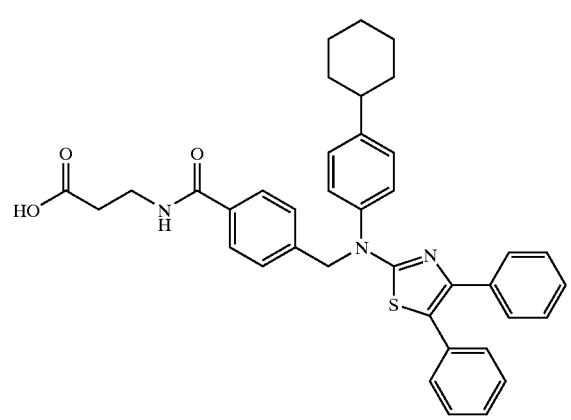
Example 38
General Procedure (A)
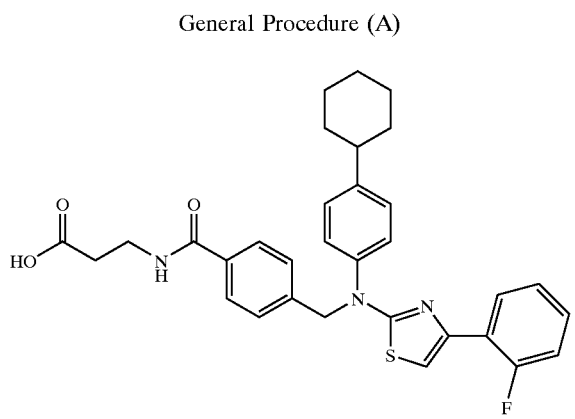
Example 39
General Procedure (A)
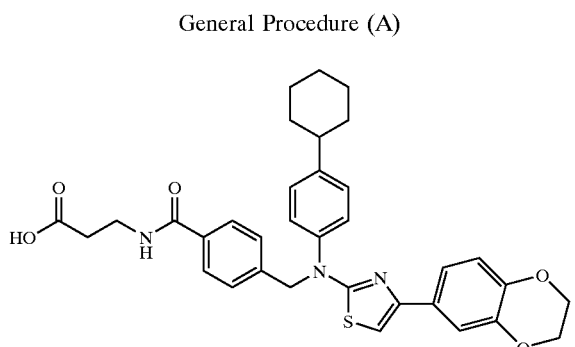
Example 40
General Procedure (A)
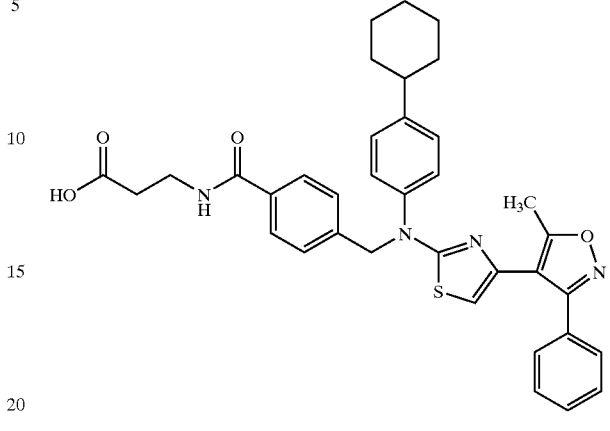
Example 41
General Procedure (A)
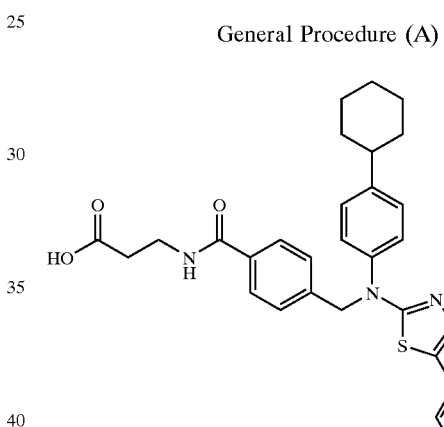
Example 42
General Procedure (A)
3-[4-({(4-Cyclohex-1-enylphenyl)-[4-(4-trifluoromethoxyphenyl)thiazol-2-yl]amino}methyl)benzoylamino]propionic acid
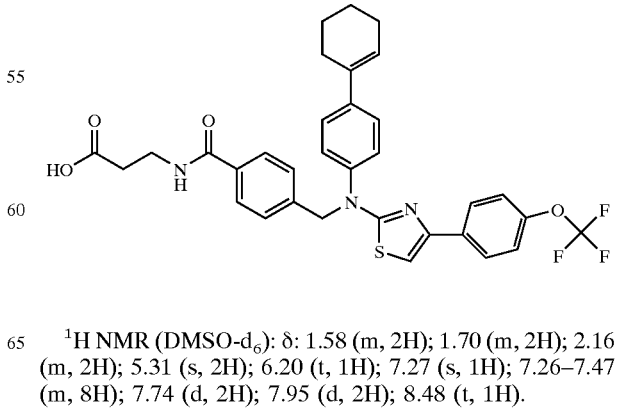
$^1$H NMR (DMSO-$d_6$): δ: 1.58 (m, 2H); 1.70 (m, 2H); 2.16 (m, 2H); 5.31 (s, 2H); 6.20 (t, 1H); 7.27 (s, 1H); 7.26–7.47 (m, 8H); 7.74 (d, 2H); 7.95 (d, 2H); 8.48 (t, 1H).

Example 43

General Procedure (A)

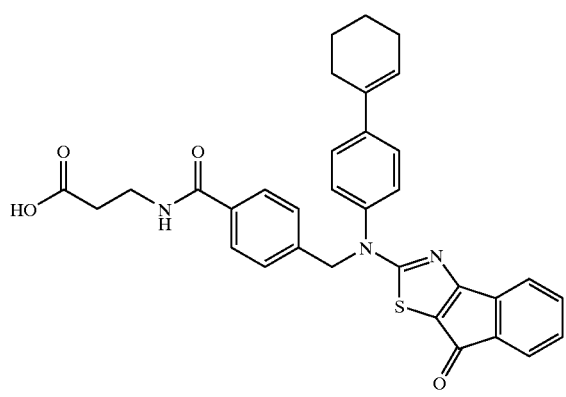

Example 44

General Procedure (A)

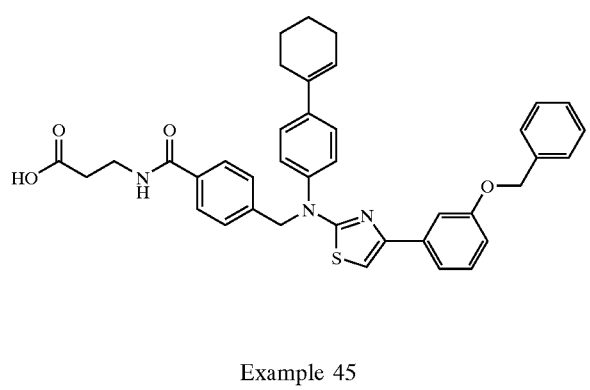

Example 45

General Procedure (A)

3-(4-{[[4-(3,5-Bis-trifluoromethylphenyl)thiazol-2-yl]-(4-cyclohex-1-enyl-phenyl)amino]methyl}benzoylamino)propionic acid

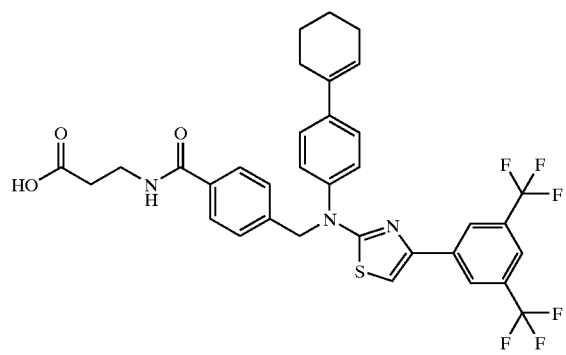

HPLC-MS (Method (A)): m/z: 674 (M+1); Rt=8.63 min.

Example 46

General Procedure (A)

3-[4-({(4-Cyclohex-1-enylphenyl)-[4-(3-phenylisoxazol-5-yl)thiazol-2-yl]amino}methyl)benzoylamino]propionic acid

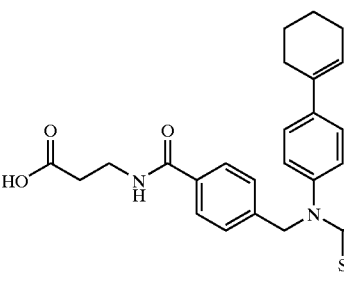

$^1$H NMR (DMSO-d$_6$): δ: 1.58 (m, 2H); 1.70 (m, 2H); 2.17 (m, 2H); 2.27 (m, 2H); 5.32 (s, 2H); 6.20 (t, 1H); 7.26 (s, 1H); 7.75 (d, 2H); 7.91 (d, 2H); 8.44 (t, 1H).

Example 47

General Procedure (A)

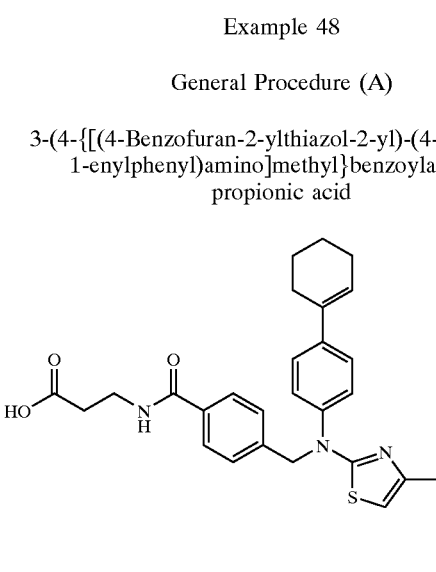

Example 48

General Procedure (A)

3-(4-{[(4-Benzofuran-2-ylthiazol-2-yl)-(4-cyclohex-1-enylphenyl)amino]methyl}benzoylamino)propionic acid HPLC-MS (Method (A)): m/z: 578 (M+1); Rt=8.27 min.

Example 49

General Procedure (A)

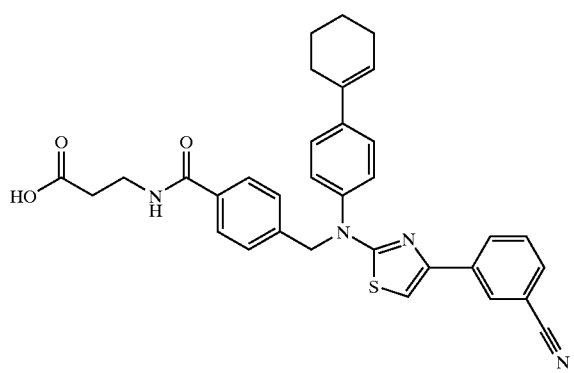

Example 50

General Procedure (A)

3-(4-{[(4-Benzo[1,3]dioxol-5-ylthiazol-2-yl)-(4-cyclohex-1-enylphenyl)amino]methyl}benzoylamino)propionic acid

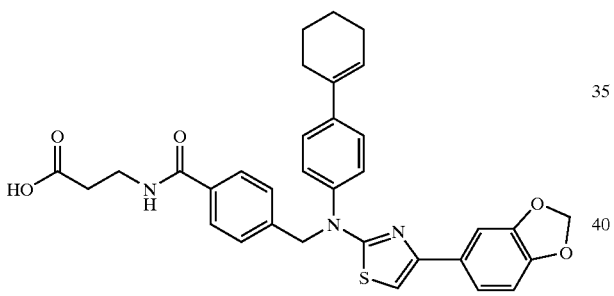

$^1$H NMR (DMSO-$d_6$): δ: 1.57 (m, 2H); 1.68 (m, 2H); 2.16 (m, 2H); 5.28 (s, 2H); 6.01 (s, 2H); 6.18 (t, 1H); 7.72 (m, 2H); 8.43 (t, 1H).

Example 51

General Procedure (A)

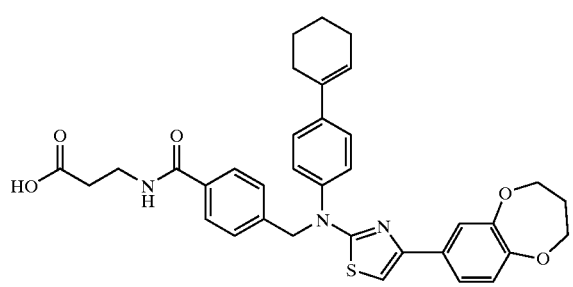

Example 52

General Procedure (A)

3-[4-({(4-Cyclohex-1-enylphenyl)-[4-(3,4-dichlorophenyl)thiazol-2-yl]amino}methyl)benzoylamino]propionic acid

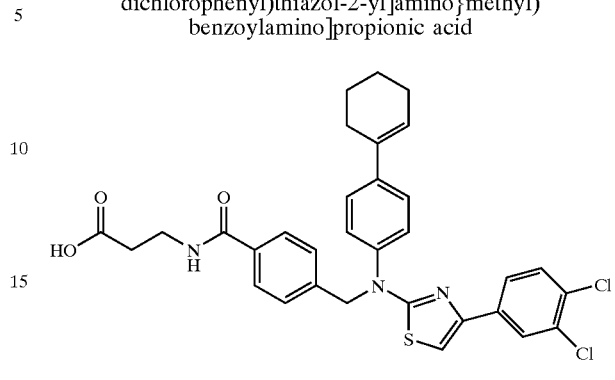

HPLC-MS (Method (A)): m/z: 606 (M+1); Rt=8.53 min.

Example 53

General Procedure (A)

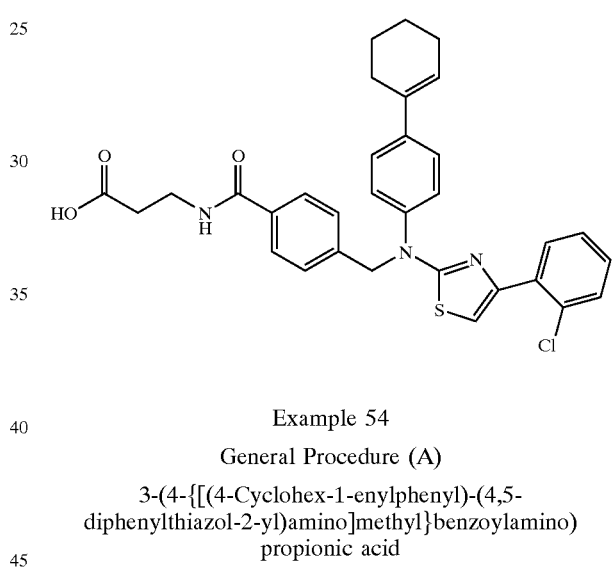

Example 54

General Procedure (A)

3-(4-{[(4-Cyclohex-1-enylphenyl)-(4,5-diphenylthiazol-2-yl)amino]methyl}benzoylamino)propionic acid

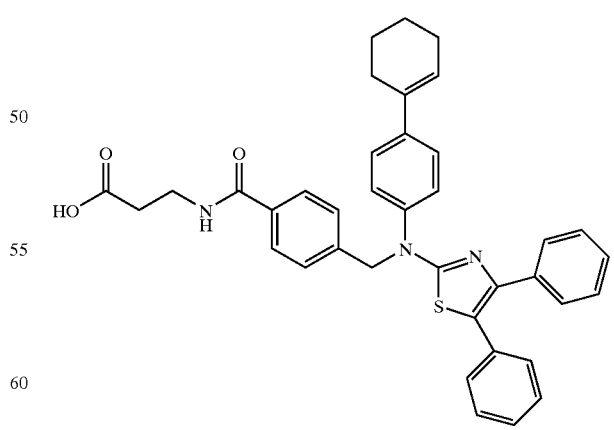

$^1$H NMR (DMSO-$d_6$): δ: 1.58 (m, 2H); 1.70 (m, 2H); 2.16 (m, 2H); 2.34 (m, 2H); 3.43 (q, 2H); 5.29 (s, 2H); 6.19 (t, 1H); 7.19–7.29 (m, 8H); 7.40–7.47 (m, 8H); 7.76 (d, 2H); 8.44 (t, 1H).

Example 55

General Procedure (A)

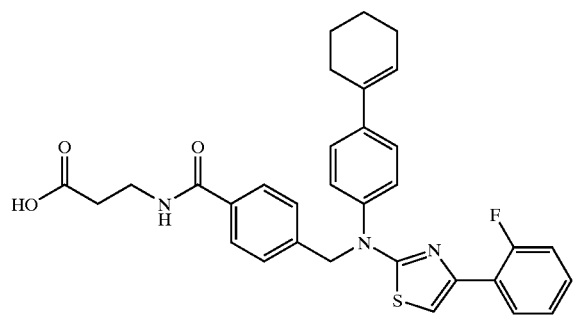

HPLC-MS (Method (A)): m/z: 556 (M+1); Rt=8.23 min.

Example 56

General Procedure (A)

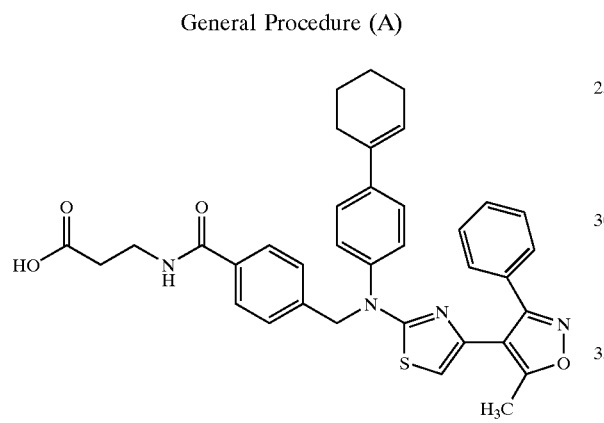

Example 57

General Procedure (A)

3-(4-{[[4-(4-Chlorophenyl)-5-phenylthiazol-2-yl]-(4-cyclohex-1-enylphenyl)amino]methyl}benzoylamino)propionic acid

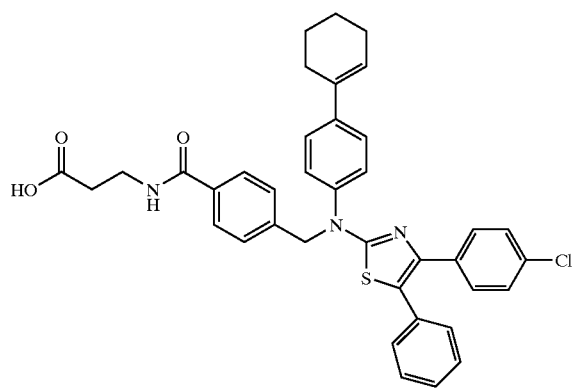

$^1$H NMR (DMSO-$d_6$): δ: 1.58 (m, 2H); 1.70 (m, 2H); 2.16 (m, 2H); 2.34 (m, 2H); 3.43 (q, 2H); 5.30 (s, 2H); 6.20 (t, 1H); 7.22–7.47 (m, 15H); 7.77 (d, 2H); 8.48 (t, 1H).

Example 58

General Procedure (A)

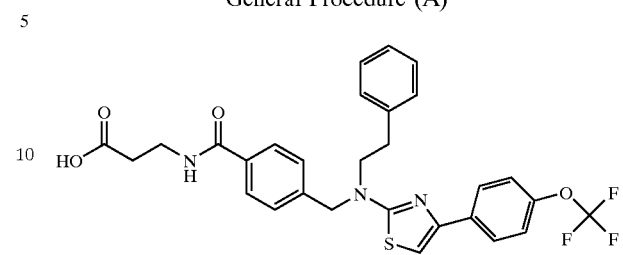

Example 59

General Procedure (A)

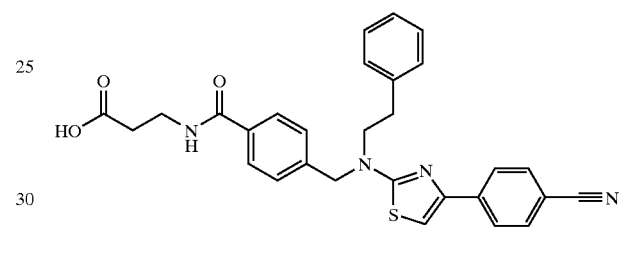

Example 60

General Procedure (A)

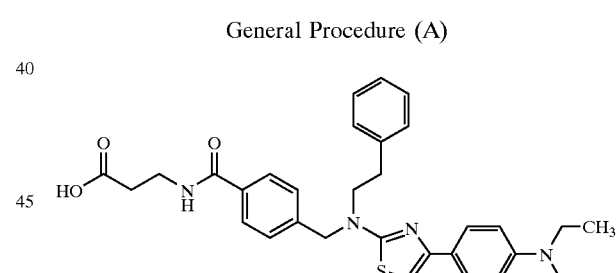

Example 61

General Procedure (A)

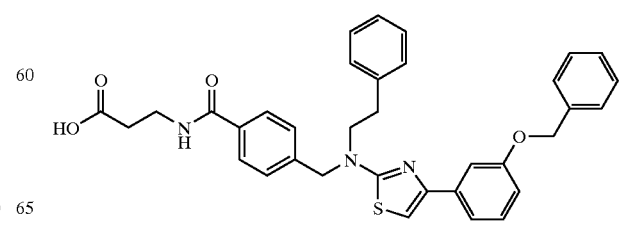

Example 62
General Procedure (A)
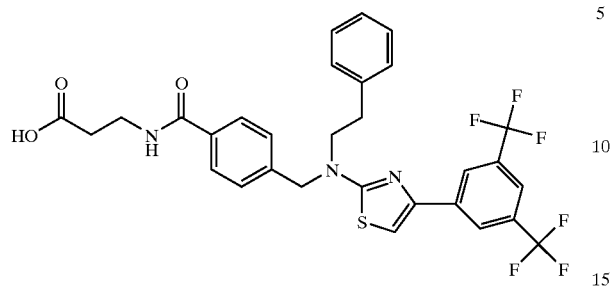
Example 63
General Procedure (A)
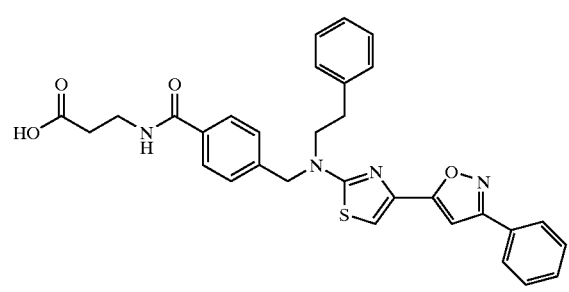
Example 64
General Procedure (A)
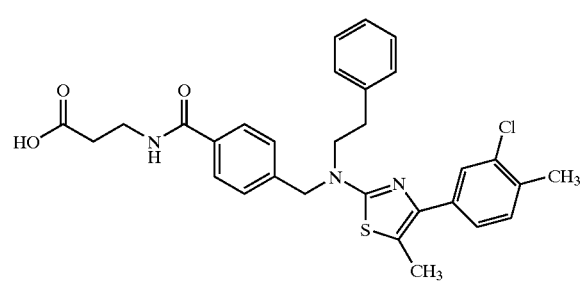
Example 65
General Procedure (A)
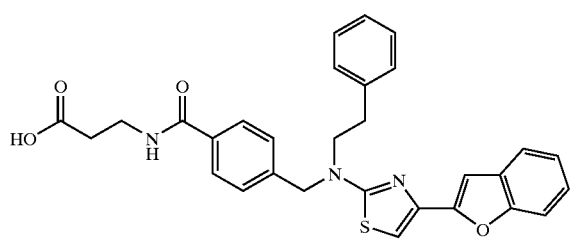
Example 66
General Procedure (A)
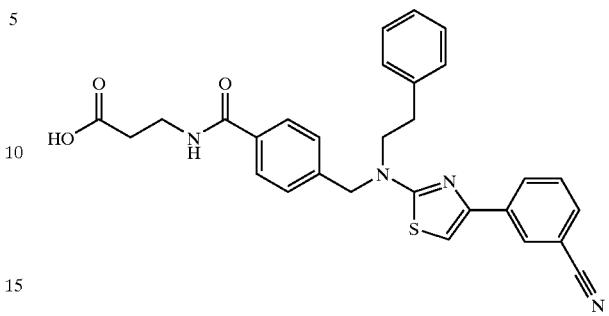
Example 67
General Procedure (A)
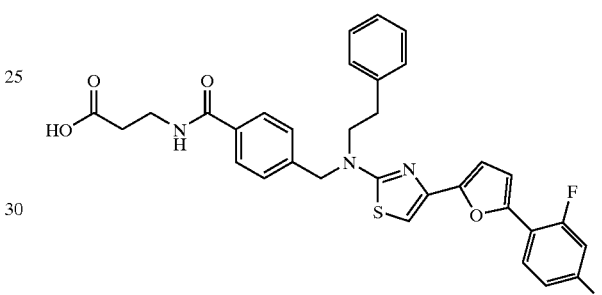
Example 68
General Procedure (A)
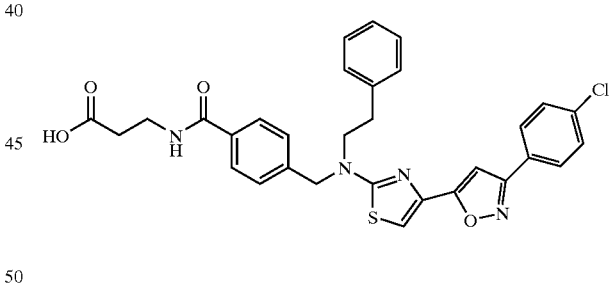
Example 69
General Procedure (A)
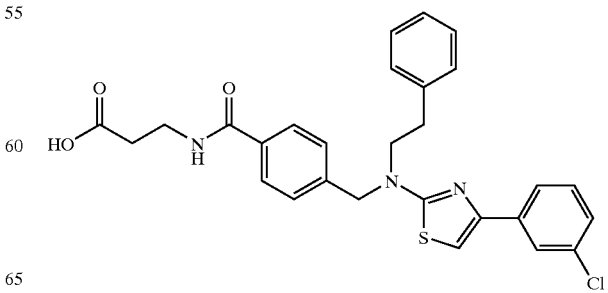

41
Example 70
General Procedure (A)
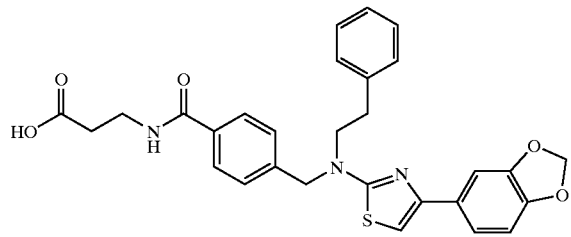
Example 71
General Procedure (A)
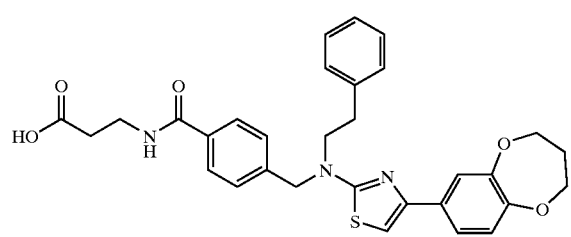
Example 72
General Procedure (A)
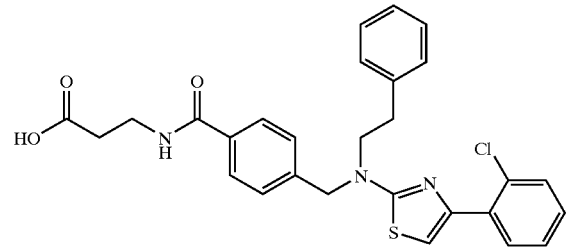
Example 73
General Procedure (A)
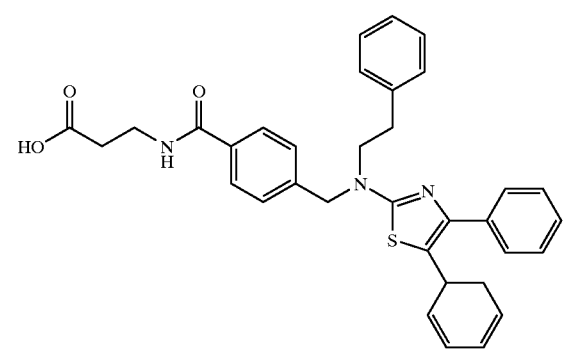
42
Example 74
General Procedure (A)
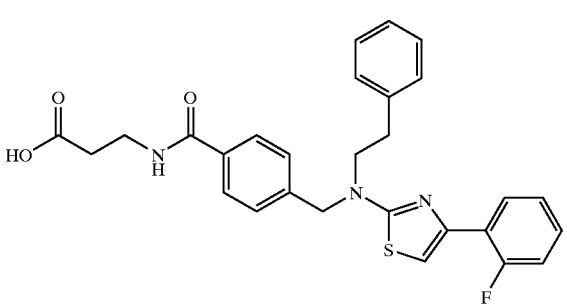
Example 75
General Procedure (A)
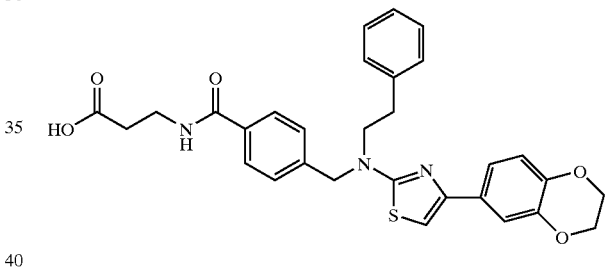
Example 76
General Procedure (A)
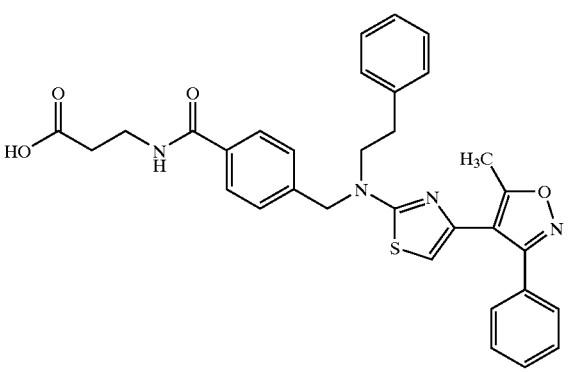

Example 77
General Procedure (A)
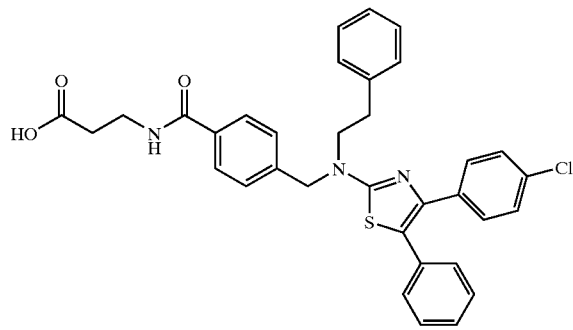
Example 78
General Procedure (A)
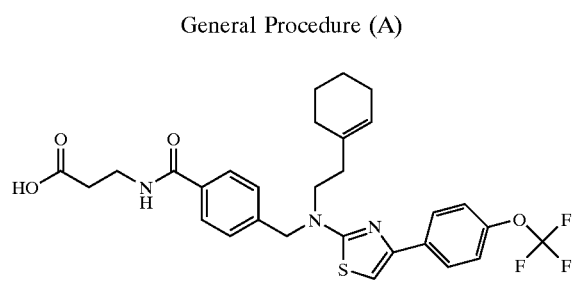
Example 79
General Procedure (A)
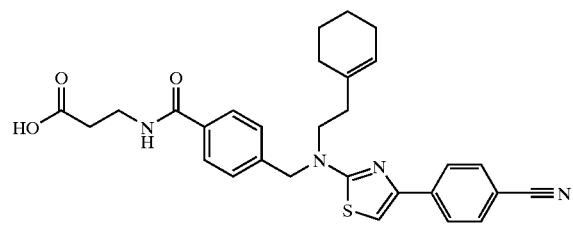
Example 80
General Procedure (A)
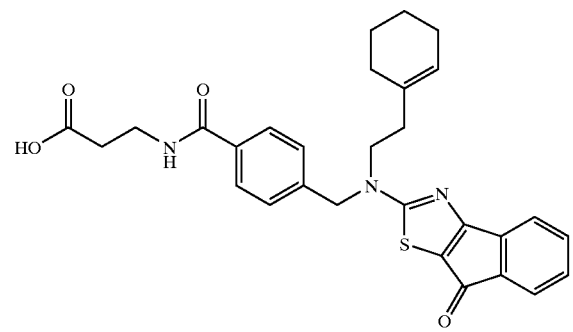
Example 81
General Procedure (A)
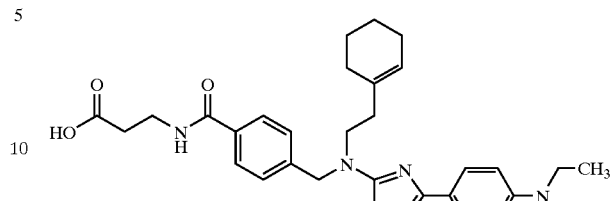
Example 82
General Procedure (A)
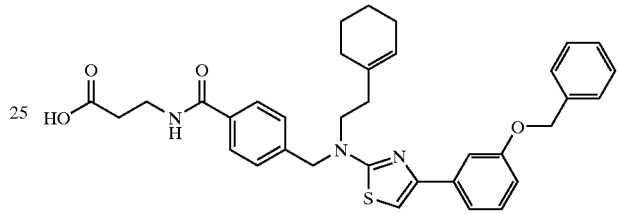
Example 83
General Procedure (A)
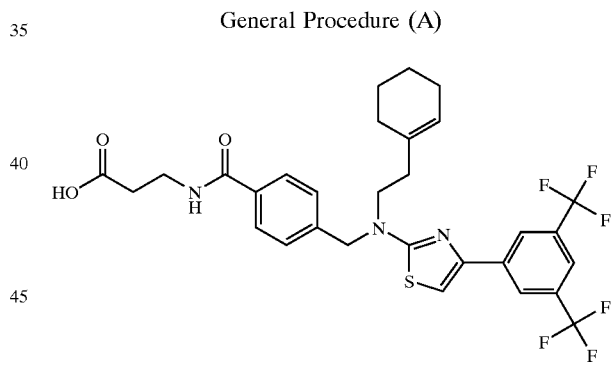
Example 84
General Procedure (A)
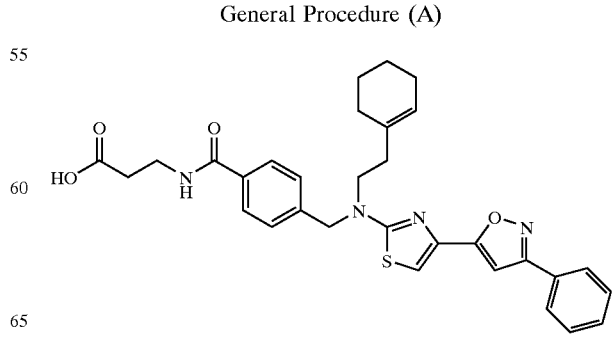

Example 85
General Procedure (A)
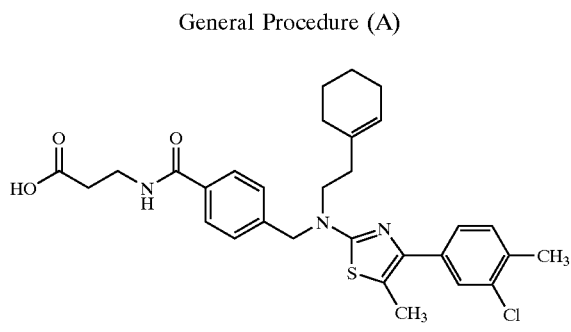
Example 89
General Procedure (A)
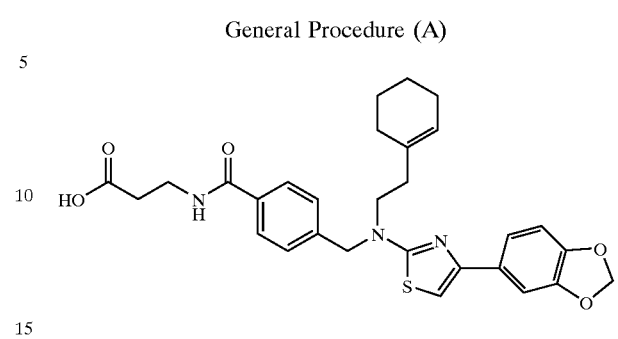
Example 86
General Procedure (A)
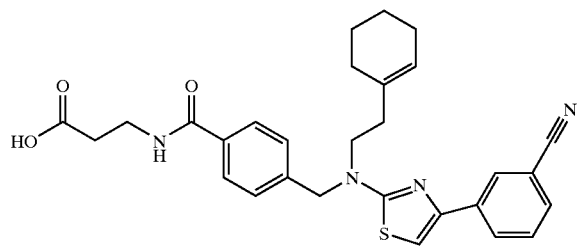
Example 90
General Procedure (A)
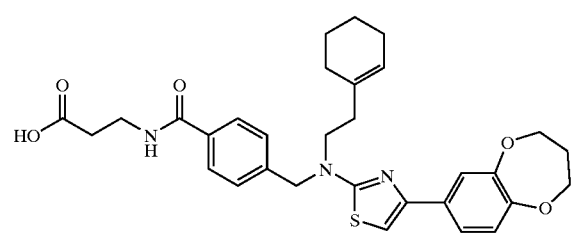
Example 87
General Procedure (A)
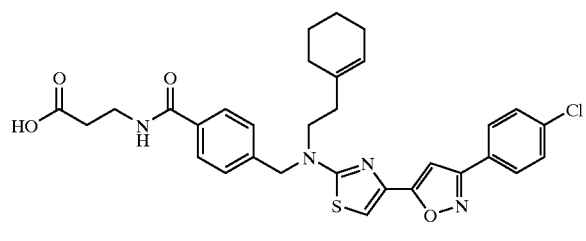
Example 91
General Procedure (A)
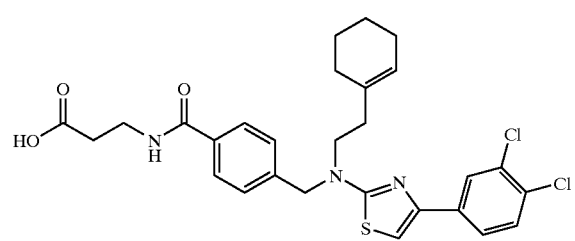
Example 88
General Procedure (A)
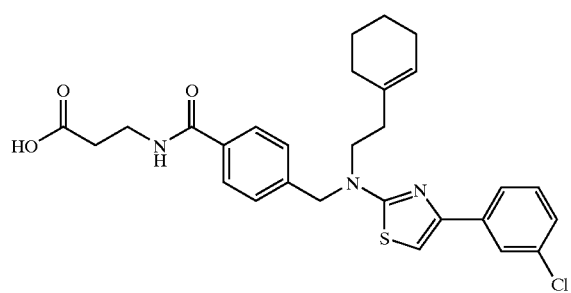
Example 92
General Procedure (A)
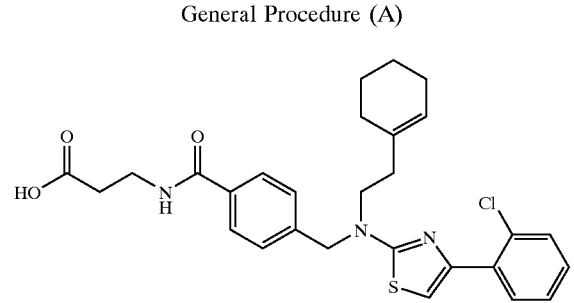

Example 93
General Procedure (A)
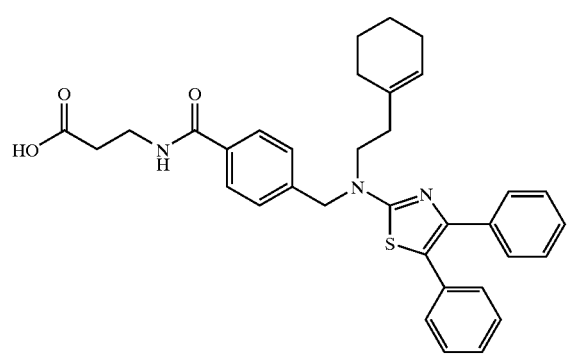
Example 94
General Procedure (A)
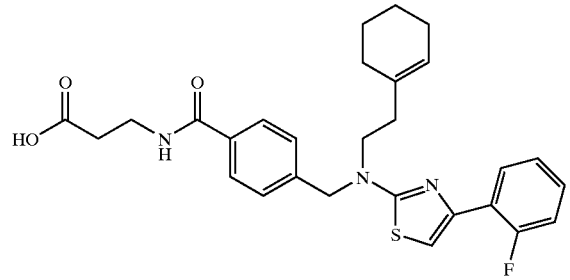
Example 95
General Procedure (A)
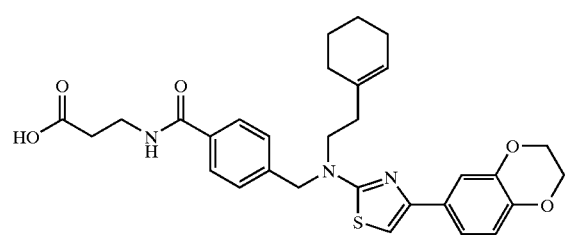
Example 96
General Procedure (A)
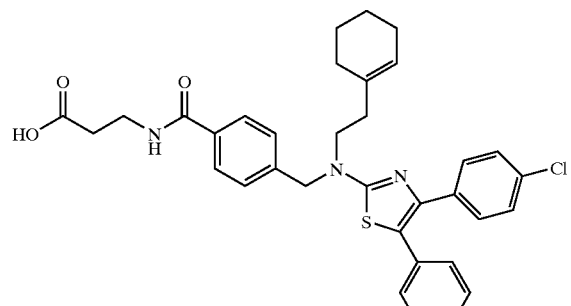
Example 97
General Procedure (A)
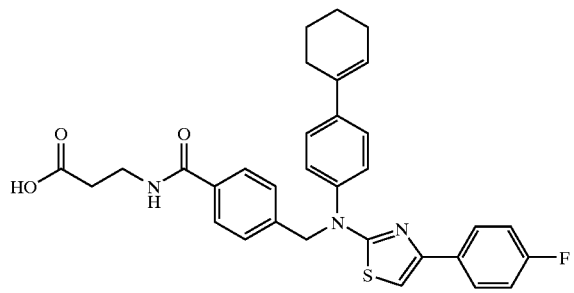
Example 98
General Procedure (A)
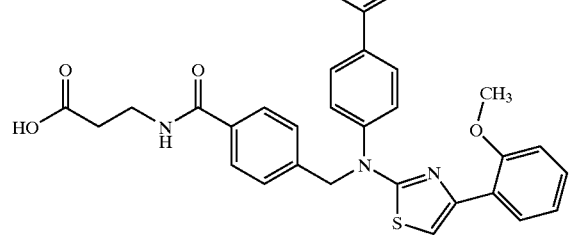

Example 99
General Procedure (A)
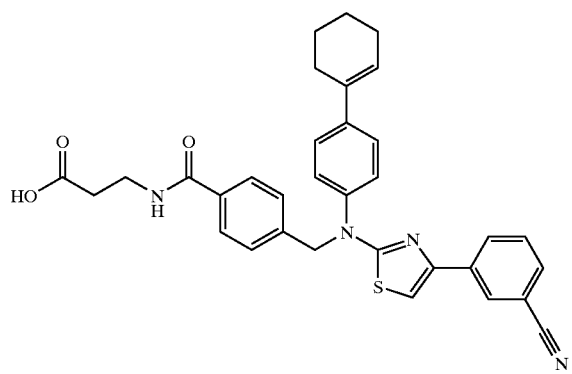
Example 100
General Procedure (A)
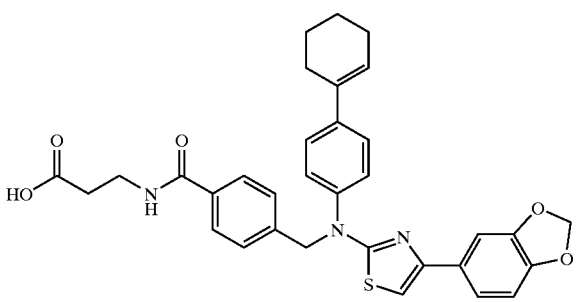
Example 101
General Procedure (A)
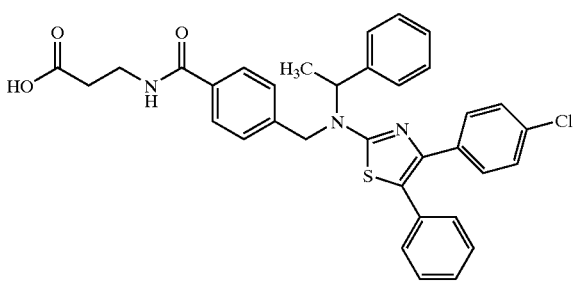
Example 102
General Procedure (A)
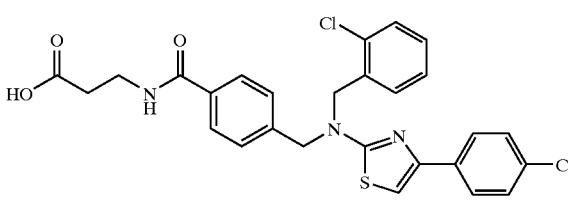
Example 103
General Procedure (A)
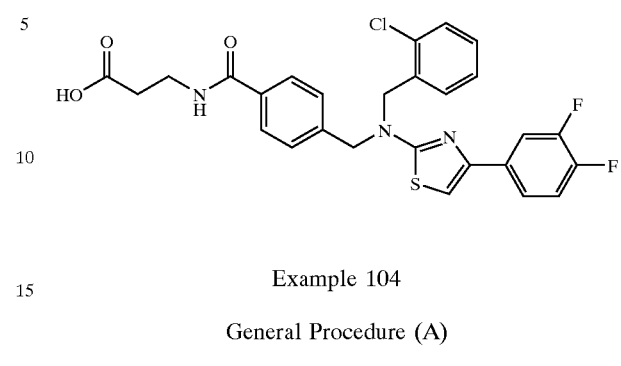
Example 104
General Procedure (A)
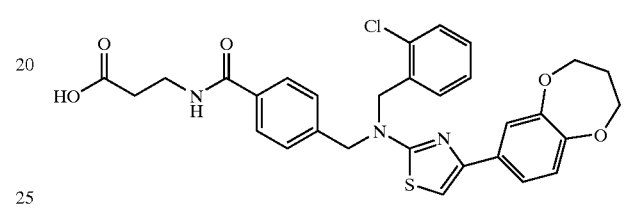
Example 105
General Procedure (A)
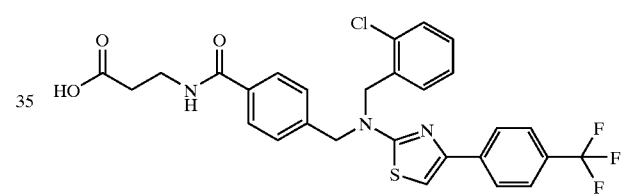
Example 106
General Procedure (A)
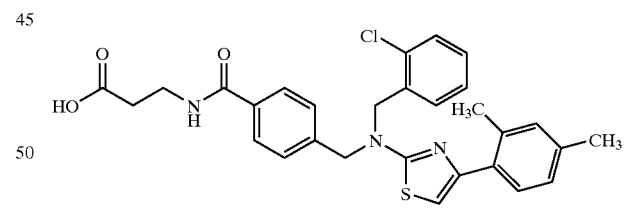
Example 107
General Procedure (A)
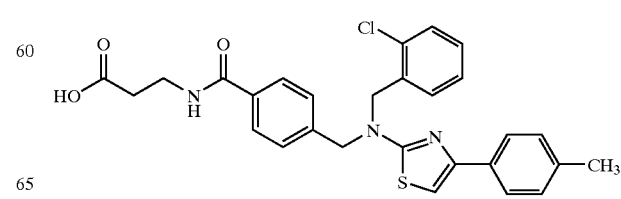

51

Example 108

General Procedure (A)

Example 109

General Procedure (A)

Example 110

General Procedure (A)

Example 111

General Procedure (A)

52

Example 112

General Procedure (A)

Example 113

General Procedure (A)

Example 114

General Procedure (A)

Example 115

General Procedure (A)

Example 116
General Procedure (A)
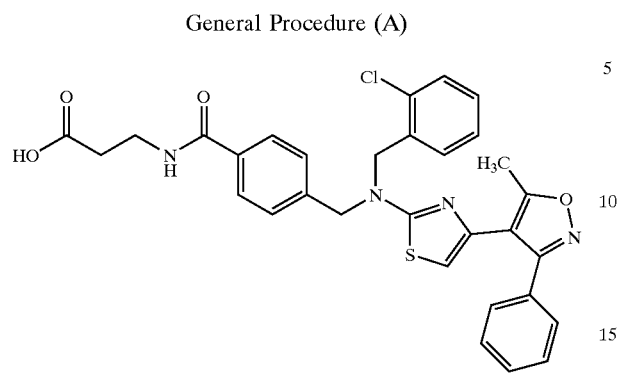
Example 117
General Procedure (A)
3-(4-{[[4-(3,4-Dichlorophenyl)thiazol-2-yl]-(1,2,3,4-tetrahydronaphthalen-1-yl)amino]methyl}benzoylamino)propionic acid
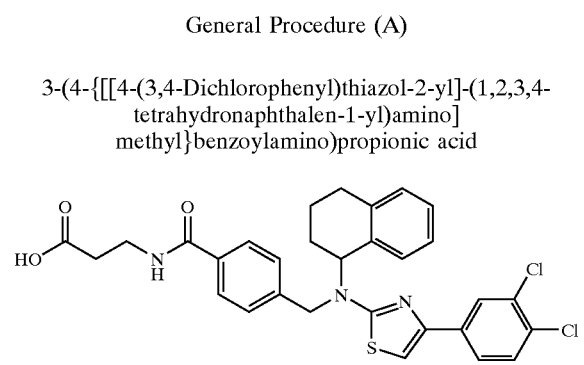
HPLC-MS (Method (A)): m/z: 581 (M+1); Rt: 6.40 min.
Example 118
General Procedure (A)
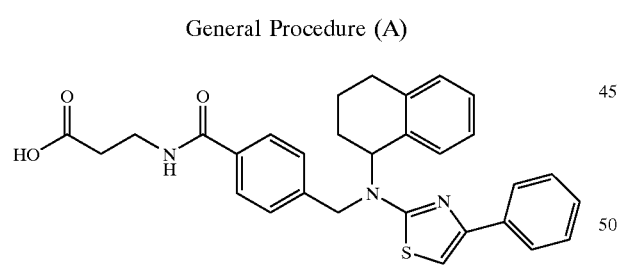
Example 119
General Procedure (A)
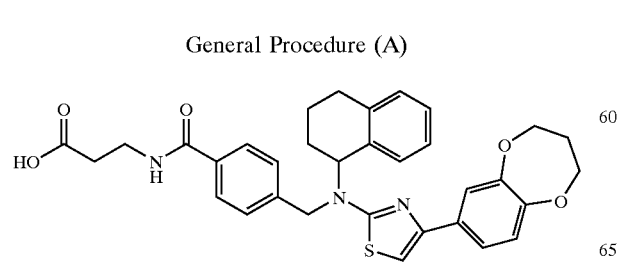
Example 120
General Procedure (A)
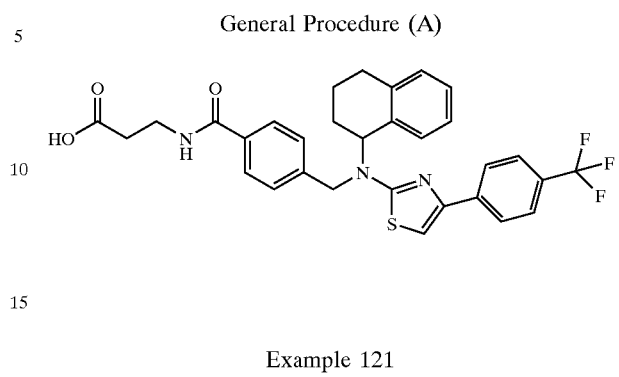
Example 121
General Procedure (A)
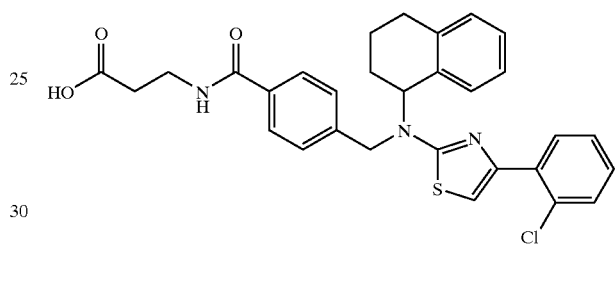
Example 122
General Procedure (A)
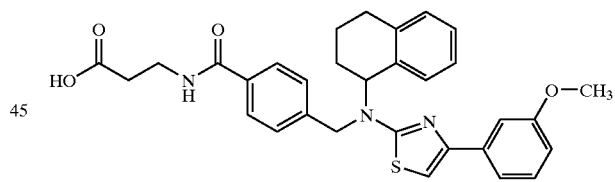
Example 123
General Procedure (A)
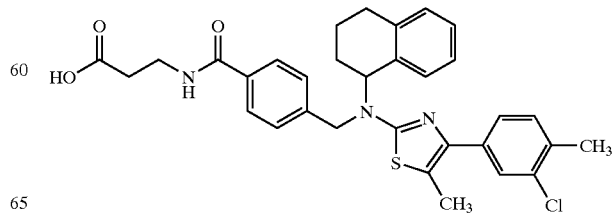

Example 124
General Procedure (A)
Example 127
General Procedure (A)
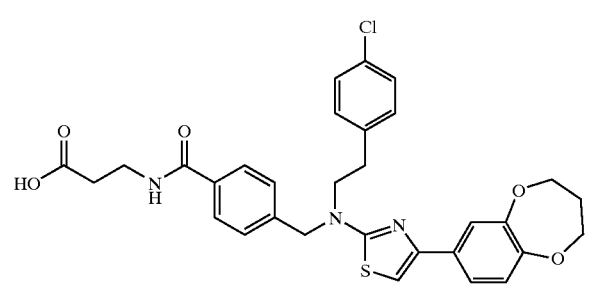
Example 125
General Procedure (A)
Example 128
General Procedure (A)
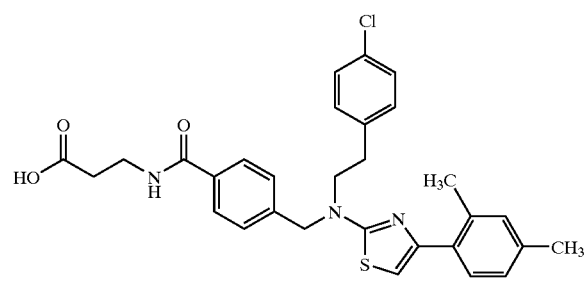
Example 126
General Procedure (A)
Example 129
General Procedure (A)
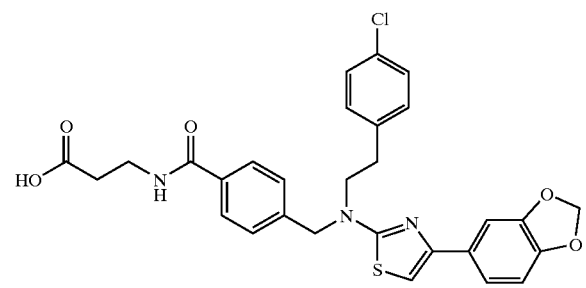

Example 130
General Procedure (A)
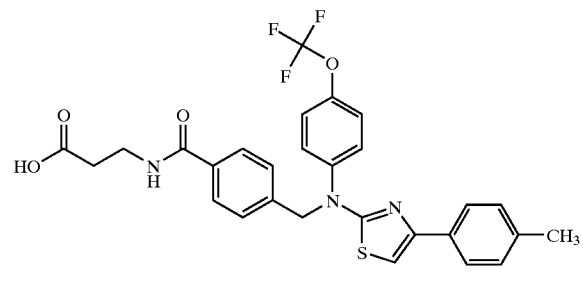
Example 131
General Procedure (A)
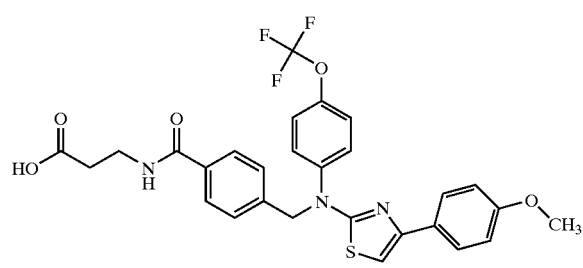
Example 132
General Procedure (A)
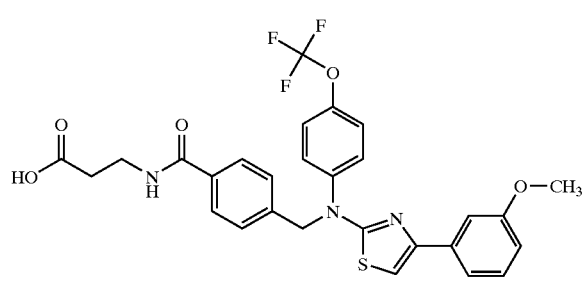
Example 133
General Procedure (A)
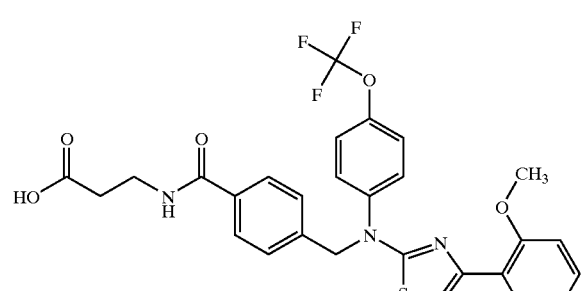
Example 134
General Procedure (A)
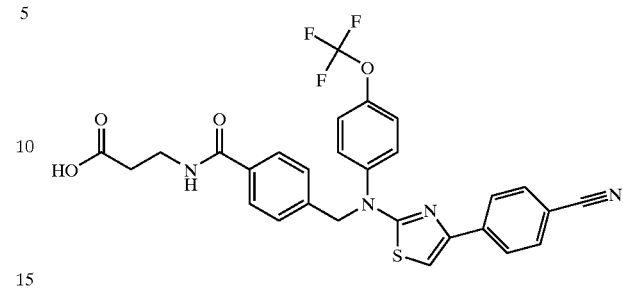
Example 135
General Procedure (A)
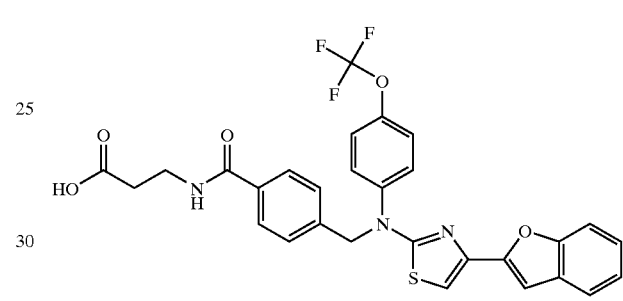
Example 136
General Procedure (A)
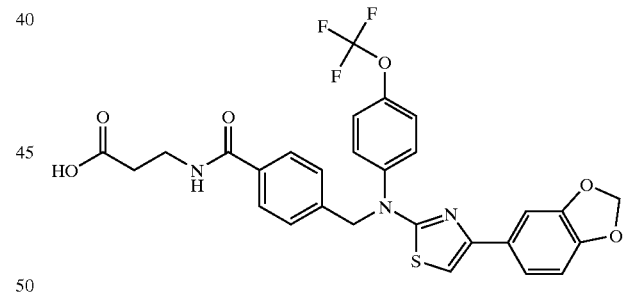
Example 137
General Procedure (A)
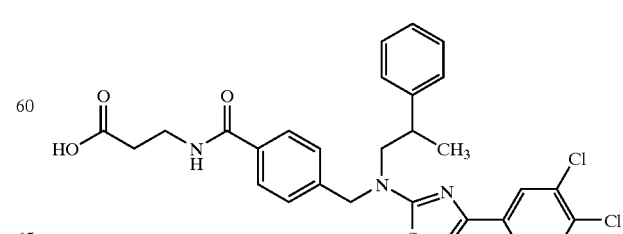

Example 138
General Procedure (A)
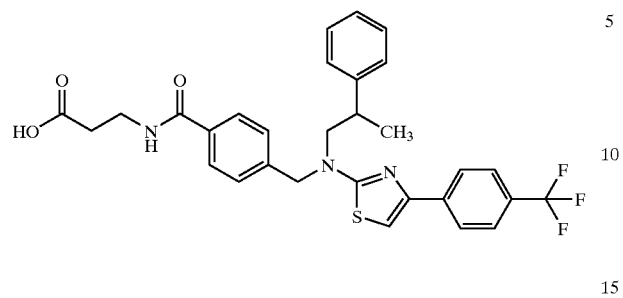
Example 139
General Procedure (A)
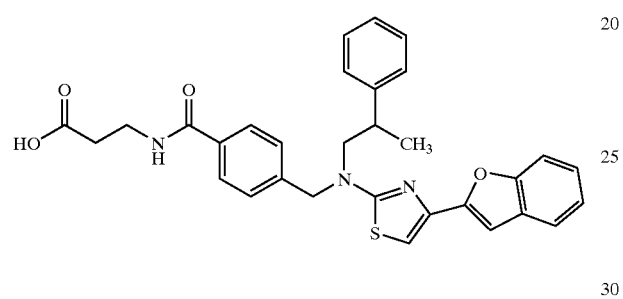
Example 140
General Procedure (A)
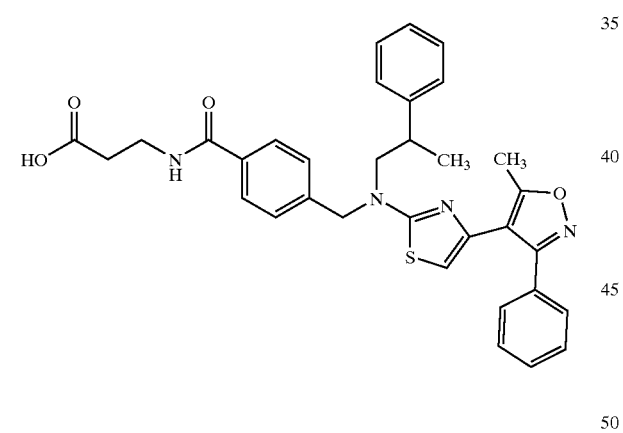
Example 141
General Procedure (A)
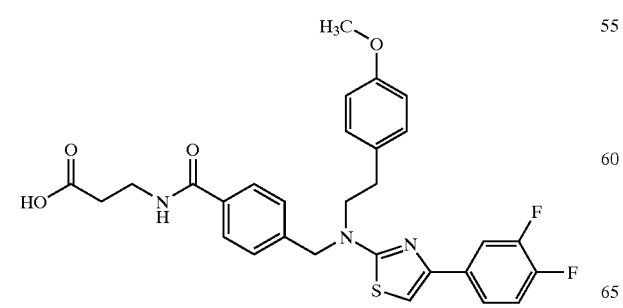
Example 142
General Procedure (A)
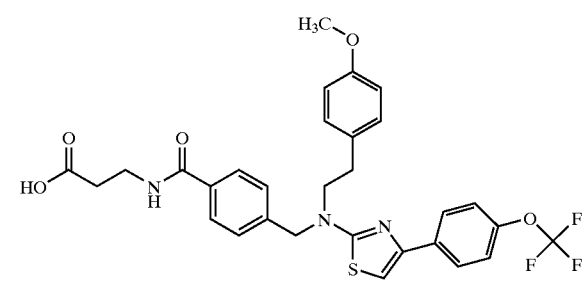
Example 143
General Procedure (A)
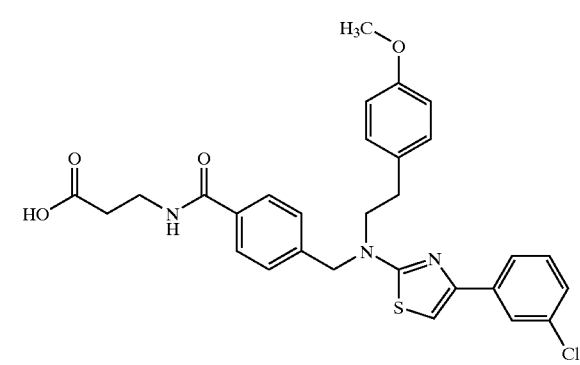
Example 144
General Procedure (A)
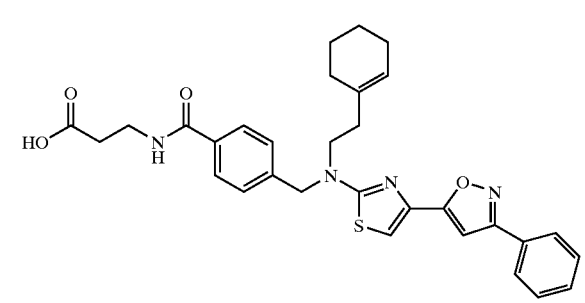
Example 145
General Procedure (A)
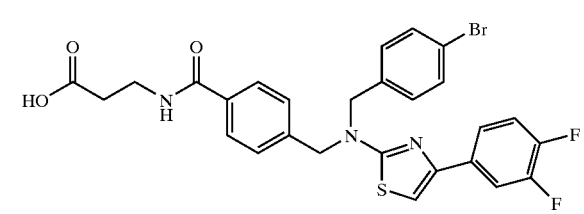

Example 146
General Procedure (A)
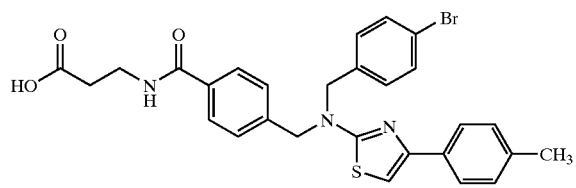
Example 147
General Procedure (A)
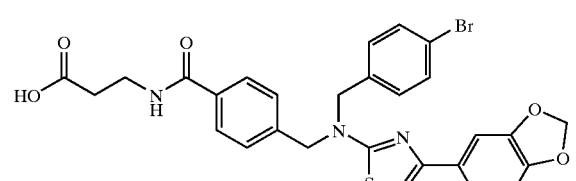
Example 148
General Procedure (A)
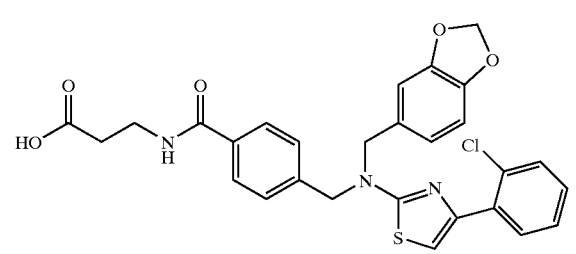
Example 149
General Procedure (A)
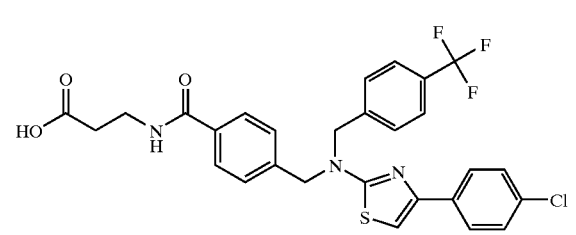
Example 150
General Procedure (A)
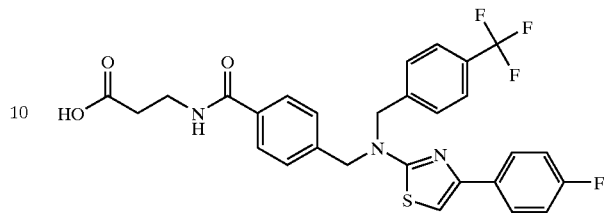
Example 151
General Procedure (A)
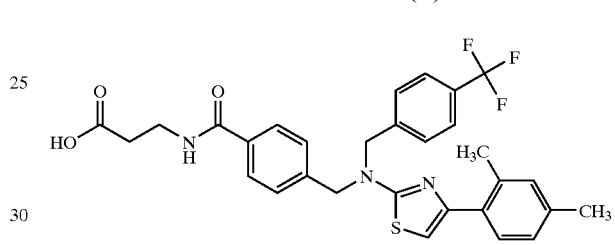
Example 152
General Procedure (A)
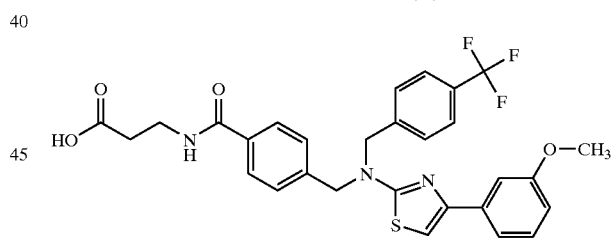
Example 153
General Procedure (A)
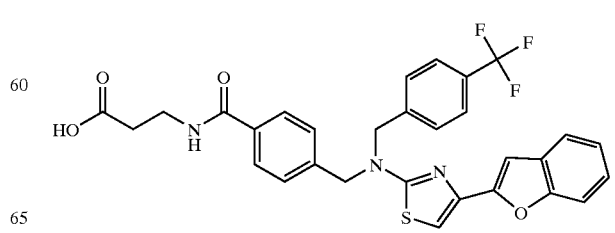

Example 154
General Procedure (A)
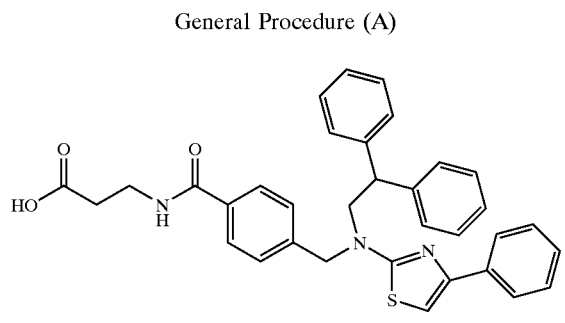
Example 155
General Procedure (A)
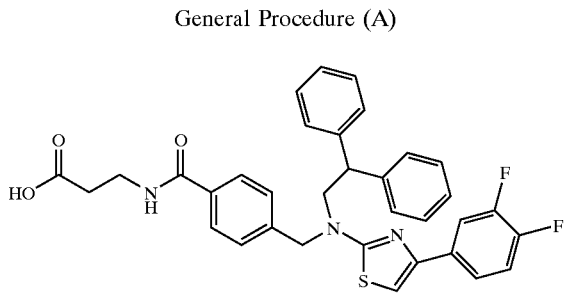
Example 156
General Procedure (A)
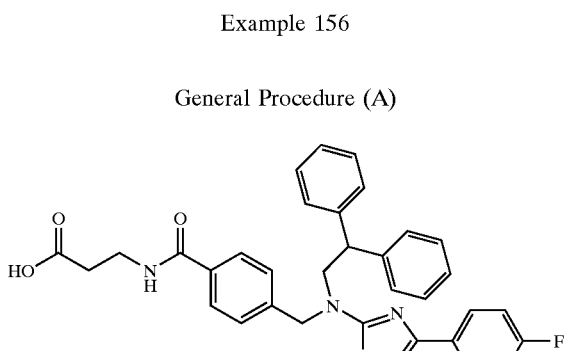
Example 157
General Procedure (A)
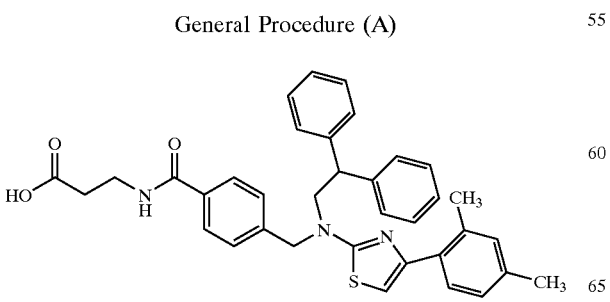
Example 158
General Procedure (A)
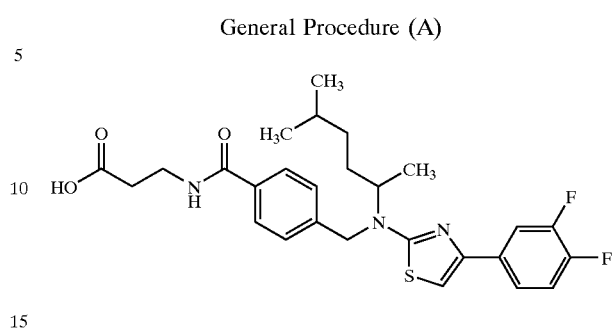
Example 159
General Procedure (A)
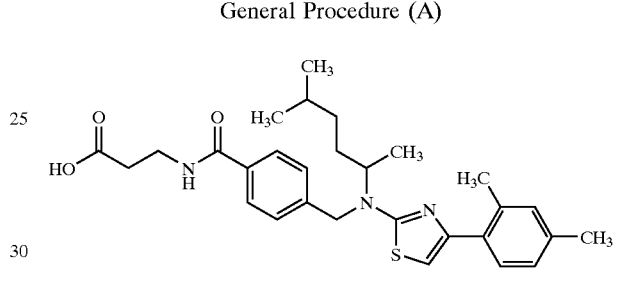
Example 160
General Procedure (A)
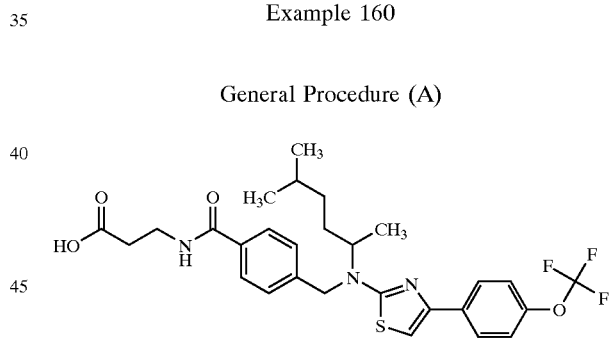
Example 161
General Procedure (A)
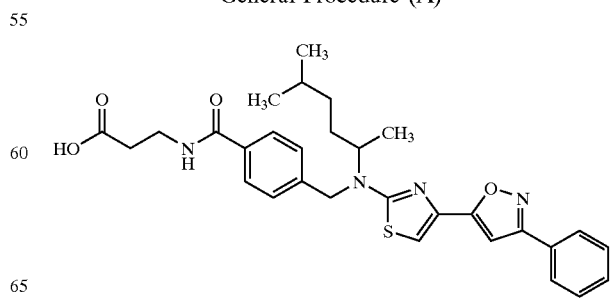

65
Example 162
General Procedure (A)
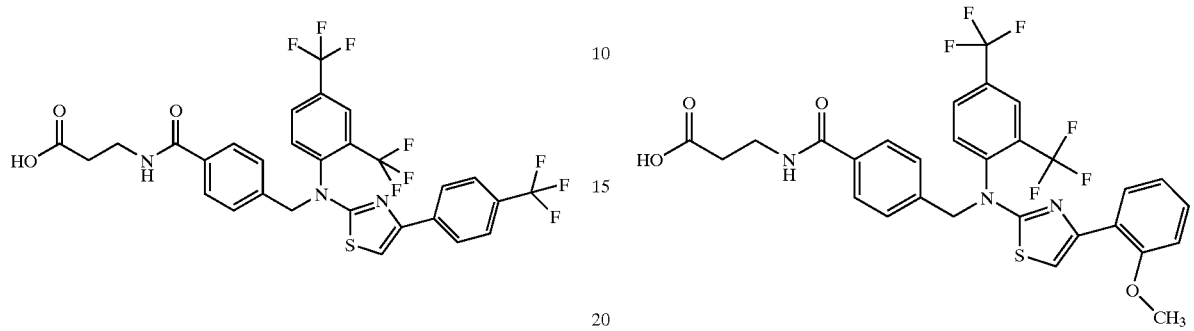
Example 163
General Procedure (A)
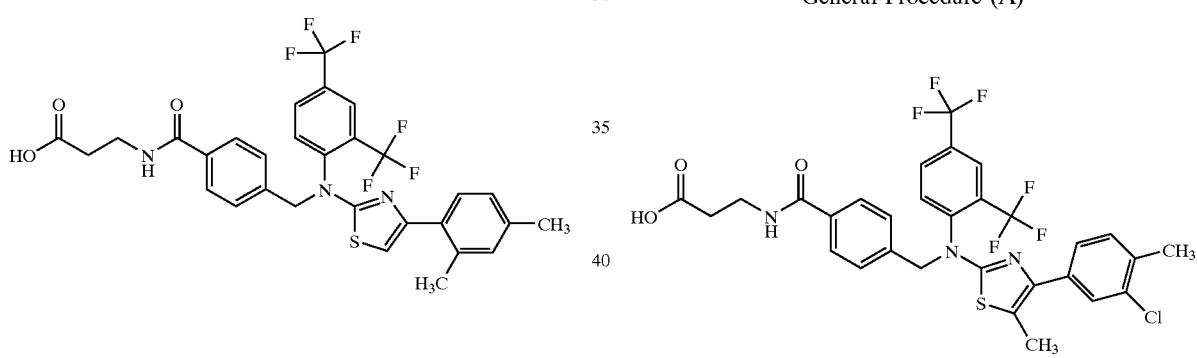
Example 164
General Procedure (A)
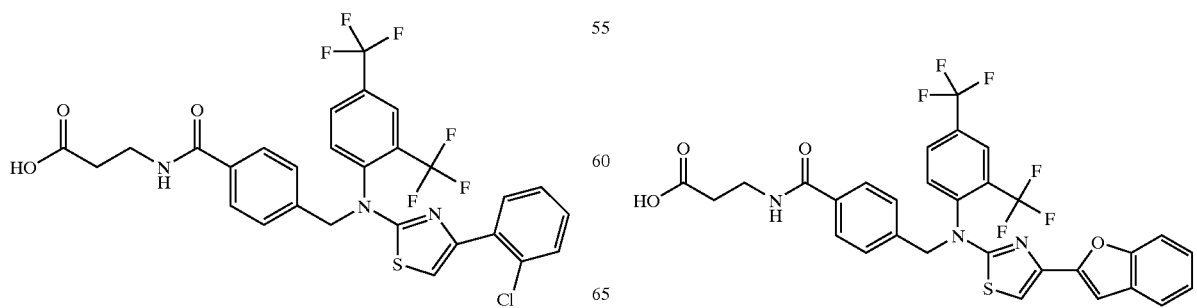
66
Example 165
General Procedure (A)
Example 166
General Procedure (A)
Example 167
General Procedure (A)

Example 168
General Procedure (A)
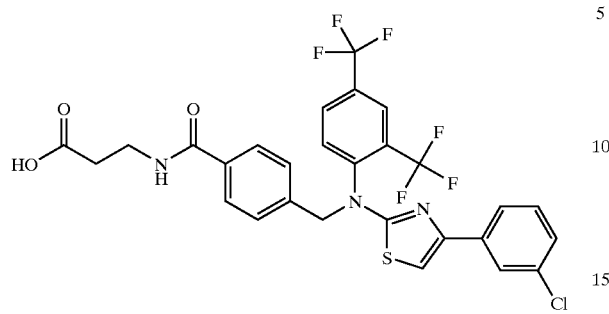
Example 169
General Procedure (A)
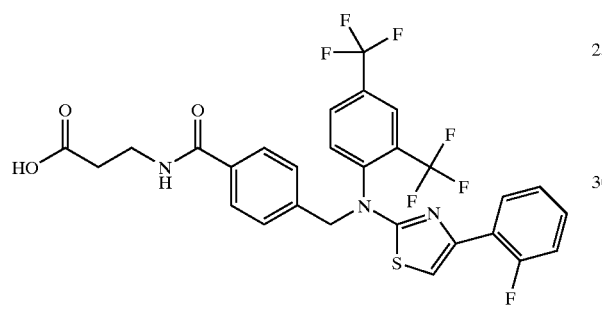
Example 170
General Procedure (A)
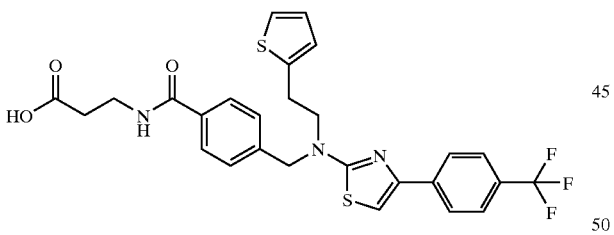
Example 171
General Procedure (A)
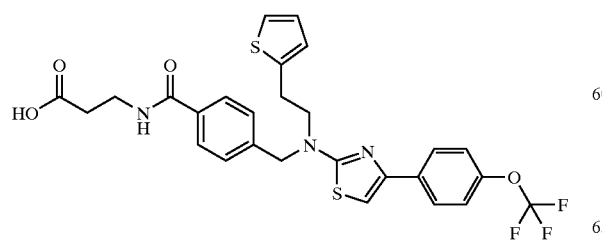
Example 172
General Procedure (A)
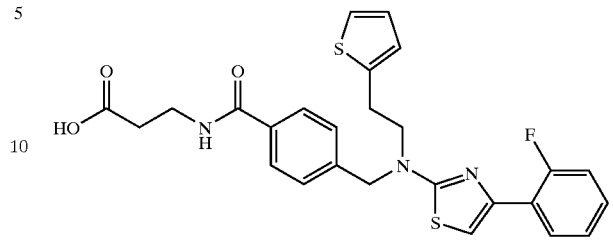
Example 173
General Procedure (A)
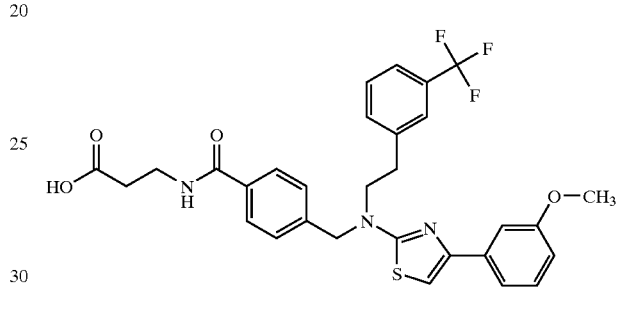
Example 174
General Procedure (A)
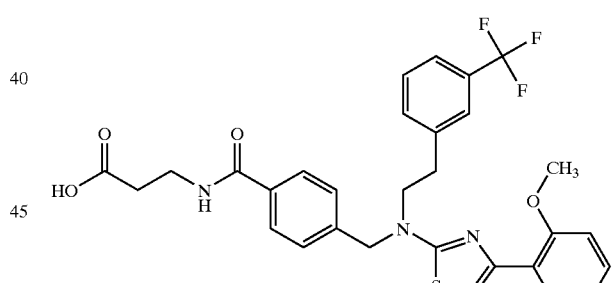
Example 175
General Procedure (A)
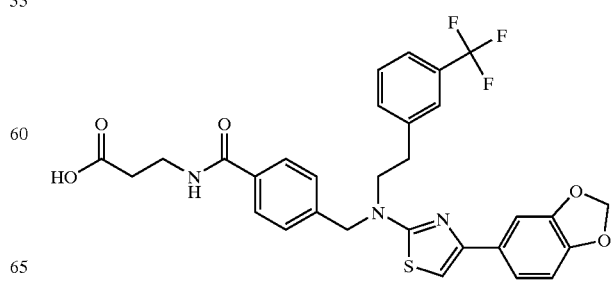

Example 176

General Procedure (A)

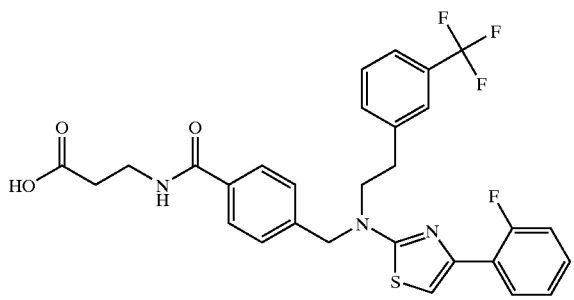

Example 177

General Procedure (A)

3-(4-{[[4-(4-Fluorophenyl)thiazol-2-yl]-(4-trifluoromethylsulfanylphenyl)amino]methyl}benzoylamino)propionic acid

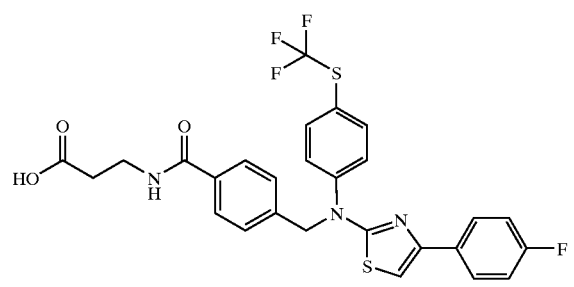

$^1$H NMR (DMSO-d$_6$): δ: 3.44 (q, 2H); 5.39 (s, 2H); 7.20–7.24 (m, 2H); 7.36 (s, 1H); 7.41 (d, 2H); 7.69–7.77 (m, 6H); 7.89 (m, 2H); 8.43 (t, 1H).

Example 178

General Procedure (A)

3-(4-{[[4-(2-Chlorophenyl)thiazol-2-yl]-(4-trifluoromethylsulfanylphenyl)amino]methyl}benzoylamino)propionic acid

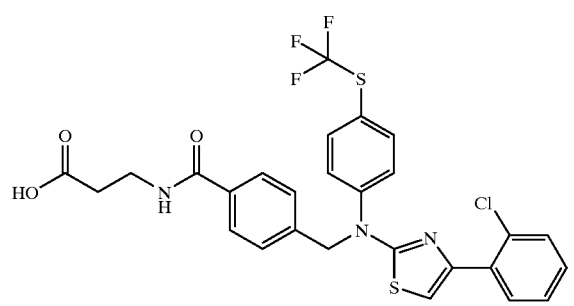

$^1$H NMR (DMSO-d$_6$): 3.44 (m, 2H); 5.29 (s, 1H); 5.37 (s, 1H); 7.40 (m, 6H); 7.72 (m, 7H); 8.43 (t, 1H).

Example 179

General Procedure (A)

3-(4-{[[4-(4-Methoxyphenyl)thiazol-2-yl]-(4-trifluoromethylsulfanylphenyl)amino]methyl}benzoylamino)propionic acid

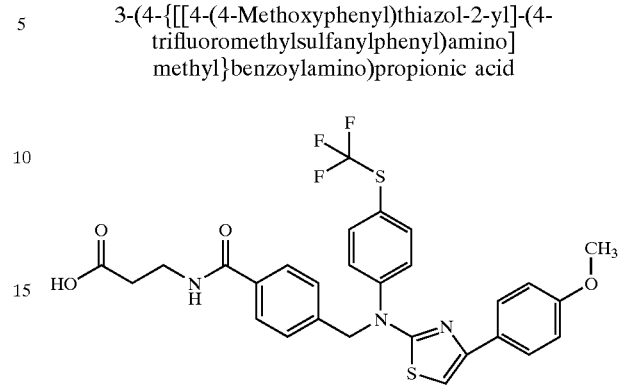

HPLC-MS (Method (A)): m/z: 588 (M+1); Rt: 5.63 min.

Example 180

General Procedure (A)

3-(4-{[[4-(3-Methoxyphenyl)thiazol-2-yl]-(4-trifluoromethylsulfanylphenyl)amino]methyl}benzoylamino)propionic acid

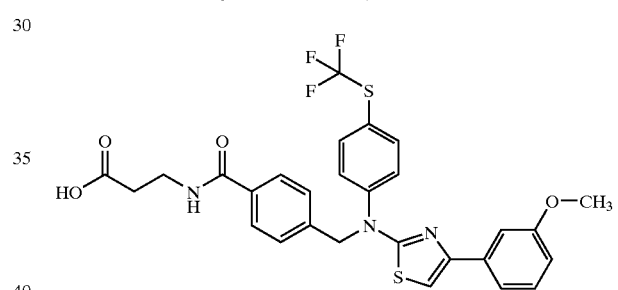

$^1$H NMR (DMSO-d$_6$): δ: 3.46 (m, 2H); 3.78 (s, 3H); 5.38 (s, 2H); 6.88 (m, 1H); 7.30 (t, 1H); 7.41 (m, 5H); 7.72 (m, 6H); 8.43 (t, 1H).

Example 181

General Procedure (A)

3-(4-{[[4-(2-Methoxyphenyl)thiazol-2-yl]-(4-trifluoromethylsulfanylphenyl)amino]methyl}benzoylamino)propionic acid

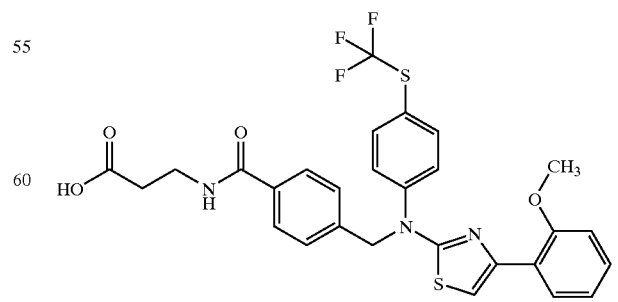

HPLC-MS (Method (A)): m/z: 588 (M+1); Rt: 5.93 min.

Example 182

General Procedure (A)

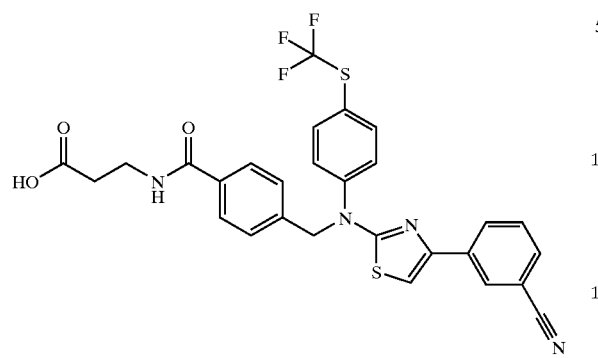

Example 183

General Procedure (A)

3-(4-{[[4-(3-Chlorophenyl)thiazol-2-yl]-(4-trifluoromethylsulfanylphenyl)amino]methyl}benzoylamino)propionic acid

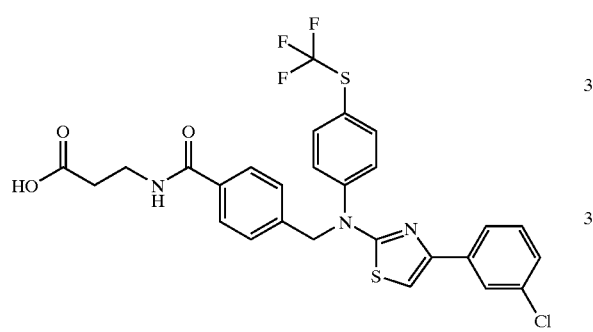

$^1$H NMR (DMSO-$d_6$): δ: 3.43 (m, 2H); 5.39 (s, 2H); 7.35 (d, 2H); 7.42 (d, 2H); 7.52 (s, 1H); 7.76 (m, 7H); 7.88 (s, 1H); 8.43 (t, 1H).

Example 184

General Procedure (A)

3-(4-{[[4-(2-Fluorophenyl)thiazol-2-yl]-(4-trifluoromethylsulfanylphenyl)amino]methyl}benzoylamino)propionic acid

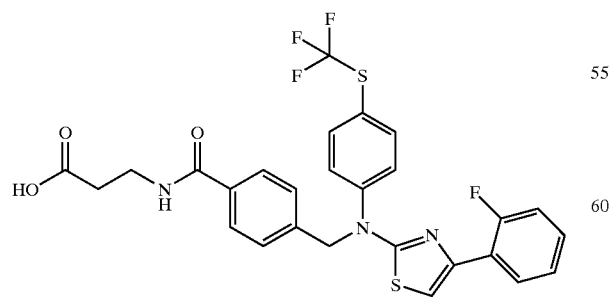

$^1$H NMR (DMSO-$d_6$): δ: 3.44 (q, 2H); 5.31 (s, 2H); 7.27–7.54 (m, 6H); 7.69–7.78 (m, 6H); 8.42 (t, 1H).

Example 185

General Procedure (A)

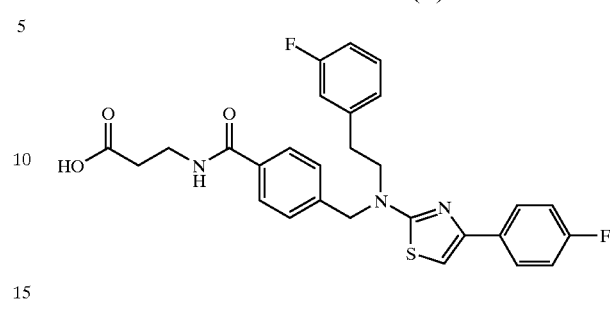

Example 186

General Procedure (A)

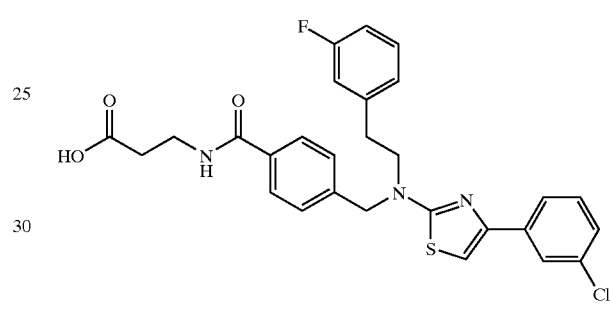

Example 187

General Procedure (A)

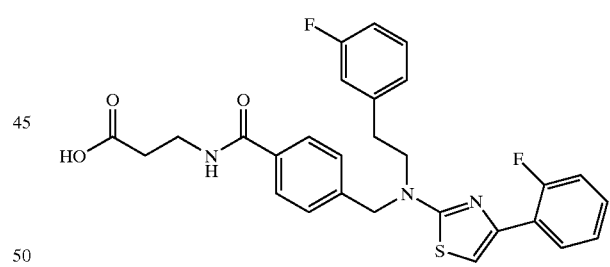

Example 188

General Procedure (A)

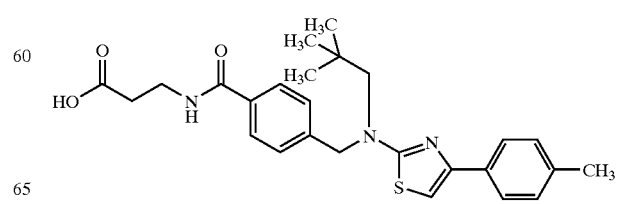

Example 189
General Procedure (A)
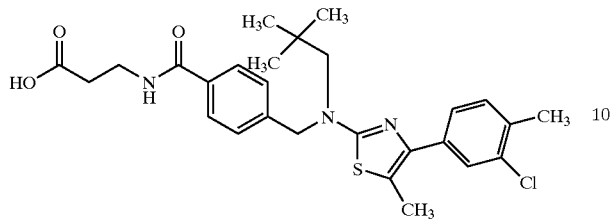
Example 190
General Procedure (A)
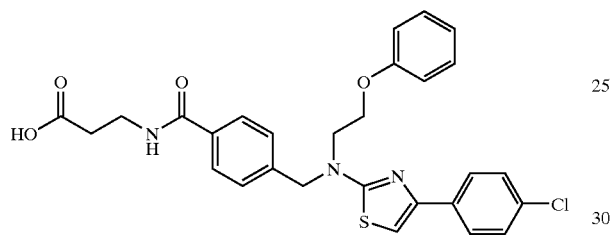
Example 191
General Procedure (A)
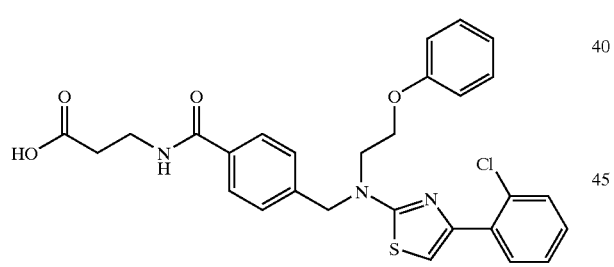
Example 192
General Procedure (A)
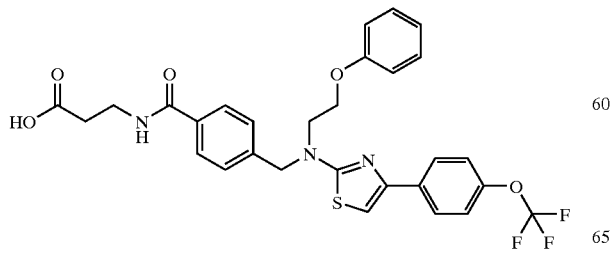
Example 193
General Procedure (A)
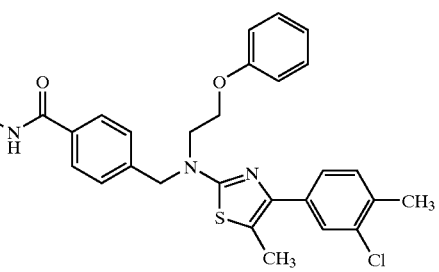
Example 194
General Procedure (A)
Example 195
General Procedure (A)
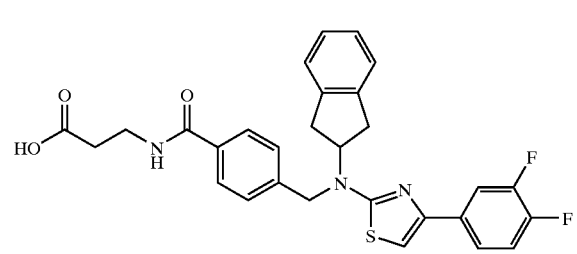

75
Example 196
General Procedure (A)
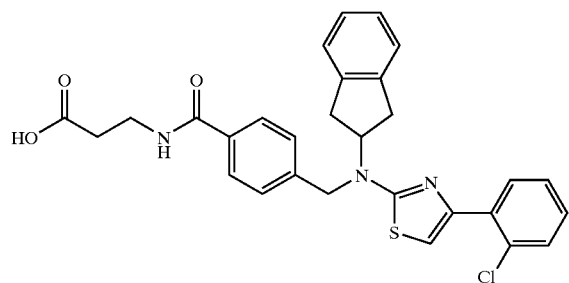
Example 197
General Procedure (A)
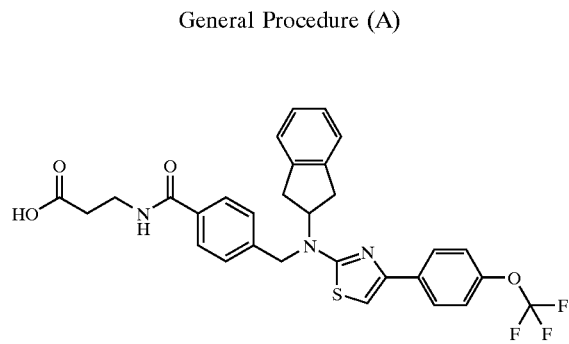
Example 198
General Procedure (A)
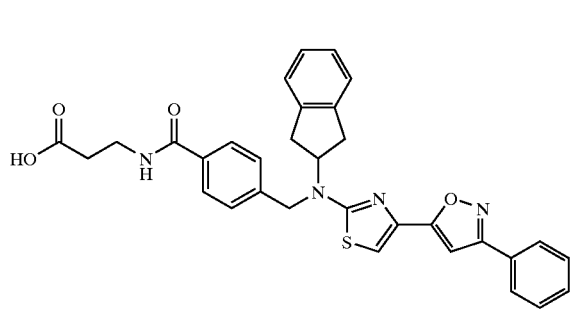
76
Example 199
General Procedure (A)
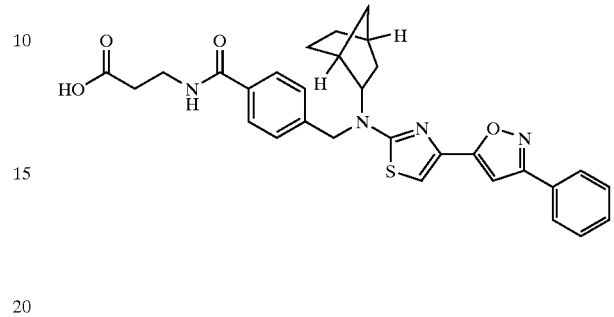
Example 200
General Procedure (A)
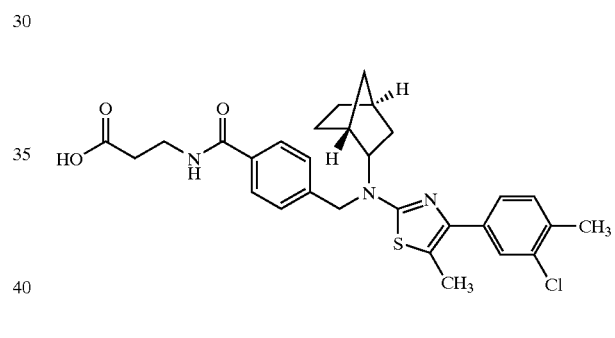
Example 201
General Procedure (A)
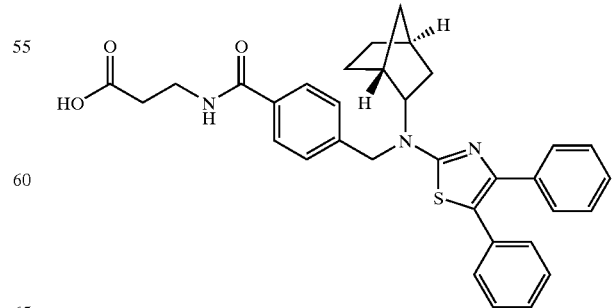

77
Example 202
General Procedure (A)
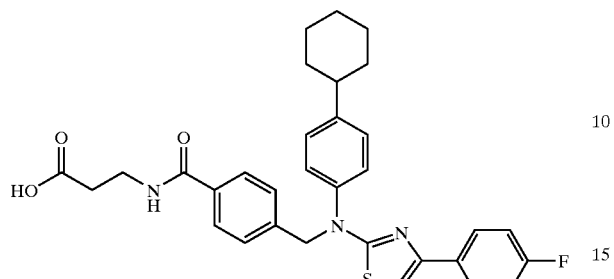
Example 203
General Procedure (A)
3-[4-({(4-Cyclohexylphenyl)-[4-(2,4-dimethylphenyl)-thiazol-2-yl]amino}methyl)benzoylamino]propionic acid
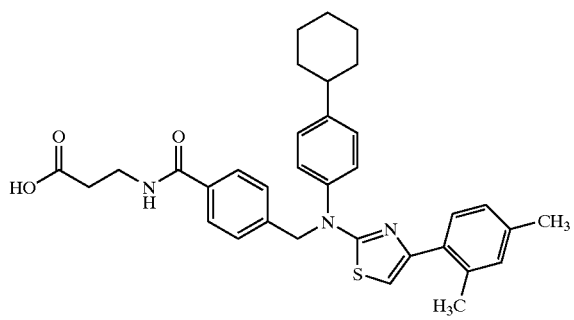
HPLC-MS (Method (A)): m/z: 568 (M+1); Rt: 6.53 min.
Example 204
General Procedure (A)
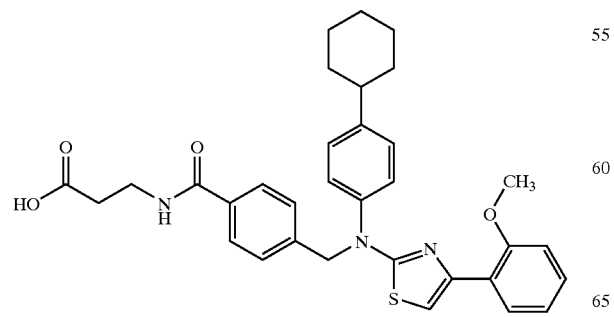
78
Example 205
General Procedure (A)
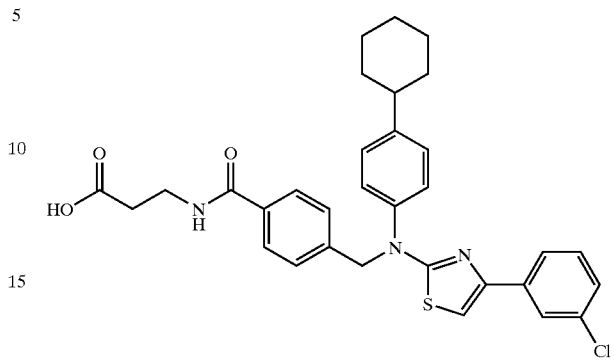
Example 206
General Procedure (A)
Example 207
General Procedure (A)
Example 208
General Procedure (A)
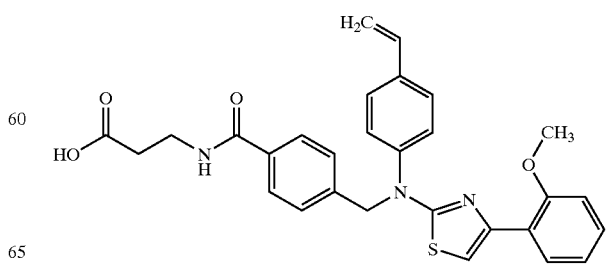

Example 209

General Procedure (A)

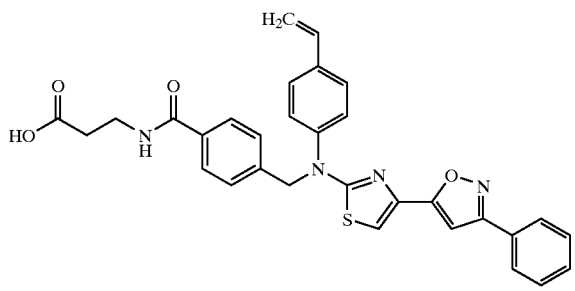

Example 210

General Procedure (A)

3-(4-{[[4-(3-Chloro-4-methylphenyl)-5-methylthiazol-2-yl]-(4-vinylphenyl)amino]methyl}benzoylamino)propionic acid

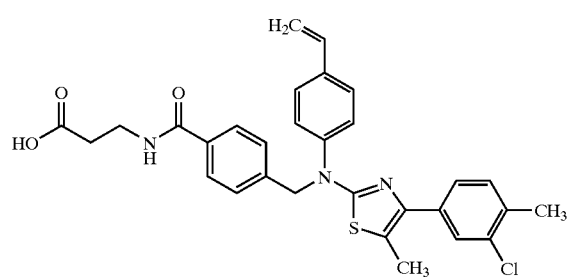

$^1$H NMR (DMSO-d$_6$): δ: 3.42 (m, 2H); 5.25 (s, 2H); 5.80 (d, 1H); 6.70 (m, 1H); 7.44 (m, 9H); 7.75 (d, 2H); 8.41 (t, 1H).

Example 211

General Procedure (A)

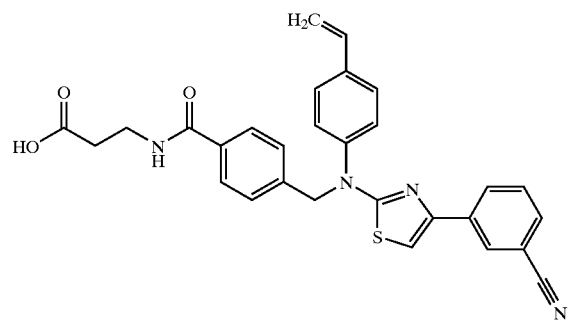

Example 212

General Procedure (A)

3-(4-{[[4-(2-Fluorophenyl)thiazol-2-yl]-(4-vinylphenyl)amino]methyl}benzoylamino)propionic acid

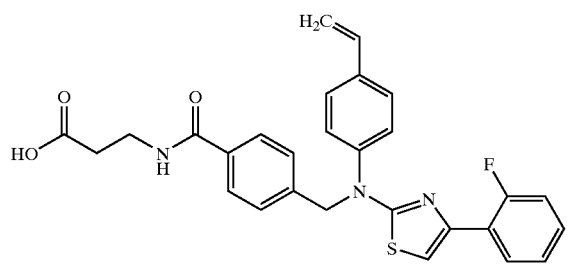

$^1$H NMR (DMSO-d$_6$): δ: 3.43 (q, 2H); 5.33 (s, 2H); 5.83 (d, 1H); 6.73 (m, 1H); 7.14 (s, 1H); 7.14–7.54 (m 9H); 7.75 (d, 2H); 8.04 (t, 1H); 8.42 (t, 1H).

Example 213

General Procedure (A)

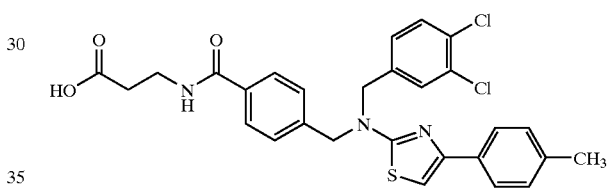

Example 214

General Procedure (A)

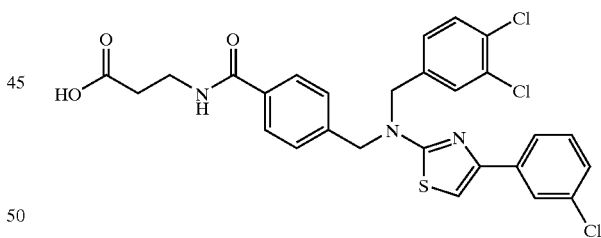

Example 215

General Procedure (A)

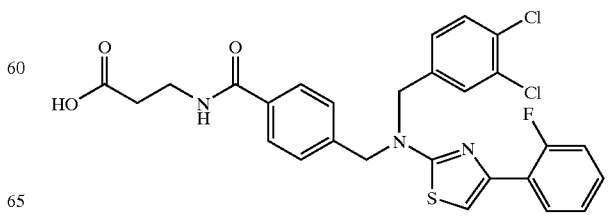

Example 216

General Procedure (A)

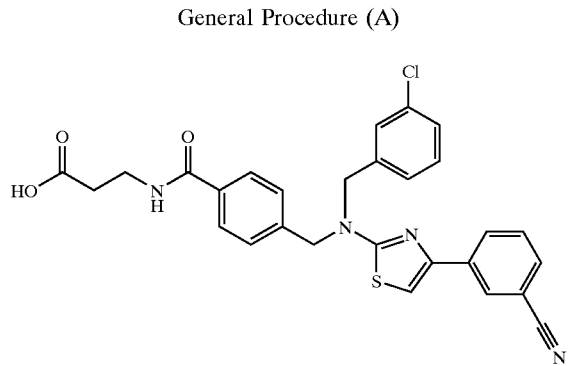

Example 217

General Procedure (A)

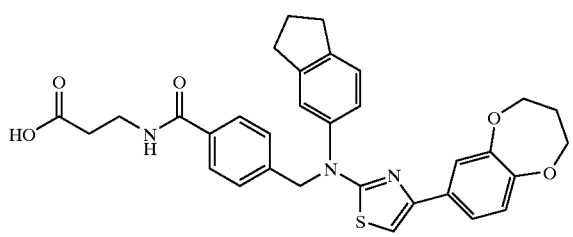

Example 218

General Procedure (A)

3-[4-({Indan-5-yl-[4-(4-trifluoromethylphenyl)thiazol-2-yl]amino}methyl)benzoylamino]propionic acid

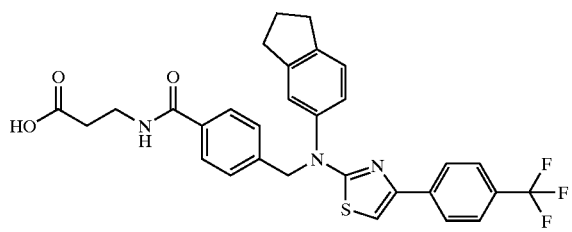

HPLC-MS (Method (A)): m/z: 566 (M+1); Rt: 6.07 min.

Example 219

General Procedure (A)

3-[4-({[4-(2-Chlorophenyl)thiazol-2-yl]indan-5-ylamino}methyl)benzoylamino]propionic acid

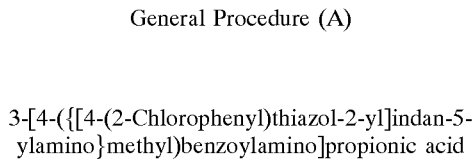

$^1$H NMR (DMSO-d$_6$): δ: 2.03 (m, 2H); 2.85 (t, 4H); 3.43 (q, 2H); 5.25 (s, 2H); 7.17 (m, 2H); 7.26 (d, 1H); 7.32–7.43 (m, 5H); 7.50 (d, 1H); 7.75 (d, 2H); 7.86 (d, 1H); 8.42 (t, 1H).

Example 220

General Procedure (A)

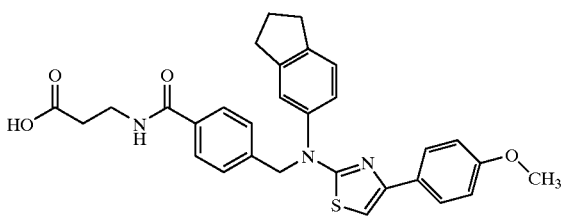

Example 221

General Procedure (A)

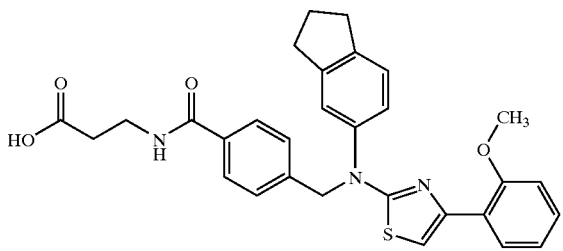

Example 222

General Procedure (A)

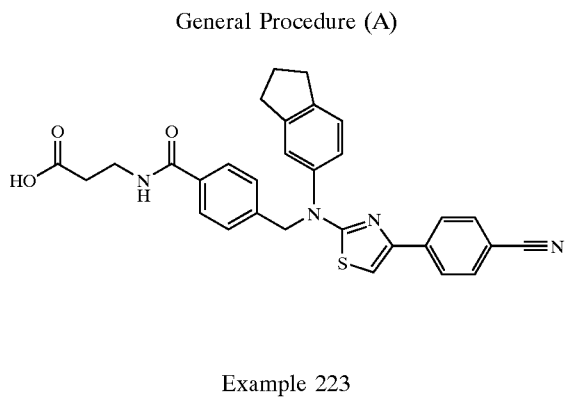

Example 223

General Procedure (A)

3-[4-({indan-5-yl-[4-(4-trifluoromethoxyphenyl)thiazol-2-yl]amino}methyl)benzoylamino]propionic acid

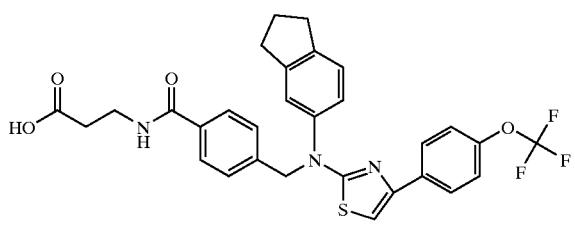

HPLC-MS (Method (A)): m/z: 582 (M+1); Rt: 6.10 min.

Example 224

General Procedure (A)

3-[4-{[4-(3-Chloro-4-methylphenyl)-5-methylthiazol-2-yl]indan-5-ylamino}methyl)benzoylamino]propionic acid

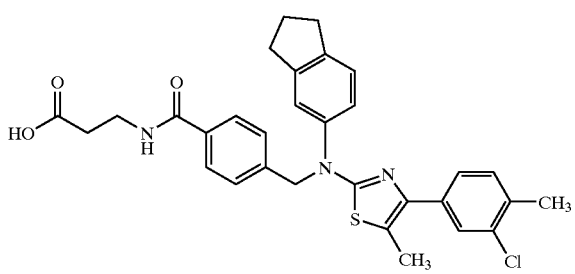

$^1$H NMR (DMSO-$d_6$): δ: 2.03 (m, 2H); 2.84 (t, 4H); 3.43 (q, 2H); 5.20 (s, 2H); 7.14 (d, 2H); 7.24 (d, 1H); 7.28 (s, 1H); 7.39–7.43 (m, 4H); 7.75 (d, 2H); 8.42 (t, 1H).

Example 225

General Procedure (A)

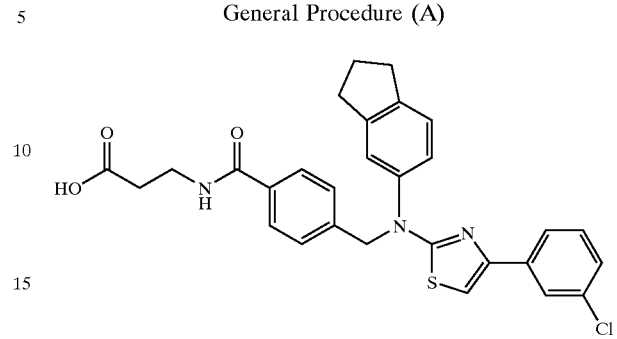

Example 226

General Procedure (A)

Example 227

General Procedure (A)

3-[4-({[4-(2-Fluorophenyl)thiazol-2-yl]indan-5-ylamino}methyl)benzoylamino]propionic acid

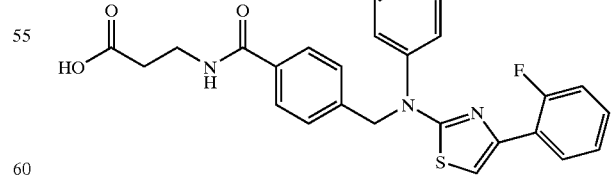

$^1$H NMR (DMSO-$d_6$): δ: 2.03 (m, 2H); 2.84 (t, 4H); 3.43 (q, 2H); 5.28 (s, 2H); 7.07 (s, 1H); 7.17 (d, 1H); 7.24–7.34 (m, 5H); 7.44 (d, 2H); 7.75 (d, 2H); 8.04 (t, 1H) 8.42 (t, 1H).

Example 228

General Procedure (A)

3-[4-({(4-tert-Butylphenyl)-[4-(3,4-dichlorophenyl)thiazol-2-yl]amino}methyl)benzoylamino]propionic acid

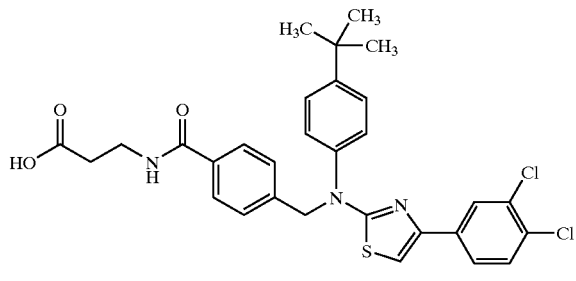

¹H NMR (DMSO-d₆): 1.27 (s, 9H); 3.44 (q, 2H); 5.29 (s, 2H); 7.38–7.47 (m, 7H); 7.62 (d, 1H); 7.75 (d, 2H); 7.81 (d, 1H); 8.05 (s, 1H); 8.42 (t, 1H).

Example 229

General Procedure (A)

3-[4-({(4-tert-Butylphenyl)-[4-(4-chlorophenyl)thiazol-2-yl]amino}methyl)benzoylamino]propionic acid

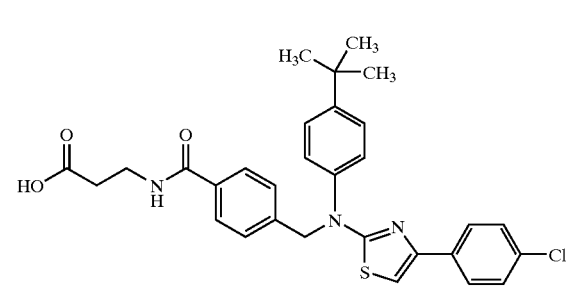

¹H NMR (DMSO-d₆): δ: 1.28 (s, 9H); 3.44 (q, 2H); 5.30 (s, 2H); 7.23 (s, 1H); 7.38–7.46 (m, 8H); 7.75 (d, 2H); 7.86 (d, 1H); 8.42 (t, 1H).

Example 230

General Procedure (A)

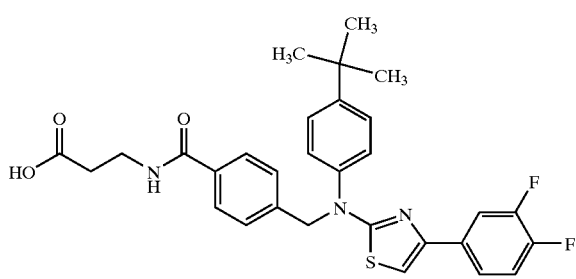

Example 231

General Procedure (A)

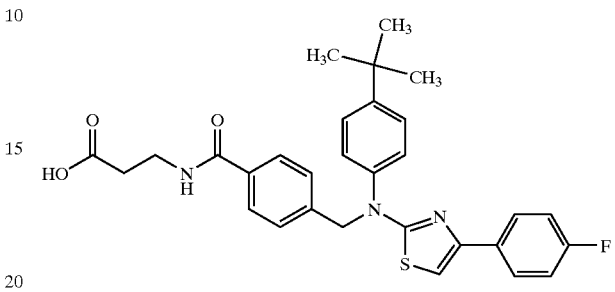

Example 232

General Procedure (A)

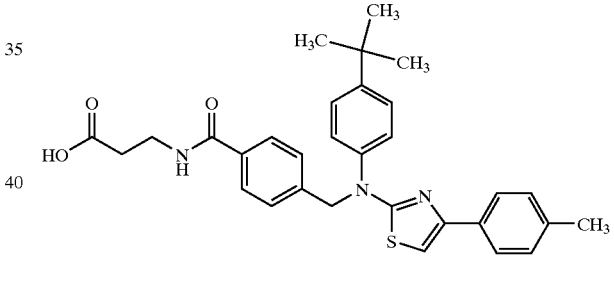

Example 233

General Procedure (A)

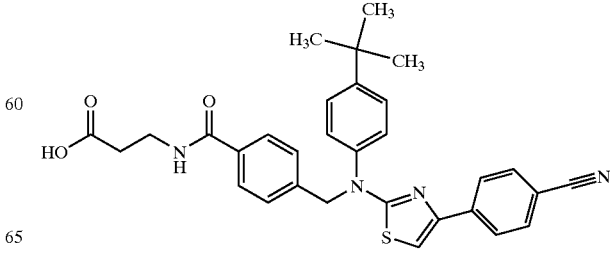

Example 234

General Procedure (A)

3-[4-({(4-tert-Butylphenyl)-[4-(4-trifluoromethoxyphenyl)thiazol-2-yl]amino}methyl)benzoylamino]propionic acid $^1$H NMR (DMSO-d$_6$): δ: 1.27 (s, 9H); 3.43 (q, 2H); 5.30 (s, 2H); 7.24 (s, 1H); 7.35–7.48 (m, 8H); 7.75 (d, 2H); 7.95 (d, 1H); 8.42 (t, 1H).

Example 235

General Procedure (A)

Example 236

General Procedure (A)

Example 237

General Procedure (A)

Example 238

General Procedure (A)

Example 239

General Procedure (A)

Example 240

General Procedure (A)

Example 241

General Procedure (A)

Example 242

General Procedure (A)

Example 243

General Procedure (A)

Example 241

General Procedure (A)

Example 245

General Procedure (A)

Example 246

General Procedure (A)

Example 247

General Procedure (A)

Example 248

General Procedure (A)

Example 249

General Procedure (A)

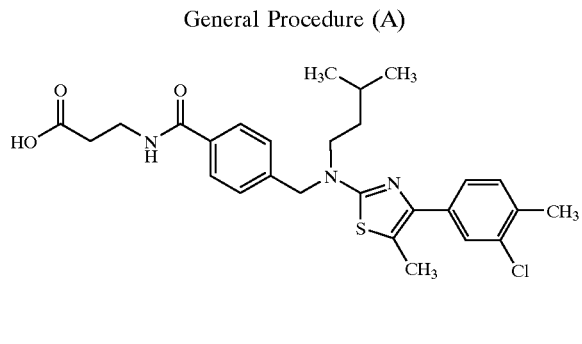

The compounds in the following examples 250–405 were all found to be hits when screened at 140 nM concentration (a "hit" is defined as a compound at the given concentration that is able to displace >40% of labelled glucagon from the human glucagon receptor):

Example 250

General Procedure (A)

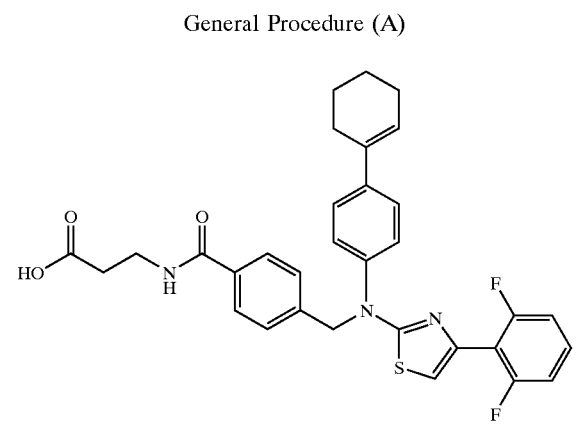

Example 251

General Procedure (A)

3-[4-({(4-Cyclohex-1-enylphenyl)-[4-(2,4-dimethylphenyl)thiazol-2-yl]amino}methyl)benzoylamino]propionic acid

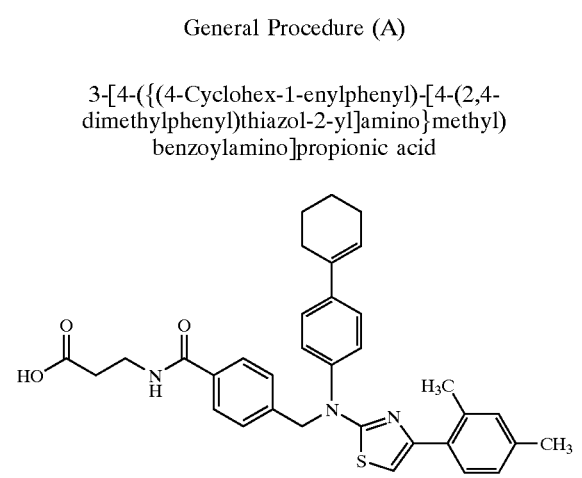

HPLC-MS (Method (A)): m/z=530 (M+1); $R_t$=5.70 min.

Example 252

General Procedure (A)

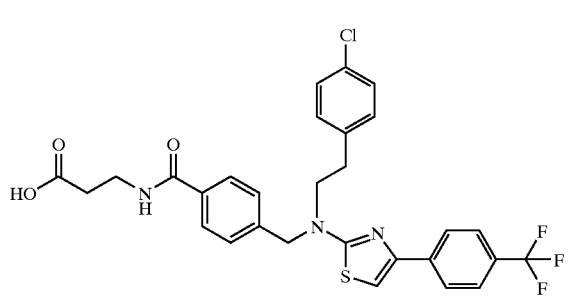

Example 253

General Procedure (A)

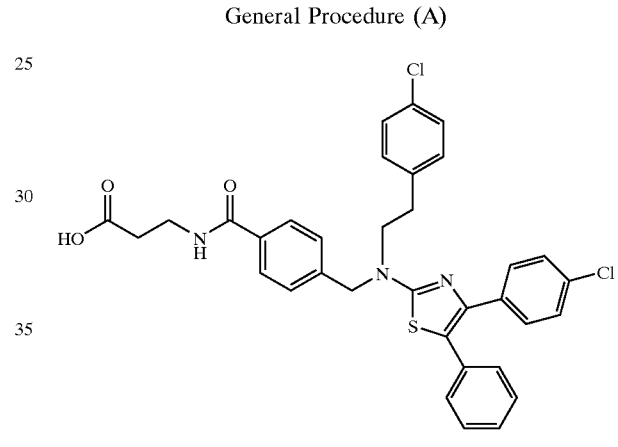

Example 254

General Procedure (A)

3-(4-{[[4-(4-Nitrophenyl)thiazol-2-yl]-(4-trifluoromethoxyphenyl)amino]methyl}benzoylamino)propionic acid

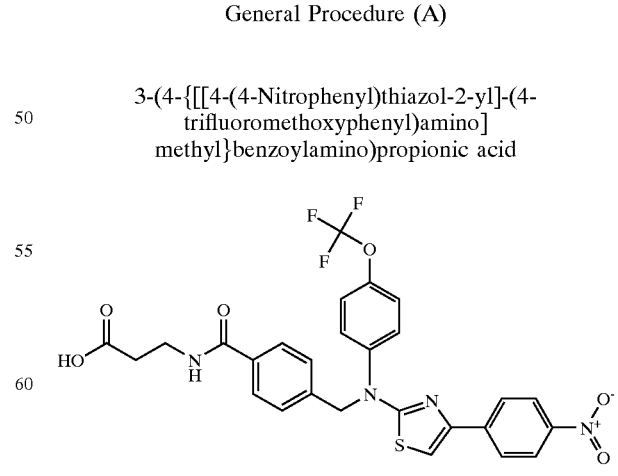

HPLC-MS (Method (A)): m/z=587 (M+1); $R_t$=5.60 min.

Example 255

General Procedure (A)

3-(4-{[(4-Biphenyl-4-ylthiazol-2-yl)-(4-trifluoromethoxyphenyl)amino]methyl}benzoylamino)propionic acid

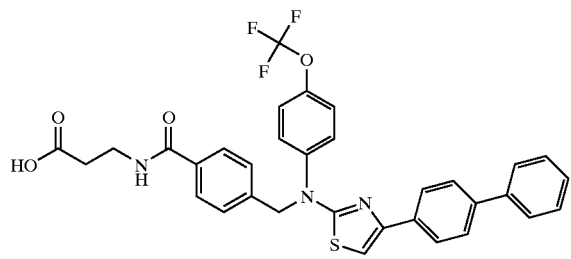

HPLC-MS (Method (A)): m/z=618 (M+1); $R_t$=6.40 min.

Example 256

General Procedure (A)

3-(4-{[(4-Naphthalen-2-ylthiazol-2-yl)-(4-trifuoromethoxyphenyl)amino]methyl}benzoylamino)propionic acid

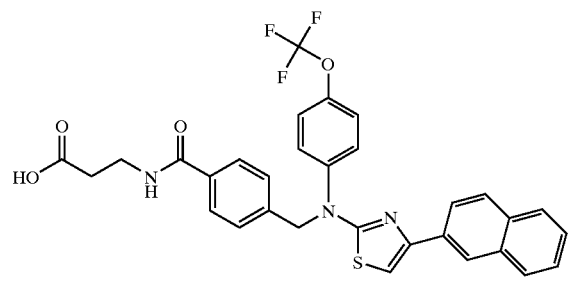

HPLC-MS (Method (A)): m/z=592 (M+1); $R_t$=6.10 min.

Example 257

General Procedure (A)

3-(4-{[[4-(3,4-Dichlorophenyl)thiazol-2-yl]-(4-trifluoromethoxyphenyl)amino]methyl}benzoylamino)propionic acid

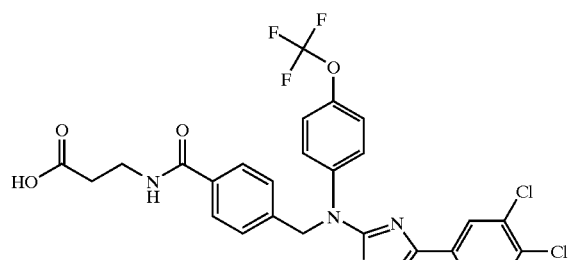

HPLC-MS (Method (A)): m/z=611 (M+1); $R_t$=6.30 min.

Example 258

General Procedure (A)

3-(4-{[[4-(4-Chlorophenyl)thiazol-2-yl]-(4-trifluoromethoxyphenyl)amino]methyl}benzoylamino)propionic acid

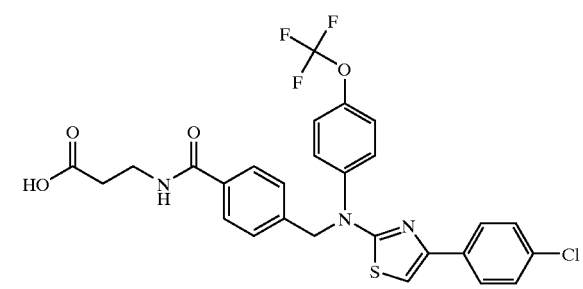

HPLC-MS (Method (A)): m/z=576 (M+1); $R_t$=6.00 min.

Example 259

General Procedure (A)

3-[4-({(4-Trifluoromethoxyphenyl)-[4-(4-trifluoromethylphenyl)thiazol-2-yl]amino}methyl)benzoylamino]propionic acid

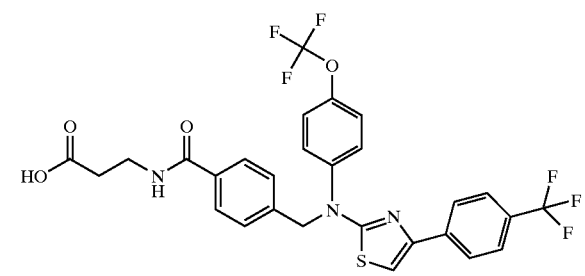

$^1$H NMR (300 MHz, DMSO-$d_6$): δ=2.5 (below DMSO), 3.44 (2H, q), 5.38 (2H, s), 7.46 (4H, m), 7.53 (1H, s), 7.68 (2H, d), 7.8 (4H, m), 8.08 (2H, d), 8.49 (1H, t), 12.2 (1H, bs); HPLC-MS (Method (A)): m/z=610 (M+1); $R_t$=1.20 min; HPLC-MS (Method (B)): m/z=610 (M+1); $R_t$=5.14 min.

Example 260

General Procedure (A)

3-(4-{[[4-(2,4-Dimethylphenyl)thiazol-2-yl]-(4-trifluoromethoxyphenyl)amino]methyl}benzoylamino)propionic acid

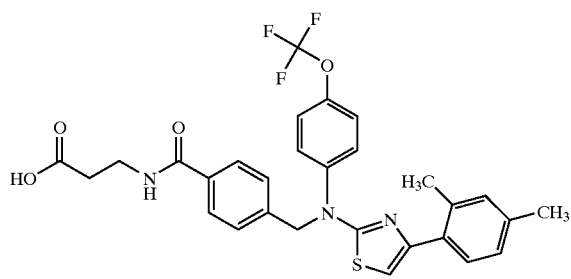

HPLC-MS (Method (A)): m/z=570 (M+1); $R_t$=5.83 min.

Example 261

General Procedure (A)

3-(4-{[[4-(2-Chlorophenyl)thiazol-2-yl]-(4-trifluoromethoxyphenyl)amino]methyl}benzoylamino)propionic acid

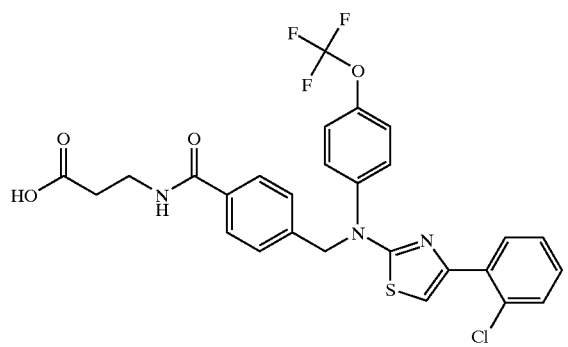

HPLC-MS (Method (A)): m/z=577 (M+1); $R_t$=5.83 min.

Example 262

General Procedure (A)

3-(4-{[(5-Methyl-4-phenylthiazol-2-yl)-(4-trifluoromethoxyphenyl)amino]methyl}benzoylamino)propionic acid

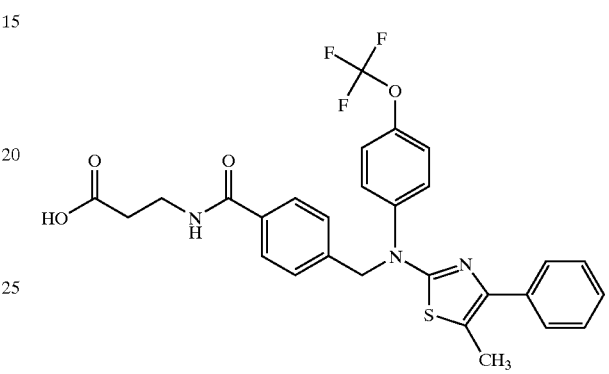

HPLC-MS (Method (A)): m/z=556 (M+1); $R_t$=5.50 min.

Example 263

General Procedure (A)

3-[4-({(4-Trifluoromethoxyphenyl)-[4-(4-trifluoromethoxyphenyl)thiazol-2-yl]amino}methyl)benzoylamino]propionic acid

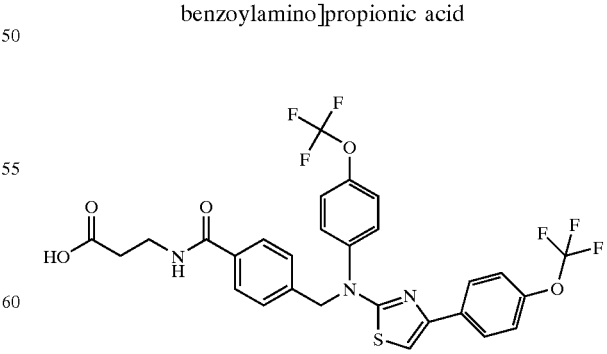

HPLC-MS (Method (A)): m/z=626 (M+1); $R_t$=6.17 min.

Example 264

General Procedure (A)

3-(4-{[[4-(3,5-Bis-trifluoromethylphenyl)thiazol-2-yl]-(4-trifluoromethoxyphenyl)amino]methyl}benzoylamino)propionic acid

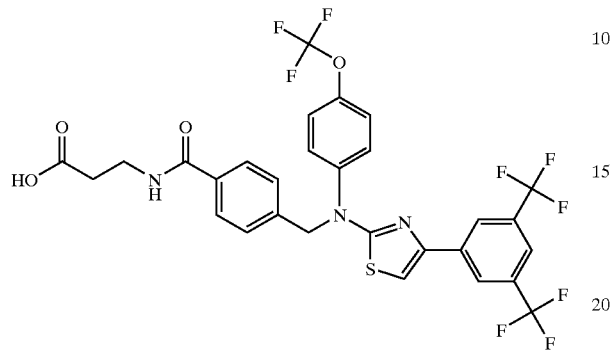

Example 265

General Procedure (A)

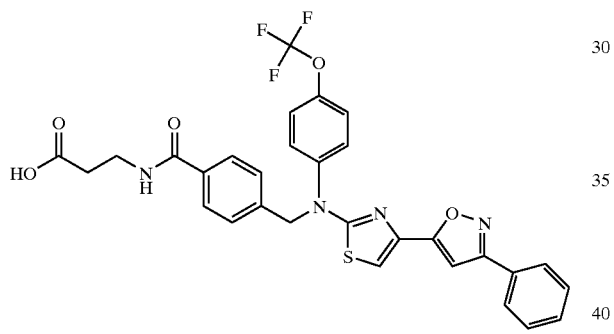

Example 266

General Procedure (A)

3-(4-{[[4-(3-Chlorophenyl)thiazol-2-yl]-(4-trifluoromethoxyphenyl)amino]methyl}benzoylamino)propionic acid

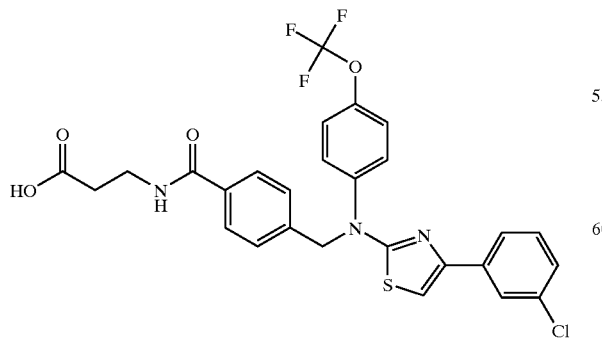

HPLC-MS (Method (A)): m/z=576 (M+1); $R_t$=5.97 min.

Example 267

General Procedure (A)

3-(4-{[(4,5-Diphenylthiazol-2-yl)-(4-trifluoromethoxyphenyl)amino]methyl}benzoylamino)propionic acid

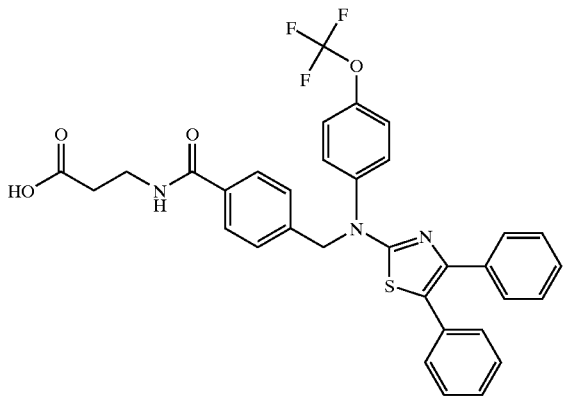

HPLC-MS (Method (A)): m/z=618 (M+1); $R_t$=6.33 min.

Example 268

General Procedure (A)

3-(4-{[[4-(2-Fluorophenyl)thiazol-2-yl]-(4-trifluoromethoxyphenyl)amino]methyl}benzoylamino)propionic acid

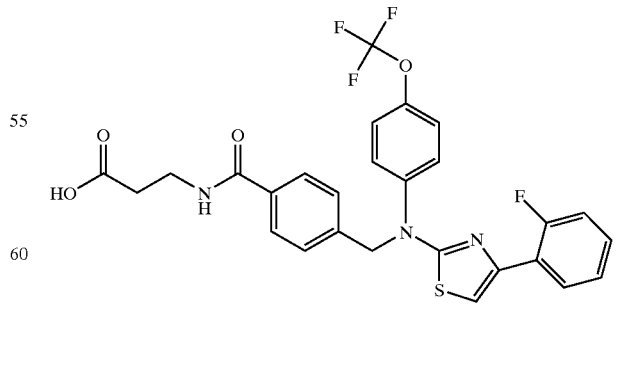

HPLC-MS (Method (A)): m/z=560 (M+1); $R_t$=5.80 min.

Example 269

General Procedure (A)

3-(4-{[[4-(4-Chlorophenyl)-5-phenylthiazol-2-yl]-(4-trifluoromethoxyphenyl)amino]ethyl}benzoylamino)propionic acid

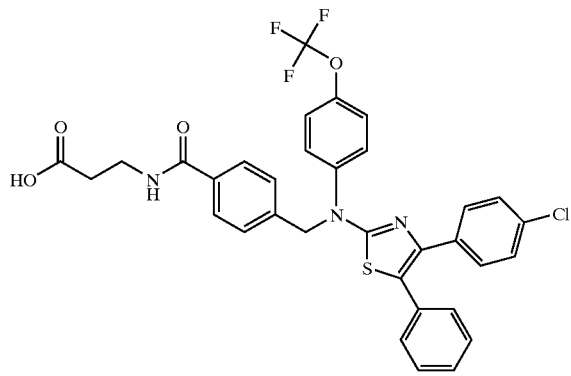

HPLC-MS (Method (A)): m/z=653 (M+1); $R_t$=6.80 min.

Example 270

General Procedure (A)

3-[4-({(4-Bromophenyl)-[4-(4-nitrophenyl)thiazol-2-yl]amino}methyl)benzoylamino]propionic acid

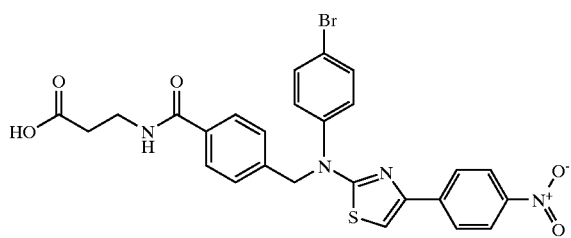

HPLC-MS (Method (A)): m/z=582 (M+1); $R_t$=5.50 min.

Example 271

General Procedure (A)

3-[4-({(4-Bromophenyl)-[4-(3,4-dichlorophenyl)thiazol-2-yl]amino}methyl)benzoylamino]propionic acid

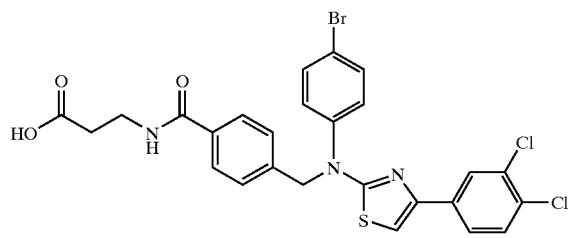

HPLC-MS (Method (A)): m/z=606 (M+1); $R_t$=6.23 min.

Example 272

General Procedure (A)

3-(4-{[(4-Bromophenyl)-(4-phenylthiazol-2-yl)amino]methyl}benzoylamino)propionic acid

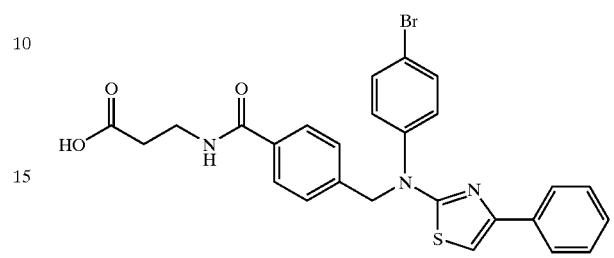

HPLC-MS (Method (A)): m/z 537 (M+1); $R_t$=5.43 min.

Example 273

General Procedure (A)

3-[4-({(4-Bromophenyl)-[4-(4-fluorophenyl)thiazol-2-yl]amino}methyl)benzoylamino]propionic acid

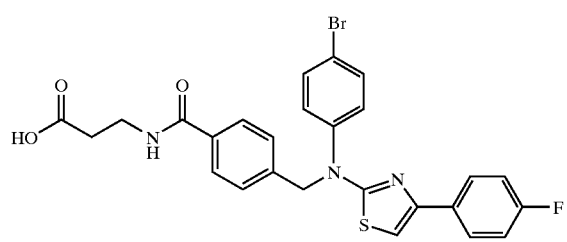

HPLC-MS (Method (A)): m/z=555 (M+1); $R_t$=5.53 min.

Example 274

General Procedure (A)

3-[4-({(4-Bromophenyl)-[4-(4-trifluoromethylphenyl)thiazol-2-yl]amino}methyl)benzoylamino]propionic acid

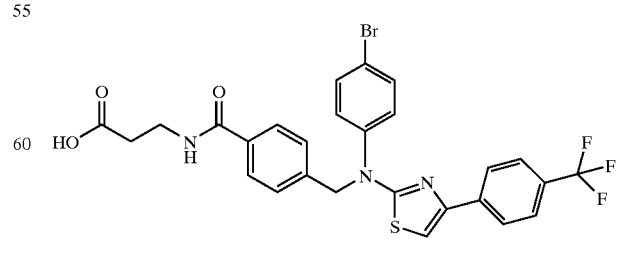

HPLC-MS (Method (A)): m/z=605 (M+1); $R_t$=6.00 min.

Example 275

General Procedure (A)

3-[4-({(4-Bromophenyl)-[4-(4-pentylphenyl)thiazol-2-yl]amino}methyl)benzoylamino]propionic acid

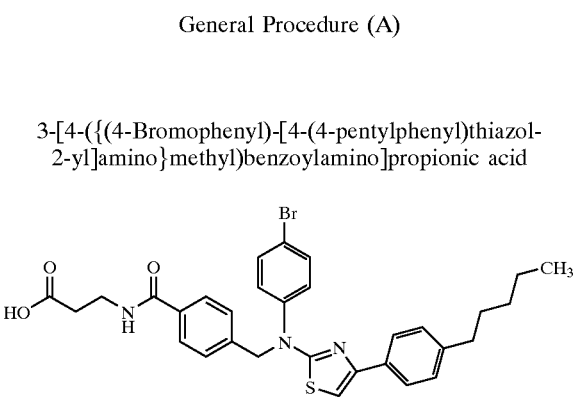

$^1$H NMR (300 MHz, DMSO-d$_6$): δ=2.58 (2H, t), 3.44 (2H, q), 5.32 (2H, s), 7.20 (1H, s), 7.22 (2H, d), 7.43 (2H, d), 7.45 (2H, d), 7.61 (2H, d), 7.77 (4H, m), 8.48 (1H, t), 12.2 (1H, bs); HPLC-MS (Method (A)): m/z=608 (M+1); R$_t$=7.03 min; HPLC-MS (Method (B)): m/z=608 (M+1); R$_t$=5.89 min.

Example 276

General Procedure (A)

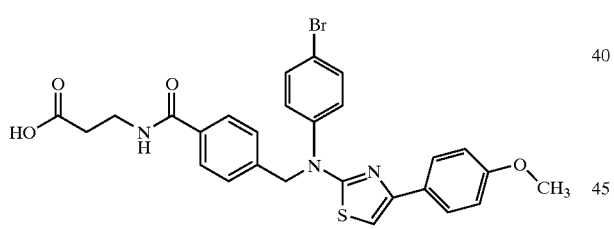

Example 277

General Procedure (A)

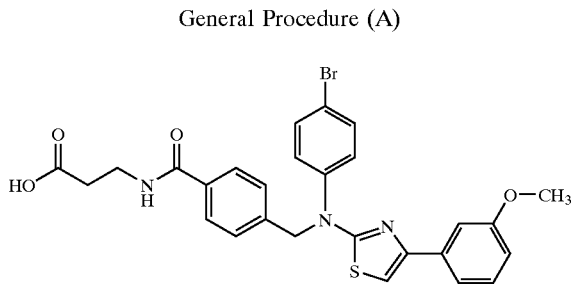

Example 278

General Procedure (A)

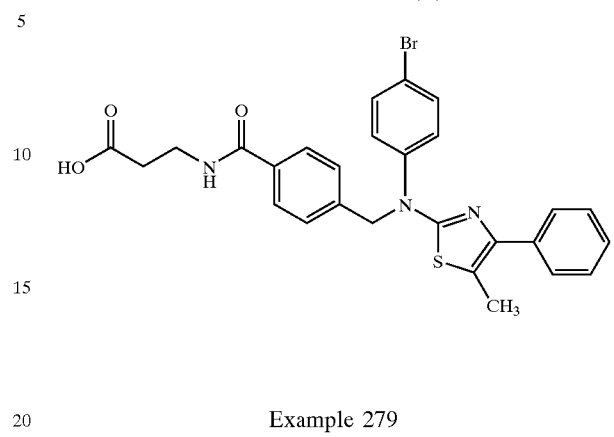

Example 279

General Procedure (A)

3-[4-({(4-Bromophenyl)-[4-(3-bromophenyl)thiazol-2-yl]amino}methyl)benzoylamino]propionic acid HPLC-MS (Method (A)): m/z 616 (M+1); R$_t$=5.93 min.

Example 280

General Procedure (A)

3-[4-({(4-Bromophenyl)-[4-(4-trifluoromethoxyphenyl)thiazol-2-yl]amino}methyl)benzoylamino]propionic acid HPLC-MS (Method (A)): m/z=621 (M+1); R$_t$=6.07 min.

Example 281

General Procedure (A)

3-[4-({(4-Bromophenyl)-[4-(4-trifluoromethoxyphenyl)thiazol-2-yl]amino}methyl)benzoylamino]propionic acid

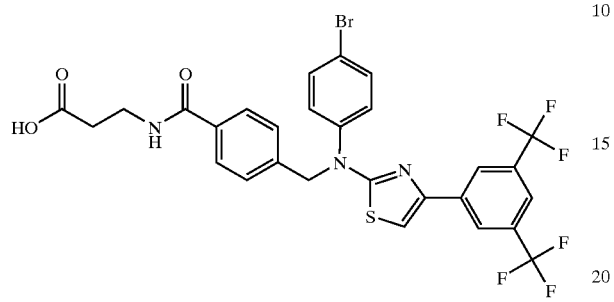

HPLC-MS (Method (A)): m/z=673 (M+1); $R_t$=6.40 min.

Example 282

General Procedure (A)

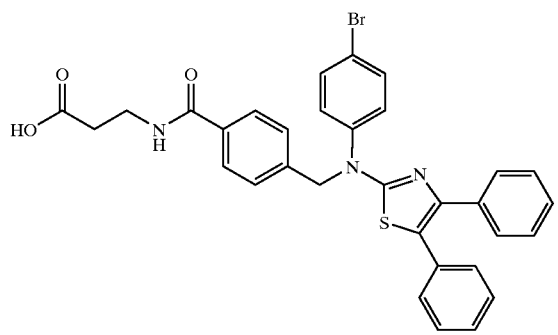

Example 283

General Procedure (A)

3-[4-({(4-Bromophenyl)-[4-(2-fluorophenyl)thiazol-2-yl]amino}methyl)benzoylamino]propionic acid

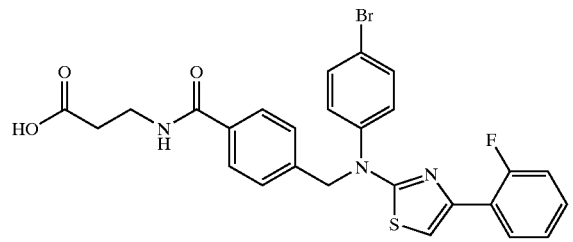

HPLC-MS (Method (A)): m/z=555 (M+1); $R_t$=5.67 min.

Example 284

General Procedure (A)

3-[4-({(4-Bromophenyl)-[4-(4-chlorophenyl)-5-phenylthiazol-2-yl]amino}methyl)benzoylamino]propionic acid

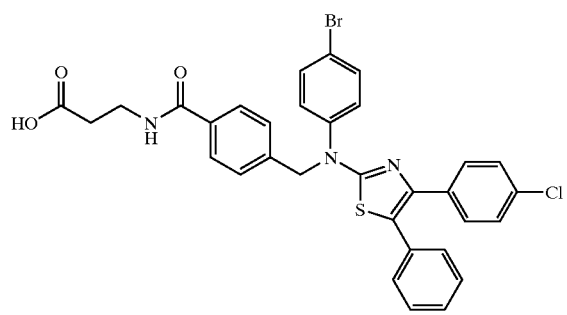

HPLC-MS (Method (A)): m/z=647 (M+1); $R_t$=6.73 min.

Example 285

General Procedure (A)

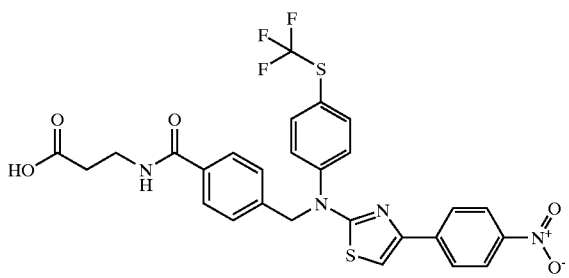

Example 286

General Procedure (A)

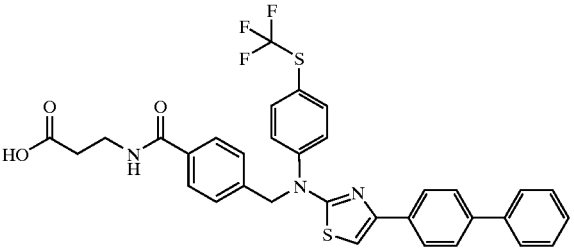

Example 287

General Procedure (A)

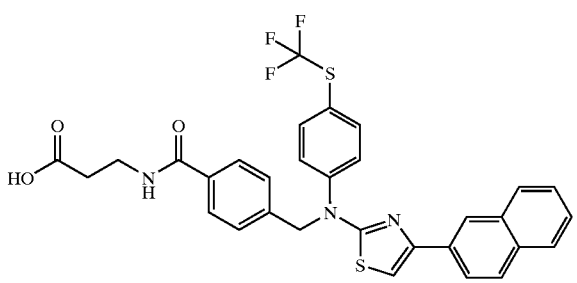

Example 288

General Procedure (A)

3-(4-{[[4-(3,4-Dichlorophenyl)thiazol-2-yl]-(4-trifluoromethylsulfanylphenyl)amino]methyl}benzoylamino)propionic acid

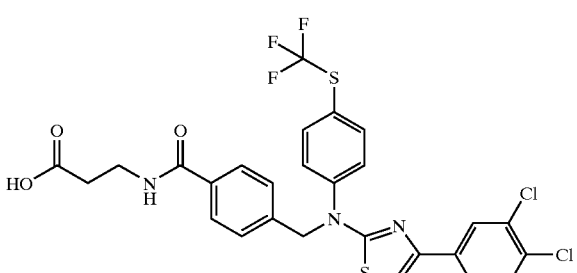

HPLC-MS (Method (A)): m/z=627 (M+1); $R_t$=6.53 min.

Example 289

General Procedure (A)

3-(4-{[[4-(4-Bromophenyl)thiazol-2-y]-(4-trifluoromethylsulfanylphenyl)amino]methyl}benzoylamino)propionic acid

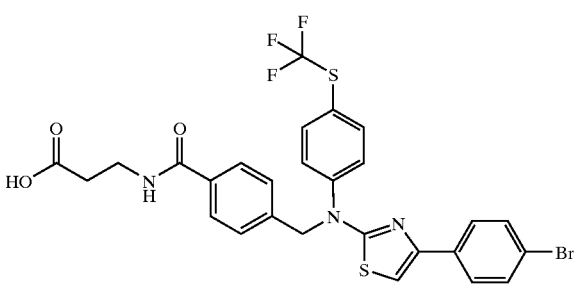

HPLC-MS (Method (A)): m/z=637 (M+1); $R_t$=6.30 min.

Example 290

General Procedure (A)

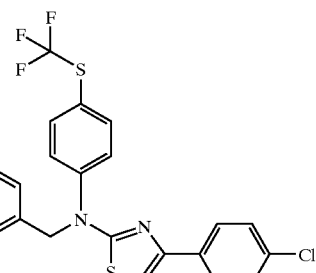

Example 291

General Procedure (A)

3-(4-{[[4-(4-Chlorophenyl)thiazol-2-yl]-(4-trifluoromethylsulfanylphenyl)amino]methyl}benzoylamino)propionic acid HPLC-MS (Method (A)): m/z=593 (M+1); $R_t$=6.20 min.

Example 292

General Procedure (A)

3-(4-{[[4-(3,4-Difluorophenyl)thiazol-2-yl]-(4-trifluoromethylsulfanylphenyl)amino]methyl}benzoylamino)propionic acid

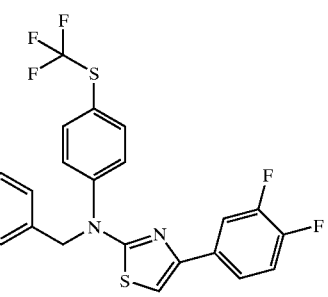

HPLC-MS (Method (A)): m/z=594 (M+1); $R^t$=6.00 min.

Example 293

General Procedure (A)

3-(4-{[[4-(4-Trifluoromethylphenyl)thiazol-2-yl]-(4-trifluoromethylsulfanylphenyl)amino]methyl}benzoylamino)propionic acid

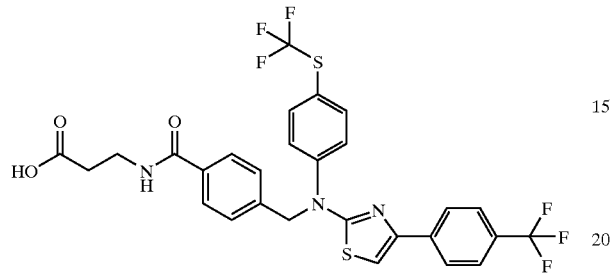

$^1$H NMR (300 MHz, DMSO-d$_6$): δ=2.5 (below DMSO), 3.42 (2H, q), 5.41 (2H, s), 7.43 (2H, d), 7.63 (1H, s), 7.7 (8H, m), 8.06 (2H, d), 8.47 (1H, t), 12.2 (1H, bs); HPLC-MS (Method (A)): m/z=626 (M+1); R$_t$=6.30 min; HPLC-MS (Method (B)): m/z=626 (M+1); R$_t$=5.39 min.

Example 294

General Procedure (A)

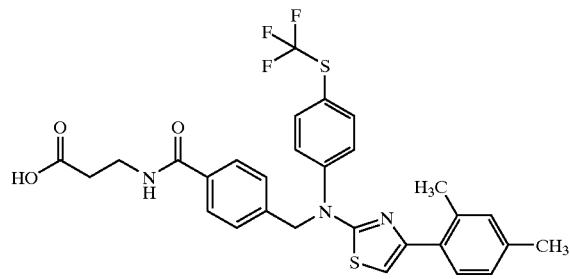

Example 295

General Procedure (A)

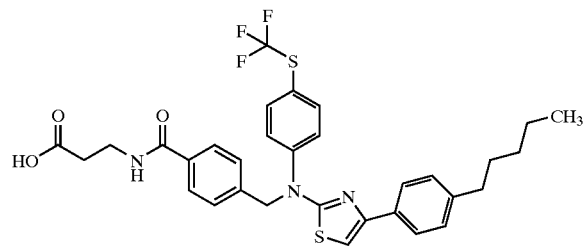

Example 296

General Procedure (A)

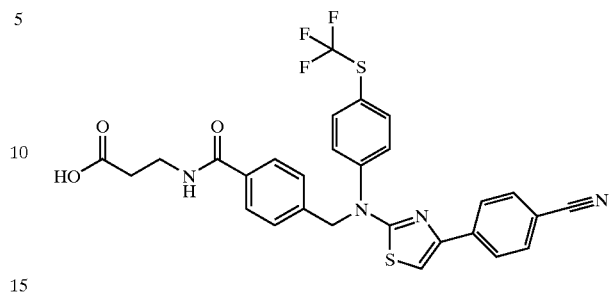

Example 297

General Procedure (A)

3-(4-{[[4-(4-Trifluoromethoxyphenyl)thiazol-2-yl]-(4-trifluoromethylsulfanylphenyl)amino]methyl}benzoylamino)propionic acid

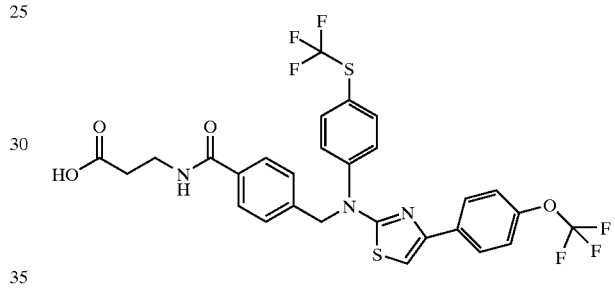

$^1$H NMR (300 MHz, DMSO-d$_6$): δ=2.5 (below DMSO), 3.4 (below water), 5.41 (2H, s), 7.4 (6H, m), 7.50 (1H, s), 7.7–7.8 (4H, m), 7.98 (2H, d), 8.49 (1H, t), 12.2 (1H, bs); HPLC-MS (Method (A)): m/z=642 (M+1); R$_t$=6.40 min; HPLC-MS (Method (B)): m/z=642 (M+1); R$_t$=5.40 min.

Example 298

General Procedure (A)

3-(4-{[[4-(3,5-Bis-trifluoromethylphenyl)thiazol-2-yl]-(4-trifluoromethylsulfanylphenyl)amino]methyl}benzoylamino)propionic acid

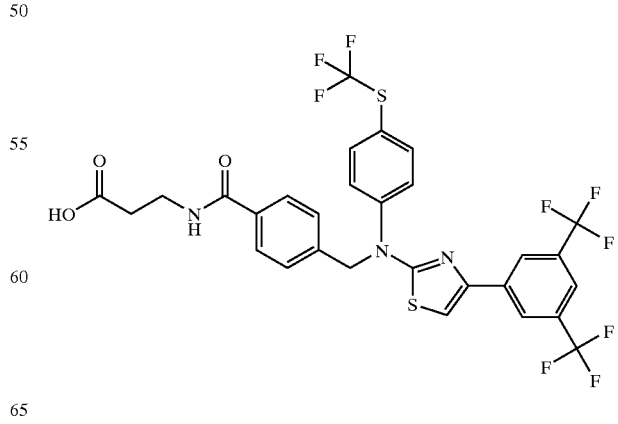

HPLC-MS (Method (A)): m/z=694 (M+1); R$_t$=6.70 min.

Example 299

General Procedure (A)

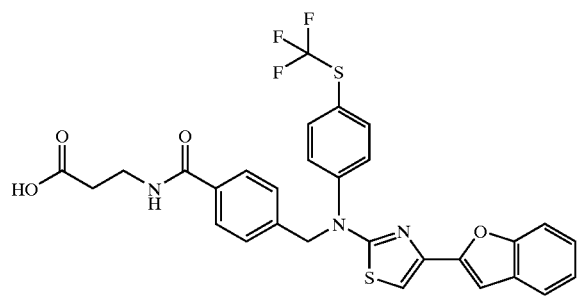

Example 300

General Procedure (A)

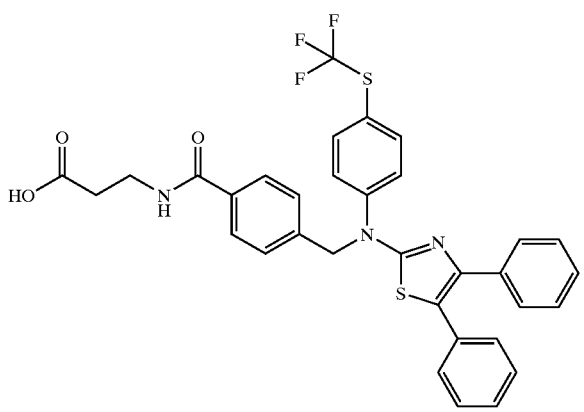

Example 301

General Procedure (A)

3-(4-{[[4-(4-Chlorophenyl)-5-phenylthiazol-2-yl]-(4-trifluoromethylsulfanylphenyl)amino]methyl}benzoylamino)propionic acid

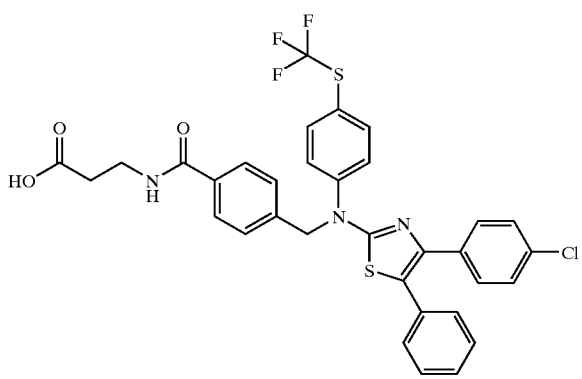

HPLC-MS (Method (A)): m/z=669 (M+1); $R_t$=7.07 min.

Example 302

General Procedure (A)

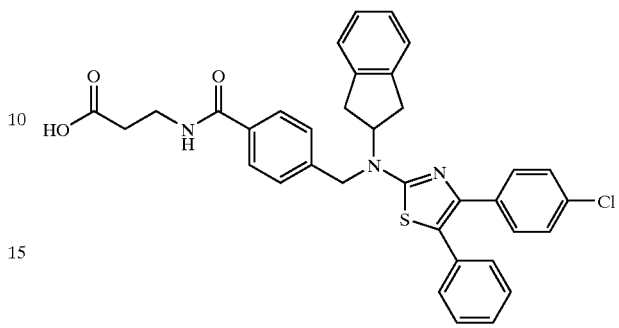

Example 303

General Procedure (A)

3-(4-{[[4-(4-Bromophenyl)thiazol-2-yl]-(4-cyclohexylphenyl)amino]methyl}benzoylamino)propionic acid

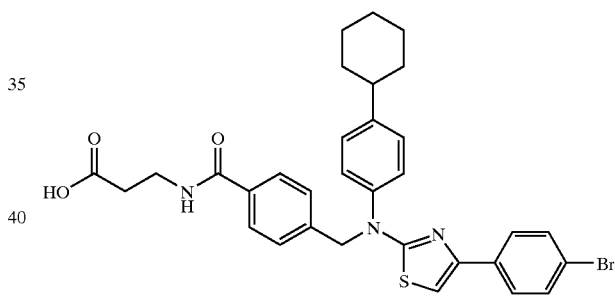

HPLC-MS (Method (A)): m/z=619 (M+1); $R_t$=7.03 min.

Example 304

General Procedure (A)

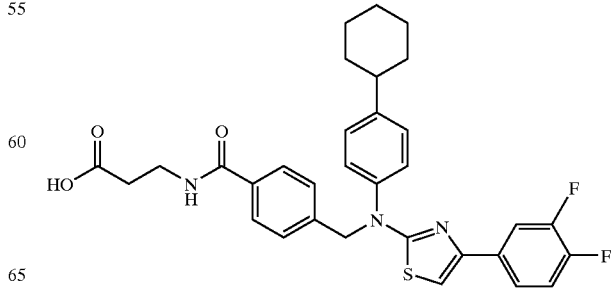

Example 305

General Procedure (A)

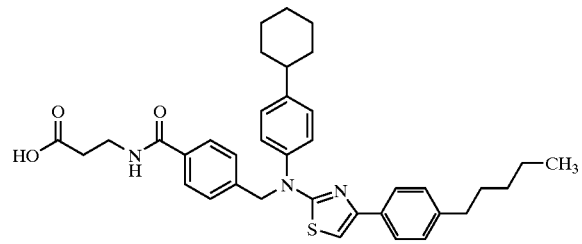

Example 306

General Procedure (A)

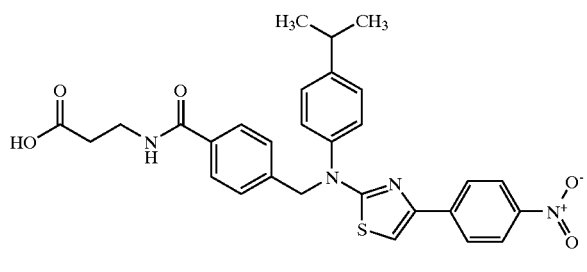

Example 307

General Procedure (A)

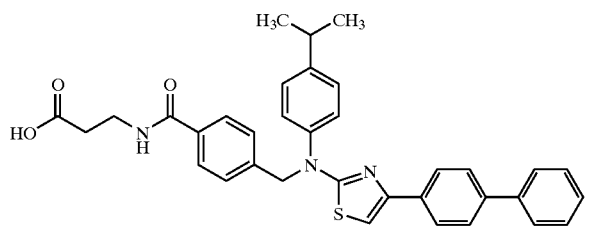

Example 308

General Procedure (A)

3-(4-{[[4-(4-Bromophenyl)thiazol-2-yl]-(4-isopropylphenyl)amino]methyl}benzoylamino)propionic acid

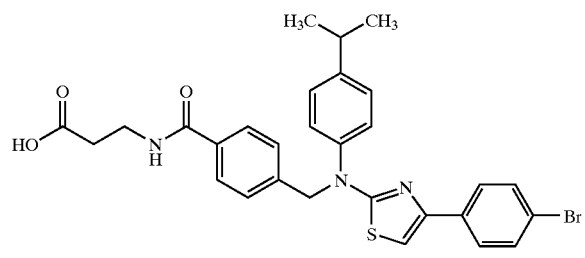

HPLC-MS (Method (A)): m/z=579 (M+1); R$_t$=6.27 min.

Example 309

General Procedure (A)

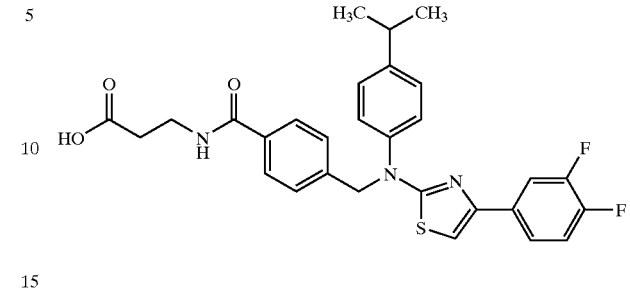

Example 310

General Procedure (A)

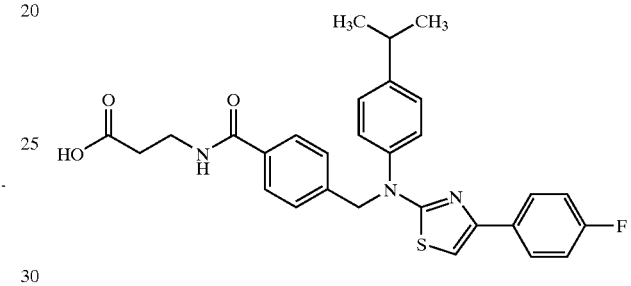

Example 311

General Procedure (A)

3-[4-({(4-isopropylphenyl)-[4-(4-trifluoromethylphenyl)thiazol-2-yl]amino}methyl)benzoylamino]propionic acid

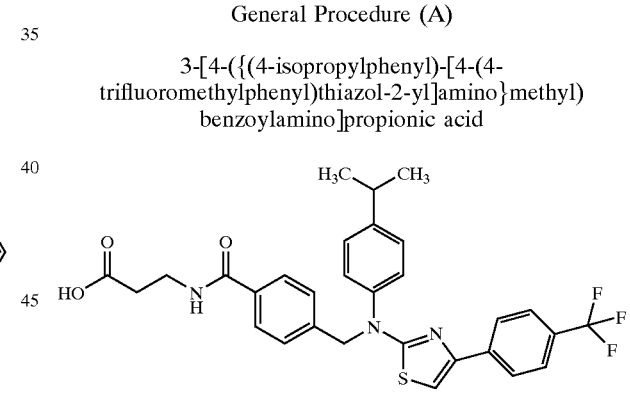

HPLC-MS (Method (A)): m/z=568 (M+1); R$_t$=6.30 min.

Example 312

General Procedure (A)

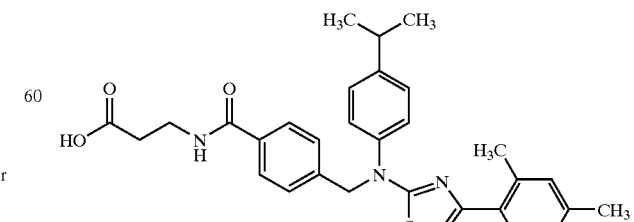

Example 313
General Procedure (A)
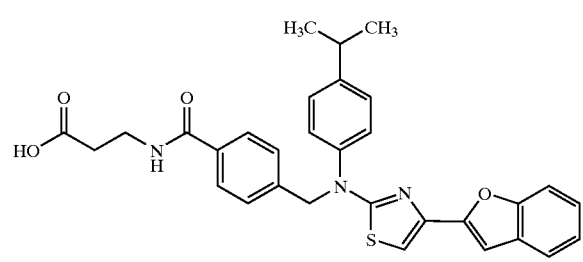
Example 314
General Procedure (A)
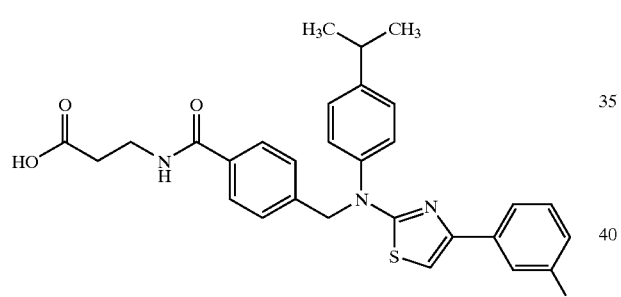
Example 315
General Procedure (A)
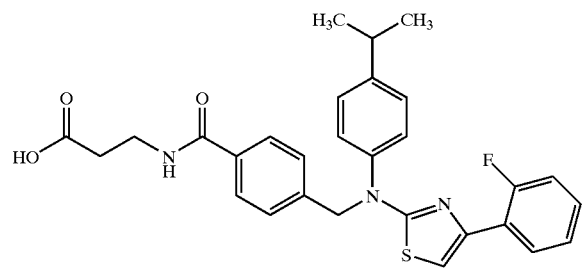
Example 316
General Procedure (A)
3-(4-{[[4-(4-Chlorophenyl)-5-phenylthiazol-2-yl]-(4-isopropylphenyl)amino]methyl}benzoylamino) propionic acid
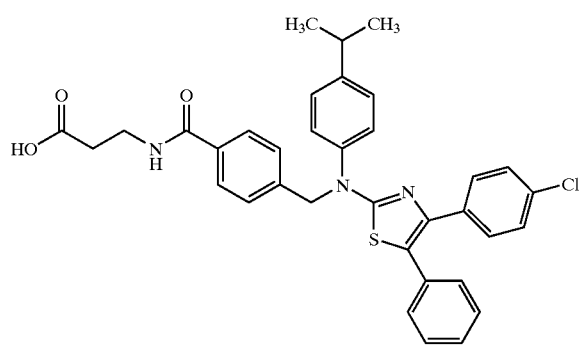
HPLC-MS (Method (A)): m/z 611 (M+1), R$_t$=7.03 min.
Example 317
General Procedure (A)
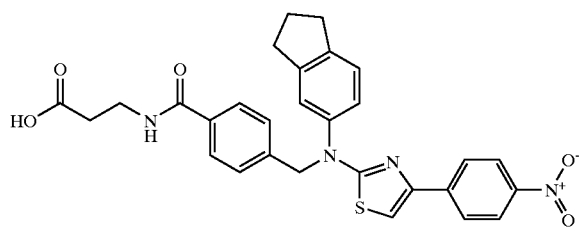
Example 318
General Procedure (A)
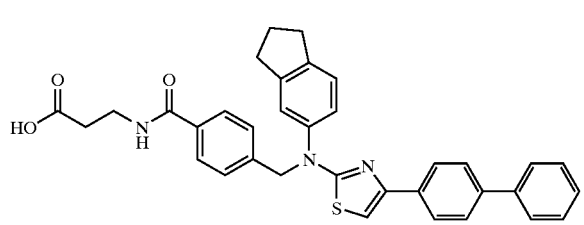

Example 319

General Procedure (A)

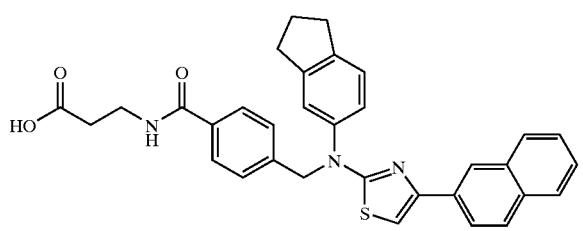

Example 320

General Procedure (A)

3-[4-({[4-(3,4-Dichlorophenyl)thiazol-2-yl]indan-5-ylamino}methyl)benzoylamino]propionic acid

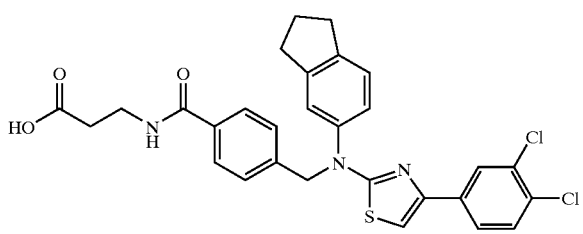

HPLC-MS (Method (A)): m/z 567 (M+1); $R_t$=6.43 min.

Example 321

General Procedure (A)

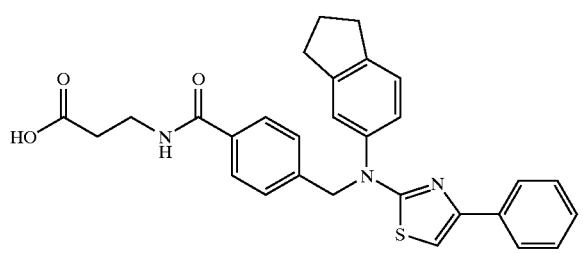

Example 322

General Procedure (A)

3-[4-({[4-(4-Chlorophenyl)thiazol-2-yl]indan-5-ylamino}methyl)benzoylamino]propionic acid

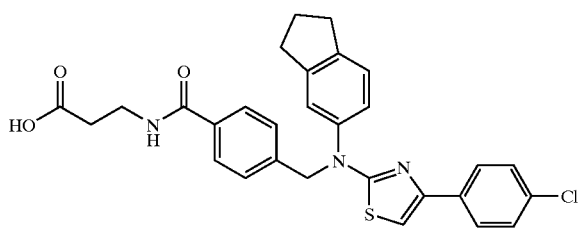

$^1$H NMR (300 MHz, DMSO-$d_6$): δ=2.05 (2H, p), 2.5 (below DMSO), 2.86 (4H, t), 3.4 (below water), 5.29 (2H, s), 7.17 (1H, dd), 7.23 (1H, s), 7.27 (1H, d), 7.31 (1H, d), 7.44 (4H, m), 7.78 (2H, d), 7.88 (2H, d), 8.47 (1H, t), 12.2 (1H, bs); HPLC-MS (Method (A)): m/z=532 (M+1); $R_t$=6.03 min; HPLC-MS (Method (A)): m/z=532 (M+1); $R_t$=5.15 min.

Example 323

General Procedure (A)

3-[4-({[4-(3,4-Difluorophenyl)thiazol-2-yl]indan-5-ylamino}methyl)benzoylamino]propionic acid

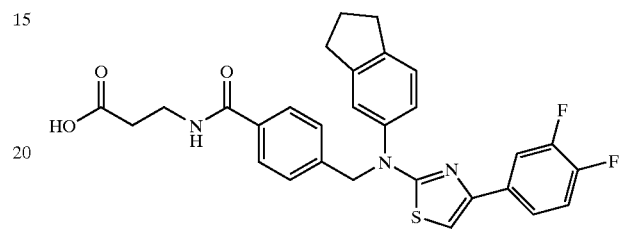

HPLC-MS (Method (A)): m/z=534 (M+1); $R_t$=5.87 min.

Example 324

General Procedure (A)

3-[4-({[4-(4-Fluorophenyl)thiazol-2-yl]indan-5-ylamino}methyl)benzoylamino]propionic acid

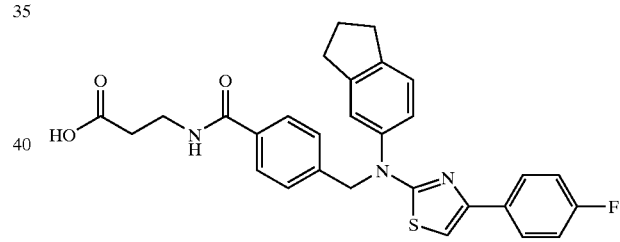

HPLC-MS (Method (A)): m/z=516 (M+1); $R_t$=5.67 min.

Example 325

General Procedure (A)

3-[4-({[4-(2,4-Difluorophenyl)thiazol-2-yl]indan-5-ylamino}methyl)benzoylamino]propionic acid

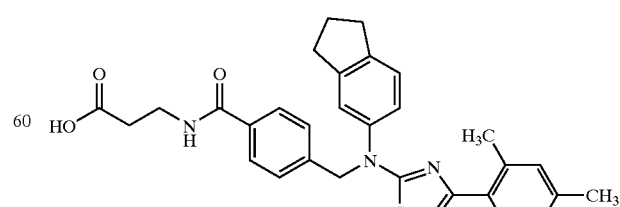

HPLC-MS (Method (A)): m/z=526 (M+1); $R_t$=5.47 min.

Example 326

General Procedure (A)

3-[4-({[4-(3,5-Bis-trifluoromethylphenyl)thiazol-2-yl]indan-5-ylamino}methyl)benzoylamino]propionic acid

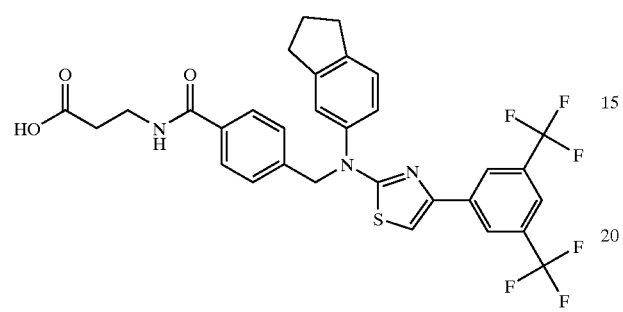

HPLC-MS (Method (A)): m/z=634 (M+1); $R_t$=6.67 min.

Example 327

General Procedure (A)

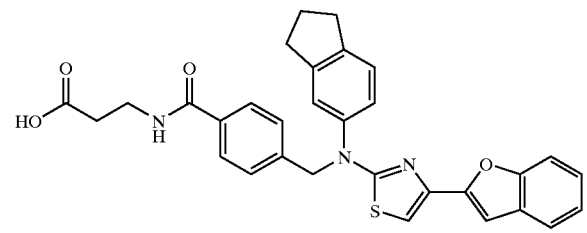

Example 328

General Procedure (A)

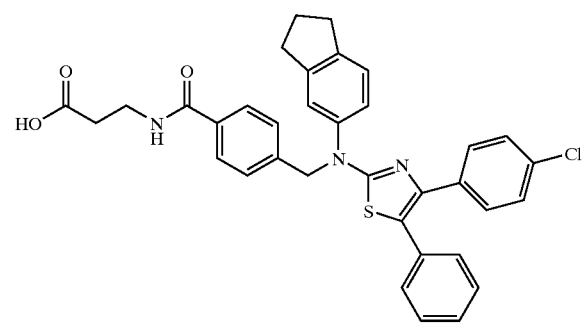

Example 329

General Procedure (A)

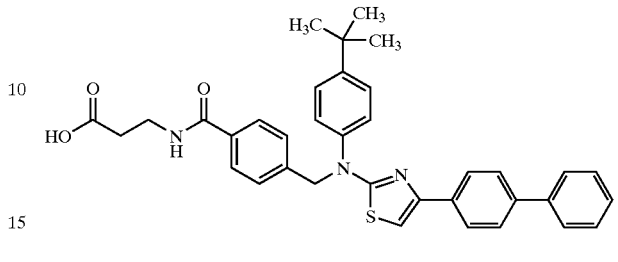

Example 330

General Procedure (A)

3-[4-({(4-tert-Butylphenyl)-[4-(4-trifluoromethylphenyl)thiazol-2-yl]amino}methyl)benzoylamino]propionic acid

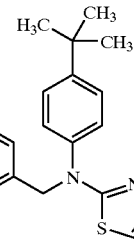

HPLC-MS (Method (A)): m/z=582 (M+1); $R_t$=6.50 min.

Example 331

General Procedure (A)

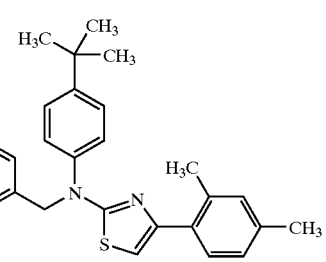

119
Example 332
General Procedure (A)
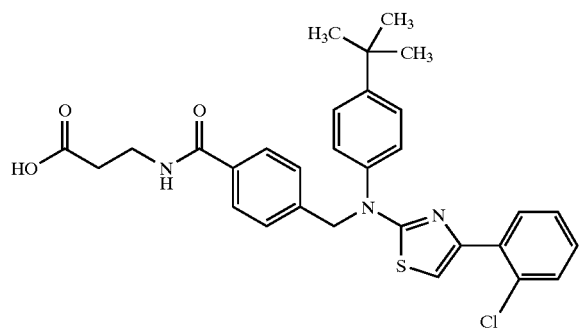
Example 333
General Procedure (A)
3-(4-{[[4-(3,5-Bis-trifluoromethylphenyl)thiazol-2-yl]-(4-tert-butylphenyl)amino]methyl}benzoylamino)propionic acid
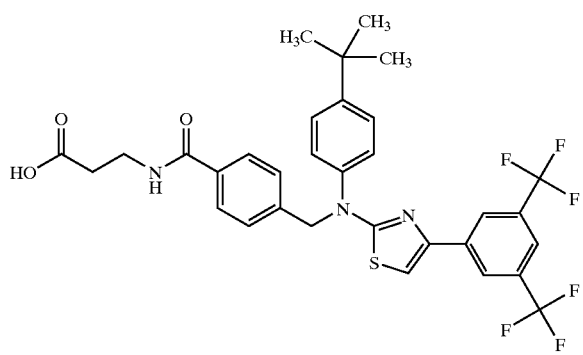
HPLC-MS (Method (A)): m/z=650 (M+1); $R_t$=6.93 min.
Example 334
General Procedure (A)
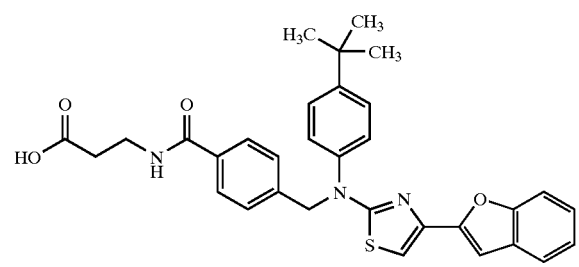
120
Example 335
General Procedure (A)
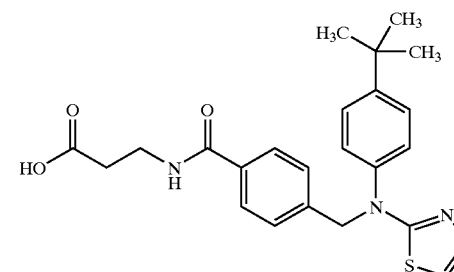
Example 336
General Procedure (A)
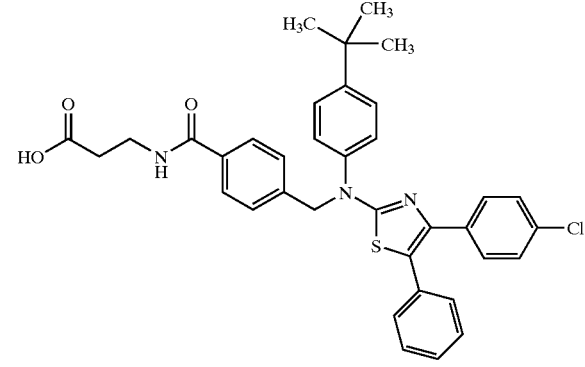
Example 337
General Procedure (A)
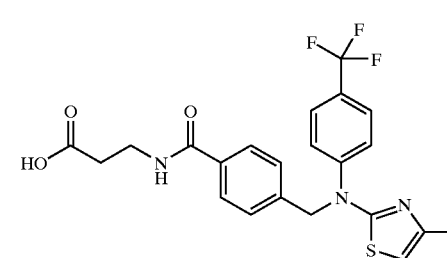

Example 338

General Procedure (A)

3-(4-{[[4-(4-Bromophenyl)thiazol-2-yl]-(4-trifluoromethylphenyl)amino]methyl}benzoylamino)propionic acid

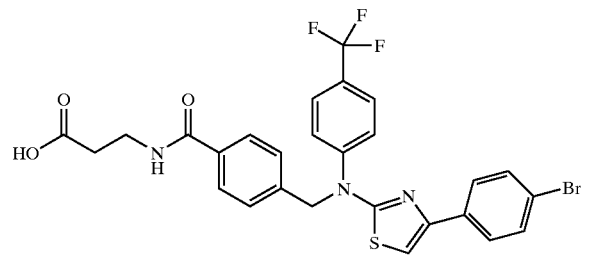

HPLC-MS (Method (A)): m/z=605 (M+1); $R_t$=5.97 min.

Example 339

General Procedure (A)

3-(4-{[[4-(4-Chlorophenyl)thiazol-2-yl]-(4-trifluoromethylphenyl)amino]methyl}benzoylamino)propionic acid

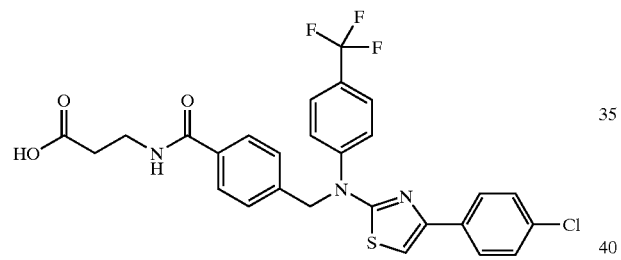

HPLC-MS (Method (A)): m/z=560 (M+1); $R_t$=5.87 min;
HPLC-MS (Method (B)): m/z=560 (M+1); $R_t$=5.10 min.

Example 340

General Procedure (A)

3-(4-{[[4-(3,4-Difluorophenyl)thiazol-2-yl]-(4-trifluoromethylphenyl)amino]methyl}benzoylamino)propionic acid

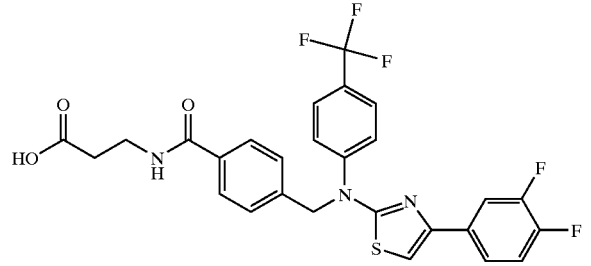

HPLC-MS (Method (A)): m/z=562 (M+1); $R_t$=5.67 min.

Example 341

General Procedure (A)

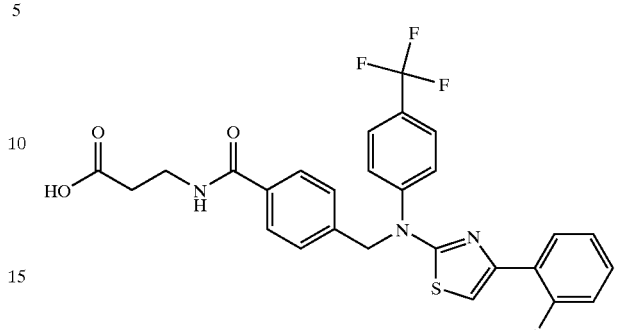

Example 342

General Procedure (A)

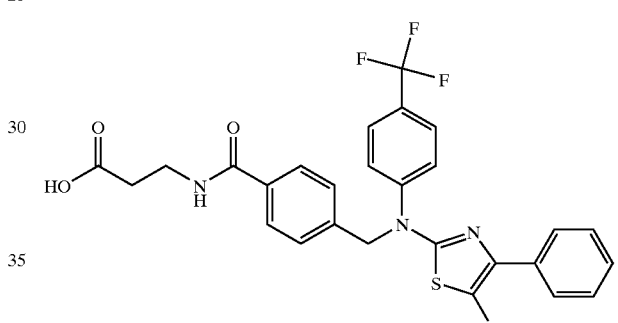

Example 343

General Procedure (A)

3-(4-{[[4-(3-Bromophenyl)thiazol-2-yl]-(4-trifluoromethylphenyl)amino]methyl}benzoylamino)propionic acid

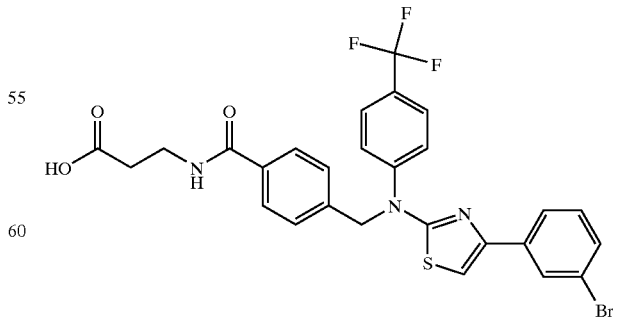

HPLC-MS (Method (A)): m/z=605 (M+1); $R_t$=5.93 min.

Example 344

General Procedure (A)

3-(4-{[[4-(3-Chlorophenyl)thiazol-2-yl]-(4-trifluoromethylphenyl)amino]methyl}benzoylamino)propionic acid

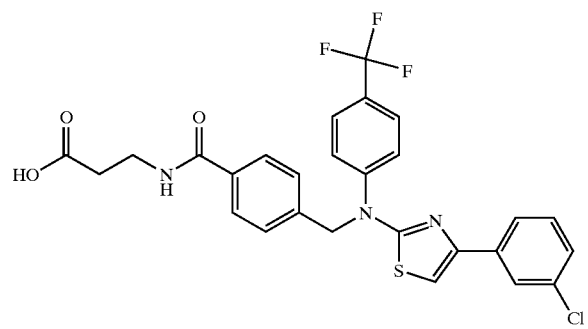

HPLC-MS (Method (A)): m/z=560 (M+1); $R_t$=5.83 min.

Example 345

General Procedure (A)

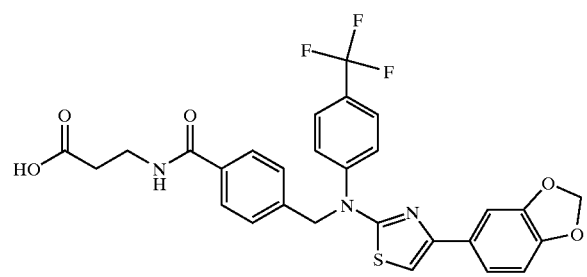

Example 346

General Procedure (A)

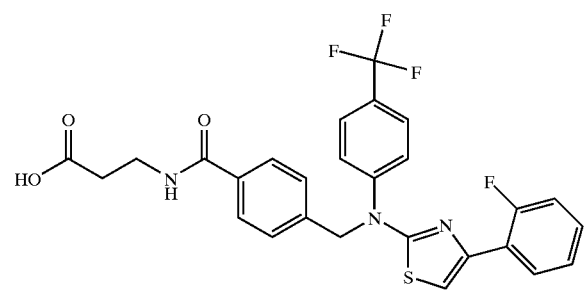

Example 347

General Procedure (A)

3-(4-{[[4-(4-Chlorophenyl)-5-phenylthiazol-2-yl]-(4-trifluoromethylphenyl)amino]methyl}benzoylamino)propionic acid

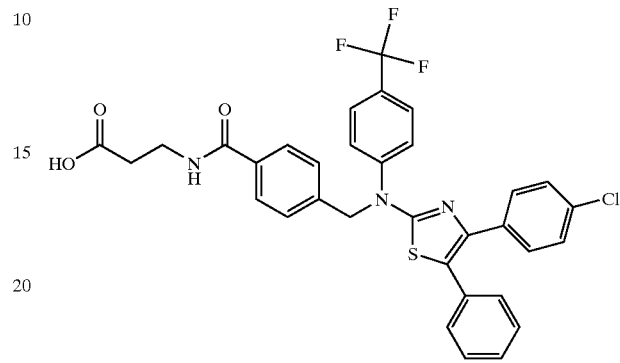

HPLC-MS (Method (A)): m/z=637 (M+1); $R_t$=6.70 min.

Example 348

General Procedure (A)

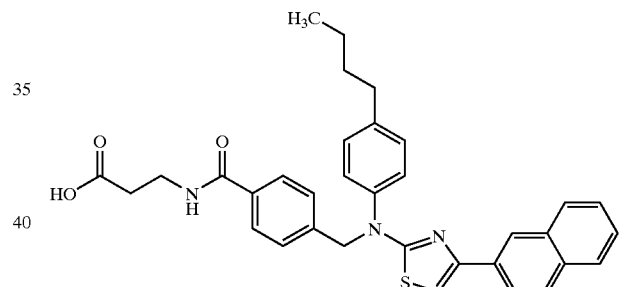

Example 349

General Procedure (A)

3-[4-({(4-Butylphenyl)-[4-(4-chlorophenyl)thiazol-2-yl]amino}methyl)benzoylamino]propionic acid

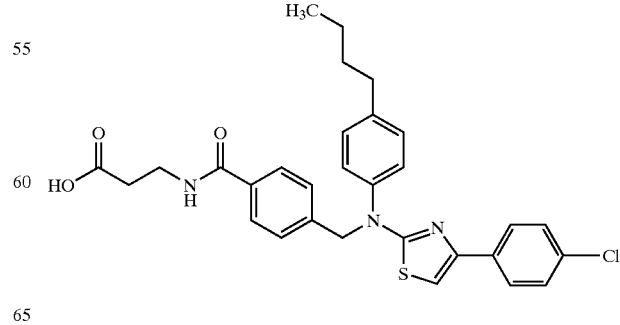

HPLC-MS (Method (A)): m/z=549 (M+1); $R_t$=6.60 min.

Example 350

General Procedure (A)

3-[4-({(4-Butylphenyl)-[4-(4-pentylphenyl)thiazol-2-yl]amino}methyl)benzoylamino]propionic acid

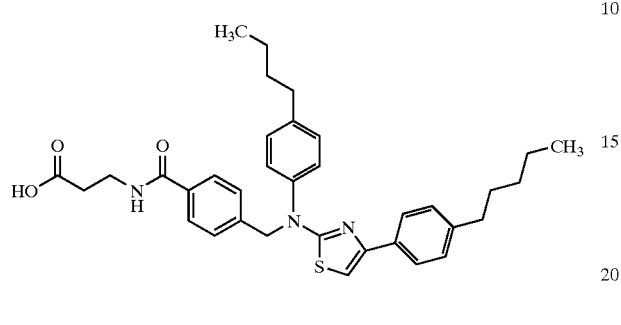

HPLC-MS (Method (A)): m/z=584 (M+1); $R_t$=7.57 min.

Example 351

General Procedure (A)

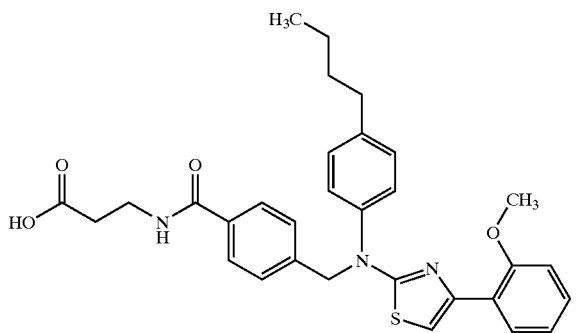

Example 352

General Procedure (A)

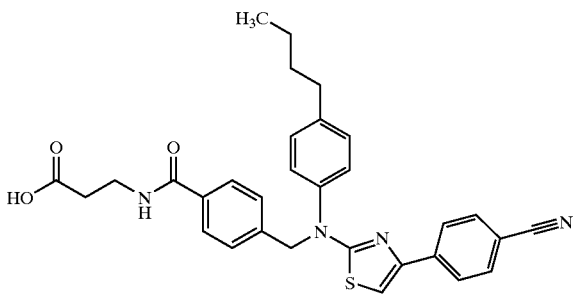

Example 353

General Procedure (A)

3-(4-{[[4-(3-Bromophenyl)thiazol-2-yl]-(4-butylphenyl)amino]methyl}benzoylamino)propionic acid

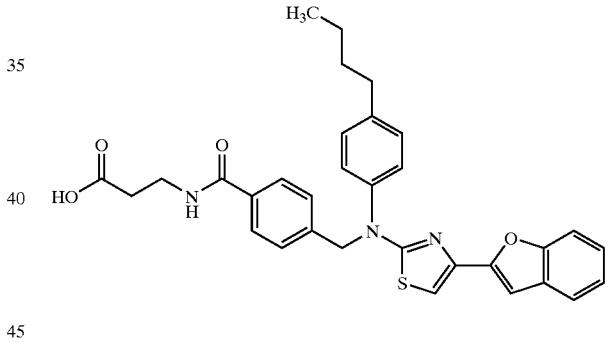

HPLC-MS (Method (A)): m/z=593 (M+1); $R_t$=6.67 min.

Example 354

General Procedure (A)

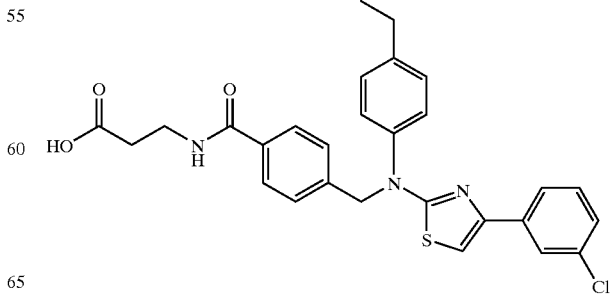

Example 355

General Procedure (A)

Example 356

General Procedure (A)

3-[4-({[4-(3,4-Dichlorophenyl)thiazol-2-yl]-p-tolylamino}methyl)benzoylamino]propionic acid

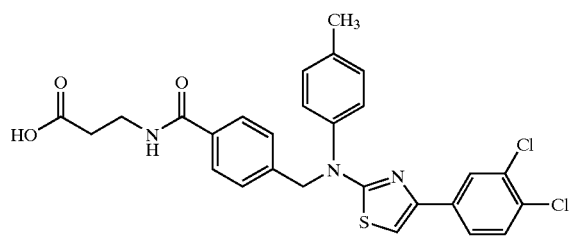

HPLC-MS (Method (A)): m/z=541 (M+1); $R_t$=6.07 min.

Example 357

General Procedure (A)

3-[4-({[4-(4-Chlorophenyl)thiazol-2-yl]-p-tolylamino}methyl)benzoylamino]propionic acid

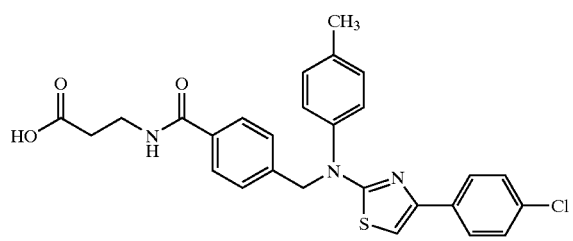

HPLC-MS (Method (A)): m/z=507 (M+1); $R_t$=5.70 min.

Example 358

General Procedure (A)

3-[4-({[4-(4-Pentylphenyl)thiazol-2-yl]-p-tolylamino}methyl)benzoylamino]propionic acid

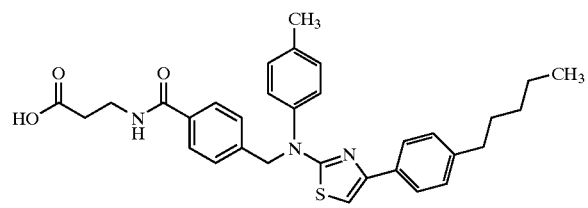

HPLC-MS (Method (A)): m/z=542 (M+1); $R_t$=6.73 min.

Example 359

General Procedure (A)

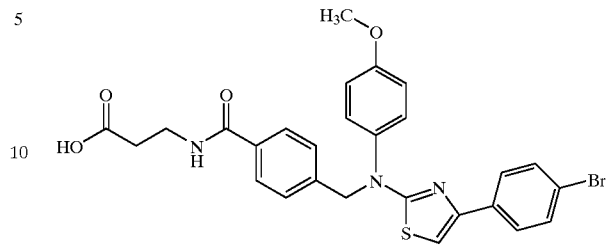

Example 360

General Procedure (A)

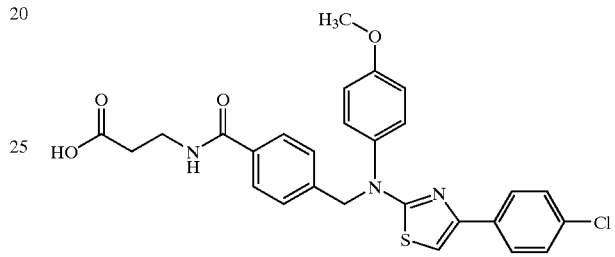

Example 361

General Procedure (A)

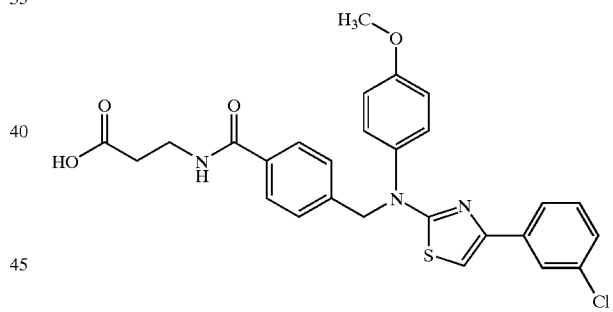

Example 362

General Procedure (A)

3-[4-({(4-Chlorophenyl)-[4-(4-nitrophenyl)thiazol-2-yl]amino}methyl)benzoylamino]propionic acid

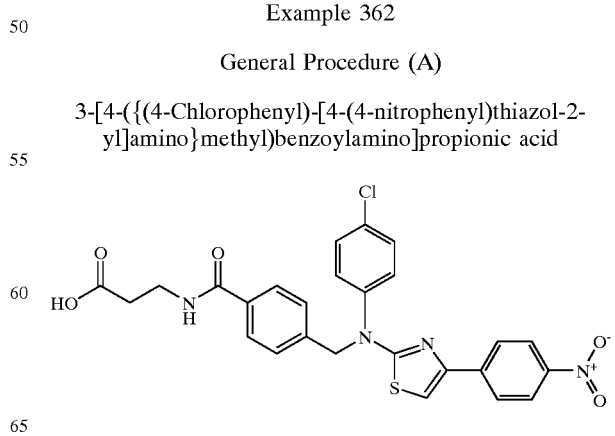

HPLC-MS (Method (A)): m/z 537 (M+1); $R_t$=5.40 min.

Example 363

General Procedure (A)

3-(4-{[(4-Biphenyl-4-ylthiazol-2-yl)-(4-chlorophenyl)amino]methyl}benzoylamino)propionic acid

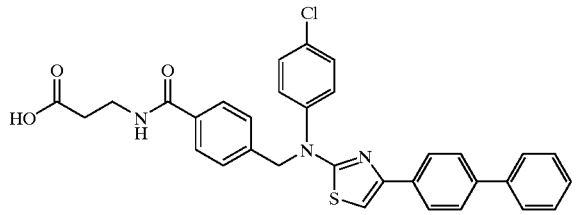

HPLC-MS (Method (A)): m/z=569 (M+1); $R_t$ 6.20 min.

Example 364

General Procedure (A)

3-[4-({(4-Chlorophenyl)-[4-(4-trifluoromethylphenyl)thiazol-2-yl]amino}methyl)benzoylamino]propionic acid

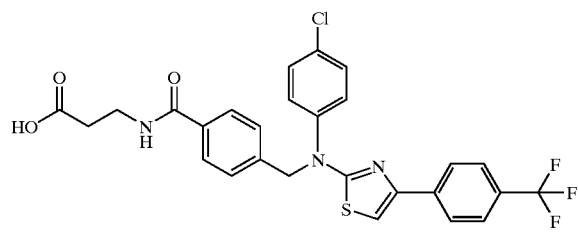

$^1$H NMR (300 MHz, DMSO-$d_6$): δ=2.5 (below DMSO), 3.43 (2H, q), 5.35 (2H, s), 7.44 (2H, d), 7.5–7.6 (5H, m), 7.76 (4H, m), 8.09 (2H, d), 8.49 (1H, t), 12.2 (1H, bs); HPLC-MS (Method (A)): m/z=560 (M+1); $R_t$=5.90 min; HPLC-MS (Method (B)): m/z=560 (M+1); $R_t$=4.95 min.

Example 365

General Procedure (A)

3-[4-({(4-Chlorophenyl)-[4-(4-pentylphenyl)thiazol-2-yl]amino}methyl)benzoylamino]propionic acid

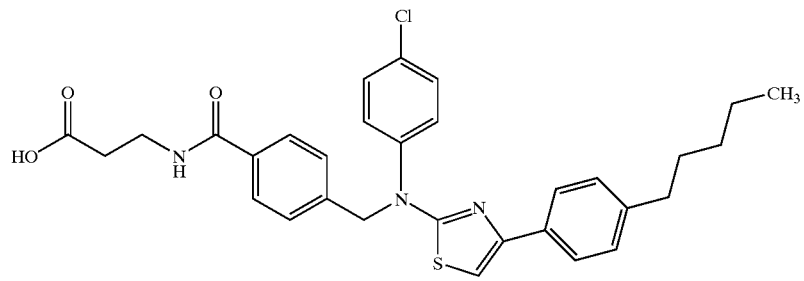

HPLC-MS (Method (A)): m/z=562 (M+1); $R_t$=6.90 min. HPLC-MS (Method (B)): m/z=562 (M+1); $R_t$=5.90 min. $^1$H NMR (300 MHz, DMSO-$d_6$): δ=0.89 (3H, t), 1.3 (4H, m), 1.59 (2H, p), 2.58 (2H, t), 3.4 (below water), 5.33 (2H, s), 7.2 (3H, m), 7.42 (2H, d), 7.51 (4H, m), 7.78 (4H, m), 8.46 (1H, t), 12.2 (1H, bs).

Example 366

General Procedure (A)

3-[4-({(4-Chlorophenyl)-[4-(4-trifluoromethoxyphenyl)thiazol-2-yl]amino}methyl)benzoylamino]propionic acid

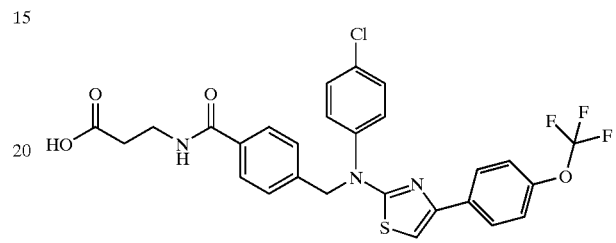

$^1$H NMR (300 MHz, DMSO-$d_6$): δ=2.5 (below DMSO), 3.45 (2H, q), 5.32 (2H, s), 7.37 (1H, s), 7.4 (4H, m), 7.53 (4H, m), 7.78 (2H, d), 7.98 (2H, d), 8.49 (1H, t), 12.2 (1H, bs); HPLC-MS (Method (A)): m/z=576 (M+1); $R_t$=6.00 min; HPLC-MS (Method (B)): m/z=576 (M+1); $R_t$=5.17 min.

Example 367

General Procedure (A)

3-(4-{[[4-(3,5-Bis-trifluoromethylphenyl)thiazol-2-yl]-(4-chlorophenyl)amino]methyl}benzoylamino)propionic acid

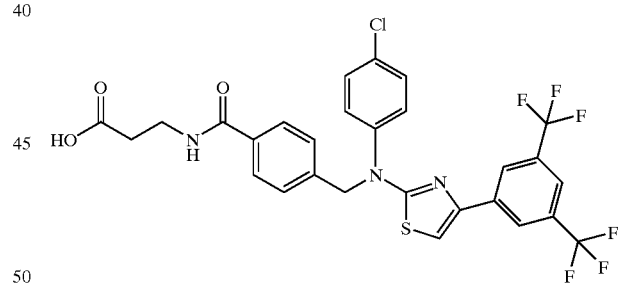

HPLC-MS (Method (A)): m/z=628 (M+1); $R_t$=6.30 min.

Example 368

General Procedure (A)

3-[4-({(4-Chlorophenyl)-[4-(3-chlorophenyl)thiazol-2-yl]amino}methyl)benzoylamino]propionic acid

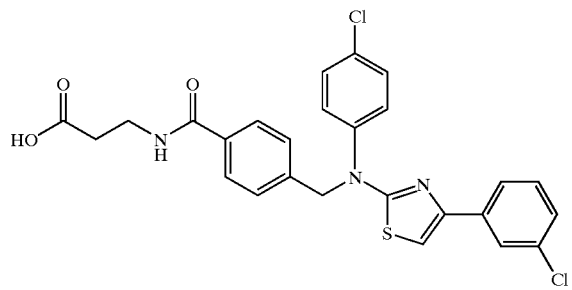

HPLC-MS (Method (A)): m/z=527 (M+1); $R_t$=5.73 min.

Example 369

General Procedure (A)

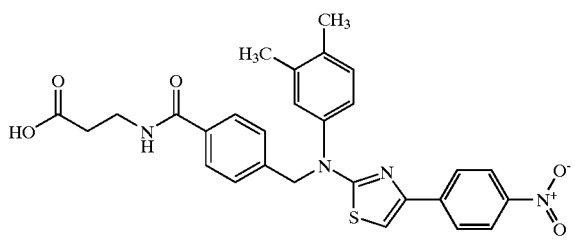

Example 370

General Procedure (A)

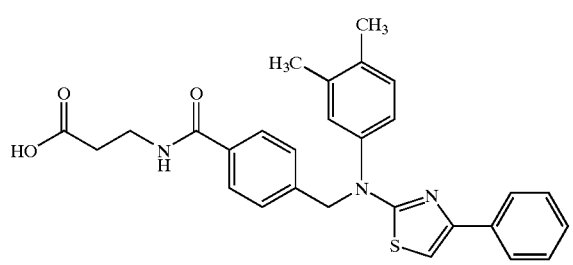

Example 371

General Procedure (A)

3-[4-({(3,4-Dimethylphenyl)-[4-(4-trifluoromethylphenyl)thiazol-2-yl]amino}methyl)benzoylamino]propionic acid

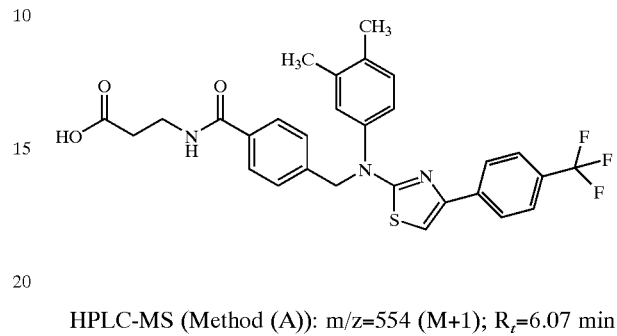

HPLC-MS (Method (A)): m/z=554 (M+1); $R_t$=6.07 min.

Example 372

General Procedure (A)

3-[4-({(3,4-Dimethylphenyl)-[4-(2,4-dimethylphenyl)thiazol-2-yl]amino}methyl)benzoylamino]propionic acid

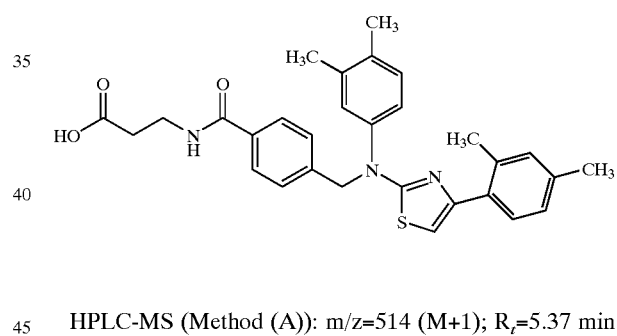

HPLC-MS (Method (A)): m/z=514 (M+1); $R_t$=5.37 min.

Example 373

General Procedure (A)

3-[4-({(3,4-Dimethylphenyl)-[4-(4-pentylphenyl)thiazol-2-yl]amino}methyl)benzoylamino]propionic acid

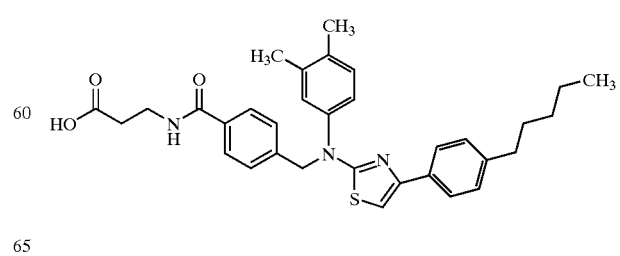

HPLC-MS (Method (A)): m/z=556 (M+1); $R_t$=6.93 min.

Example 374
General Procedure (A)
3-(4-{[[4-(3-Chlorophenyl)thiazol-2-yl]-(3,4-dimethylphenyl)amino]methyl}benzoylamino)propionic acid
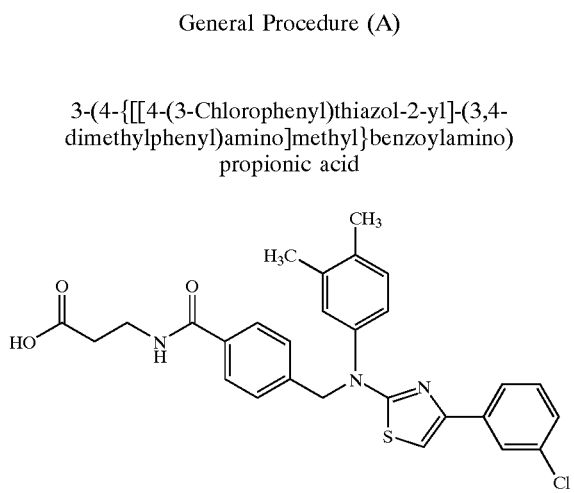
HPLC-MS (Method (A)): m/z=521 (M+1); $R_t$=5.90 min.
Example 375
General Procedure (A)
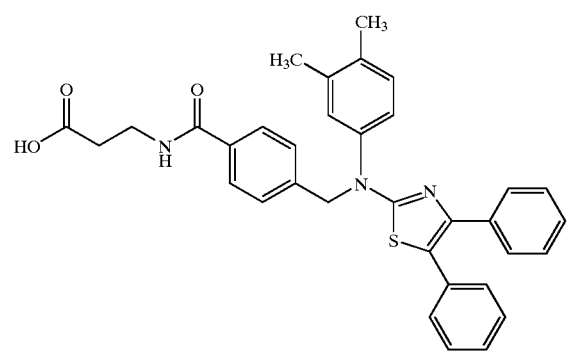
Example 376
General Procedure (A)
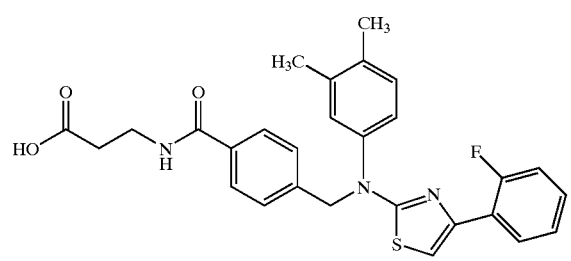
Example 377
General Procedure (A)
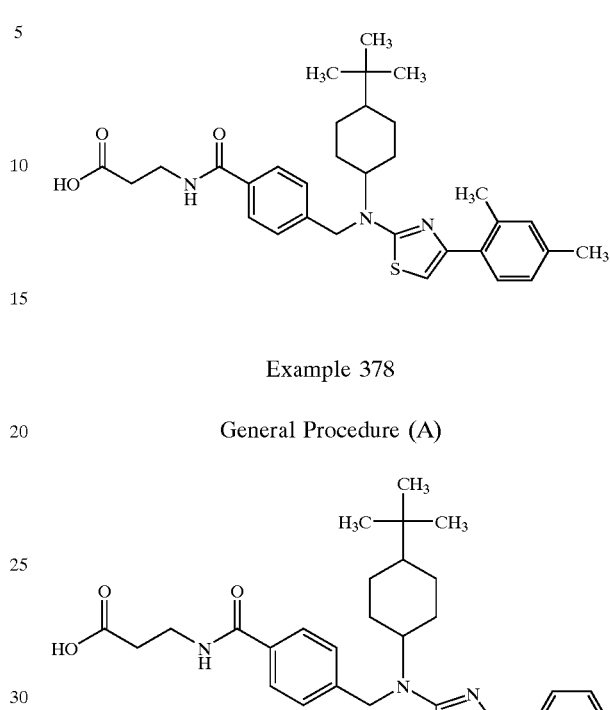
Example 378
General Procedure (A)
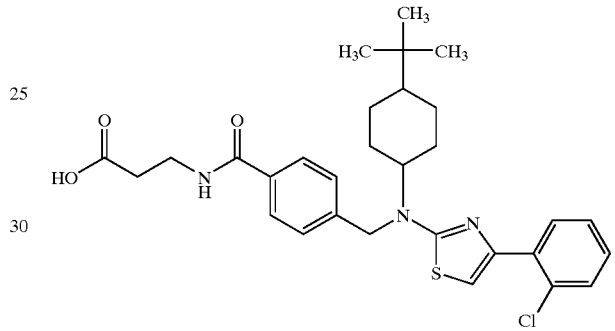
Example 379
General Procedure (A)
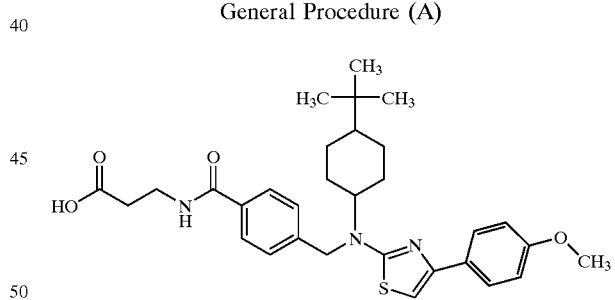
Example 380
General Procedure (A)
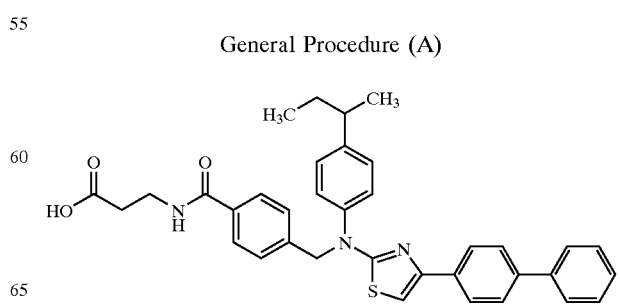

Example 381

General Procedure (A)

3-[4-({(4-sec-Butylphenyl)-[4-(3,4-dichlorophenyl)thiazol-2-yl]amino}methyl)benzoylamino]propionic acid

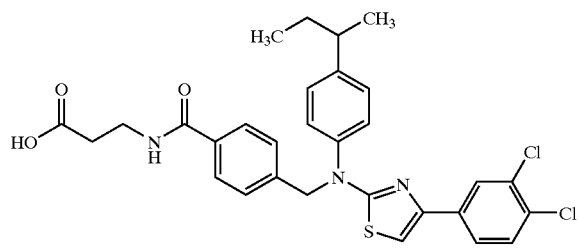

HPLC-MS (Method (A)): m/z=583 (M+1); $R_t$=6.90 min.

Example 382

General Procedure (A)

3-[4-({(4-sec-Butylphenyl)-[4-(4-chlorophenyl)thiazol-2-yl]amino}methyl)benzoylamino]propionic acid

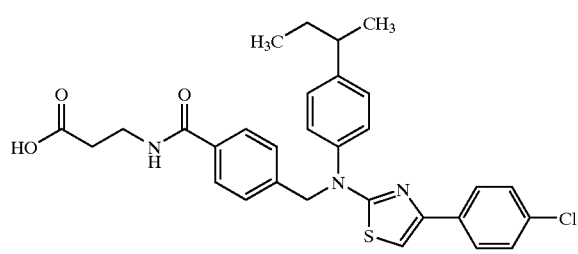

HPLC-MS (Method (A)): m/z=549 (M+1); $R_t$=6.50 min.

Example 383

General Procedure (A)

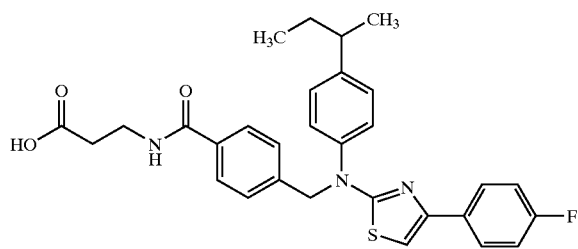

Example 384

General Procedure (A)

3-[4-({(4-sec-Butylphenyl)-[4-(4-pentylphenyl)thiazol-2-yl]amino}methyl)benzoylamino]propionic acid

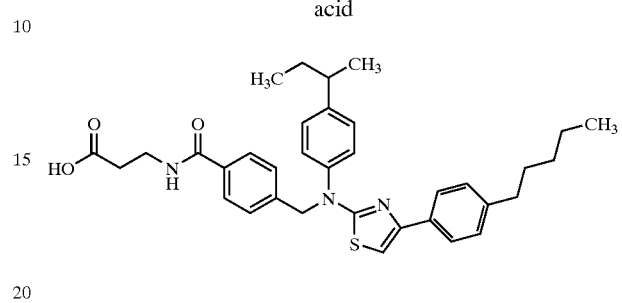

HPLC-MS (Method (A)): m/z=584 (M+1); $R_t$=7.50 min.

Example 385

General Procedure (A)

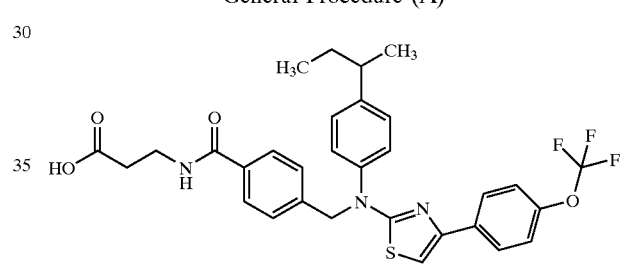

Example 386

General Procedure (A)

3-(4-{[[4-(3,5-Bis-trifluoromethylphenyl)thiazol-2-yl]-(4-sec-butylphenyl)amino]methyl}benzoylamino)propionic acid

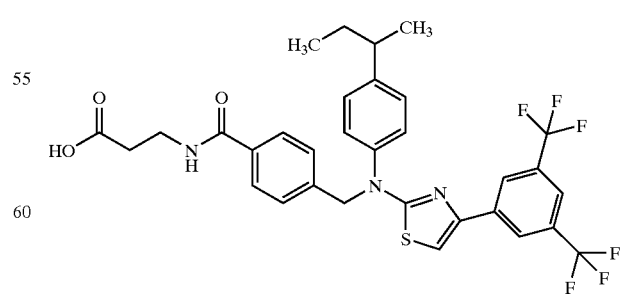

HPLC-MS (Method (A)): m/z=650 (M+1); $R_t$=7.07 min.

Example 387

General Procedure (A)

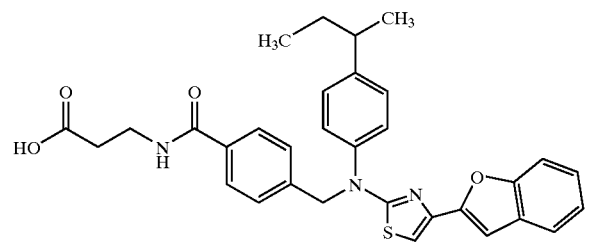

Example 388

General Procedure (A)

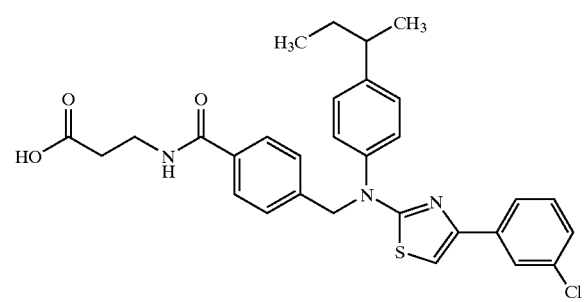

Example 389

General Procedure (A)

3-(4-{[(4-Naphthalen-2-ylthiazol-2-yl)-(4-propylphenyl)amino]methyl}benzoylamino) propionic acid

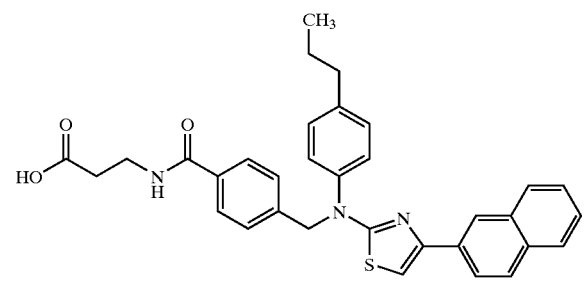

Example 390

General Procedure (A)

3-(4-{[[4-(4-Chlorophenyl)thiazol-2-yl]-(4-propylphenyl)amino]methyl}benzoylamino) propionic acid

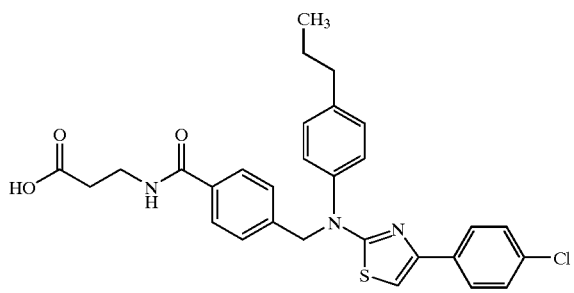

HPLC-MS (Method (A)): m/z=535 (M+1); $R_t$=6.30 min.

Example 391

General Procedure (A)

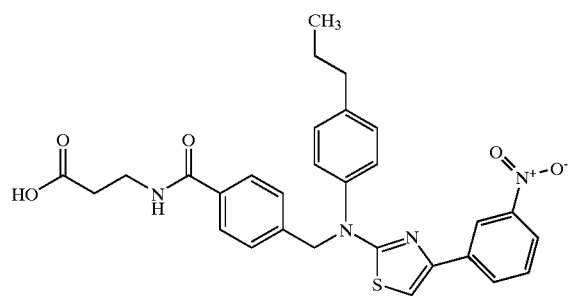

Example 392

General Procedure (A)

3-(4-{[[4-(3,5-Bis-trifluoromethylphenyl)thiazol-2-yl]-(4-propylphenyl)amino]methyl}benzoylamino) propionic acid

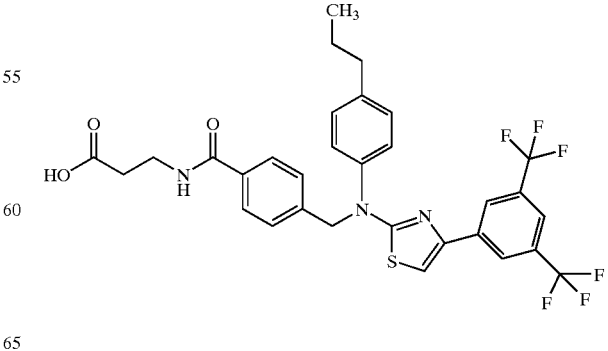

HPLC-MS (Method (A)): m/z=636 (M+1); $R_t$=6.87 min.

Example 393

General Procedure (A)

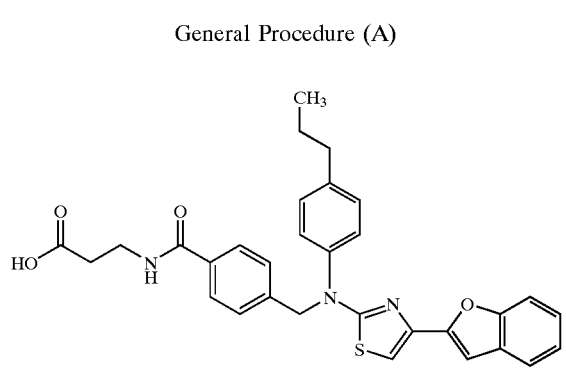

Example 394

General Procedure (A)

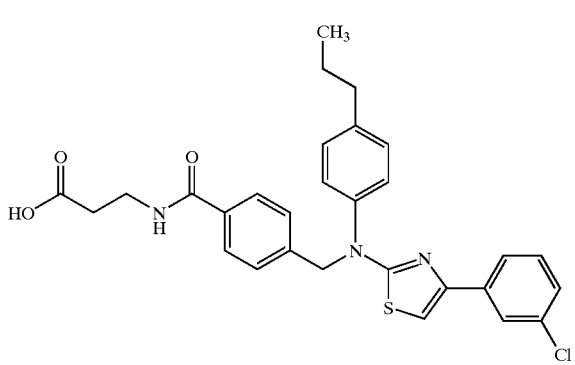

Example 395

General Procedure (A)

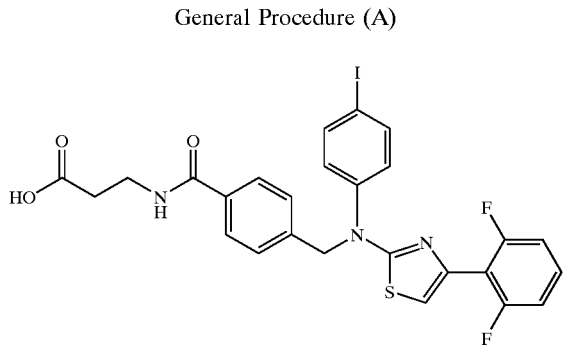

Example 396

General Procedure (A)

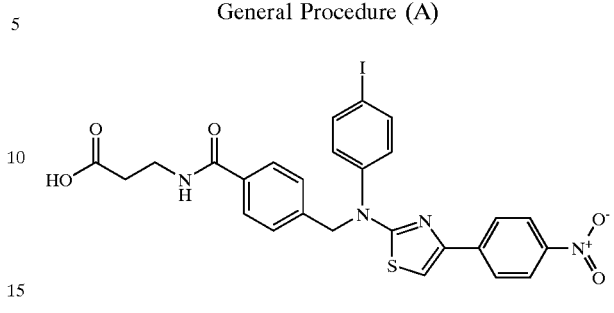

Example 397

General Procedure (A)

3-(4-{[(4-Biphenyl-4-ylthiazol-2-yl)-(4-iodophenyl)amino]methyl}benzoylamino)propionic acid

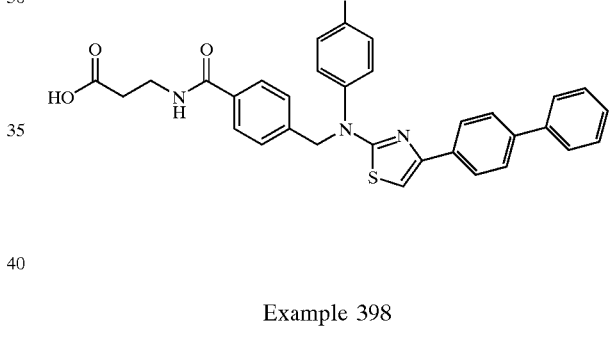

Example 398

General Procedure (A)

3-(4-{[[4-(3,4-Dichlorophenyl)thiazol-2-yl]-(4-iodophenyl)amino]methyl}benzoylamino)propionic acid

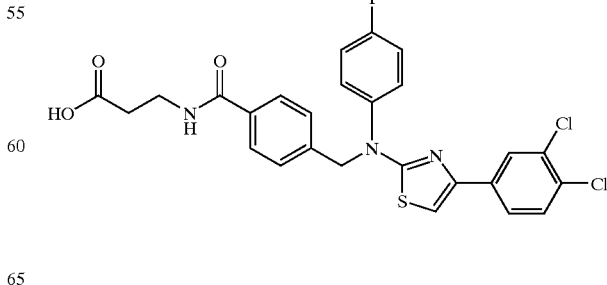

HPLC-MS (Method (A)): m/z=653 (M+1); $R_t$=6.37 min.

Example 399

General Procedure (A)

3-(4-{[[4-(4-Chlorophenyl)thiazol-2-yl]-(4-iodophenyl)amino]methyl}benzoylamino)propionic acid

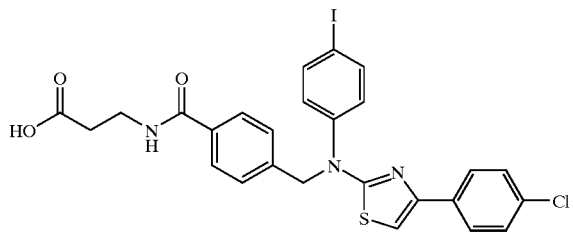

HPLC-MS (Method (A)): m/z=618 (M+1); $R_t$=6.03 min.

Example 400

General Procedure (A)

3-(4-{[[4-(3,4-Difluorophenyl)thiazol-2-yl]-(4-iodophenyl)amino]methyl}benzoylamino)propionic acid

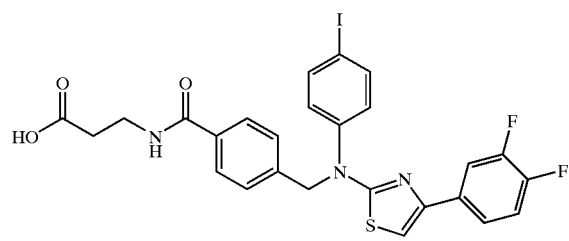

HPLC-MS (Method (A)): m/z=620 (M+1); $R_t$=5.80 min.

Example 401

General Procedure (A)

3-(4-{[[4-(4-Fluorophenyl)thiazol-2-yl]-(4-iodophenyl)amino]methyl}benzoylamino)propionic acid

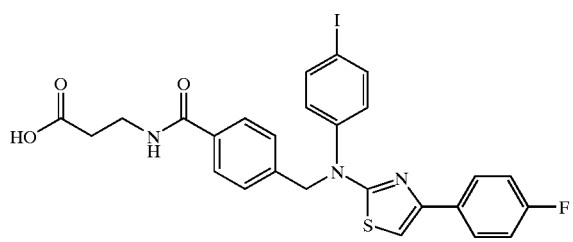

HPLC-MS (Method (A)): m/z=602 (M+1); $R_t$=5.67 min.

Example 402

General Procedure (A)

3-(4-{[[4-(2,4-Dimethylphenyl)thiazol-2-yl]-(4-iodophenyl)amino]methyl}benzoylamino)propionic acid

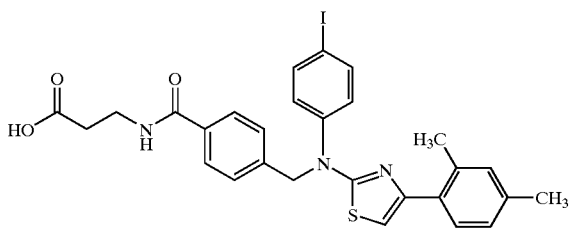

HPLC-MS (Method (A)): m/z=612 (M+1); $R_t$=5.87 min.

Example 403

General Procedure (A)

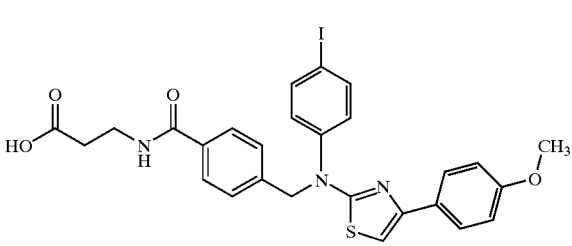

Example 404

General Procedure (A)

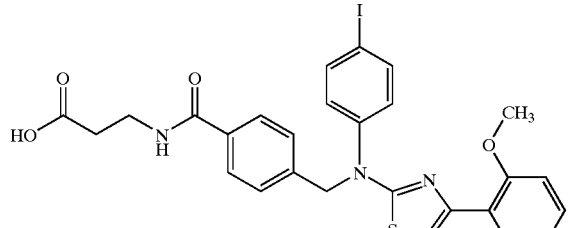

Example 405

General Procedure (A)

3-(4-{[[4-(2-Fluorophenyl)thiazol-2-yl]-(4-iodophenyl)amino]methyl}benzoylamino)propionic acid

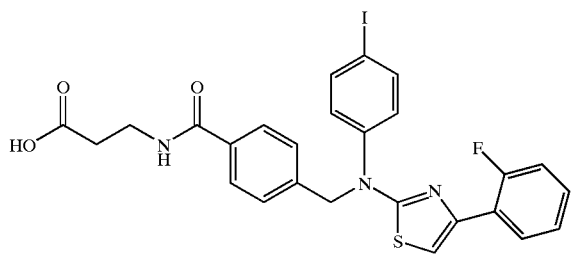

HPLC-MS (Method (A)): m/z=602 (M+1); $R_t$=5.83 min.

Example 406

3-[4-({(4-Cyclohex-1-enylphenyl)-[5-(4-trifluoromethoxyphenyl)-[1,3,4]thiadiazol-2-yl]amino}methyl)benzoylamino]propionic acid

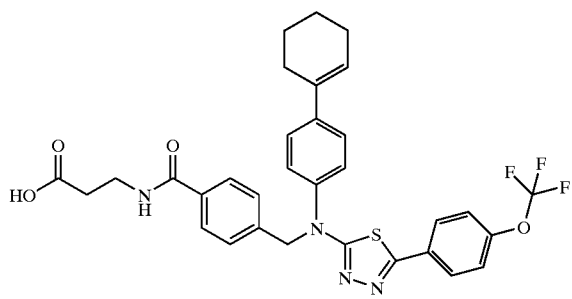

Fmoc-beta-ala-wang resin (10 g, 5.7 mmol) was added a solution of 20% piperidine in DMF (80 ml) and shaken for ½ hour at room temperature. The resin was drained and washed successively with DMF, 5% HOBt in DMF and DMF (each 80 ml).

The resin was drained and added a solution of 4-formylbenzoic acid (3.42 g, 22.8 mmol) and HOBt (3.49 g, 22.8 mmol) in DMF (50 ml) immediately followed by addition of diisopropylcarbodiimide (3.53 ml, 22.8 mmol). The mixture was diluted with DMF (20 ml) and shaken at room temperature for 16 hours. The resin was drained and washed successively with DMF and DCM (each 80 ml).

To the drained resin was added a solution of 4-cyclohexenylaniline (3.95 g, 22.8 mmol) in a 1:1 mixture of trimethyl orthoformate and DMF (50 ml) followed by acetic acid (7 ml) and the mixture was shaken for 2.5 hour at room temperature.

A solution of sodium cyanoborohydride (1.89 g, 28.5 mmol) in a mixture of MeOH and DMF (15 ml each) was added and the mixture was shaken at room temperature for 16 hours. The resin was drained and washed with MeOH, DMF and DCM. The resin was dried in vacuo at 40° C. for 16 hours to afford the resin-bound 3-{4-[(4-cyclohex-1-enylphenylamino)methyl]benzoylamino}propionic acid.

To this resin (2.0 g, 1.14 mmol) was added a 1.2 M solution of di-2-pyridylthionocarbonate in NMP (20 ml) and the mixture was shaken at 70° C. for 16 hours. The resin was drained and washed with DMF and DCM.

The drained resin was added 25% hydrazine monohydrate in water (1.45 ml) in NMP (20 ml) and the mixture was shaken at room temperature for 16 hours. The resin was drained and washed with DMF and DCM to afford the resin-bound thiosemicarbazide.

This resin (2.0 g, 1.14 mmol) was added a solution of 4-(trifluoromethoxy)benzaldehyde (2.61 g, 13.73 mmol) in DMF (17 ml) followed by trimethylorthoformate (17 ml) and acetic acid glacial (2.9 ml) at room temperature and the mixture was shaken for 4 hours at room temperature and washed with DMF.

The resin was drained and added a 0.2 M solution of iron(III) chloride (1.3 g, 8.0 mmol) in DCM:MeOH (2:1 v/v, 40 ml). The resin was shaken over night. The resin was drained and the addition of a 0.2 M solution of iron(III) chloride was repeated. The mixture was shaken for 23 hours, and the resin was drained and washed successively with NMP and DCM, MeOH and DCM (each 20 ml).

The resin was added a 1:1 mixture of TFA and DCM (20 ml) and shaken for 30 minutes at room temperature. The resin was filtered and washed with DCM (3×20 ml). The combined filtrates were evaporated in vacuo.

Purification by preparative HPLC afforded the title compound (0.05 g).

$^1$H NMR (DMSO-$d_6$) selected data: δ 1.60 (2H, m), 1.74 (2H, m), 2.18 (2H, m), 2.35 (2H, m), 2.50 (below DMSO-signal), 3.42 (2H, m), 5.32 (2H, s), 6.22 (1H, t), 7.39–7.52 (8H, m), 7.78 (2H, d), 7.90 (2H, d), 8.50 (1H, t); HPLC-MS (Method (A)): m/z: 623 (M+1); Rt: 7.93 min.

Example 407

3-[4-({(4-Cyclohex-1-enylphenyl)-[5-(4-trifluoromethoxyphenyl)-6H-[1,3,4]thiadiazin-2-yl]amino}methyl)benzoylamino]propionic acid

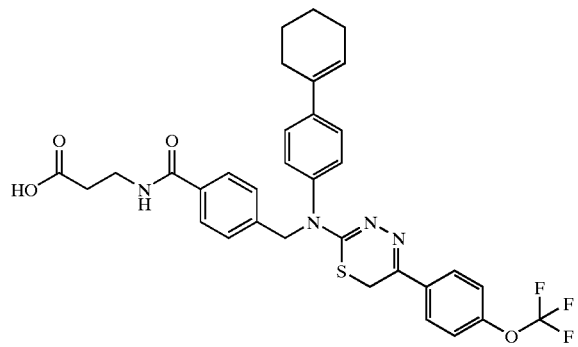

To the above resin-bound thiosemicarbazide (2.0 g, 1.14 mmol) was added a solution of 2-bromo-1-[4-(trifluoromethoxy)phenyl]ethan-1-one (3.0 g, 10.6 mmol) in NMP (20 ml) at room temperature. Acetic acid (4 ml) was added to the resin and the mixture was shaken at room temperature for 16 hours. The resin was drained and washed successively with DMF, MeOH and DCM (each 20 ml).

The resin was added a 1:1 mixture of TFA and DCM (20 ml) and shaken for 30 minutes. The resin was drained and washed with DCM (3×20 ml). The combined filtrates were evaporated in vacuo. Purification by preparative HPLC afforded the title compound (0.01 g).

$^1$H NMR (CDCl$_3$) selected data: δ 1.25–1.42 (2H, m), 1.54–1.70 (2H, m), 1.70–1.84 (2H, m), 2.12–2.29 (2H, m), 2.30–2.42 (2H, m), 2.58–2.70 (2H, m), 3.55–3.74 (4H, m), 5.28 (2H, s), 6.16 (1H, t), 6.99–7.08 (2H, d), 7.20–7.40 (7H, m below CDCl$_3$ signal), 7.60–7.74 (2H, d), 7.82–7.92 (2H, m); HPLC-MS (Method (A)): m/z: 637 (M+1); Rt: 6.47 min.

Example 408

General Procedure (A)

3-[4-({[4-(4-tert-Butylphenyl)thiazol-2-yl]indan-5-ylamino}methyl)benzoylamino]propionic acid

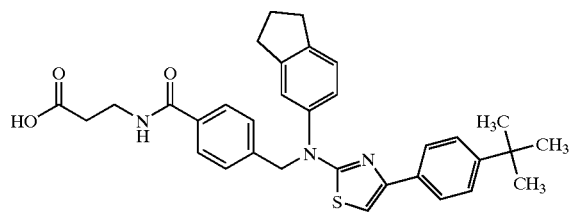

$^1$H NMR (DMSO-d$_6$, selected data): δ 1.29 (9H, s), 2.50 (below DMSO), 3.42 (2H, q), 5.27 (2H, s), 7.07 (1H, s), 7.10–7.17 (3H, m), 7.40 (2H, d), 7.43 (2H, d), 7.75 (4H, m), 8.47 (1H, t).

Example 409

General Procedure (A)

3-(4-{[[4-(4-tert-Butylphenyl)thiazol-2-yl]-(5,6,7,8-tetrahydronaphthalen-2-yl)amino]methyl}benzoylamino)propionic acid

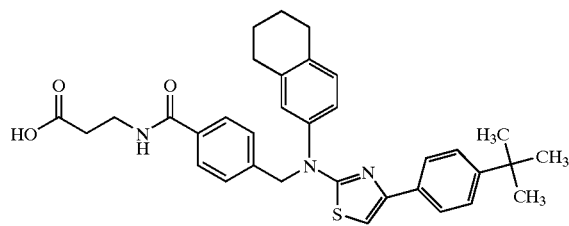

HPLC-MS (Method B): m/z: 568 (M+1); Rt=5.88 min.

Example 410

General Procedure (A)

3-[4-({(4-tert-Butylphenyl)-[4-(4-tert-butylphenyl)thiazol-2-yl]amino}methyl)benzoylamino]propionic acid

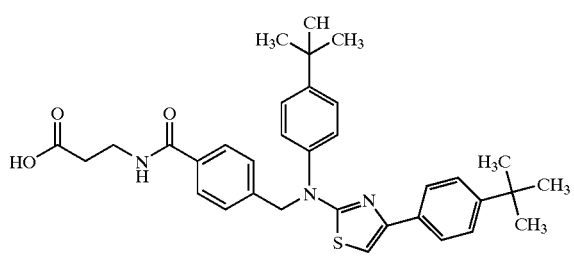

HPLC-MS (Method B): m/z: 570 (M+1); Rt=5.92 min.

Example 411

General Procedure (A)

3-(4-{[[4-(4-tert-Butylphenyl)thiazol-2-yl]-(4-cyclohexylphenyl)amino]methyl}benzoylamino)propionic acid

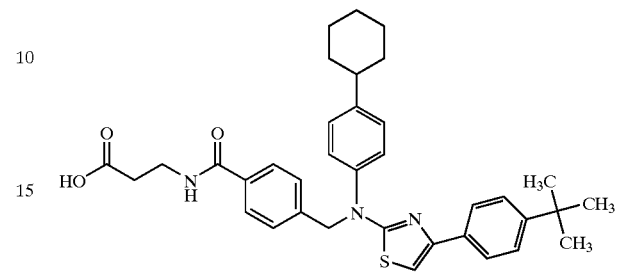

HPLC-MS (Method B): m/z: 596 (M+1); Rt=6.32 min.

Example 412

General Procedure (A)

3-(4-{[[4-(4-tert-Butylphenyl)thiazol-2-yl]-(4-cyclohex-1-enylphenyl)amino]methyl}benzoylamino)propionic acid

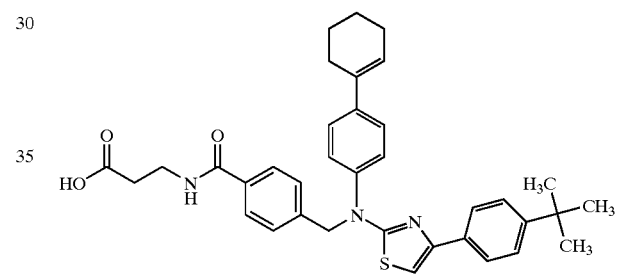

HPLC-MS (Method B): m/z: 594 (M+1); Rt=6.25 min.

Example 413

General Procedure (A)

3-(4-{[[4-(3,4-Dichlorophenyl)thiazol-2-yl]-(4-isopropyl-3-methylphenyl)amino]methyl}benzoylamino)propionic acid

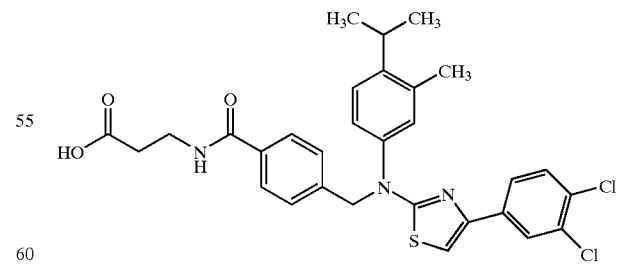

The cleaved residue was purified by preparative HPLC using acetonitrile (45% to 97.5%), water and TFA (2.5%) as eluent and evaporated yielding 0.03 g of the title compound.

$^1$H NMR (DMSO-d$_6$) selected data: δ 8.46 (t, 1H), 8.05 (m, 1H), 7.86–7.70 (m, 3H), 7.60 (d, 1H), 7.44 (d, 2H); 7.39

(s, 1H), 7.27 (m, 3H), 5.28 (s, 2H), 3.06 (m, 1H), 2.29 (s, 3H), 1.18 (d, 3H), 1.16 (d, 3H); HPLC-MS (Method A): m/z=582 (M+1); $R_t$=6.90 min.

Example 414

General Procedure (A)

3-[4-({(4-isopropyl-3-methylphenyl)-[4-(4-pentylphenyl)thiazol-2-yl]amino}methyl)benzoylamino]propionic acid

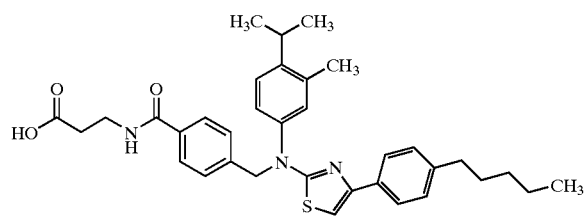

The cleaved residue was purified by preparative HPLC using acetonitrile (55% to 97.5%), water and TFA (2.5%) as eluent and evaporated yielding 0.10 g of the title compound.

$^1$H NMR (DMSO-$d_6$) selected data: δ 8.46 (t, 1H), 7.79–7.69 (dd, 4H), 7.43 (d, 2H), 7.30–7.16 (m, 5H), 7.08 (s, 1H); 5.28 (s, 2H), 3.42 (q, 2H), 3.10 (m, 1H), 2.56 (m, 2H), 2.29 (s, 3H), 1.59 (m, 2H), 1.30 (m, 4H), 1.18 (d, 3H), 1.16 (d, 3H), 0.86 (t, 3H); HPLC-MS (Method A): m/z=584 (M+1); $R_t$=7.47 min.

Example 415

General Procedure (A)

3-(4-{[[4-(4-Chlorophenyl)thiazol-2-y]-(4-isopropyl-3-methylphenyl)amino]methyl}benzoylamino)propionic acid

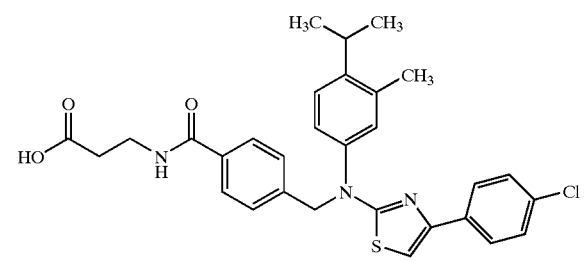

The cleaved residue was purified by preparative HPLC using acetonitrile (45% to 97.5%), water and TFA (2.5%) as eluent and evaporated yielding 0.07 g of the title compound.

$^1$H NMR (DMSO-$d_6$) selected data: δ 8.45 (t, 1H), 7.88–7.72 (dd, 4H), 7.43 (dd, 4H), 7.27 (m, 3H), 7.23 (s, 1H); 5.28 (s, 2H), 3.06 (m, 1H), 2.29 (s, 3H), 1.18 (d, 3H), 1.16 (d, 3H); HPLC-MS (Method A): m/z=548 (M+1); $R_t$=6.50 min.

Example 416

General Procedure (A)

3-(4-{[[4-(3,4-Difluorophenyl)thiazol-2-yl](4-isopropyl-3-methylphenyl)amino]methyl}benzoylamino)propionic acid

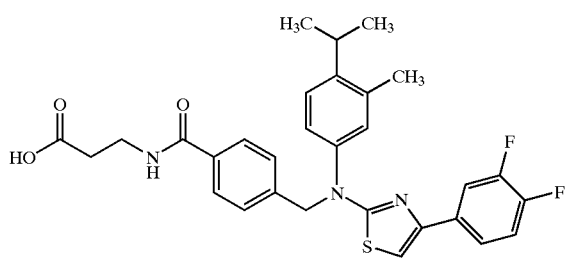

The cleaved residue was purified by preparative HPLC using acetonitrile (42% to 97.5%), water and TFA (2.5%) as eluent and evaporated yielding 0.05 g of the title compound.

$^1$H NMR (DMSO-$d_6$) selected data: δ 8.45 (t, 1H), 7.87 (m, 2H), 7.76 (dd, 2H), 7.69 (m, 1H), 7.44 (dd, 3H); 7.27 (m, 4H), 5.28 (s, 2H), 3.08 (m, 1H), 2.29 (s, 3H), 1.18 (d, 3H), 1.16 (d, 3H); HPLC-MS (Method A): m/z=550 (M+1); $R_t$=6.43 min.

Example 417

General Procedure (A)

3-[4-({(4-Isopropyl-3-methylphenyl)-[4-(4-trifluoromethylphenyl)thiazol-2-yl]amino}methyl)benzoylamino]propionic acid

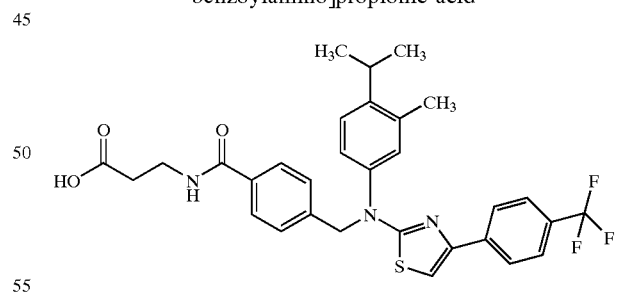

The cleaved residue was purified by preparative HPLC using acetonitrile (45% to 97.5%), water and TFA (2.5%) as eluent and evaporated yielding 0.08 g of the title compound.

$^1$H NMR (DMSO-$d_6$) selected data: δ 12.17 (broad, 1H), 8.45 (t, 1H), 8.05 (dd, 2H), 7.75 (m, 4H), 7.46 (dd, 2H), 7.41 (s, 1H), 7.28 (m, 3H), 5.30 (s, 2H), 3.42 (m, 2H), 3.09 (m, 1H), 2.29 (s, 3H), 1.18 (d, 3H), 1.17 (d, 3H); HPLC-MS (Method A): m/z=582 (M+1); $R_t$=6.77 min.

Example 418

General Procedure (A)

3-(4-{[[4-(3,5-Bis-trifluoromethylphenyl)thiazol-2-yl]-(4-isopropyl-3-methylphenyl)amino]methyl}benzoylamino)propionic acid

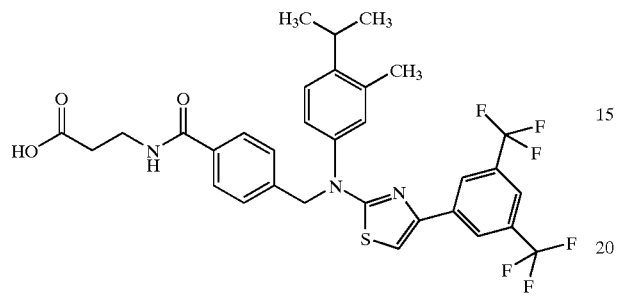

The cleaved residue was purified by preparative HPLC using acetonitrile (53% to 97.5%), water and TFA (2.5%) as eluent and evaporated yielding 0.09 g of the title compound.

$^1$H NMR (DMSO-$d_6$) selected data: δ 12.22 (broad, 1H), 8.46 (m, 3H), 8.00 (t, 1H), 7.77 (dd, 2H), 7.72 (s, 1H), 7.45 (dd, 2H), 7.35–7.26 (m, 3H), 5.28 (s, 2H), 3.42 (m, 2H), 3.08 (m, 1H), 2.30 (s, 3H), 1.19 (d, 3H), 1.17 (d, 3H); HPLC-MS (Method A): m/z=650 (M+1); $R_t$=7.17 min.

Example 419

General Procedure (A)

3-(4-{[[4-(4-Pentylphenyl)thiazol-2-yl]-(5,6,7,8-tetrahydronaphthalen-2-yl)amino]methyl}benzoylamino)propionic acid

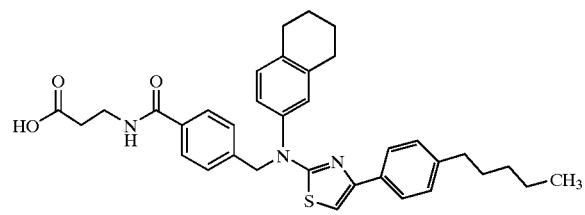

The cleaved residue was purified by preparative HPLC using acetonitrile (54% to 97.5%), water and TFA (2.5%) as eluent and evaporated yielding 0.15 g of the title compound.

$^1$H NMR (DMSO-$d_6$) selected data: δ 8.47 (t, 1H), 7.75 (m, 4H), 7.43 (dd, 2H), 7.22–7.09 (m, 5H); 7.08 (s, 1H), 5.27 (s, 2H), 3.43 (m, 2H), 2.70.(m, 4H), 2.56 (m, 2H), 1.72 (m, 4H), 1.57 (m, 2H), 1.28 (m, 4H), 0.86 (t, 3H); HPLC-MS (Method A): m/z=582 (M+1); $R_t$=7.47 min.

Example 420

General Procedure (A)

3-(4-{[[4-(3,4-Difluorophenyl)thiazol-2-yl]-(5,6,7,8-tetrahydronaphthalen-2-yl)amino]methyl}benzoylamino)propionic acid

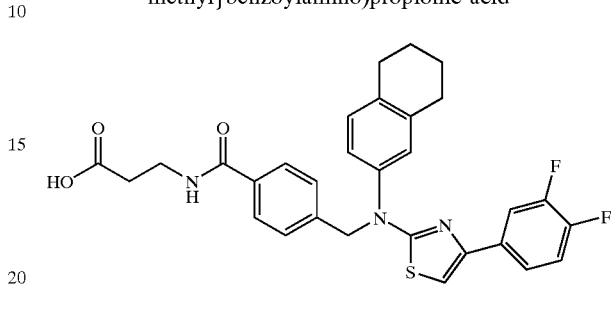

The cleaved residue was purified by preparative HPLC using acetonitrile (41% to 97.5%), water and TFA (2.5%) as eluent and evaporated yielding 0.16 g of the title compound.

$^1$H NMR (DMSO-$d_6$) selected data: δ 8.45 (t, 1H), 7.86 (m, 1H), 7.76 (dd, 2H), 7.68 (m, 1H); 7.43 (m, 3H), 7.26 (s, 1H), 7.19–7.06 (m, 3H), 5.27 (s, 2H), 3.42 (m, 2H), 2.69 (m, 4H), 1.72 (m, 4H); HPLC-MS (Method A): m/z=548 (M+1); $R_t$=6.37 min.

Example 421

General Procedure (A)

3-[4-({(5,6,7,8-Tetrahydronaphthalen-2-yl)-[4-(4-trifluoromethoxyphenyl)thiazol-2-yl]amino}methyl)benzoylamino]propionic acid

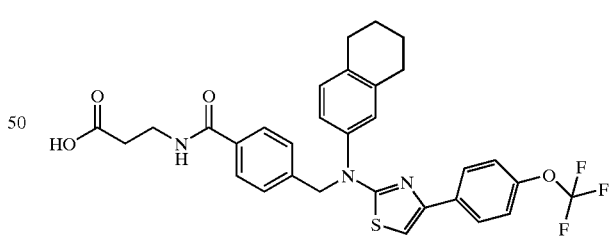

The cleaved residue was purified by preparative HPLC using acetonitrile (45% to 97.5%), water and TFA (2.5%) as eluent and evaporated yielding 0.17 g of the title compound.

$^1$H NMR (DMSO-$d_6$) selected data: δ 8.45 (t, 1H), 7.96 (dd, 2H), 7.76 (dd, 2H), 7.43 (dd, 2H), 7.36 (dd, 2H); 7.25 (s, 1H), 7.20–7.08 (m, 3H), 5.27 (s, 2H), 3.43 (m, 2H), 2.70 (m, 4H), 1.72 (m, 4H); HPLC-MS (Method A): m/z=596 (M+1); $R_t$=6.73 min.

Example 422

General Procedure (A)

3-[4-({(5,6,7,8-Tetrahydronaphthalen-2-yl)-[4-(4-trifluoromethylphenyl)thiazol-2-yl]amino}methyl)benzoylamino]propionic acid

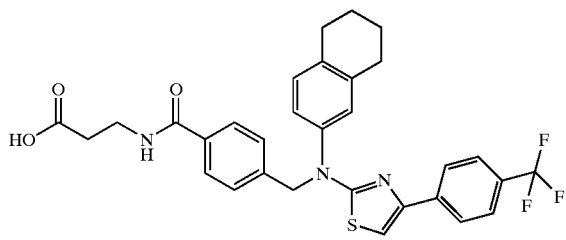

The cleaved residue was purified by preparative HPLC using acetonitrile (45% to 97.5%), water and TFA (2.5%) as eluent and evaporated yielding 0.17 g of the title compound.

$^1$H NMR (DMSO-d$_6$) selected data: δ 8.45 (t, 1H), 8.06 (dd, 2H), 7.75 (m, 4H), 7.45 (dd, 2H), 7.41 (s, 1H), 7.20–7.09 (m, 3H), 5.29 (s, 2H), 3.42 (m, 2H), 2.70 (m, 4H), 1.72 (m, 4H); HPLC-MS (Method A): m/z=580 (M+1); R$_t$=6.67 min.

Example 423

General Procedure (A)

3-(4-{[[4-(3,5-Bis-trifluoromethylphenyl)thiazol-2-yl]-(5,6,7,8-tetrahydronaphthalen-2-yl)amino]methyl}benzoylamino)propionic acid

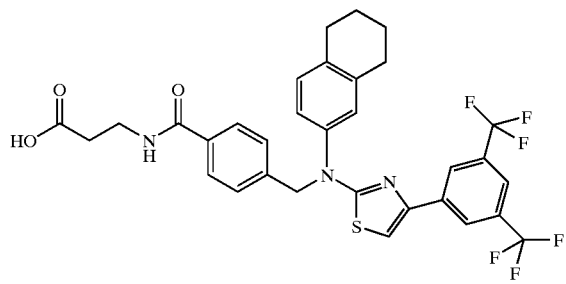

The cleaved residue was purified by preparative HPLC using acetonitrile (45% to 97.5%), water and TFA (2.5%) as eluent and evaporated yielding 0.19 g of the title compound.

$^1$H NMR (DMSO-d$_6$) selected data: δ 12.19 (broad, 1H), 8.46 (m, 3H), 7.99 (t, 1H), 7.76 (dd, 2H), 7.72 (s, 1H), 7.45 (dd, 2H), 7.10–7.23 (m, 3H), 5.28 (s, 2H), 3.42 (m, 2H), 2.71 (m, 4H), 1.73 (m, 4H); HPLC-MS (Method A): m/z=648 (M+1); R$_t$ 7.10 min.

Example 424

General Procedure (A)

3-(4-{[[4-(3,4-Dichlorophenyl)thiazol-2-yl]-(5,6,7,8-tetrahydronaphthalen-2-yl)amino]methyl}benzoylamino)propionic acid

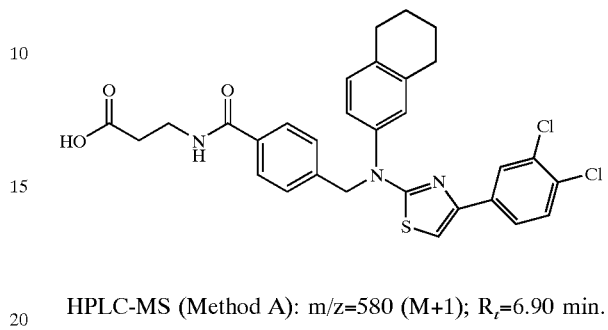

HPLC-MS (Method A): m/z=580 (M+1); R$_t$=6.90 min.

Example 425

General Procedure (A)

3-[4-({Indan-5-yl-[4-(2,2,3,3-tetrafluoro-2,3-dihydro-benzo[1,4]dioxin-6-yl)-thiazol-2-yl]amino}-methyl)benzoylamino]-propionic acid

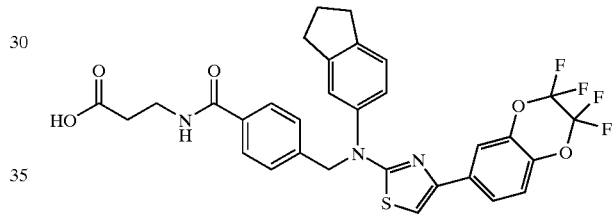

$^1$H NMR (DMSO-d$_6$): δ=8.48 (t, 1H), 7.90 (d, 1H), 7.83 (dd, 1H), 7.76 (d, 2H), 7.50 (d, 1H), 7.42 (d, 2H), 7.33 (s, 2H), 7.27 (d, 1H), 7.15 (dd, 1H), 5.30 (s, 2H), 3.43 (q, 2H); 2.87 (t, 4H), 2.03 (m, 2H), HPLC-MS (Method B): m/z=628 (M+1); R$_t$=5.69 min.

Preparation of the Intermediate, 2-Bromo-1-(2,2,3,3-tetrafluoro-2,3-dihydrobenzo[1,4]dioxin-6-yl)ethanone:

All equipment was dried at 120° C. for some hours in an oven.

Under an atmosphere of nitrogen in a dried three-necked 500 mL round bottom flask equipped with a separatory funnel and a condenser was added magnesium chips (7.31 g, 0.30 mol) and diethyl ether (20 mL). With magnetic stirring, iodomethane (4.7 mL, 75 mmol) was added dropwise to the Mg and the reaction was commenced. Iodomethane (14 mL, 0.22 mol) in diethyl ether (30 mL) was added slowly while maintaining reflux. After finished addition the mixture was stirred for 1½ hour. 6-Cyano-2,2,3,3-tetrafluoro-1,4-benzodioxene (35 g, 0.15 mol) was dissolved in toluene (60 mL) and added to the reaction mixture. The mixture was heated to 80° C. for 1 hour without condenser to remove the diethyl ether. Additional 6-cyano-2,2,3,3-tetrafluoro-1,4-benzodioxene (25 g, 0.11 mol) was added and the mixture was heated at reflux temperature for 16 hours. The mixture was cooled with an ice bath and hydrochloric acid (6 M, 150 mL) was added carefully and the mixture was then heated to reflux for 1.5 hour. After cooling, the mixture was partitioned between ethyl acetate and water, and washed with aqueous sodium hydrogen carbonate. The combined organic phases were dried (magnesium sulphate) and concentrated in vacuo. The residual oil was purified by chromatography on silica gel eluting with a mixture of ethyl acetate and heptane (2:8). This afforded 1-(2,2,3,3-Tetrafluoro-2,3-dihydrobenzo[1,4]dioxin-6-yl)ethanone (22 g, 34%).

$^1$H NMR (CDCl$_3$): δ=7.80 (dd, 1H), 7.77 (d, 1H), 7.23 (d, 1H), 2.69 (s, 3H); HPLC-MS (Method A): m/z=251 (M+1); Rt=4.27 min.

1-(2,2,3,3-Tetrafluoro-2,3-dihydrobenzo[1,4]dioxin-6-yl)ethanone (1.50 g, 6 mmol) was dissolved in THF (30 mL). CuBr$_2$ (2.68 g, 12.0 mmol) was added and the suspension was stirred under nitrogen overnigth at room temperature. The suspension was filtered through celite and evaporated in vacuo to afford 2-bromo-1-(2,2,3,3-tetrafluoro-2,3-[1,4]dioxin-6-yl)ethanone as an oil which was used without further purification or characterisation.

Example 426

General Procedure (A)

3-[4-({Indan-5-yl-[4-(4-trifluoromethylsulfanylphenyl)thiazol-2-yl]amino}methyl)benzoylamino]propionic acid

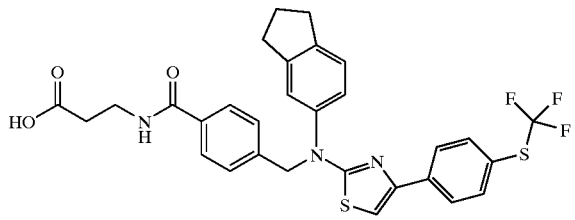

$^1$H NMR (CDCl$_3$): δ=7.66 (d, 4H), 7.55 (d, 2H), 7.45 (t, 1H), 7.35–25 (m, 3H), 7.10 (s, 1H), 6.95 (dd, 1H), 6.88 (s, 1H), 5.27 (s, 2H), 3.70 (q, 2H); 2.92 (q, 4H), 2.70 (t, 2H), 2.12 (m, 2H), HPLC-MS (Method B): m/z=598 (M+1); R$_t$=5.60 min.

Preparation of the Intermediate, 2-bromo-1-(4-trifluoromethylsulfanylphenyl)ethanone:

4-(Trifluoromethylthio)acetophenone (5 g, 22.7 mmol) was dissolved in THF (100 mL). CuBr$_2$ (10.1 g, 45.4 mmol) was added and the suspension was stirred under nitrogen overnigth at room temperature. The suspension was filtered through celite and evaporated to an oil which was purified by silicagel column purification using ethylacetate/heptane (2:8) as eluent to give 2.1 g of 2-bromo-1-(4-trifluoromethylsulfanylphenyl)ethanone.

$^1$H NMR (CDCl$_3$): δ=8.02 (d, 2H), 7.78 (d, 2H), 4.44 (s, 2H), HPLC-MS (Method B): m/z=299 (M+1); Rt=4.46 min.

Example 427

General Procedure (A)

3-[4-({(5,6,7,8-Tetrahydronaphthalen-2-yl)-[4-(4-trifluoromethylsulfanylphenyl)thiazol-2-yl]amino}methyl)benzoylamino]propionic acid

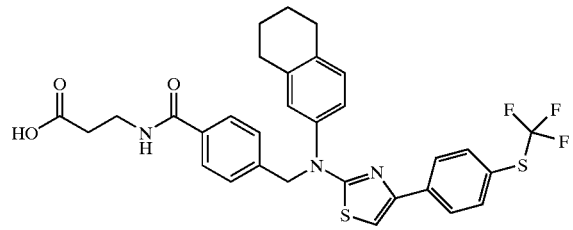

$^1$H NMR (CDCl$_3$): δ=7.69 (dd, 4H), 7.54 (d, 2H), 7.42 (t, 1H), 7.35 (d, 2H), 7.16 (d, 1H), 6.99 (s, 1H), 6.92 (dd, 1H), 6.68 (s, 1H), 5.27 (s, 2H), 3.70 (q, 2H); 2.72 (m, 6H), 1.80 (br s, 4H),

HPLC-MS (Method B): m/z=612 (M+1); R$_t$=5.81 min.

Example 428

General Procedure (A)

3-[4-({(4-Cyclohexylphenyl)-[4-(4-trifluoromethylsulfanylphenyl)thiazol-2-yl]amino}methyl)benzoylamino]propionic acid

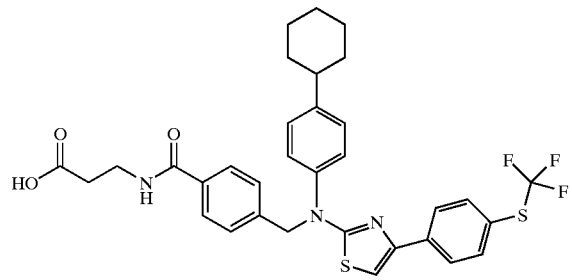

$^1$H NMR (CDCl$_3$): δ=7.70 (dd, 4H), 7.56 (d, 2H), 7.42 (t, 1H), 7.32 (d, 4H), 7.18 (d, 2H), 6.68 (s, 1H), 5.31 (s, 2H), 3.70 (q, 2H); 2.74 (t, 2H), 2.54 (m, 1H), 1.95–1.70 (m, 5H), 1.50–1.15 (m, 5H), HPLC-MS (Method B): m/z=640 (M+1); R$_t$=6.24 min.

General Procedure (B)

General procedure (B) may be used for solution phase preparation of compounds of general formula (I$_b$), (I$_c$) and (I$_d$):

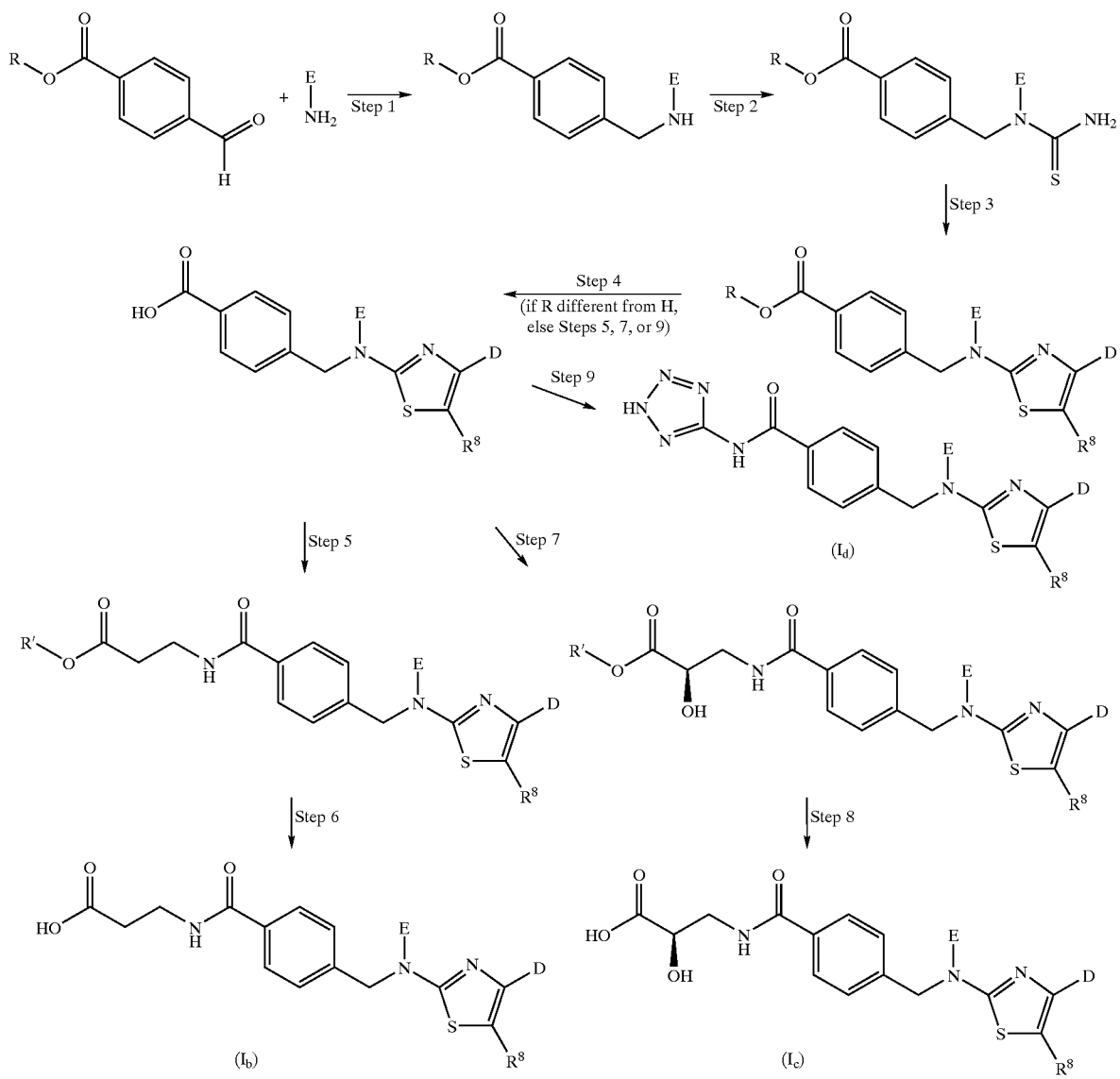

wherein

R and R' independently are hydrogen or $C_{1-6}$-alkyl, $R^8$ is as defined above, and E and D independently are aryl or heteroaryl and are both optionally substituted as defined above.

Step 2 is a formation of a thiourea from a secondary amine. This is a known reaction and can be done in a one- or in a two-step procedure. In the one-step procedure the amine (the product from step 1) is heated with potassium (or sodium or mmonium) thiocyanate in hydrochloric acid (see eg K. Nagarajan et al., *Indian J. Chem.*, 24B, 840–4 (1985)). Alternatively, the amine as the hydrochloride salt is heated in an anhydrous solvent with potassium (or sodium) thiocyanate (see eg Fernandes L. & Ganapathi K., *Proc. Indian Acad. Sci.*, Sect. A., 33, 364–367 (1951)).

The two-step procedure is first a reaction with a synthetic equivalent of H-NCS, eg acyl-isothiocyanates as ethoxycarbonyl-acetyl-, or benzoylisothiocyanates followed by hydrolysis of the acyl moiety (see eg H. Hartmann & I Reuther, *J. Prakt. Chem.*, 315 (1), 144–8 (1973), B. Stanovik & M. Tisler, *Monatsh. Chem.*, 104, 1034–9 (1973), Douglass & Dains, *J. Am Chem. Soc.*, 56, 1408–9 (1934) and Durant et al., *J. Med. Chem.*, 9, 22–27 (1966)).

Step 3 is formation of an aminothiazole from the 1,1-disubstituted thiourea obtained in step 2 by reaction with α-bromo (or chloro) ketones. This reaction is well known (see eg Zhang, M. Q. et al, *J. Heterocycl. Chem.*, 28, 673–683 (1991) & Birkinshaw T, et al., *J. Chem. Soc., Perkin Trans.* 1, 2, 147–153 (1984)) and is normally performed at ambient temperature or at elevated temperature, up to the temperature of the boiling point of the solvent(s). The solvent can be one (or a mixture of two or more) of the following: dioxane, THF, DCM, 1,2-di-chloropropane, acetonitrile, acetone, ethanol, methanol, DMF, N-methylpyrrolidone, DMSO, toluene and ethyl acetate. The reaction can optionally be performed in the presence of a base, such as triethylamine (see eg Phred B. et al., *J. Heterocycl. Chem.* 24, 1509–1520 (1987)) or in the presence of an acid such as acetic acid.

If the product from step 3 is a benzoic acid ester, then the ester is hydrolysed (step 4). This step is similar to similar transformations described in 00/69810.

Steps 5 & 6 are coupling of the benzoic acid with a β-alanine ester followed by hydrolysis of the ester. These steps are similar to similar transformations described in WO 00/69810.

Steps 7 & 8 are coupling of the benzoic acid with an (R)-isoserine ester followed by hydrolysis of the ester. These steps are similar to similar transformations described in WO 00/69810.

Step 9 is coupling of the benzoic acid with 5-aminotetrazole hydrate. This step is similar to similar transformations described in WO 00/69810.

This general procedure (B) is further illustrated in the following examples:

Example 429

General Procedure (B). Alternative Mode of Preparation of the Compound of Example 366

3-[4-({(4-Chlorophenyl)-[4-(4-trifluoromethoxyphenyl)thiazol-2-yl]amino}methyl)benzoylamino]propionic acid

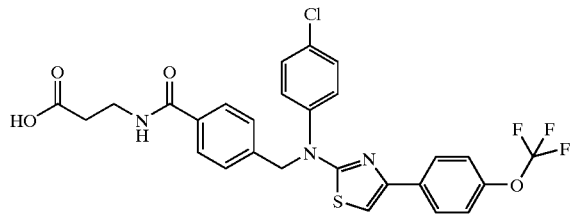

Step 1, 4-[(4-Chlorophenylamino)methyl]benzoic acid:

4-Formylbenzoic acid (15 g, 100 mmol) was suspended in methanol (500 mL) and 4-chloroaniline (12.7 g, 100 mmol) was added. The resulting suspension was heated at reflux temperature for 30 minutes and subsequently cooled to approximately 35° C. Acetic cid glacial (50 mL) was added followed by sodium cyanoborohydride (4.96 g, 80 mmol) in portions. The mixture was stirred at room temperature for 30 minutes. The mixture was concentrated in vacuo to approximately 150 mL by rotary evaporation. Water (150 mL) was added and the resulting suspension was stirred at room temperature for 16 hours. Filtration, washing with water and drying afforded 26.8 g (100%) 4-[(4-chlorophenylamino)methyl]benzoic acid as a solid.

$^1$H NMR (DMSO-d$_6$): δ=4.31 (2H, d), 6.54 (4H, "d"), 7.05 (2H, d), 7.45 (2H, d), 7.89 (2H, d), 12.8 (1H, bs). HPLC-MS (Method B): m/z=262 (M+1); Rt=3.62 min.

Step 2, 4-[1-(4-Chlorophenyl)thioureidomethyl]benzoic acid:

A mixture of 4-[(4-chlorophenylamino)methyl]benzoic acid (33.3 g, 127 mmol) and potassium thiocyanate (37 g, 382 mmol) in 1 N hydrochloric acid (500 mL) was refluxed for 16 hours. The suspension was filtered and washed with water. The solid was mixed with potassium thiocyanate (37 g, 382 mmol) and 1 N hydrochloric acid (500 mL) and the mixture was again refluxed for 16 hours. Filtration, washing with water and re-submission to the reaction conditions above afforded 30.2 g (70%) of 4-[1-(4-chlorophenyl)thioureidomethyl]benzoic acid as a solid.

HPLC-MS (Method B): m/z: 321 (M+1); Rt:=2.99 min. $^1$H NMR (DMSO-d$_6$): δ=5.44 (2H, s), 7.14 (2H, d), 7.39 (4H, "t"), 7.85 (2H, d), 12.9 (1H, bs).

Step 3, 4-({(4-chlorophenyl)-[4-(4-trifluoromethoxyphenyl)thiazol-2-yl]amino}methyl)benzoic acid:

4-[1-(4-Chlorophenyl)thioureidomethyl]benzoic acid (29 g, 88.8 mmol) was dissolved in DMF (300 mL) and acetic acid (40 mL) and 2'-bromo-4-trifluoromethoxyacetophenoe (25.1 g, 88.8 mmol) were added and the resulting mixture was stirred at room temperature for 16 hours. Ethyl acetate (500 mL) was added and the mixture was washed with water (2×500 mL), saturated aqueous sodium chloride (500 mL) and saturated aqueous ammonium chloride (500 mL). Drying (MgSO$_4$) and concentration in vacuo afforded 48 g (quant.) of 4-({(4-chlorophenyl)-[4-(4-trifluoromethoxyphenyl)thiazol-2-yl]amino}methyl)benzoic acid as an oil.

HPLC-MS (Method B): m/z: 505 (M+1); Rt:=5.59 min. $^1$H NMR (DMSO-d$_6$): δ=5.35 (2H, s), 7.36 (1H, s), 7.39 (2H, d), 7.47–7.57 (6H, m), 7.90 (2H, d), 7.97 (2H, d), 12.7 (1H, bs).

Step 4, Not Relevant

Step 5, 3-[4-({(4-Chlorophenyl)-[4-(4-trifluoromethoxyphenyl)thiazol-2-yl]amino}methyl)benzoylamino]propionic acid methyl ester:

4-({(4-Chlorophenyl)-[4-(4-trifluoromethoxyphenyl)thiazol-2-yl]amino}methyl)benzoic acid (47 g, 93 mmol) was dissolved in DMF (500 mL) and 1-hydoxybenzotriazole (18.9 g, 140 mmol) and 1-ethyl-3-(3-dimethylaminopropyl)carbodiimide hydrochloride (26.7 g, 140 mmol) were added and the mixture was stirred at room temperature for 1.5 hours. Di PEA (i 9.1 mL, 111 mmol) and 3-aminopropionic acid methyl ester hydrochloride (15.5 g, 111 mmol) were added to the mixture and the resulting mixture was stirred at room temperature for 16 hours. Ethyl acetate (500 mL) was added and the mixture was washed with water (500 mL). The aqueous phase was extracted with ethyl acetate (500 mL). The combined organic phases were washed with water (2×500 mL) and saturated aqueous ammonium chloride (2×300 mL), dried (Na$_2$SO$_4$) and concentrated in vacuo to afford 60 g (quant.) of crude 3-[4-({(4-chlorophenyl)-[4-(4-trifluoromethoxyphenyl)thiazol-2-yl]amino}methyl)benzoylamino]propionic acid methyl ester as a solid. Recrystallisation from ethanol afforded 31.2 g (55%) pure product.

HPLC-MS (Method B): m/z: 590 (M+1); Rt:=5.50 min.

Step 6: 3-[4-({(4-Chlorophenyl)-[4-(4-trifluoromethoxyphenyl)thiazol-2-yl]amino}methyl)benzoylamino]propionic acid:

3-[4-({(4-Chlorophenyl)-[4-(4-trifluoromethoxyphenyl)thiazol-2-yl]amino}methyl)benzoylamino]propionic acid methyl ester (18.7 g, 31.7 mmol) was dissolved in ethanol (500 mL) and 1 N sodium hydroxide (63 mL, 63 mmol) was added. The resulting mixture was stirred at room temperature for 16 hours. The mixture was filtered, washed with ethanol and dried in vacuo at 40° C. for 16 hours to afford 8.0 g (42%) of the title compound as the sodium salt.

HPLC-MS (Method B): m/z: 576 (M+1); Rt:=5.12 min. $^1$H NMR (DMSO-d$_6$): δ=2.13 (2H, t), 3.37 (m, below water), 5.31 (2H, s), 7.34–7.39 (5H, m), 7.50 (4H, m), 7.74 (2H, d), 7.97 (2H, d), 8.78 (1H, bs).

The above filtrate was added 1 N hydrochloric acid (80 mL) and water (200 mL) and the mixture was extracted with ethyl acetate (300 mL). The organic phase was washed with water (300 mL), dried and concentrated in vacuo to afford 6.63 g (36%) of the title compound as a solid.

HPLC-MS (Method B): m/z: 576 (M+1); Rt:=5.13 min. $^1$H NMR (DMSO-d$_6$): δ=2.47 (m, below DMSO), 3.43 (2H, q), 5.32 (2H, s), 7.36 (1H, s), 7.41 (4H, "t"), 7.39 (5H, m), 7.51 (4H, m), 7.76 (2H, d), 7.97 (2H, d), 8.48 (1H, t), 12.2 (1H, bs).

Microanalyis: Calculated for C$_{27}$H$_{21}$N$_3$Cl$_1$F$_3$O$_4$S$_1$: C: 56,30%, H: 3,67%, N: 7,30%. Found: C: 56,08%, H: 3,81%, N: 7,25%.

Example 430

General Procedure (B)

3-[4-({(4-Chlorophenyl)-[4-(4-chlorophenyl)thiazol-2-yl]amino}methyl)benzoylamino]propionic acid

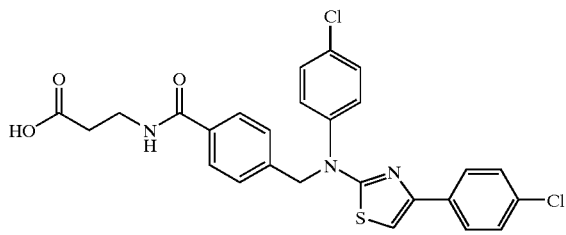

HPLC-MS (Method B): m/z: 526 (M+1); Rt=4.90 min. $^1$H NMR (CDCl$_3$): δ=2.70 (2H, t), 3.71 (2H, q), 5.25 (2H, s), 6.71 (1H, s), 6.77 (1H, t), 7.24 (2H, d), 7.31 (4H, m), 7.41 (2H, d), 7.68 (2H, d), 7.75 (2H, d).

Example 431

General Procedure (B)

4-({(4-Chlorophenyl)-[4-(4-chlorophenyl)thiazol-2-yl]amino}methyl)-N-(2H-tetrazol-5-yl)benzamide

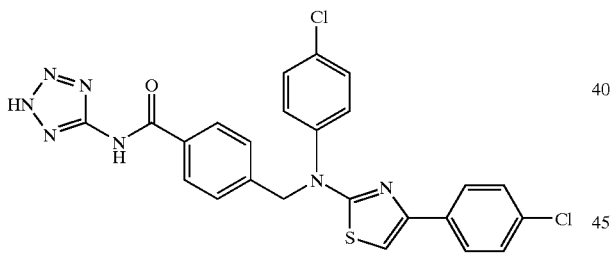

Step 9:

4-({(4-Chlorophenyl)-[4-(4-chlorophenyl)thiazol-2-yl]amino}methyl)benzoic acid (0.15 g, 0.33 mmol) was dissolved in DMF (5 mL) and 1-hydroxybenzotriazol (49 mg, 0.36 mmol), 1-ethyl-3-(3-dimethylaminopropyl)carbodiimide hydrochloride (69 mg, 0.36 mmol), and triethylamine (51 μL, 0.36 mmol) were added and the resulting mixture was stirred at room temperature for 15 minutes. 5-Aminotetrazole hydrate (34 mg, 0.33 mmol) was added and the resulting mixture was stirred at room temperature for 16 hours. Water was added and the mixture was stirred at room temperature for 1 hour and filtered. Washing with water and drying in vacuo afforded 145 mg (84%) of the title compound as a solid.

HPLC-MS (Method B): m/z: 522 (M+1); Rt:=5.04 min. $^1$H NMR (DMSO-d$_6$): δ=5.37 (2H, s), 7.36 (1H, s); 7.44–7.59 (8H, m), 7.87 (2H, d), 8.03 (2H, d), 12.2 (1H, s).

Example 432

General Procedure (B)

4-({(4-Chlorophenyl)-[4-(4-trifluoromethoxyphenyl)thiazol-2-yl]amino}methyl)-N-(2H-tetrazol-5-yl)benzamide

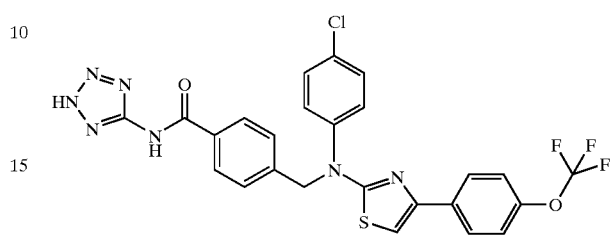

HPLC-MS (Method B): m/z: 572 (M+1); Rt=5.31 min.

Example 433

General Procedure (B)

4-({Indan-5-yl-[4-(4-trifluoromethoxyphenyl)-thiazol-2-yl]amino}methyl)-N-(2H-tetrazol-5-yl)benzamide

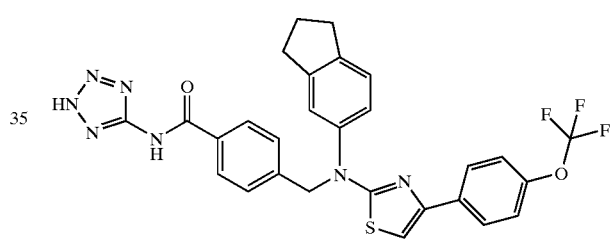

HPLC-MS (Method B): m/z: 578 (M+1); Rt=5.46 min.

Example 434

General Procedure (B)

4-({Indan-5-yl-[4-(4-trifluoromethylphenyl)thiazol-2-yl]amino}methyl)-N-(2H-tetrazol-5-yl)benzamide

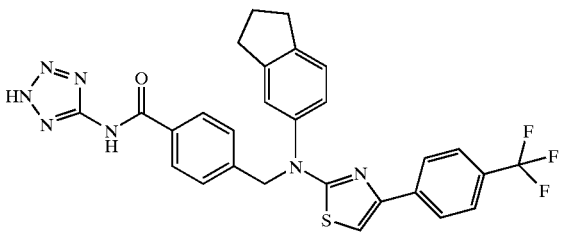

HPLC-MS (Method B): m/z: 562 (M+1); Rt=5.39 min. $^1$H NMR (DMSO-d$_6$): δ=5.35 (2H, s), 7.23 (1H, dd), 7.28 (1H, d), 7.36 (1H, bs), 7.42 (1H, s), 7.56 (H, d), 7.74 (2H, d), 8.05 (4H, "t").

Example 435

General Procedure (B)

2(R)-Hydroxy-3-[4-({indan-5-yl-[4-(4-trifluoromethoxyphenyl)thiazol-2-yl]amino}methyl)benzoylamino]propionic acid

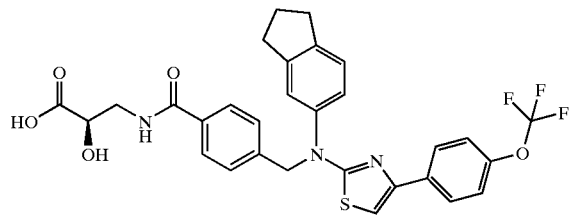

Step 7, 2(R)-Hydroxy-3-[4-({indan-5-yl-[4-(4-trifluoromethoxyphenyl)thiazol-2-yl]amino}methyl)benzoylamino]propionic acid methyl ester:

4-({Indan-5-yl-[4-(4-trifluoromethoxyphenyl)thiazol-2-yl]amino}methyl)benzoic acid (0.44 g, 0.86 mmol) was dissolved in DMF (10 mL) and 1-hydroxybenzotriazole (0.18 g, 1.29 mmol) and 1-ethyl-3-(3-dimethylaminopropyl)carbodiimide hydrochloride (0.25 g, 1.29 mmol) were added and the resulting mixture was stirred at room temperature for 1.5 hours. 3-Amino-2(R)-hydroxypropionic acid methyl ester hydrochloride, (R-isoserine methyl ester hydrochloride), prepared as described in WO 02/00612, (0.16 g, 1.03 mmol) and DIPEA (225 µL, 1.29 mmol) were added and the resulting mixture was stirred at room temperature for 16 hours. Ethyl acetate (100 mL) was added and the mixture was washed with water (2×80 mL). The organic phase was dried (MgSO$_4$) and concentrated in vacuo. The residue (0.35 g) was purified by column chromatography on silica gel eluting with a mixture of ethyl acetate and heptane (1:1). This afforded 0.10 g (19%) of 2(R)-Hydroxy-3-[4-({indan-5-yl-[4-(4-trifluoromethoxyphenyl)thiazol-2-yl]amino}methyl)benzoylamino]propionic acid methyl ester.

$^1$H NMR (CDCl$_3$): δ=2.10 (2H, p), 2.90 (4H, m), 3.81 (5H, m), 4.39 (1H, bs), 5.26 (2H, s), 6.50 (1H, t), 6.66 (1H, t), 7.04 (1H, dd), 7.14 (1H, s), 7.21 (3H, "d"), 7.46 (2H, d), 7.69 (2H, d), 7.84 (2H, d).

Step 8, 2(R)-Hydroxy-3-[4-({indan-5-yl-[4-(4-trifluoromethoxyphenyl)thiazol-2-yl]amino}methyl)benzoylamino]propionic acid:

2(R)-Hydroxy-3-[4-({indan-5-yl-[4-(4-trifluoromethoxyphenyl)thiazol-2-yl]amino}methyl)benzoylamino]propionic acid methyl ester (0.10 g, 0.16 mmol) was dissolved in methanol (5 mL) and 1 N aqueous sodium hydroxide (0.16 mL, 0.16 mmol) was added and the resulting mixture was stirred at room temperature for 16 hours. 1 N hydrochloric acid (0.17 mL) and water (50 mL) were added and the mixture was extracted with ethyl acetate (50 mL). The organic phase was washed with water (50 mL), dried (MgSO4) and concentrated in vacuo. This afforded 0.06 g (61%) of the title compound.

$^1$H NMR (CDCl$_3$): δ=2.09 (2H, m), 2.88 (4H, m), 3.78 (1H, m), 3.87 (1H, m), 4.37 (1H, t), 5.24 (2H, s), 6.65 (1H, s), 7.00 (1H, t), 7.02 (1H, d), 7.13 (1H, s), 7.19 (3H, "d"), 7.45 (2H, d), 7.68 (2H, d), 7.82 (2H, d).

HPLC-MS (Method B): m/z: 598 (M+1); Rt=5.12 min.

Example 436

General Procedure (B)

2(R)-Hydroxy-3-[4-({indan-5-yl-[4-(4-trifluoromethylphenyl)thiazol-2-yl]amino}methyl)benzoylamino]propionic acid

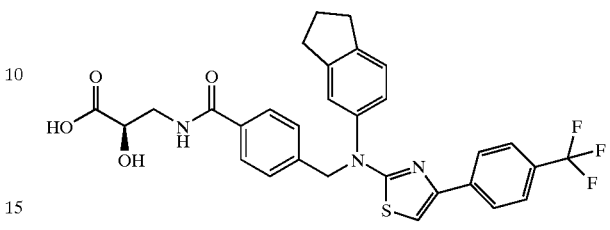

HPLC-MS (Method B): m/z: 582 (M+1); Rt=5.05 min.

In the following examples, details as to how step 2 has been carried out are given. The other steps are very similar to the corresponding steps given in the example above.

Example 437

General Procedure (B). Alternative Mode of Preparation of the Compound of Example 339

3-(4-{[[4-(4-Chlorophenyl)thiazol-2-yl]-(4-trifluoromethylphenyl)amino]methyl}benzoylamino)propionic acid

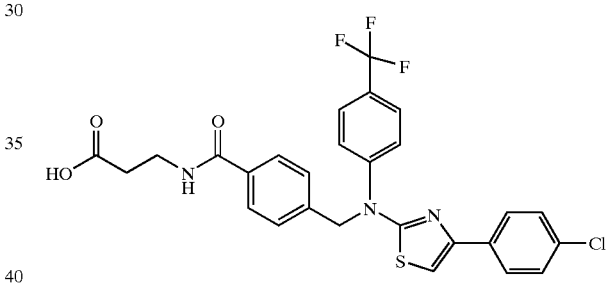

Step 2:

4-[(4-Trifluoromethylphenylamino)methyl]benzoic acid methyl ester (1.00 g; 3.23 mmol) was dissolved in DCM (10 mL), and Fmoc isothiocyanate (0.91 g; 3.23 mmol) was added. The resulting mixture was stirred at room temperature for 16 hours. The mixture was concentrated in vacuo, and the residue was purified by flash chromatography using DCM as eluent. This afforded 1.79 g (94%) of [(4-trifluoromethylphenyl)-(4-mehoxycarbonylbenzyl)thiocarbamoyl]carbamic acid 9H-fluoren-9-ylmethyl ester.

$^1$H NMR (CDCl$_3$): δ=3.88 ppm (s, 3H); 4.05 (t, 1H); 4.30 (d, 2H); 5.52 (s, 2H); 7.15–7.30 (m, 5H); 7.30–7.45 (m, 7H); 7.53 (d, 2H); 7.72 (d, 2H); 7.95 (d, 2H).

[(4-Trifluoromethylphenyl)-(4-mehoxycarbonylbenzyl)thiocarbamoyl]carbamic acid 9H-fluoren-9-ylmethyl ester (1.70 g; 2.87 mmol) was dissolved in a mixture of piperidine and DCM (1:4, 20 mL). The mixture was stirred at room temperature for 30 minutes and then evaporated to dryness in vacuo. The residue was purified by column chromatography eluting with dichloromethane, to give an oil, which was subsequently crystallised from ethyl acetate/heptane to afford 495 mg (46%) of 4-[1-(4-trifluoromethylphenyl)thioureidomethyl]benzoic acid methyl ester.

$^1$H NMR (CDCl$_3$): δ=3.88 ppm (s, 3H); 5.62 (s, 2H); 5.65 (bs, 2H); 7.20 (d, 2H); 7.40 (d, 2H); 7.65 (d, 2H); 7.96 (d, 2H).

Example 438

General Procedure (B)

3-[4-({(9H-Fluoren-2-yl)-[4-(4-trifluoromethoxyphenyl)thiazol-2-yl]amino}methyl)benzoylamino]propionic acid

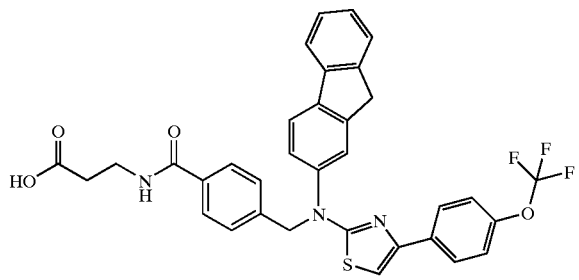

Step 2:

4-[(9H-Fluoren-2-ylamino)methyl]benzoic acid methyl ester (10 g, 30.36 mmol) was dissolved in dichloromethane (160 mL) and ethoxycarbonyl isothiocyanate (4.65 mL, 39.47 mmol) was added and the resulting mixture was stirred at room temperature for 16 hours. The mixture was concentrated in vacuo to afford 14 g (100%) of [(9H-fluoren-2-yl)-(4-mehoxycarbonylbenzyl)thiocarbamoyl]carbamic acid ethyl ester.

$^1$H NMR (DMSO-$d_6$): δ=10.18 (s, 1H), 7.90–7.80 (m, 4H), 7.56–7.50 (m, 3H), 7.42 (s, 1H), 7.38–7.30 (m, 3H), 7.17 (d, 1H), 5.64 (s, 2H), 3.88–3.80 (m, 5H), 0.92 (t, 3H); HPLC-MS (Method A): m/z=461 (M+1); Rt=5.26 min.

[(9H-Fluoren-2-yl)-(4-mehoxycarbonylbenzyl)thiocarbamoyl]carbamic acid ethyl ester (14 g, 30.36 mmol) was dissolved in warmethanol (96%, 160 mL) and the solution was added 4 N aqueous sodium hydroxide (76 mL, 304 mmol) and the resulting mixture was refluxed for 16 hours. The mixture was concentrated in vacuo to remove ethanol and the residue was suspended in water (150 mL) and carefully added 4 N hydrochloric acid (76 mL, 304 mmol). The suspension was stirred for ½ hour at 25° C. and filtered, washed with water and dried in vacuo at 40° C. for 16 hours to afford 11.4 g (100%) of 4-{[1-(9H-Fluoren-2-yl)thioureido]methyl)benzoic acid.

$^1$H NMR (DMSO-$d_6$): δ=12.88 (broad, 1H), 7.88–7.84 (m, 4H), 7.58 (d, 1H), 7.46–7.38 (m, 5H), 7.09 (d, 1H), 5.53 (s, 2H), 3.87 (s, 2H); HPLC-MS (Method A): m/z=375 (M+1); $R_t$=3.91 min.

Data for the title compound:

$^1$H NMR (DMSO-$d_6$): δ=8.47 (t, 1H), 8.02–7.87 (m, 4H), 7.77 (dd, 2H), 7.71 (s, 1H), 7.59 (d, 1H); 7.48 (m, 3H), 7.40 (m, 3H), 7.36 (d, 1H), 7.30 (s, 1H), 5.37 (s, 2H), 3.94 (s, 2H), 2.48 (m, 2H); HPLC-MS (Method A): m/z=630 (M+1); $R_t$=8.17 min.

Example 439

General Procedure (B). Alternative Mode of Preparation of the Compound of Example 259

3-[4-({(4-Trifluoromethoxyphenyl)-[4-(4-trifluoromethylphenyl)thiazol-2-yl]amino}methyl)benzoylamino]propionic acid

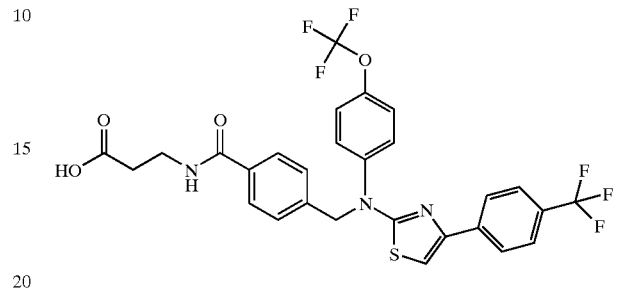

Step 2:

4-[(4-Trifluoromethoxyphenylamino)methyl]benzoic acid methyl ester (15 g, 46.11 mmol) was dissolved in dichloromethane (220 mL) and ethoxycarbonyl isothiocyanate (7.05 mL, 59.95 mmol) was added and the resulting mixture was stirred at room temperature for 16 hours. The mixture was concentrated in vacuo to afford 21 g (100%) of [(4-trifluoromethoxyphenyl)-(4-mehoxycarbonylbenzyl)thiocarbamoyl]carbamic acid ethyl ester.

$^1$H NMR (DMSO-$d_6$): δ=10.44 (s, 1H), 7.89 (dd, 2H), 7.51 (dd, 2H), 7.36–7.28 (m, 4H), 5.61 (s, 2H); 3.88–3.80 (m, 5H), 0.91 (t, 3H); HPLC-MS (Method A): m/z=457 (M+1); Rt=4.95 min.

[(4-Trifluoromethoxyphenyl)-(4-mehoxycarbonylbenzyl)thiocarbamoyl]carbamic acid ethyl ester (21 g, 46.11 mmol) was dissolved in warm ethanol (96%, 250 mL) and added 4 N aqueous sodium hydroxide (115 mL, 460 mmol). The resulting mixture was refluxed for 16 hours. After cooling, the mixture was evaporated in vacuo to remove ethanol and the residue was suspended in water (400 mL) and carefully added 4 N hydrochloric acid (115 mL, 460 mmol). The water was decanted from the oil and the residual oil was dissolved in dichloromethane, dried over MgSO$_4$ and evaporated. The amorphous residue was partly dissolved in ethyl acetate, filtered and evaporated to afford 17 g (100%) of 4-[1-(4-trifluoromethoxyphenyl)thioureidomethyl]benzoic acid.

HPLC-MS (Method A): m/z=371 (M+1); Rt=3.58 min.

Data for the title compound:

M.p.: 103–105° C.

$^1$H NMR (DMSO-$d_6$): δ=12.22 (broad, 1H), 8.48 (t, 1H), 8.07 (d, 2H), 7.77 (dd, 4H), 7.65 (d, 2H), 7.52 (s, 1H); 7.44 (m, 4H), 5.35 (s, 2H), 3.43 (m, 2H); HPLC-MS (Method A): m/z=610 (M+1); $R_t$=8.02 min.

General Procedure (C)

General procedure (C) may be used for solution phase preparation of compounds of general formula (I$_b$), (I$_c$) and (I$_d$):

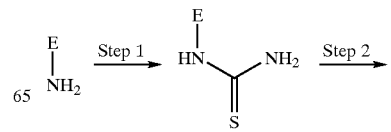

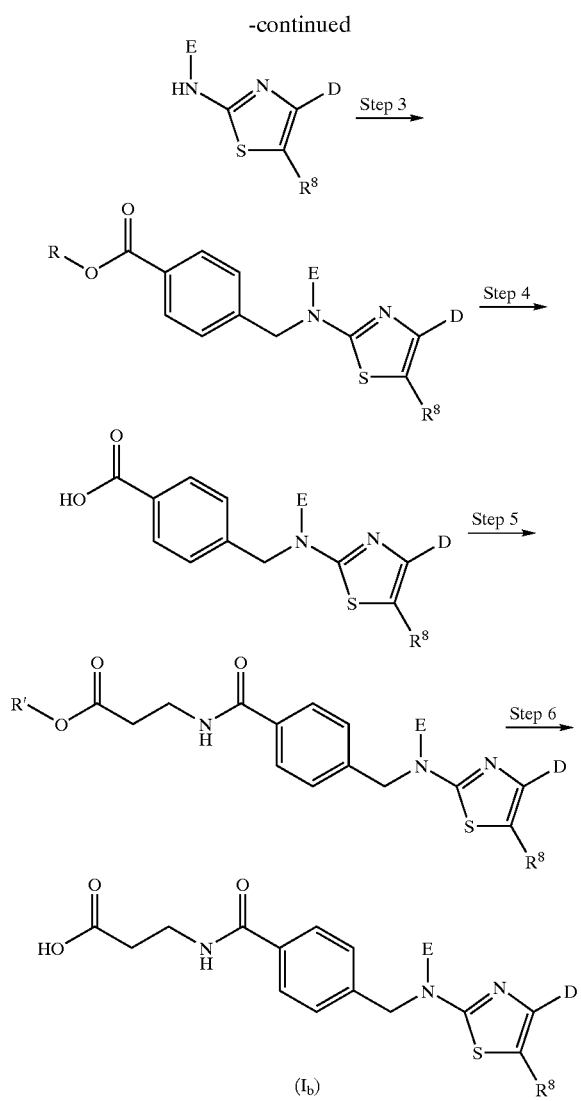

wherein

E and D independently are aryl or heteroaryl and are both optionally substituted as defined above, R⁸ is as defined above, and R and R' independently are hydrogen or $C_{1-6}$-alkyl, Similarly, by using steps 7 and 8 of general procedure (B) compounds of formula (1%) are accessible from the benzoic acid intermediate and by using step 9 of General Procedure (B) compounds of general formula ($I_d$) are accessible.

Step 1 is a formation of a thiourea from a primary amine, E-NH₂. This is a known reaction and can be done in a one step procedure: The amine is heated with potassium (or sodium or ammonium) thiocyanate in hydrochloric acid (see eg K. Nagarajan et al., Indian J. Chem., 24B, 840–4 (1985)). Alternatively, the amine as the hydrochloride salt is heated in an anhydrous solvent with potassium (or sodium) thiocyanate (see eg Fernandes L. & Ganapathi K., Proc. Indian Acad. Sci., Sect. A., 33, 364–367 (1951)).

Step 2 is formation of an aminothiazole from the N-substituted thiourea obtained in step 1 by reaction with α-bromo (or chloro) ketones. This reaction is well known (see eg Zhang, M. Q. et al, J. Heterocycl. Chem., 28, 673–683 (1991) & Birkinshaw T, et al., J. Chem. Soc., Perkin Trans. 1, 2, 147–153 (1984)) and is normally performed at ambient temperature or at elevated temperature, up to the temperature of the boiling point of the solvent(s). The solvent can be one (or a mixture of two or more) of the following: dioxane, THF, DCM, 1,2-dichloro-propane, acetonitrile, acetone, ethanol, methanol, DMF, N-methylpyrrolidone, DMSO, toluene and ethyl acetate. The reaction can optionally be performed in the presence of a base, such as triethylamine (see eg Phred B. et al., J. Heterocycl. Chem. 24, 1509–1520 (1987)) or in the presence of an acid such as acetic acid.

Step 3 is an alkylation of the exocyclic nitrogen atom of the 2-aminothiazole heterocycle obtained in step 2. The reaction is known (see e.g. Gupta & Singh, J. Indian Chem. Soc., 42, 336–338 (1965)) and is usually performed by reaction of the 2-aminothiazole with a benzyl halide in the presence of a base, such as sodium hydride, sodium amide, or potassium 20 carbonate in a solvent such as DMF, DMSO, NMP, acetonitrile, tetrahydrofuran, or 1,4-dioxane or in mixtures of two or more of these solvents. Optionally, catalytic or stoichiometric amounts of potassium, sodium, or tetraalkyl ammonium iodide can be added. The reaction temperature is usually from room temperature to the boiling point of the solvent.

Step 4 is a hydrolysis of the ester obtained in step 3. This step is similar to similar transformations described in WO 00/69810.

Steps 5 & 6 are coupling of the benzoic acid with a β-alanine ester followed by hydrolysis of the ester. These steps are similar to similar transformations described in WO 00/69810.

This general procedure (C) is further illustrated in the following example

Example 440

General Procedure (C). Alternative Mode of Preparation of the Compound of Examples 339 & 437

3-(4-{[[4-(4-Chlorophenyl)thiazol-2-yl]-(4-trifluoromethylphenyl)amino]methyl}benzoylamino) propionic acid

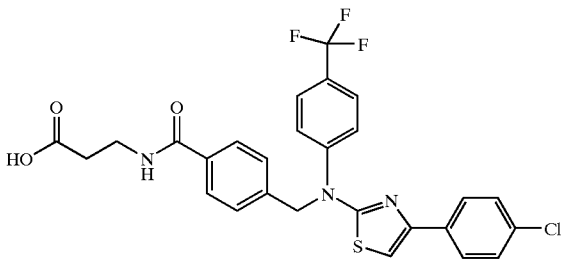

4-Trifluoromethylaniline (2.00 g; 12.4 mmol) and potassium thiocyanate (4.82 g; 49.7 mmol) was suspended in 1N aqueous HCl (20 ml). A clear solution was obtained upon heating to reflux (after 1 hour, a precipitate started to form). The mixture was refluxed overnight, then cooled to room temperature and extracted with ethyl acetate. The organic phase was washed with brine and dried with anhydrous sodium sulphate. Solvent was removed, and the residual oil was striped twice from acetonitril, to give a quantitative yield of (4-trifluoromethylphenyl)thiourea.

¹H-NMR(DMSO-$d_6$, selected peaks): δ 7.15 ppm (d, 2H); 7.25 (d, 2H); 10.2 (s, 1H). HPLC-MS (Method B): m/z: 221 (M+1), Rt: 2.69 min.

(4-Trifluoromethylphenyl)thiourea (5.00 g; 22.7 mmol) was dissolved in ethanol (45 mL) by gentle heating. Then, α-bromo-p-chloroacetophenone (5.30 g; 22.70 mmol) and DIPEA (3.22 g; 24.9 mmol) was added. The resulting solution was stirred for 16 hours at ambient temperature. The mixture was then concentrated in vacuo, and the residue dissolved in ethyl acetate. The DIPEA hydrobromide, which crystallized out of solution, was removed by filtration. The filtrate was washed with water (2×50 mL) and brine (50 mL), and dried over anhydrous sodium sulphate. The solvent was removed by rotary evaporation to give 7.00 g (93%) of [4-(4-chlorophenyl)thiazol-2-yl]-(4-trifluoromethylphenyl)amine as an oil. The material was pure enough for use in the next step (a crystalline sample can be obtained by re-crystallization in heptane).

$^1$H-NMR (DMSO-$d_6$): δ=6.84 ppm (s, 1H); 7.33 (d, 2H); 7.41 (d, 2H); 7.52 (d, 2H); 7.75 (d, 2H); 8.28 (bs, 1H). HPLC-MS (Method (B)): m/z: 355 (M+1), Rt=5.60 min.

[4-(4-Chlorophenyl)thiazol-2-yl]-(4-trifluoromethylphenyl)amine (0.335 mg; 0.95 mmol) was dissolved in acetonitril (4 ml) and methyl 4-(bromomethyl) benzoate (238 mg; 1.04 mmol), potassium carbonate (195 mg; 1.41 mmol) and sodium iodide (212 mg; 1.41 mmol) were added. The reaction mixture was heated to 60° C. for 3 days, then filtered while still hot. The solvent was removed by rotary evaporation, then the residue was dissolved in ethyl acetate (50 ml) and washed with water (50 ml) and brine (50 ml). The organic phase was dried with sodium sulphate, and taken to dryness by rotary evaporation. The residue was striped once with acetonitril to give pure 4-{[[4-(4-chlorophenyl)thiazol-2-yl]-(4-trifluoromethyl-phenyl)amino]methyl}benzoic acid methyl ester as an oil. Yield; 454 mg (96%).

$^1$H-NMR(CDCl$_3$): δ 3.90 ppm (s, 3H); 5.85 (s, 2H); 6.80 (s, 1H); 7.35 (d, 2H); 7.42 (d, 2H); 7.51 (d, 2H); 7.62 (d, 2H); 7.74 (d, 2H); 7.98 (d, 2H). HPLC-MS (Method B): m/z: 503 (M+1), Rt: 6.14 min.

4-{[[4-(4-Chlorophenyl)thiazol-2-yl]-(4-trifluoromethylphenyl)amino]methyl}benzoic acid methyl ester was subsequently converted to the title compound as described in General procedure (B), steps 4, 5, and 6.

Data for the title compound:
$^1$H-NMR(CDCl$_3$): δ 2.68 ppm (t, 2H); 3.71 (q, 2H); 5.32 (s, 2H); 6.75 (t, 1H); 6,80 (s, 1H); 7.32 (d, 2H); 7.41 (d, 2H); 7.50 (d, 2H); 7.61 (d, 2H); 7.68 (d, 2H); 7.73 (d, 2H).

General Procedure (D)

General procedure (D) may be used for solid phase preparation of compounds of general formula ($I_b$):

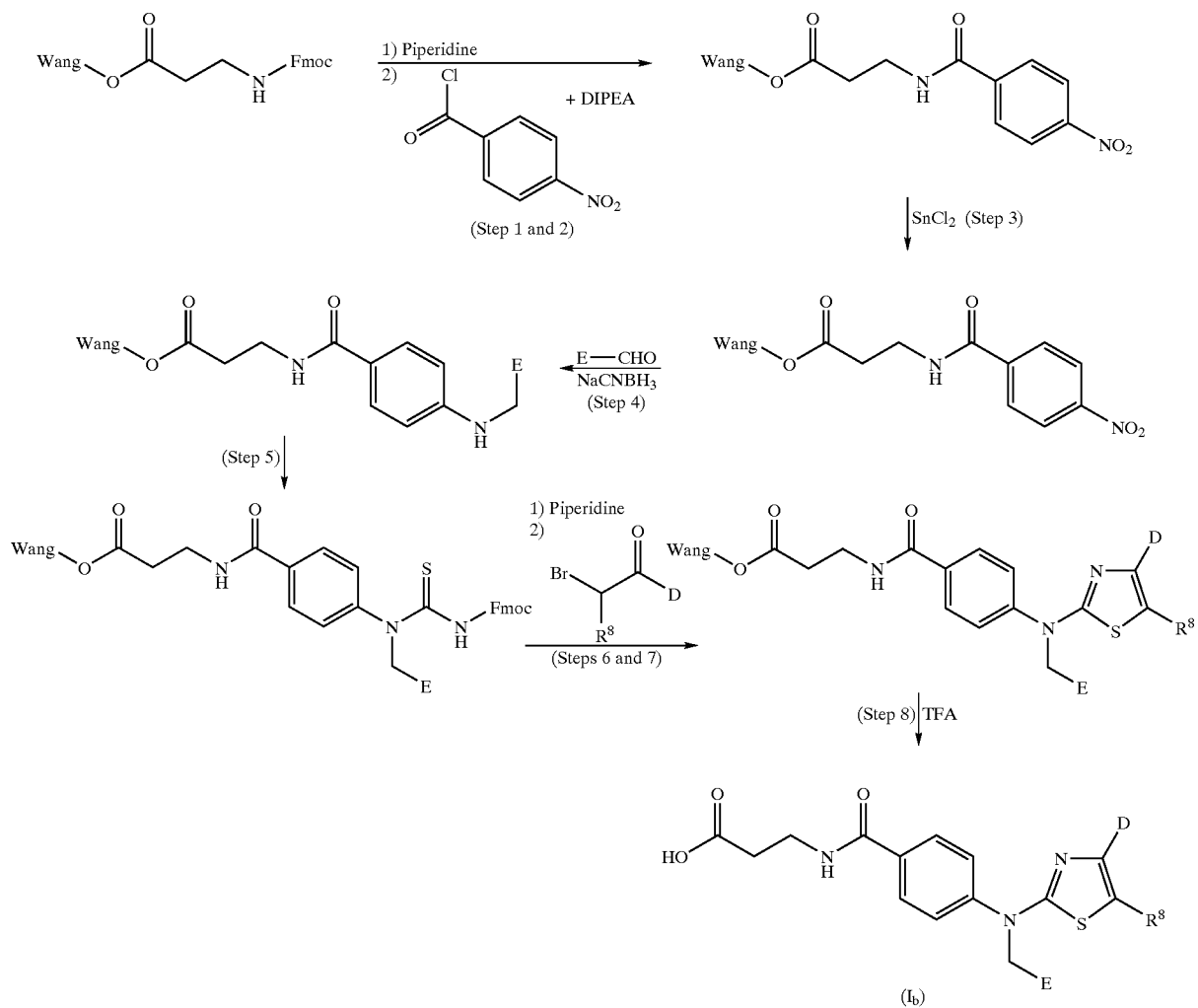

wherein

Wang is a polystyrene resin loaded with the Wang linker, and

D, E and $R^8$ are as defined above

Steps 1 to 2:

These steps are analogous to the corresponding steps described in WO 00/69810 and WO 02/00612.

Step 3:

The reduction of aromatic nitro groups on solid phase is generally known (F. Z. Dörwald, "Organic Synthesis on Solid Phase", 1st Edition Wiley-VCH: Weinheim, 2000, p. 246–247), and is performed using an excess of tin(II) chloride dihydrate in a polar organic solvent such as DMF or NMP. The reaction is performed at 20–100° C., preferable at ambient or slightly elevated temperature.

Step 4:

This reaction is generally known (F. Z. Dörwald, "Organic Synthesis on Solid Phase", 1st Edition Wiley-VCH: Weinheim, 2000, p. 239–241), and is achieved by using an excess of aldehyde, sodium cyano borohydride and a proton source such as acetic acid. The reaction is performed at 20–100° C. preferable at 40–80° C. in a polar organic solvent such as DMF or NMP.

Steps 5 and 6: Thiourea Formation

The formation of 1,1-disubstituted thioureas on solid phase from resin-bound secondary amines is a known reaction and have been described with Fmoc-isothiocyanate (P. C. Kearney et al., J. Org Chem., 1998, 63, 196–200) and Alloc-isothiocyanate (D. Dodd et al., Tetrahedron Lett., 1998, 39, 5701–4) as synthetic equivalents of H-NCS. The present methodology utilises Fmoc-isothiocyanate followed by deprotection of the Fmoc-protected thiourea with piperidine.

Step 7: Thiazole Formation

The reaction generally is known (P. C. Kearney et al., J. Org Chem., 1998, 63, 196–200 and J. Stadlwieser et al., Angew. Chem. Int. Ed. Engl., 1998, 37, 1402–4) and is performed by reacting a resin-bound thiourea with a α-haloketone under basic or acidic conditions. The reaction is normally performed at ambient temperature or at elevated temperature, up to the temperature of the boiling point of the solvent(s). The solvent can be one (or a mixture of two or more) of the following: dioxane, THF, DCM, 1,2-dichloropropane, acetonitrile, DMF, N-methylpyrrolidone, DMSO, toluene and ethyl acetate.

Step 8: Cleavage from Resin

This step is analogous to the corresponding transformations described in WO 00/69810 and WO 02/00612.

The general procedure (D) is further illustrated in the following example:

Example 441

General Procedure (D)

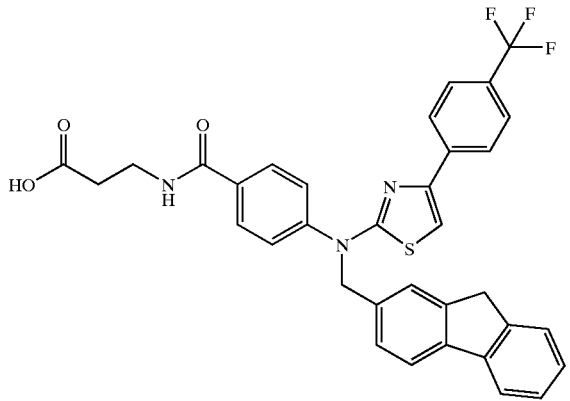

Fmoc-β-Ala-Wang resin (5.0 g, 0.31 mmol/g, 1.55 mmol) was treated with piperidine (20% in NMP, 20 ml) for 30 min and the resin was drained. This was repeated once. The resin was then washed with DMF (5×). A solution of DIPEA (3 ml) in NMP (17 ml) was added, followed by slow addition of a solution of p-nitrobenzoylchloride (2.88 g; 15.5 mmol, 10 eq.) in NMP (20 ml). The mixture was shaken for 3 h, then drained. The resin was washed with DMF (5×). Then a solution of $SnCl_2.2H_2O$ (10,5 g; 46.5 mmol, 30 eq.) in NMP (30 ml) was added. The mixture was shaken at room temperature for 16 h. The resin was drained and washed with DMF (3×) and DCM (10×), then dried under vacuum for 16 h. Yield: 5.20 g.

Dry resin (100 mg; 54 umol; 0.54 mmol/g) prepared as described above, was swelled in DCM for 30 min. 2-carboxyfluorene (194.5 mg; 1 mmol) dissolved in DMF (1 ml) was added followed by a solution of sodium cyano borohydride (138 mg; 2 mmol) in DMF—acetic acid (1.2 ml, 5:1). The reaction mixture was heated to 80° C. over night. The resin was drained for solvent and reactants, and subsequently washed with MeOH (3×), DMF (5×) and DCM (4×) to give resin bound 3-{4-[(9H-fluoren-2-ylmethyl)amino]benzoylamino}propionic acid.

Resin bound 3-{4-[(9H-fluoren-2-ylmethyl)amino]benzoylamino}propionic acid was added a solution of Fmoc isothiocyanate (90 mg, 0.3 mmol, 5 eq.) in DCM (1 ml). The resin was stirred at ambient temperature for 3 h, then drained and washed with DCM (3×) and DMF (3×). The resin was then treated with a 20% solution of piperidine in DMF (1 ml) for 15 min. Solvent was removed and the piperadine treatment was repeated once more. The resin was then washed with DMF (3×) to furnish resin bound 3-{4-[1-(9H-fluoren-2-ylmethyl)thioureido]benzoylamino}propionic acid.

To resin bound 3-{4-[1-(9H-fluoren-2-y!methyl)thioureido]benzoylamino}propionic acid was added α-bromo-p-trifluoromethylacetophenone (267 mg, 1 mmol) in DMF (1 ml). Acetic acid (200 ul) was added, and the resin was stirred at ambient temperature over night. Resin was washed with DMF (3×) and DCM (10×).

The resin was then treated with 50% TFA in DCM (2 ml) for 45 min. The resin was drained, and washed twice with 50% TFA in DCM. The combined filtrates were collected and evaporated to dryness to afford the title compound. HPLC-MS (Method (D)): m/z: 614 (M+1); Rt: 5.54 min.

Example 442
General Procedure (D)
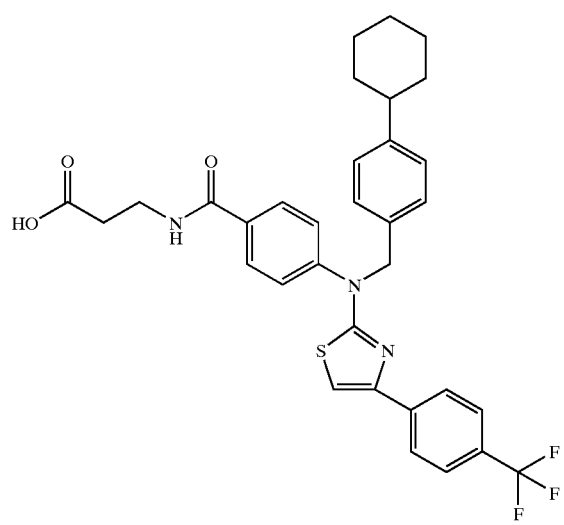
HPLC-MS (Method (A)): m/z: 608 (M+1); Rt: 6.88 min.
Example 443
General Procedure (D)
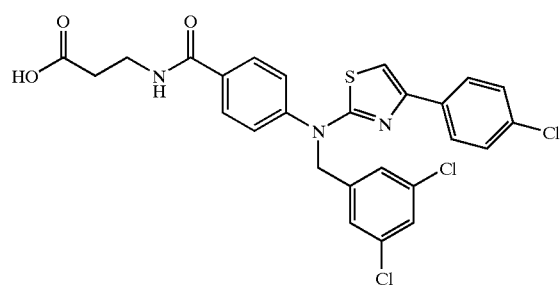
HPLC-MS (Method (A)): m/z: 561 (M+1); Rt: 6.54 min.
Example 444
General Procedure (D)
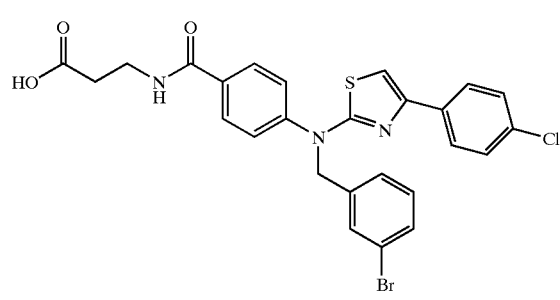
HPLC-MS (Method (A)): m/z: 571 (M+1); Rt: 6.17 min.
Example 445
General Procedure (D)
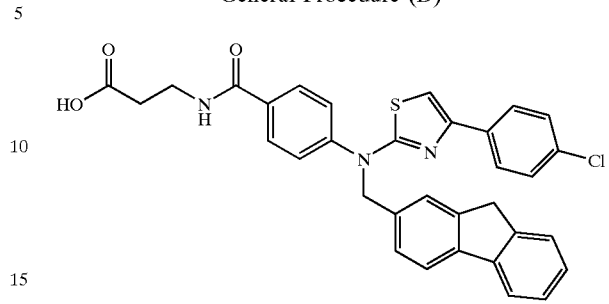
HPLC-MS (Method (A)): m/z: 580 (M+1); Rt: 6.63 min.
Example 446
General Procedure (D)
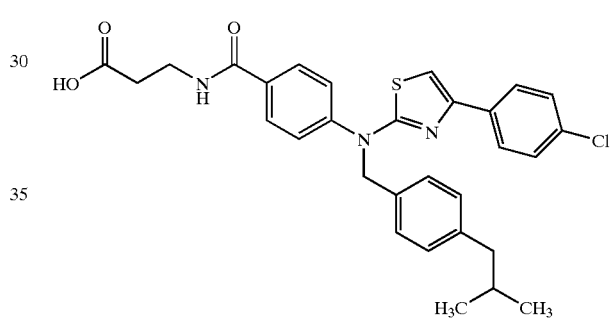
HPLC-MS (Method (A)): m/z: 548 (M+1); Rt: 6.91 min.
Example 447
General Procedure (D)
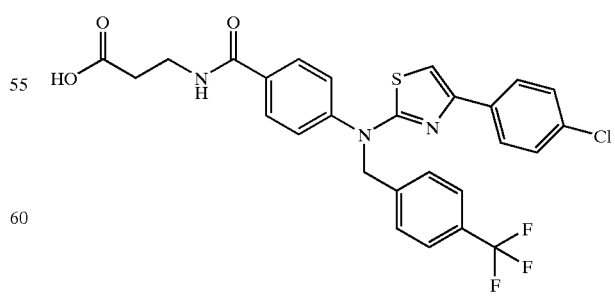
HPLC-MS (Method (A)): m/z: 560 (M+1); Rt: 6.13 min.

Example 448
General Procedure (D)
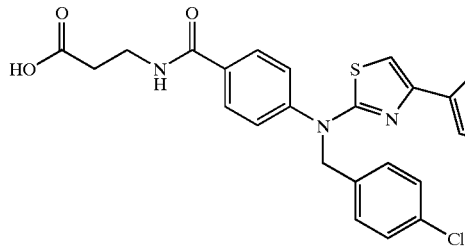
HPLC-MS (Method (A)): m/z: 526 (M+1); Rt: 6.10 min.
Example 449
General Procedure (D)
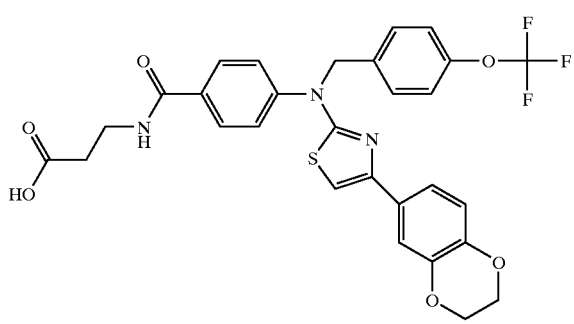
HPLC-MS (Method (A)): m/z: 600 (M+1); Rt: 5.20 min.
Example 450
General Procedure (D)
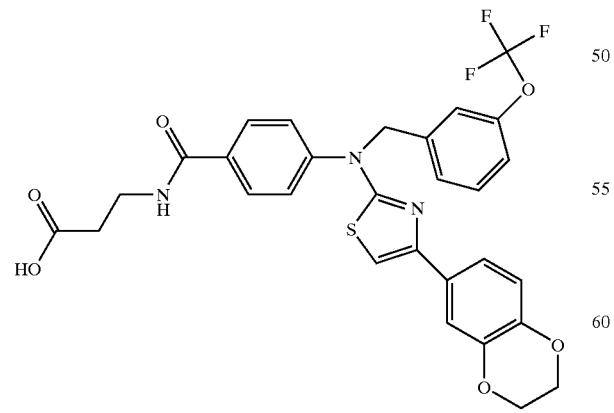
HPLC-MS (Method (A)): m/z: 600 (M+1); Rt: 5.13 min.
Example 451
General Procedure (D)
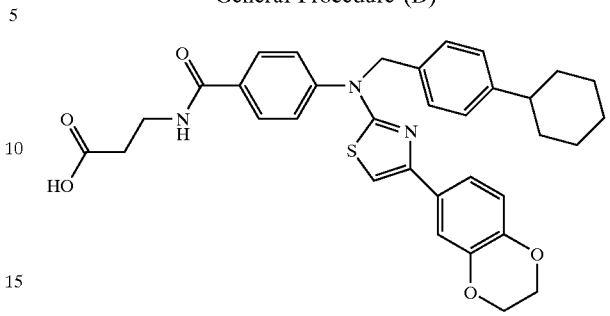
HPLC-MS (Method (A)): m/z: 598 (M+1); Rt: 6.07 min.
Example 452
General Procedure (D)
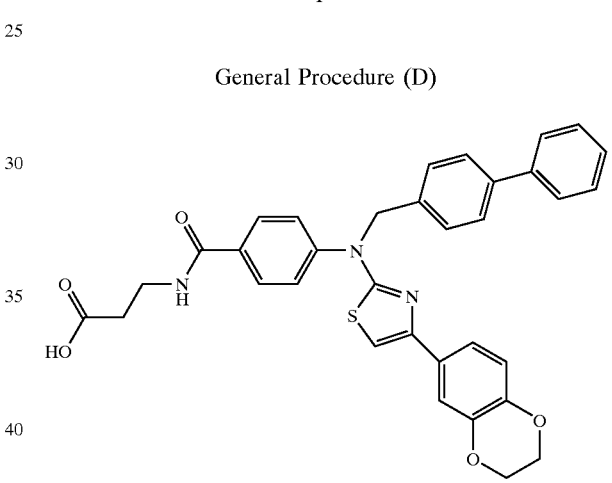
HPLC-MS (Method (A)): m/z: 592 (M+1); Rt: 5.43 min.
Example 453
General Procedure (D)
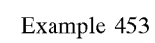
HPLC-MS (Method (A)): m/z: 622 (M+1); Rt: 6.00 min.

Example 454
General Procedure (D)
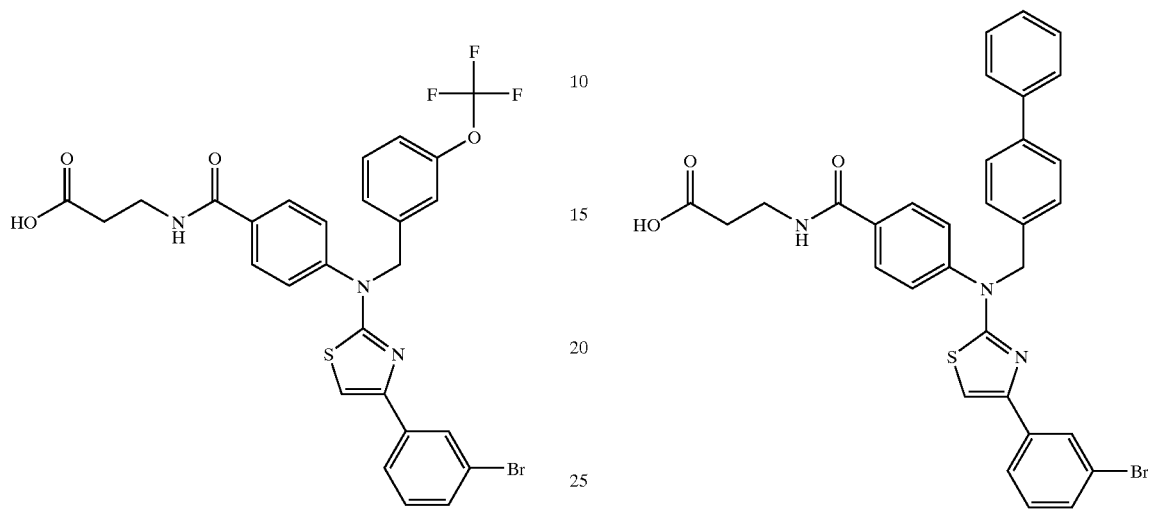
HPLC-MS (Method (A)): m/z: 622 (M+1); Rt: 5.93 min.
Example 455
General Procedure (D)
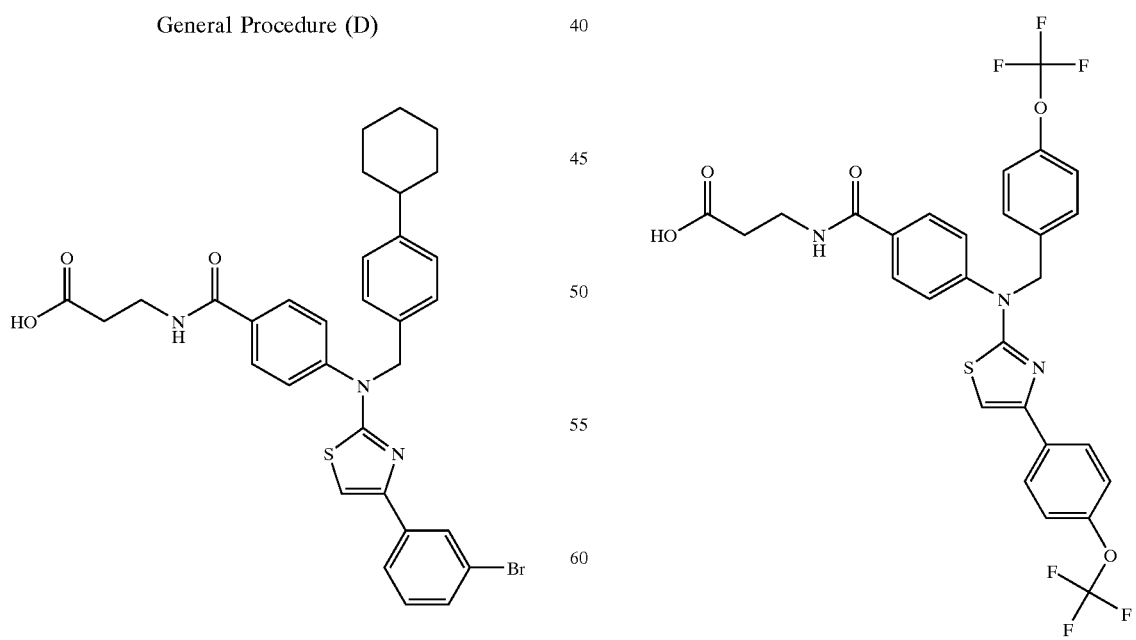
HPLC-MS (Method (A)): m/z: 619 (M+1); Rt: 7.00 min.
Example 456
General Procedure (D)
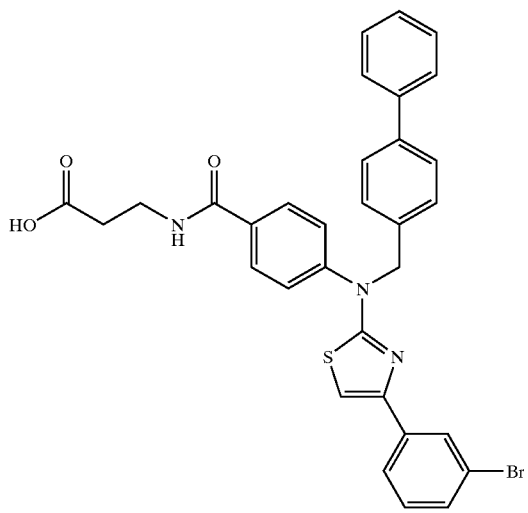
HPLC-MS (Method (A)): m/z: 613 (M+1); Rt: 6.23 min.
Example 457
General Procedure (D)
HPLC-MS (Method (A)): m/z: 626 (M+1); Rt: 6.10 min.

Example 458
General Procedure (D)
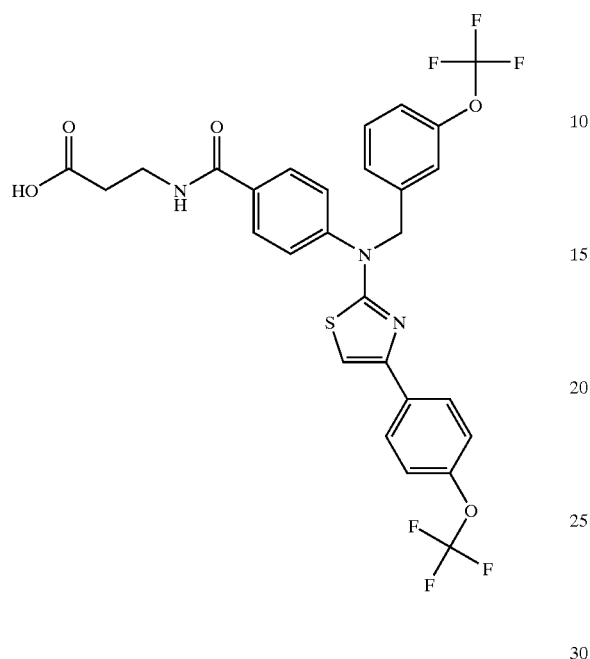
HPLC-MS (Method (A)): m/z: 626 (M+1); Rt: 6.03 min.
Example 459
General Procedure (D)
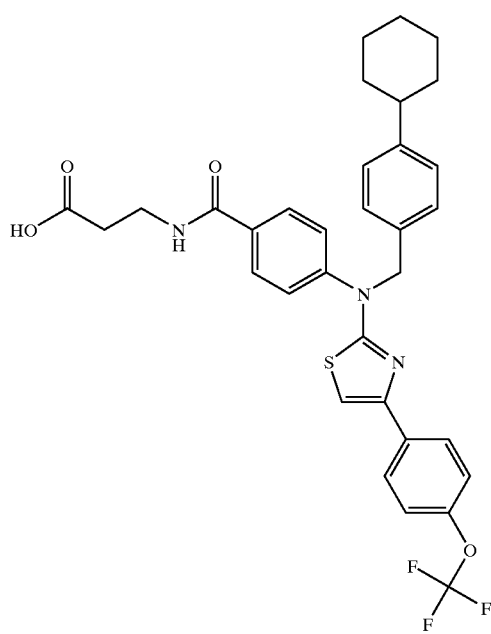
HPLC-MS (Method (A)): m/z: 624 (M+1); Rt: 7.03 min.
Example 460
General Procedure (D)
HPLC-MS (Method (A)): m/z: 618 (M+1); Rt: 5.25 min.
Example 461
General Procedure (D)
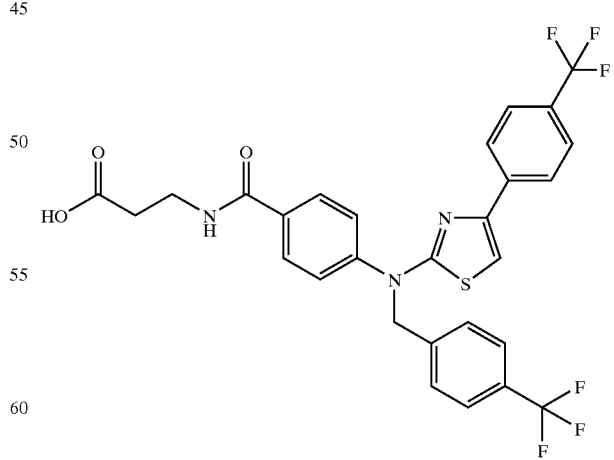
HPLC-MS (Method B): m/z: 594 (M+1); Rt: 5.17 min.

Example 462
General Procedure (D)
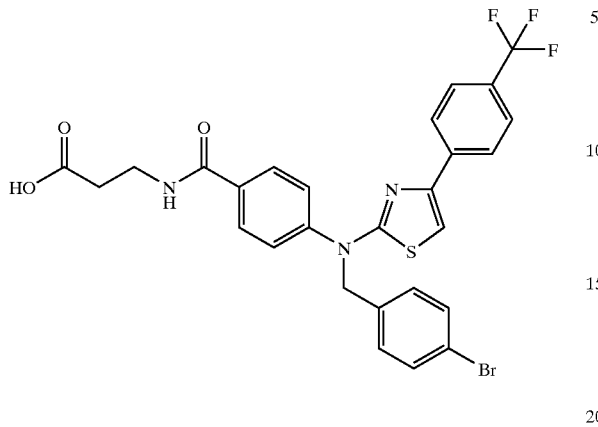
HPLC-MS (Method B): m/z: 606 (M+1); Rt: 5.20 min.
Example 463
General Procedure (D)
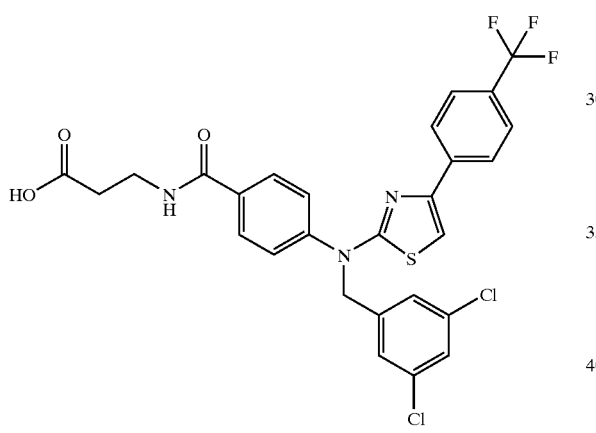
HPLC-MS (Method B): m/z: 594 (M+1); Rt: 5.45 min.
Example 464
General Procedure (D)
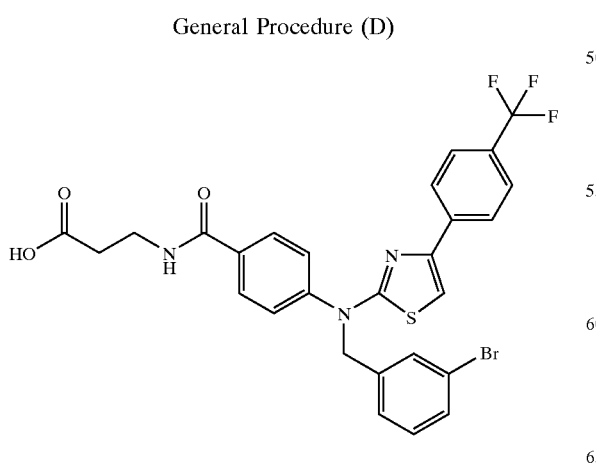
HPLC-MS (Method B): m/z: 606 (M+1); Rt: 5.14 min.
Example 465
General Procedure (D)
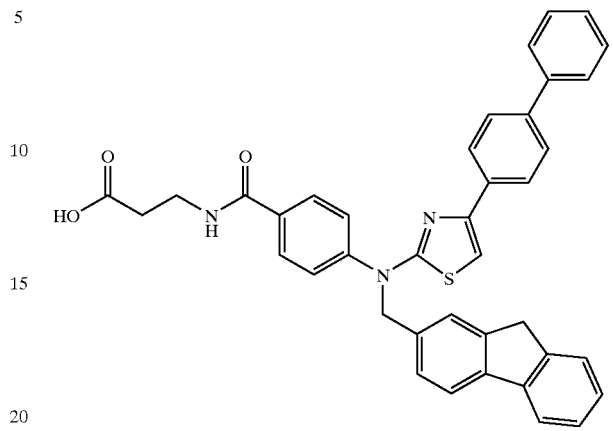
HPLC-MS (Method B): m/z: 622 (M+1); Rt: 5.74 min.
Example 466
General Procedure (D)
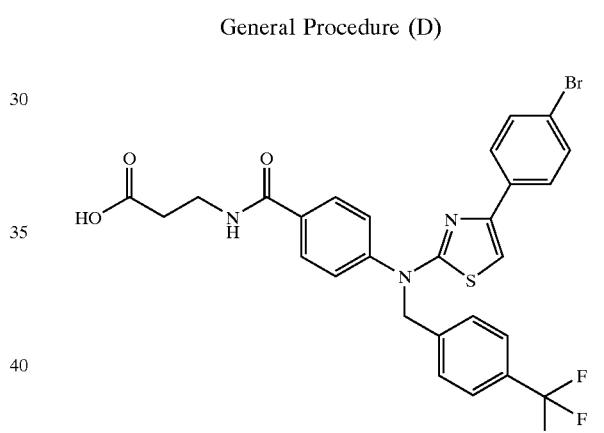
HPLC-MS (Method B): m/z: 604 (M+1); Rt: 5.20 min.
Example 467
General Procedure (D)
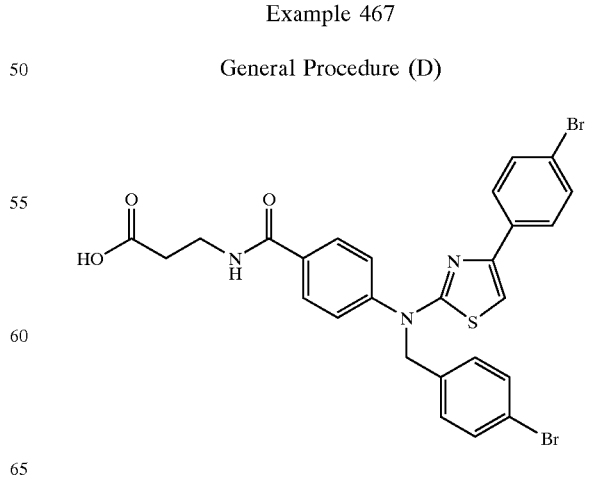
HPLC-MS (Method B): m/z: 616 (M+1); Rt: 5.22 min.

Example 468
General Procedure (D)
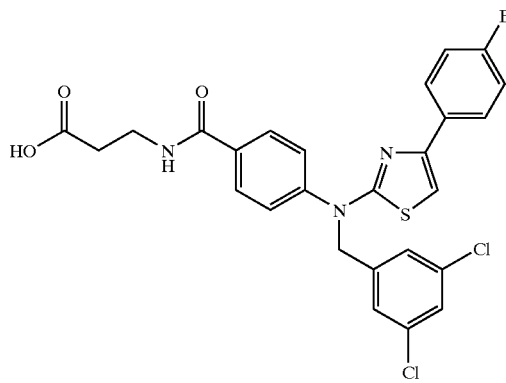
HPLC-MS (Method B): m/z: 606 (M+1); Rt: 5.47 min.
Example 469
General Procedure (D)
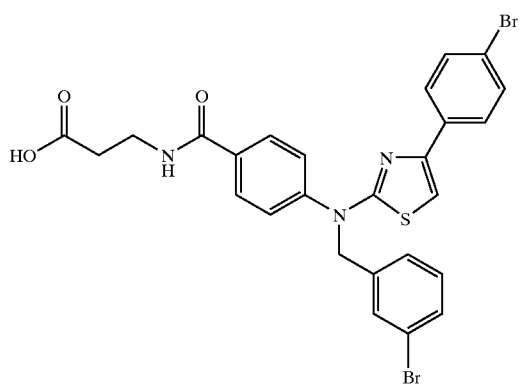
HPLC-MS (Method B): m/z: 616 (M+1); Rt: 5.17 min.
Example 470
General Procedure (D)
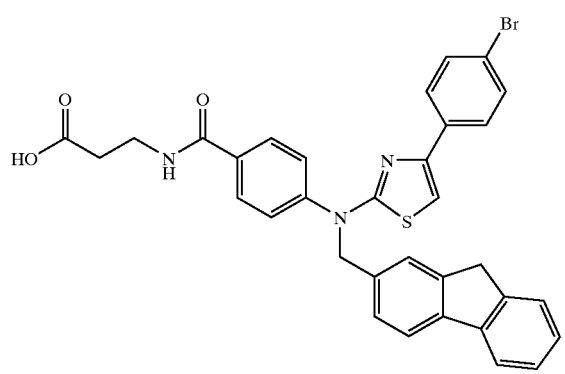
HPLC-MS (Method B): m/z: 625 (M+1); Rt: 5.56 min.
Example 471
General Procedure (D)
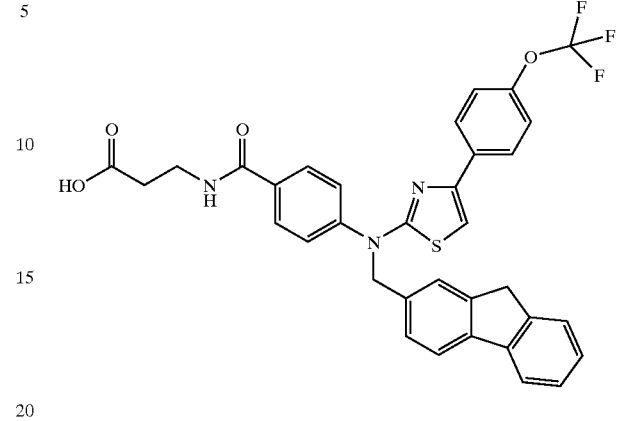
HPLC-MS (Method B): m/z: 630 (M+1); Rt: 5.57 min.
Example 472
General Procedure (D)
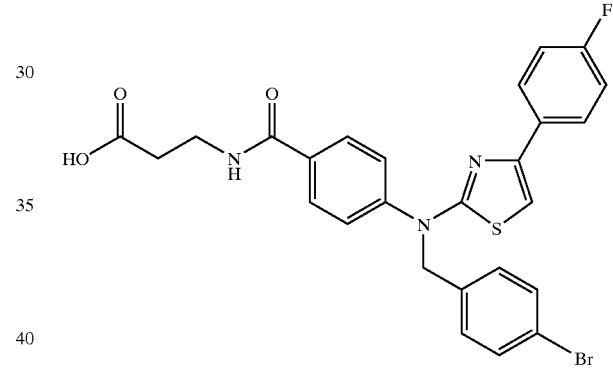
HPLC-MS (Method B): m/z: 554 (M+1); Rt: 4.79 min.
Example 473
General Procedure (D)
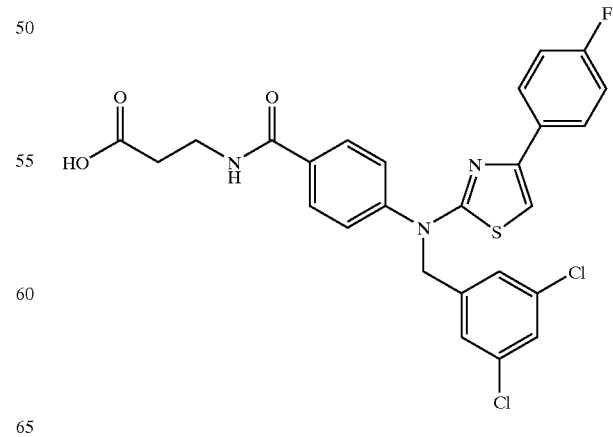
HPLC-MS (Method B): m/z: 544 (M+1); Rt: 5.03 min.

Example 474
General Procedure (D)
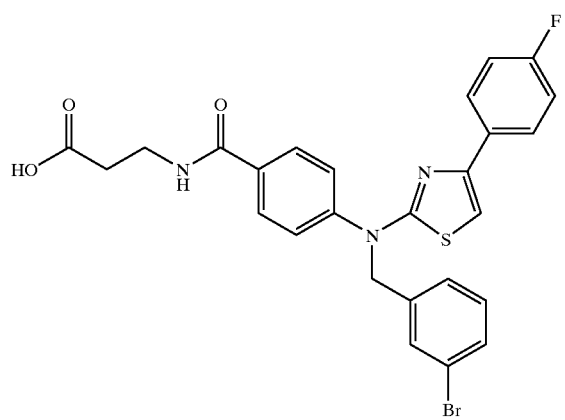
HPLC-MS (Method B): m/z: 554/557 (M+1); Rt: 4.75 min.
Example 475
General Procedure (D)
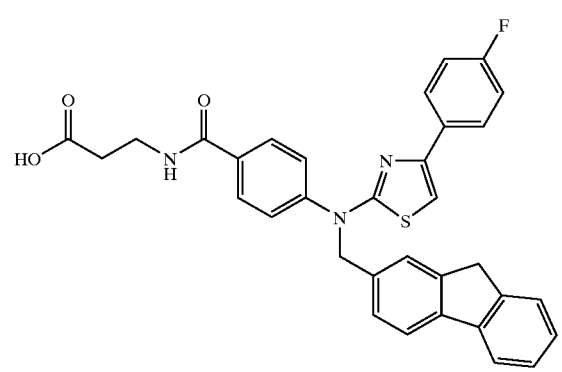
HPLC-MS (Method B): m/z: 564 (M+1); Rt: 5.14 min.
Example 476
General Procedure (D)
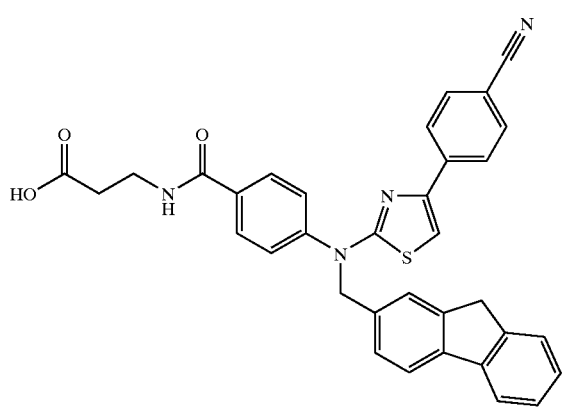
HPLC-MS (Method B): m/z: 571 (M+1); Rt: 4.84 min.
Example 477
General Procedure (D)
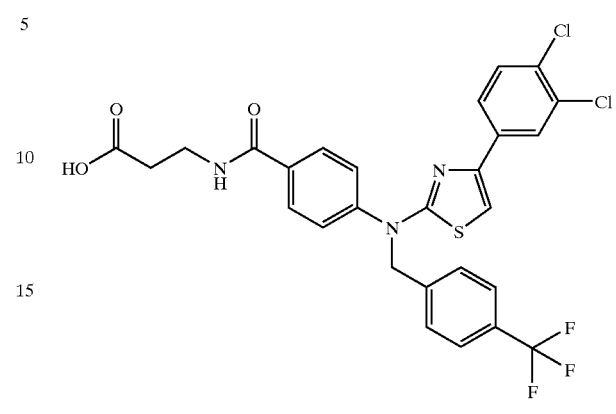
HPLC-MS (Method B): m/z: 594 (M+1); Rt: 5.42 min.
Example 478
General Procedure (D)
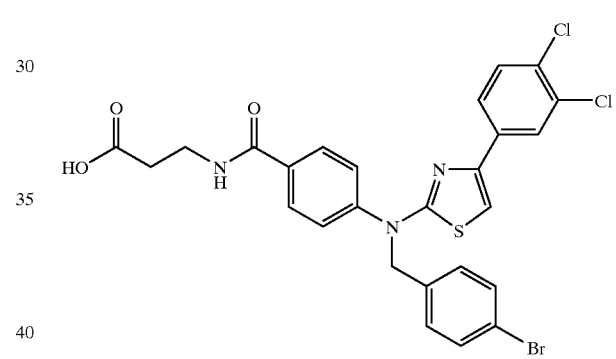
HPLC-MS (Method B): m/z: 605 (M+1); Rt: 5.45 min.
Example 479
General Procedure (D)
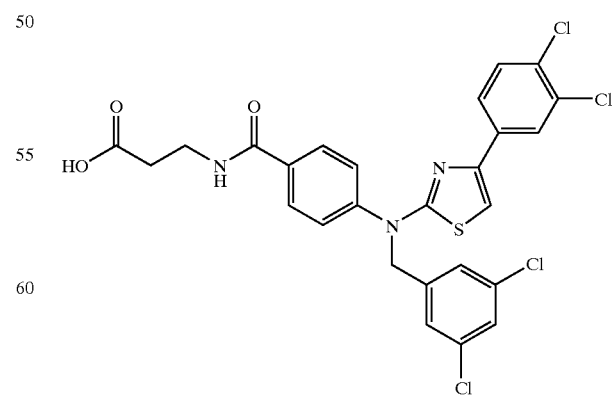
HPLC-MS (Method B): m/z: 594 (M+1); Rt: 5.73 min.

Example 480

General Procedure (D)

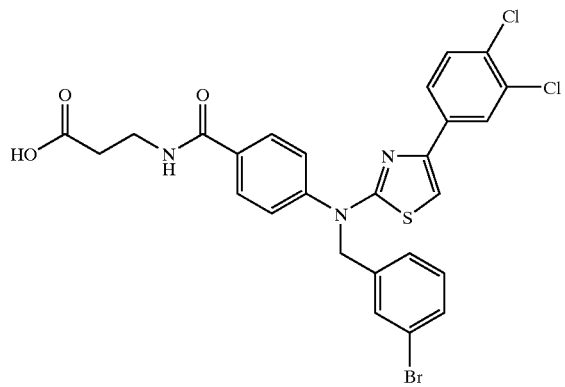

HPLC-MS (Method B): m/z: 605 (M+1); Rt: 5.43 min.

Example 481

General Procedure (D)

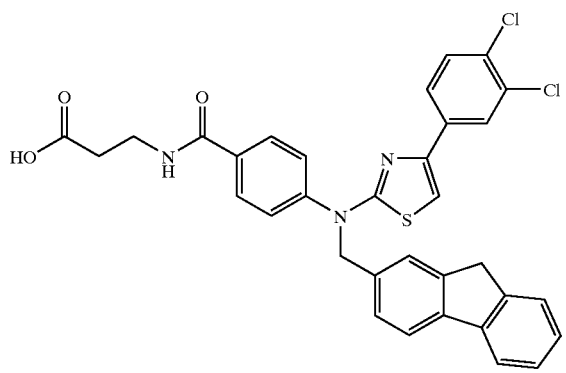

HPLC-MS (Method B): m/z: 615 (M+1); Rt: 5.80 min.

Example 482

General Procedure (D)

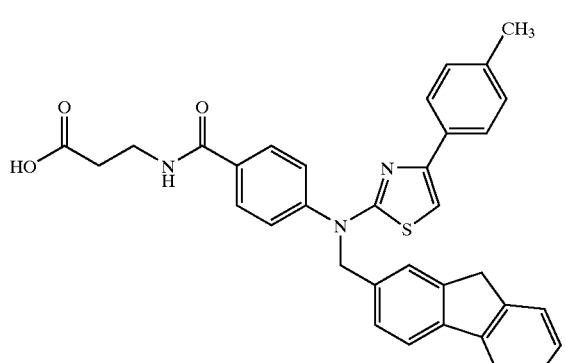

HPLC-MS (Method B): m/z: 560 (M+1); Rt: 5.33 min.

Example 483

General Procedure (D)

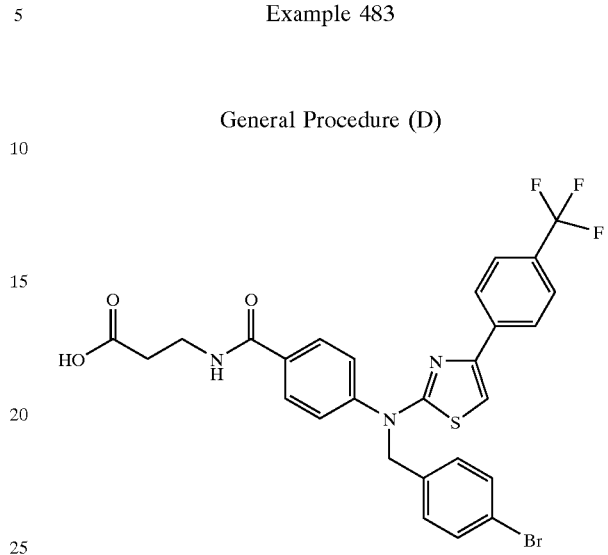

$^1$H-NMR (CDCl$_3$, selected peaks): δ 2.76 ppm (t, 2H); 3.76 (q, 2H); 5.20 (s, 2H); 6.83 (s, 1H); 7.17 (d, 2H); 7.42 (d, 2H); 7.47 (d, 2H); 7.63 (d, 2H); 7.76 (d, 2H); 7.84 (d, 2H); 8.12 (t, 1H). HPLC-MS (Method B): m/z: 604 (M+1), Rt: 5.15 min.

Example 484

General Procedure (D)

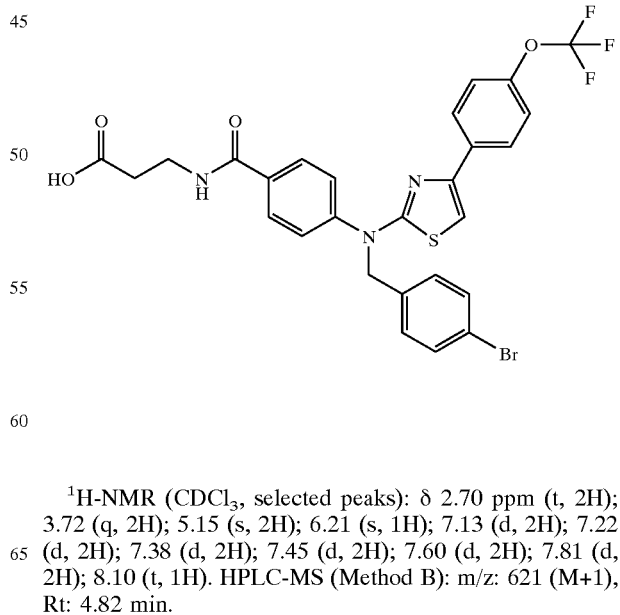

$^1$H-NMR (CDCl$_3$, selected peaks): δ 2.70 ppm (t, 2H); 3.72 (q, 2H); 5.15 (s, 2H); 6.21 (s, 1H); 7.13 (d, 2H); 7.22 (d, 2H); 7.38 (d, 2H); 7.45 (d, 2H); 7.60 (d, 2H); 7.81 (d, 2H); 8.10 (t, 1H). HPLC-MS (Method B): m/z: 621 (M+1), Rt: 4.82 min.

Example 485

General Procedure (D)

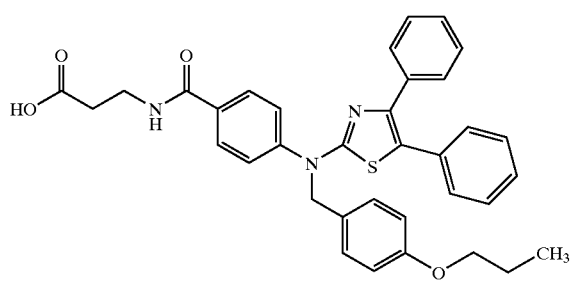

¹H-NMR (CDCl₃, selected peaks): δ 1.02 ppm (t, 3H); 1.78 (m, 2H); 2.68 (t, 2H); 3.68 (q, 2H); 3.89 (t, 2H); 5.04 (s, 2H); 6.85 (d, 2H); 7.12 (d, 2H); 7.22–7.44 (m, 12H); 7.65 (t, 1H); 7.82 (d, 2H). HPLC-MS (Method B): m/z: 592 (M+1), Rt: 5.30 min.

Example 486

General Procedure (D)

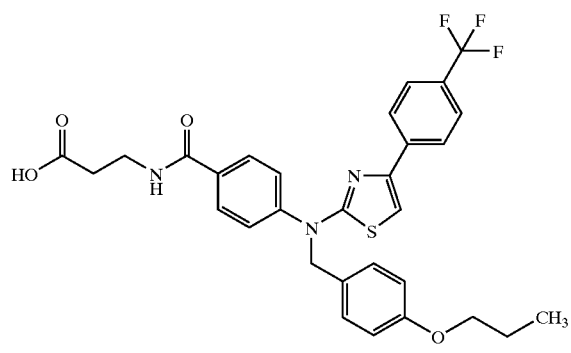

¹H-NMR (CDCl₃, selected peaks): δ 1.01 ppm (t, 3H); 1.74 (m, 2H); 2.71 (m, 2H); 3.71 (m, 2H); 3.79 (t, 2H); 5.08 (s, 2H); 6.78 (s, 1H); 6.75–6.90 (m, 2H); 7.15 (d, 2H); 7.34 (d, 2H); 7.44 (dd, 1H); 7.70–7.88 (m, 3H), 8.08 (t, 1H). HPLC-MS (Method B): m/z: 584 (M+1), Rt: 4.98 min.

Example 487

General Procedure (D)

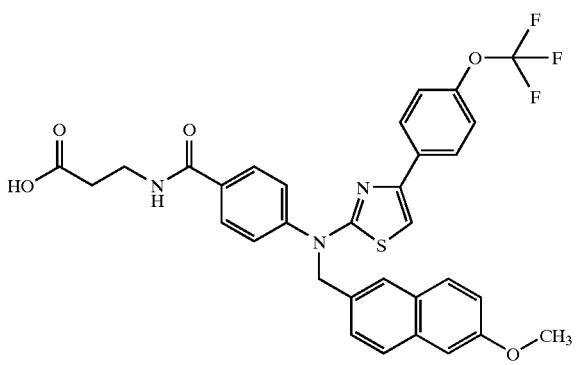

¹H-NMR (CDCl₃, selected peaks): δ 2.71 ppm (t, 2H); 3.72 (q, 2H); 3.92 (s, 3H); 5.28 (s, 2H); 6.65 (s, 1H); 7.20 (d, 2H); 7.25–7.75 (m, 14H); 7.82 (d, 2H). HPLC-MS (Method B): m/z: 622 (M+1), Rt: 5.20 min.

Example 488

General Procedure (D)

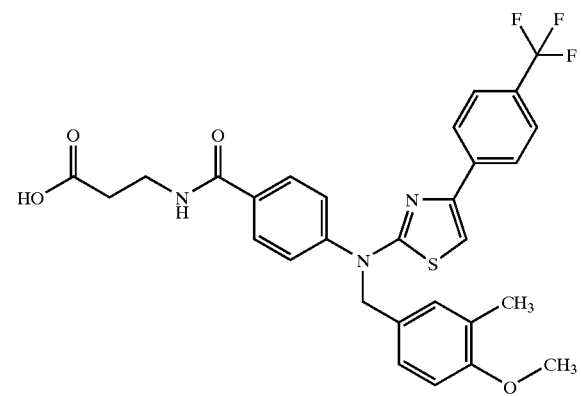

Example 489

General Procedure (D)

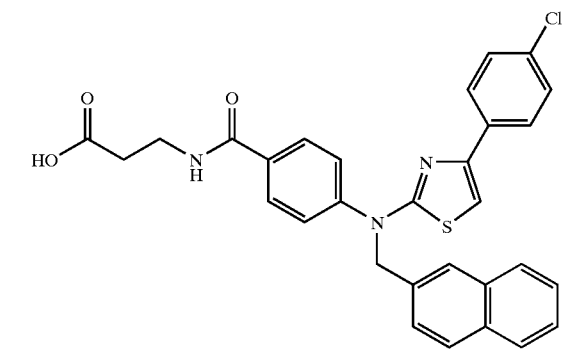

¹H-NMR (CDCl₃, selected peaks): δ 2.71 ppm (t, 2H); 3.70 (q, 2H); 5.28 (s, 2H); 6.65 (s, 1H); 7.35 (d, 2H); 7.42 (d, 2H); 7.45–7.65 (m, 4H); 7.75–7.85 (m, 4H); HPLC-MS (Method B): m/z: 543 (M+1), Rt: 4.82 min.

General Procedure (E)

General procedure (E) may be used for solution phase preparation of compounds of general formula (I_e):

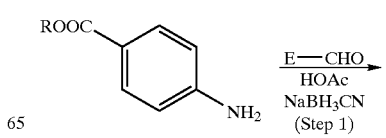

-continued

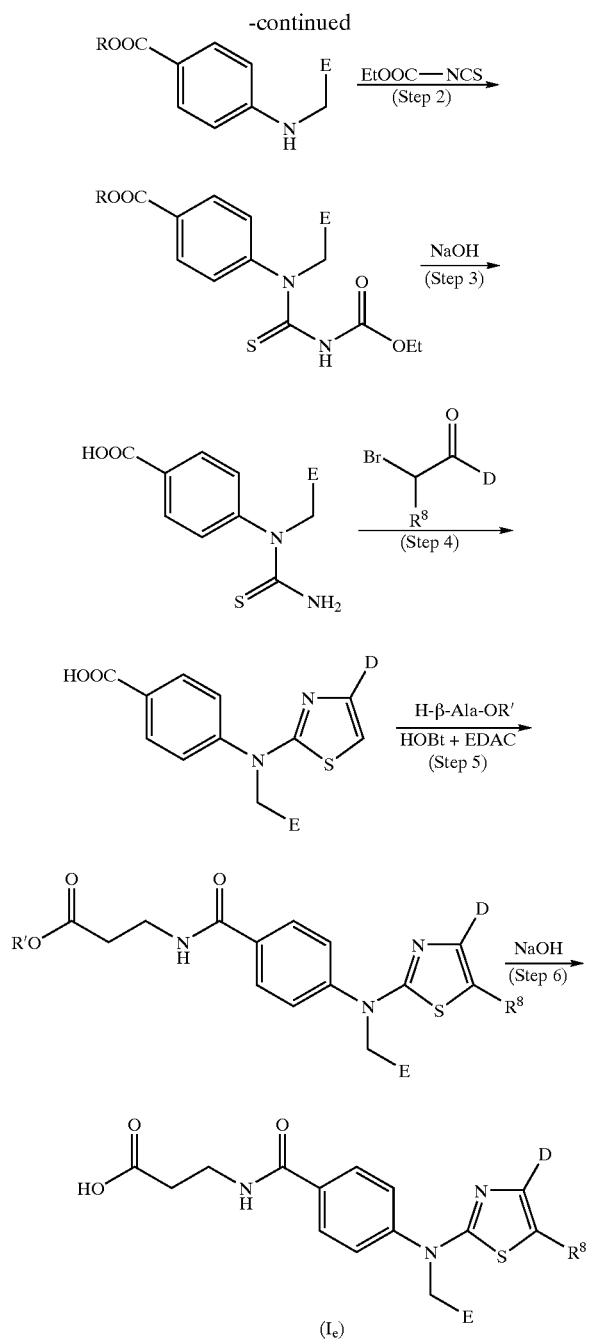

wherein D, E, and $R^8$ are as defined above, and

R and R' independently are $C_{1-6}$alkyl.

This general procedure (E) is very similar to general procedure (B) the only difference being the connectivity as the result of step 1, where in general procedure (B) the reductive amination is between E-$NH_2$ and a 4-formylbenzoic acid derivative, whereas in general procedure (E) the reductive amination is between E-CHO and a 4-aminobenzoic acid derivative.

The general procedure (E) is further illustrated in the following example

Example 490

General Procedure (E)

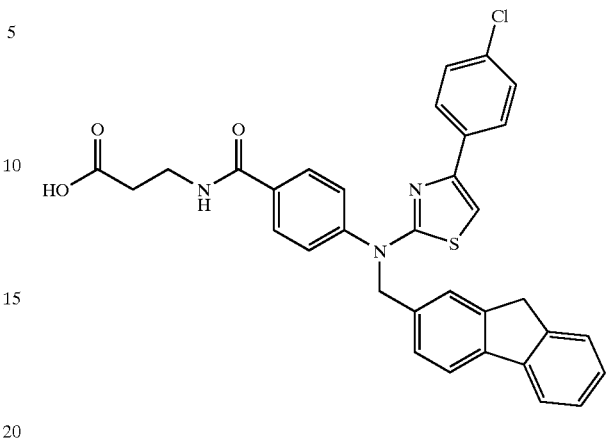

Step 1:
Methyl p-aminobenzoate (3.90 g; 20.0 mmol) and fluorine-2-carbaldehyde (3.04 g; 20.1 mmol) were suspended in methanol (120 mL). The suspension was heated to reflux. The mixture was cooled to room temperature. Acetic acid (20 mL) and sodium cyano borohydride (1.39 g; 20.1 mmol) were added. The mixture was then re-heated to reflux for 30 minutes. The suspension was cooled, and the precipitate was filtered off and washed trice with water. This afforded 5.70 g (87%) of 4-[(9H-fluoren-2-ylmethyl)amino] benzoic acid methyl ester.
$^1$H-NMR (CDCl$_3$): δ=3.85 ppm (s, 3H); 3.89 (s, 2H); 4.45 (s, 2H); 4.51 (bs, 1H); 6.62 (d, 2H); 7.26–7.40 (m, 3H); 7.55 (d, 2H); 7.75 (d, 1H), 7.78 (d, 1H); 7.85 (d, 2H). HPLC-MS (Method B): m/z: 352 (M+Na); Rt: 4.96 min.
Step 2:
4-[(9H-Fluoren-2-ylmethyl)amino]benzoic acid methyl ester (0.33 g; 1 mmol) was suspended in DCM (6 ml). Ethoxycarbonylisothiocyanate (0.17 g; 1.3 mmol) was added. The suspension was stirred at ambient temperature for 16 hours. A clear solution formed. The solvent was removed by rotary evaporation, and the residual oil was stripped twice from acetonitrile. This afforded 450 mg (99%) of [(9H-fluoren-2-ylmethyl)-(4-methoxycarbonylphenyl)thiocarbamoyl]carbamic acid ethyl ester.
$^1$H-NMR (CDCl$_3$): δ=1.12 ppm (t, 3H); 3.85 (s, 2H); 3.90 (s, 3H); 4.02 (q, 2H); 5.60 (s, 2H); 7.20 (d, 2H); 7.23–7.40 (m, 3H); 7.52 (d, 1H); 7.57 (s, 1H); 7.65 (d, 1H); 7.74 (d, 1H); 7.99 (d, 2H).
HPLC-MS (Method B): m/z: 461 (M+1); Rt: 4.95 min.
Step 3:
[(9H-Fluoren-2-ylmethyl)-(4-mehoxycarbonylphenyl) thiocarbamoyl]carbamic acid ethyl ester (0.90 g; 1.95 mmol) was dissolved in hot ethanol (20 mL). A solution of 4N aqueous sodium hydroxide (5 mL) was added, and the solution was refluxed for 16 hours. The solution was cooled and acidified with 1N aqueous hydrochloric acid (20 mL). The precipitated material was collected by filtration and washed twice with water to afford 707 mg (96%) of 4-[1-(9H-fluoren-2-ylmethyl)thioureido]benzoic acid.
$^1$H-NMR (DMSO-d$_6$): δ=3.85 ppm (s, 2H); 5.48 (s, 2H); 7.20–7.40 (m, 4H); 7.55 (d, 2H); 7.72–7.95 (m, 5H). 12.8 (bs, 1H). HPLC-MS (Method B): m/z: 375 (M+1), 397 (M+Na); Rt: 3.89 min.
Step 4:
4-[1-(9H-Fluoren-2-ylmethyl)thioureido]benzoic acid (0.70 g, 1.90 mmol) was suspended in a mixture of DMF (6 mL) and acetic acid (3 mL). α-Bromo-p-chloroacetophenone (0.49 g, 2.07 mmol) was added. A solution initially was formed, then a precipitate started to form. Additional DMF (3 mL) was added, and the mixture was heated gently until all material had dissolved. The mixture was then stirred at ambient temperature for 30 minutes. The precipitated product was collected and washed with water. Additional product was obtained from the mother liquor, by adding water at elevated temperature followed by slow cooling to allow crystallization. The combined products were collected and dried in vacuo at 40° C. This afforded 0.827 g (88%) of 4-[[4-(4-chlorophenyl)thiazol-2-yl]-(9H-fluoren-2-ylmethyl)amino]benzoic acid.

$^1$H NMR (DMSO-$d_6$): δ=3.87 ppm (s, 2H); 5.42 (s, 2H); 7.20–7.40 (m, 3H); 7.46 (m, 3H); 7.55 (d, 2H); 7.68 (d, 2H); 7.83 (d, 2H); 7.90 (d, 2H); 7.95 (d, 2H); 12.85 (bs, 1H). HPLC-MS (Method B): m/z: 509 (M+1), Rt: 5.98 min.

Step 5:

4-[[4-(4-Chlorophenyl)thiazol-2-yl]-(9H-fluoren-2-ylmethyl)amino]benzoic acid (300 mg; 0.59 mmol) was suspended in a mixture of DCM (4 mL) and DMF (4 mL). HOBt (88 mg; 0.64 mmol) and 1-ethyl-3-(3-dimethylaminopropyl)carbodiimide hydrochloride (128 mg; 0.64 mmol) were added. The mixture was stirred for 1 hour to give a clear solution. Then, β-alanine methyl ester hydrochloride (67 mg, 0.64 mmol) and DIPEA (350 µL) were added. The mixture was stirred at room temperature for 16 hours, then diluted with DCM (20 mL) and washed twice with water and once with brine. The organic phase was dried with anhydrous sodium sulphate and concentrated in vacuo to afford 310 mg (88%) of 3-{4-[[4-(4-chlorophenyl)thiazol-2-yl]-(9H-fluoren-2-ylmethyl)amino]benzoylamino}propionic acid methyl ester as a foam.

$^1$H-NMR (DMSO-$d_6$): δ=2.58 ppm (t, 2H); 3.48 (q, 2H); 3.60 (s, 3H); 3.86 (s, 2H); 5.40 (s, 2H); 7.20–7.35 (m, 4H); 7.48 (d, 2H); 7.56 (d, 2H); 7.64 (d, 2H); 7.78–7.88 (m, 4H); 7.90 (d, 2H). HPLC-MS (Method B): m/z: 595 (M+1), Rt: 5.88 min.

Step 6:

3-{4-[[4-(4-Chlorophenyl)thiazol-2-yl]-(9H-fluoren-2-ylmethyl)amino]benzoylamino}propionic acid methyl ester (200 mg; 0.337 mmol) was suspended in hot ethanol (30 mL). 4N aqueous sodium hydroxide (3 mL) was added, and the solution was gently heated until all material had dissolved. The mixture was then cooled on an ice bath and acidified with acetic acid (6 mL). Water was added until start of precipitation, then the amount of solvent was reduced to ¹⁄₁₀ by rotary evaporation. The crystalline solid thus obtained was collected by filtration, washed with water. And dried in vacuo. This afforded 124 mg (63%) of 3-{4-[[4-(4-chlorophenyl)thiazol-2-yl]-(9H-fluoren-2-ylmethyl)amino]benzoylamino}propionic acid.

$^1$H-NMR (DMSO-$d_6$): δ=2.33 ppm (t, 2H); 3.40 (q, 2H); 3.85 (s, 2H); 5.39 (s, 2H); 7.23–7.40 (m, 4H); 7.46 (d, 2H); 7.55 (m, 2H); 7.62 (d, 2H); 7.75–7.95 (m, 6H); 8.64 (t, 1H). HPLC-MS (Method B): m/z: 580 (M+1), Rt: 5.48 min.

General Procedure (F)

General procedure (F) may be used for solution phase preparation of compounds of general formula ($I_f$) and ($I_g$).

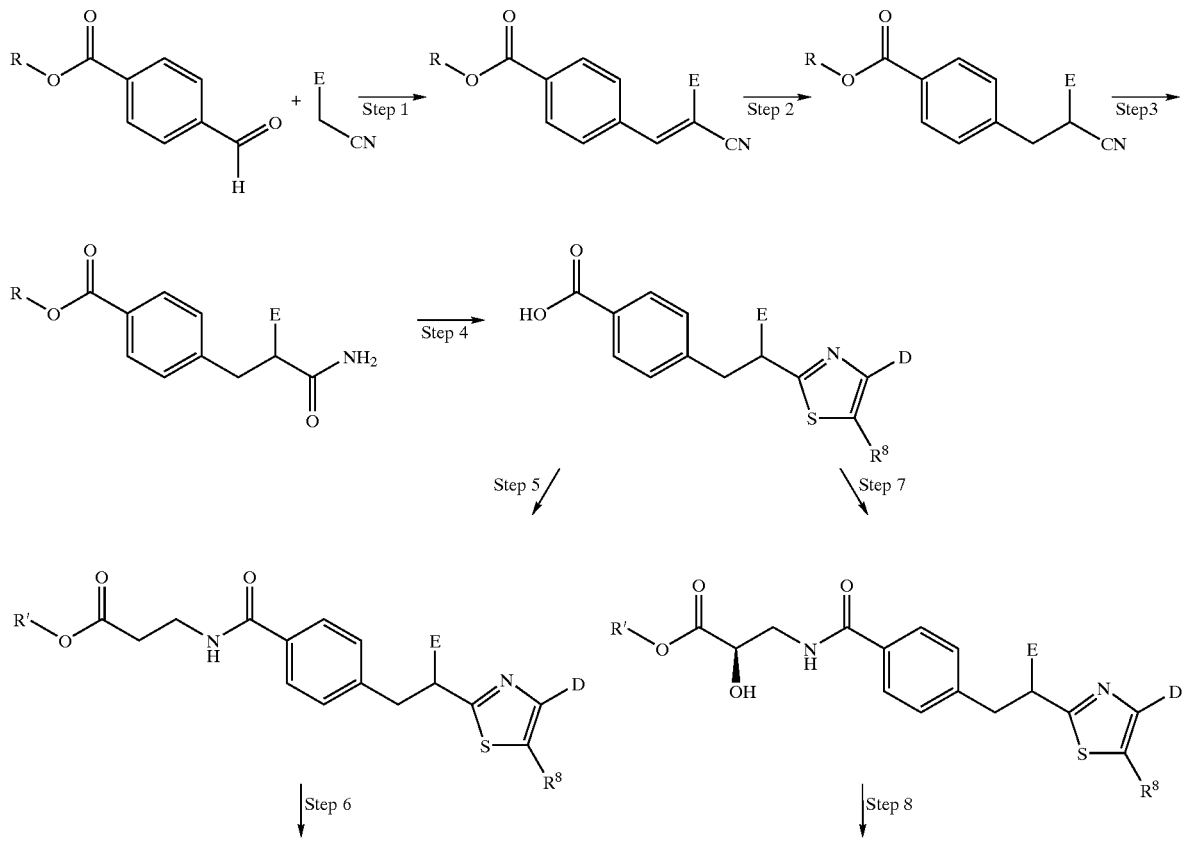

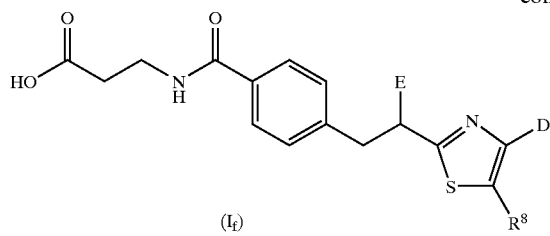

(I_f)

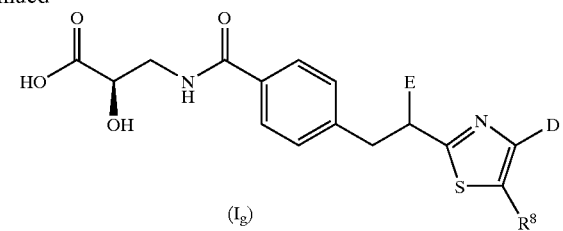

(I_g)

wherein

R and R' independently are hydrogen or $C_{1-6}$-alkyl,
$R^8$ is as defined above, and
E and D independently are aryl or heteroaryl and are both optionally substituted as defined above.

Step 1 is a Knoevenagel type reaction. Reacting a carbonyl compound with an acetonitrile in the presence of a base will lead to an α,β-unsaturated nitrile. The basic media can be 40% aqueous sodium hydroxide (see eg Wayne, V et al., *J. Med. Chem.* 1704–1719 (1996)) or solid $K_2CO_3$ in alcoholic media (see eg Ladhar, F & Gharbi, R. E I, *Synth. Commun.*, 21(3), 413–417 (1991)).

Step 2 is a reduction of a double bond to a single bond. This reaction is well known and can be performed with various types of reducing agents. Reduction with $NaBH_4$ can be performed is solvents such as THF, DMF, 2-propanol or ethanol at temperatures ranging from –30° C. to ambient temperature (see eg Wayne, V et al., *J. Med. Chem.* 1704–1719 (1996), Kulp, S. S: & Caldwell, C. B., *J. Org. Chem.* 45(1), 171–173 (1980)).

Step 3 is a formation of a thioamide from a nitrile. The sulphur source can be $P_4S_{10}/Na_2S$ in THF (see eg Brillon, D., *Synth. Commun.* 22(10) 1397–1401 (1992)) or diethyl thiophosphate in water (see eg Shabana, S., Meyer, H. J., Lawesson, S.-O., *Phosphorus Sulfur* 25, 297–306 (1985)).

Step 4 is formation of a thiazole from a thioamide obtained in step 3 by reaction with α-bromo (or chloro) ketones. This reaction is well known (see eg Reddy Sastry, C. V. et al., *Indian J. Chem Sect B*. 26, 662–665 (1987) and is normally performed at ambient temperature or at elevated temperature, up to the temperature of the boiling point of the solvent(s). The solvent can be one (or a mixture of two or more) of the following: dioxane, THF, DCM, isopropanol, acetonitrile, acetone, ethanol, methanol, DMF, N-methylpyrrolidone, DMSO, toluene and ethyl acetate. The reaction can optionally be performed in the presence of a base, such as triethylamine (see eg Elnagdi, M. H. et al., *J. Chem. Res. Miniprint*, 2, 375–384 (1997)).

Step 4: If the product from step 3 is a benzoic acid ester, then the ester is hydrolysed. This step is similar to similar transformations described in WO 00/69810.

Steps 5 & 6 are coupling of the benzoic acid with a β-alanine ester followed by hydrolysis of the ester. These steps are similar to similar transformations described in WO 00/69810.

Steps 7 & 8 are coupling of the benzoic acid with an (R)-isoserine ester followed by hydrolysis of the ester. These steps are similar to similar transformations described in WO 00/69810.

The steps 4–8 are very similar to the corresponding steps in general procedure (B).

This general procedure (F) is further illustrated in the following examples:

Example 491

General Procedure (F)

3-{4-[2-[4-(4-Chlorophenyl)thiazol-2-yl]-2-(4-trifluoromethoxyphenyl)ethyl]benzoylamino}propionic acid

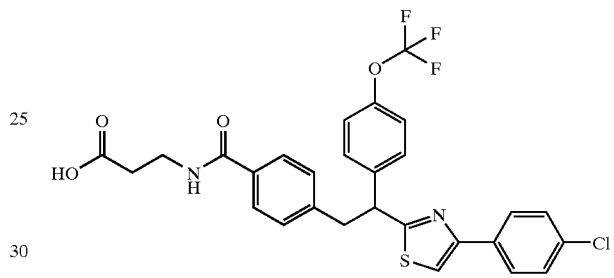

Step 1: 4-[2-Cyano-2-(4-trifluoromethoxyphenyl)vinyl]benzoic acid methyl ester:

4-Formylbenzoic acid methyl ester (8.60 g, 52.39 mmol) was dissolved in warm methanol (50 mL) and 4-trifluoromethoxyphenylacetonitrile (10.54 g, 52.39 mmol) was added. The mixture was stirred and potassium carbonate (7.75 g, 56.05 mmol) was added. The mixture was heated to 60° C. and more methanol (20 mL) was added and stirring was continued for 1 hour. The precipitate was filtered off and added in small portions to a stirred and cold 4 M hydrochloric acid solution. The precipitate was filtered off, washed with water and dried to afford 14.4 g (79%) of 4-[2-cyano-2-(4-trifluoromethoxyphenyl)vinyl]benzoic acid methyl ester.

HPLC-MS (Method D): m/z: 348 (M+1); Rt=5.14 min. $^1$H NMR (DMSO-d$_6$): δ=3.90 (s, 3H), 7.55 (d, 2H), 7.92 (d, 2H), 8.00–8.22 (m, 7H).

Step 2: 4-[2-Cyano-2-(4-trifluoromethoxyphenyl)ethyl]benzoic acid methyl ester:

A solution of 4-[2-cyano-2-(4-trifluoromethoxyphenyl)vinyl]benzoic acid methyl ester (9.0 g, 25.92 mmol) in THF (50 mL) was stirred and cooled to –20° C. A solution of sodium borohydride in THF (100 mL) was added during 20 minutes. The cooling bath was removed and the mixture was stirred for two hours at room temperature and then kept at 5° C. for 16 hours. Ice (100 g) was added and the mixture was neutralised (pH 4–5) with 1 M hydrochloric acid (50 mL). The resulting mixture was extracted with DCM and washed with brine. The organic phase was dried (MgSO$_4$), purified (Norite A), filtered and evaporated. The residue was dried at 40° C. in vacuo to afford 8.8 g (97%) of 4-[2-cyano-2-(4-trifluoromethoxyphenyl)ethyl]benzoic acid methyl ester.

$^1$H NMR (DMSO-d$_6$): δ=3.28 (m, 2H), 3.86 (s, 3H), 4.72 (t, 1H), 7.42 (m, 4H), 7.55 (2H, d), 7.92 (m, 2H).

Step 3: 4-[2-Thiocarbamoyl-2-(4-trifluoromethoxyphenyl) ethyl]benzoic acid methyl ester:

A mixture of 4-[2-cyano-2-(4-trifluoromethoxyphenyl) ethyl]benzoic acid methyl ester (8.76 g, 25.08 mmol), water (4.7 mL) and diethyl thiophosphate (4.67 mL, 27.8 mmol) was stirred and heated to 80° C. for two hours. The mixture was cooled and aqueous sodium hydrogen carbonate (100 mL, 10%) and ethyl acetate (200 mL) were added. The organic phase was washed with brine. Drying (MgSO$_4$) and concentration in vacuo afforded 7 g of the crude material, which was purified by column chromatography on silica gel eluting with a mixture of ethyl acetate:heptane 1:2, containing 2% ethanol. This afforded 2.6 g (27%.) of 4-[2-thiocarbamoyl-2-(4-trifluoromethoxy-phenyl)ethyl]benzoic acid methyl ester as a solid.

HPLC-MS (Method D): m/z: 384 (M+1); Rt: 4.51 min. $^1$H NMR (DMSO-d$_6$): δ=3.18 (dd, 1H), 3.60 (dd, 1H), 3.83 (s, 3H), 4.33 (t, 1H), 7.30 (d, 2H), 7.38 (d, 2H), 7.59 (d, 2H), 7.84 (d, 2H), 9.45 (s, 2H).

Step 4: 4-[α-[4-(4-Chlorophenyl)thiazol-2-yl]-2-(4-trifluoromethoxyphenyl)ethyl]benzoic acid:

A mixture of 4-[2-thiocarbamoyl-2-(4-trifluoromethoxyphenyl)ethyl]benzoic acid methyl ester (0.2 g, 0.52 mmol) and 2-bromo-4'-chloroacetophenone (0.12 g, 0.52 mmol) in methanol (5 mL) was refluxed for 2 hours. The solvent was evaporated and the residue was partitioned between aqueous sodium hydrogen carbonate (4 mL, 10%) and DCM (4 mL). The organic phase was filtered through silica gel (1 g), followed by wash with more DCM (4 mL). The filtrate was evaporated to afford 242 mg (92%) of crude ester intermediate as an oil. This ester was added methanol (5 mL), THF (2 mL), and 4M sodium hydroxide (0.5 mL) and the mixture was stirred for 16 hours at room temperature followed by heating to 38° C. for 1 hour. The total volume was reduced to about 3 mL and water (4 mL) was added. The mixture was acidified (pH 1–2) with 1 M hydrochloric acid. The precipitate was filtered off and dried to afford 177 mg (77%) of 4-[2-[4-(4-chlorophenyl)thiazol-2-yl]-2-(4-trifluoromethoxyphenyl)ethyl]benzoic acid as a solid.

$^1$H NMR (DMSO-d$_6$): δ=3.48 (dd, 1H), 3.75 (dd, 1H), 4.99 (t, 1H), 7.32 (m, 4H), 7.53 (d, 2H), 7.59 (d, 2H), 7.78 (d, 2H), 8.00 (d, 2H), 8.03 (s, 1H).

Steps 5 and 6: 3-{4-[2-[4-(4-Chlorophenyl)thiazol-2-yl]-2-(4-trifluoromethoxyphenyl)ethyl]benzoylamino}propionic acid:

4-[2-[4-(4-Chlorophenyl)thiazol-2-yl]-2-(4-trifluoromethoxyphenyl)ethyl]benzoic acid (0.16 g, 0.31 mmol) was dissolve in DMF (5 mL) and 1-hydroxybenzotriazole (51.48 mg, 0.38 mmol) and 1-ethyl-3-(3-dimethylaminopropyl)carbodiimide hydrochloride (73 mg, 0.38 mmol) were added and the mixture was stirred at room temperature for 1.5 hours. DI PEA (0.123 g, 0.95 mmol) and 3-aminopropionic acid methyl ester hydrochloride (66 mg, 0.48 mmol) were added to the mixture. The mixture was heated at 40° C. for 2 hours and left with stirring for 16 hours at room temperature. Ethyl acetate (5 mL) was added and the mixture was washed with water (5 mL). The aqueous phase was extracted with ethyl acetate (5 mL). The combined organic phases were washed with brine (5 mL) and water (5 mL) and concentrated in vacuo to afford crude intermediary ester compound. The ester was dissolved in a mixture of methanol (4 mL) and THF (1 mL) and 4M sodium hydroxide (0.2 mL) was added. The mixture was stirred for 16 hours at room temperature and the solvents were removed by evaporation in vacuo. Water (6 mL) was added and the pH was adjusted (1–2) by the addition of 1M hydrochloric acid. The precipitate was filtered off, washed with water and dried to afford 126 mg (69%) of the title compound as a solid.

$^1$H NMR (DMSO-d$_6$): δ=2.47 (t, 2H), 3.41 (m, 3H), 3.72 (dd, 1H, s), 4.99 (t, 1H), 7.30 (m, 4H), 7.52 (d, 2H), 7.60 (d, 2H), 7.66 (d, 2H), 8.01 (d, 2H), 8.02 (s, 1H), 8.42 (t, 1H), 12.27 (br s, 1H).

The following examples have been prepared in analogy with the methods given above.

Example 492

General Procedure (F)

3-{4-[2-[4-(4-Fluorophenyl)thiazol-2-yl]-2-(4-trifluoromethoxyphenyl)ethyl]benzoylamino}propionic acid

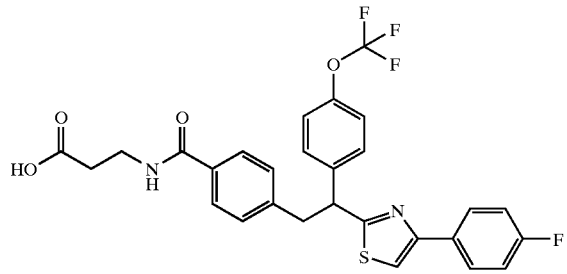

$^1$H NMR (DMSO-d$_6$): δ=2.46 (t, 2H), 3.39 (m, 3H), 3.68 (dd, 1H), 4.95 (t, 1H), 7.33 (m, 6H), 7.60 (d, 2H), 7.66 (d, 2H), 7.93 (s, 1H), 8.03 (d, 2H), 8.43 (t, 1H), 12.23 (br s, 1H).

Example 493

General Procedure (F)

3-{4-[2-[4-(3,5-Dichlorophenyl)thiazol-2-yl]-2-(4-trifluoromethoxyphenyl)ethyl]benzoylamino}propionic acid

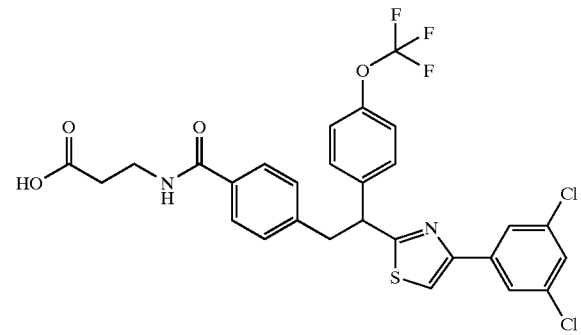

$^1$H NMR (DMSO-d$_6$): δ=2.46 (t, 2H), 3.36–3.50 (m, 3H), 3.73 (dd, 1H), 5.00 (t, 1H), 7.30 (m, 4H), 7.58 (m, 3H), 7.65 (d, 2H), 8.04 (s, 2H), 8.25 (s, 1H), 8.41 (t, 1H), 12.20 (br s, 1H).

Example 494

General Procedure (F)

3-(4-{2-(4-Trifluoromethoxyphenyl)-2-[4-(4-trifluoromethylphenyl)thiazol-2-yl]ethyl}benzoylamino)propionic acid

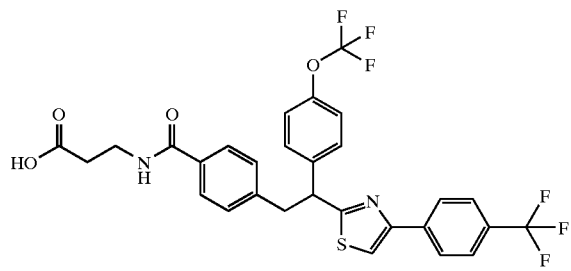

¹H NMR (DMSO-d₆): δ=2.46 (t, 2H), 3.43 (m, 3H), 3.73 (dd, 1H), 5.00 (t, 1H), 7.33 (dd, 4H), 7.58 (d, 2H), 7.65 (d, 2H), 7.80 (d, 2H), 8.15 (m, 3H), 8.41 (t, 1H), 12.28 (br s, 1H).

Example 495

General Procedure (F)

3-{4-[2-[4-(3,4-Difluorophenyl)thiazol-2-yl]-2-(4-trifluoromethoxyphenyl)ethyl]benzoylamino}propionic acid

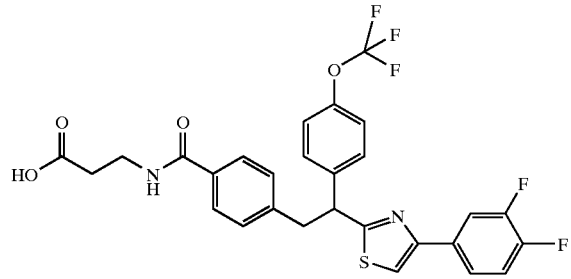

¹H NMR (DMSO-d₆): δ=2.46 (t, 2H), 3.40 (m, 3H), 3.70 (dd, 1H), 4.97 (t, 1H), 7.32 (dd, 4H), 7.53 (m, 1H), 7.59 (d, 2H), 7.65 (d, 2H), 7.85 (m, 1H), 8.02 (m, 2H), 8.40 (t, 1H), 12.25 (br s, 1H).

Example 496

General Procedure (F)

3-{4-[2-[4-(4-Cyanophenyl)thiazol-2-yl]-2-(4-trifluoromethoxyphenyl)ethyl]benzoylamino}propionic acid ¹H NMR (DMSO-d₆): δ=2.46 (t, 2H), 3.40 (m, 3H), 3.71 (dd, 1H), 4.98 (t, 1H), 7.30 (dd, 4H), 7.58 (d, 2H), 7.65 (d, 2H), 7.93 (d, 2H), 8.15 (d, 2H), 8.24 (s, 1H), 8.41 (t, 1H), 11.92 (br s, 1H).

Example 497

General Procedure (F)

3-{4-[2-[4-(3-Bromophenyl)thiazol-2-y]-2-(4-trifluoromethoxyphenyl)ethyl]benzoylamino}propionic acid ¹H NMR (DMSO-d₆): δ=2.48 (t, 2H), 3.42 (m, 3H), 3.71 (dd, 1H), 4.97 (t, 1H), 7.30 (dd, 4H), 7.41 (t, 1H), 7.54 (d, 1H), 7.57 (d, 2H), 7.65 (d, 2H), 7.96 (d, 1H), 8.10 (s, 1H), 8.15 (s, 1H), 8.40 (t, 1H), 12.26 (br s, 1H).

Example 498

General Procedure (F)

3-{4-[2-[4-(4-Methanesulfonylphenyl)thiazol-2-yl]-2-(4-trifluoromethoxyphenyl)ethyl]benzoylamino}propionic acid

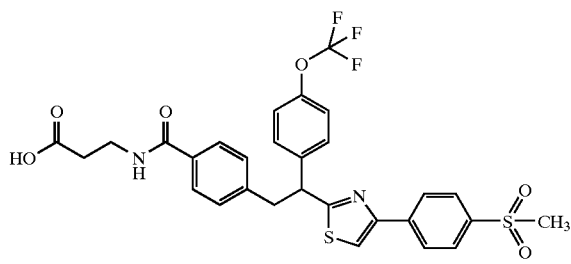

¹H NMR (DMSO-d₆): δ=2.45 (t, 2H), 3.39 (m, 3H), 3.74 (dd, 1H), 5.01 (t, 1H), 7.31 (dd, 4H), 7.58 (d, 2H), 7.64 (d, 2H), 7.97 (d, 2H), 8.23 (m, 3H), 8.42 (t, 1H), 12.41 (br s, 1H).

Example 499

General Procedure (F)

3-(4-{2-(4-Trifluoromethoxyphenyl)-2-[4-(4-trifluoromethoxyphenyl)thiazol-2-yl]ethyl}benzoylamino)propionic acid

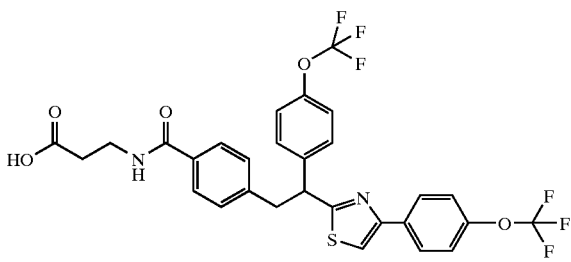

¹H NMR (DMSO-d₆): δ 2.38 (t, 2H), 3.40 (m, 3H), 3.70 (dd, 1H), 4.97 (t, 1H), 7.29 (dd, 4H), 7.44 (d, 2H), 7.56 (d, 2H), 7.64 (d, 2H), 8.02 (s, 1H), 8.07 (d, 2H), 8.47 (t, 1H).

Example 500

General Procedure (F)

3-{4-[2-(4-Biphenyl-4-yl)thiazol-2-yl)-2-(4-trifluoromethoxyphenyl)ethyl]benzoylamino}propionic acid

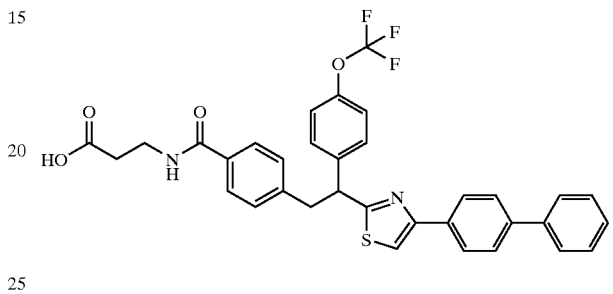

¹H NMR (DMSO-d₆): δ=2.45 (t, 2H), 3.43 (m, 3H), 3.74 (dd, 1H), 4.97 (t, 1H), 7.32 (dd, 4H), 7.38 (t, 1H), 7.50 (t, 2H), 7.61 (d, 2H), 7.66 (d, 2H), 7.73 (d, 2H), 7.76 (d, 2H), 8.00 (s, 1H), 8.06 (d, 2H), 8.41 (t, 1H), 12.42 (br s, 1H).

Example 501

General Procedure (F)

3-{4-[2-[4-(4-Bromophenyl)thiazol-2-yl]-2-(4-trifluoromethoxyphenyl)ethyl]benzoylamino}propionic acid

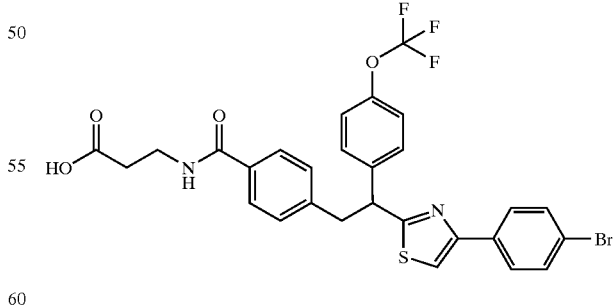

¹H NMR (DMSO-d₆): δ=2.46 (t, 2H), 3.38 (m, 3H), 3.70 (dd, 1H), 4.97 (t, 1H), 7.31 (dd, 4H), 7.57 (d, 2H), 7.66 (dd, 4H), 7.94 (d, 2H), 8.04 (s, 1H), 8.44 (t, 1H), 12.43 (br S, 1H).

Example 502

General Procedure (F)

3-{4-[2-[4-(3,4-Dichlorophenyl)thiazol-2-yl]-2-(4-trifluoromethoxyphenyl)ethyl]benzoylamino}propionic acid

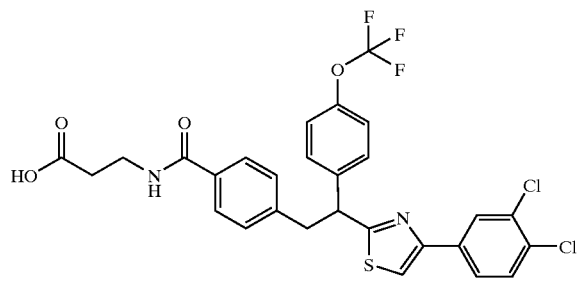

$^1$H NMR (DMSO-d$_6$): δ=2.48 (t, 2H), 3.41 (m, 3H), 3.72 (dd, 1H), 4.98 (t, 1H), 7.30 (dd, 4H), 7.59 (d, 2H), 7.66 (d, 2H), 7.72 (d, 1H), 7.97 (d, 1H), 8.16 (s, 1H), 8.22 (s, 1H), 8.44 (t, 1H), 12.25 (br s, 1H).

Example 503

General Procedure (F)

3-(4-{2-(4-tert-Butylphenyl)-2-[4-(4-trifluoromethylphenyl)thiazol-2-yl]ethyl}benzoylamino)propionic acid

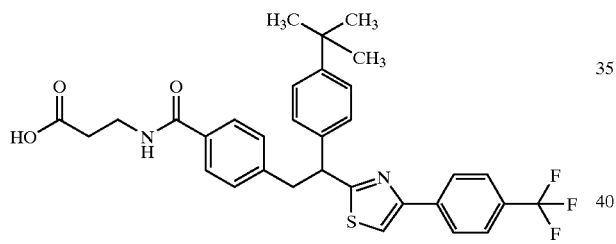

HPLC-MS (Method D): m/z: 581 (M+1); Rt=5.49 min.
$^1$H NMR (DMSO-d$_6$): δ=1.25 (s, 9H), 2.18 (t, 2H), 3.40 (m, 3H), 3.70 (dd, 1H), 4.88 (t, 1H), 7.38 (m, 6H), 7.62 (d, 2H), 7.82 (d, 2H), 8.14 (s, 1H), 8.19 (d, 2H), 8.78 (t, 1H).

Example 504

General Procedure (F)

3-(4-{2-(4-tert-Butylphenyl)-2-[4-(4-cyanophenyl)thiazol-2-yl]ethyl}benzoylamino)propionic acid

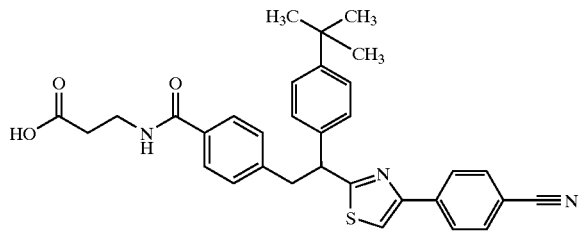

HPLC-MS (Method D): m/z: 538 (M+1); Rt=4,89 min.
$^1$H NMR (DMSO-d$_6$): δ=1.25 (s, 9H), 2.48 (t, 2H), 3.40 (m, 3H), 3.70 (dd, 1H), 4.88 (t, 1H), 7.38 (m, 6H), 7.65 (d, 2H), 7.82 (d, 2H), 8.17 (d, 2H), 8.21 (s, 1H), 8.42 (t, 1H).

Example 505

General Procedure (F)

3-{4-[2-(4-tert-Butylphenyl)-2-(4-(naphthalen-2-yl))thiazol-2-yl)ethyl]benzoylamino}propionic acid

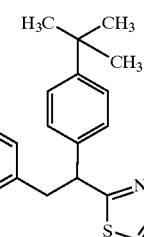

HPLC-MS (Method D): m/z: 563 (M+1); Rt=5.46 min.

$^1$H NMR (DMSO-d$_6$): δ=1.25 (s, 9H), 2.45 (t, 2H), 3.40 (m, 3H), 3.75 (dd, 1H), 4.88 (t, 1H), 7.38 (m, 4H), 7.42 (d, 2H), 7.55 (m, 2H), 7.68 (d, 2H), 7.9–8.03 (m, 3H), 8.05 (s, 1H), 8.10 (d, 1H), 8.52 (s, 1H).

Example 506

General Procedure (F)

3-(4-{2-(4-tert-Butylphenyl)-2-[4-(4-chlorophenyl)thiazol-2-yl]ethyl}benzoylamino)propionic acid

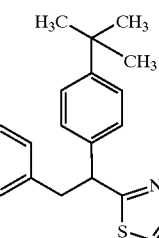

HPLC-MS (Method D): m/z: 547 (M+1); Rt=5.37 min.
$^1$H NMR (DMSO-d$_6$): δ=1.25 (s, 9H), 2.45 (t, 2H), 3.40 (m, 3H), 3.70 (dd, 1H), 4.85 (t, 1H), 7.38 (m, 6H), 7.50 (d, 2H), 7,65 (d, 2H), 7,96 (s, 1H), 8.00 (d, 2H), 8.42 (t, 1H).

Example 507

General Procedure (F)

3-(4-(2-(4-tert-Butylphenyl)-2-[4-(4-fluorophenyl)thiazol-2-yl]ethyl}benzoylamino)propionic acid

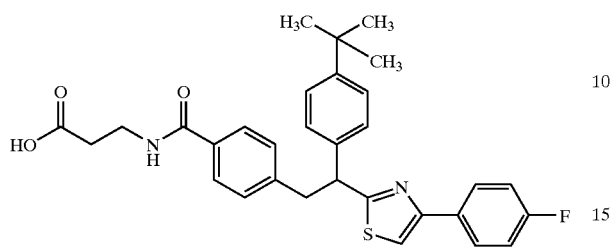

HPLC-MS (Method D): m/z: 531 (M+1); Rt=5,07 min.
¹H NMR (DMSO-d₆): δ=1.25 (s, 9H), 2.45 (t, 2H), 3.40 (m, 3H), 3.70 (dd, 1H), 4.82 (t, 1H), 7.30 (m, 6H), 7.40 (d, 2H), 7.65 (d, 2H), 7.90 (s, 1H), 7.98 (d, 2H), 8.46 (t, 1H).

Example 508

General Procedure (F)

3-(4-{2-(4-tert-Butylphenyl)-2-[4-(4-trifluoromethoxyphenyl)thiazol-2-yl]ethyl}benzoylamino)propionic acid

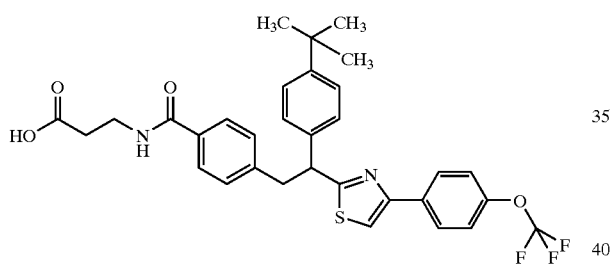

HPLC-MS (Method D): m/z: 597 (M+1); Rt=5.56 min.
¹H NMR (DMSO-d₆): δ=1.25 (s, 9H), 2.33 (t, 2H), 3.40 (m, 3H), 3.70 (dd, 1H), 4.85 (t, 1H), 7.30 (m, 6H), 7.45 (d, 2H), 7.65 (d, 2H), 7.97 (s, 1H), 8.08 (d, 2H), 8.51 (t, 1H).

Example 509

General Procedure (F)

3-(4-{2-(4-Chlorophenyl)-2-[4-(4-trifluoromethylphenyl)thiazol-2-yl]ethyl}benzoylamino)propionic acid

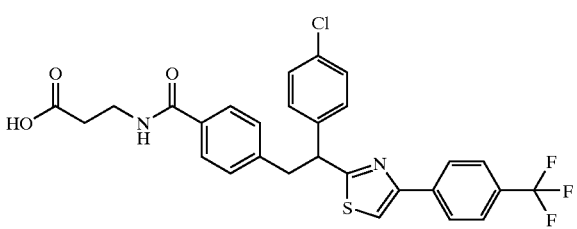

HPLC-MS (Method D): m/z: 559 (M+1); Rt=5.04 min.
¹H NMR (DMSO-d₆): δ=2.46 (t, 2H), 3.39 (m, 3H), 3.70 (dd, 1H), 4.95 (t, 1H), 7.30 (d, 2H), 7.35 (d, 2H), 7.45 (d, 2H), 7.65 (d, 2H), 7.80 (d, 2H), 8.20 (d, 2H), 8.21 (s, 1H), 8.45 (t, 1H).

Example 510

General Procedure (F)

3-(4-{2-(4-Chlorophenyl)-2-[4-(4-trifluoromethoxyphenyl)-thiazol-2-yl]-ethyl}-benzoylamino)propionic acid

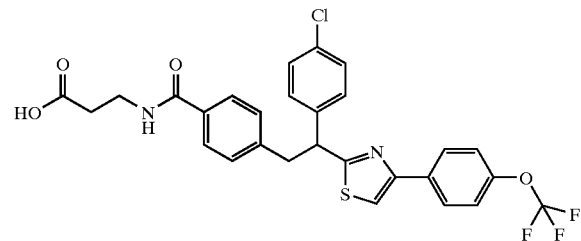

HPLC-MS (Method D): m/z: 589 (M+1); Rt=5.50 min.
¹H NMR (DMSO-d₆): δ=2.46 (t, 2H), 3.39 (m, 3H), 3.70 (dd, 1H), 4.95 (t, 1H), 7.30 (d, 2H), 7.35 (d, 2H), 7.45 (m, 4H), 7.65 (d, 2H), 8.02 (s, 1H), 8.08 (d, 2H), 8.40 (t, 1H), 12.23 (br s, 1H).

Example 511

General Procedure (F)

3-(4-{2-(4-Chlorophenyl)-2-[4-(4-trifluoromethylphenyl)thiazol-2-yl]ethyl}benzoylamino)-2R-hydroxypropionic acid

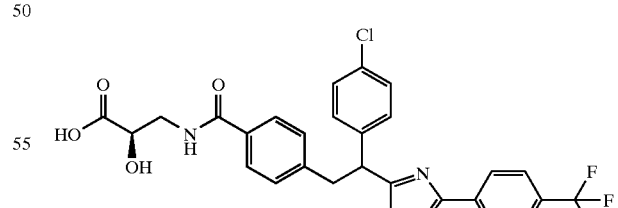

HPLC-MS (Method D): m/z: 575 (M+1); Rt=4.83 min.
¹H NMR (DMSO-d₆): δ=3.45 (m, 3H), 3.71 (dd, 1H), 4.15 (dd, 1H), 4.95 (t, 1H), 7.30 (d, 2H), 7.35 (d, 2H), 7.50 (d, 2H), 7.70 (d, 2H), 7.80 (d, 2H), 8.19 (d, 2H), 8.21 (s, 1H), 8.35 (t, 1H), 12.60 (brs, 1H).

Example 512

3-(4-{2-(4-Chlorophenyl)-2-[4-(4-trifluoromethoxyphenyl)thiazol-2-yl]vinyl}benzoylamino)propionic acid

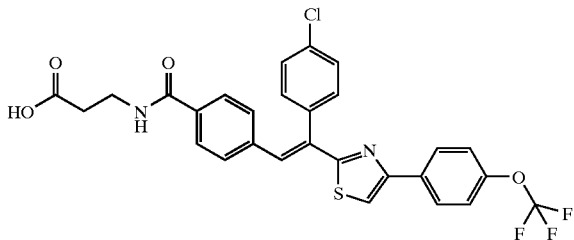

$^1$H NMR (DMSO-d$_6$): δ=2.50 (t, 2H), 3.43 (q, 2H), 7.16 (d, 2H), 7.43 (d, 2H), 7.46 (d, 2H), 7.48 (s, 1H), 7.57 (d, 2H), 7.66 (d, 2H), 8.14 (d, 2H), 8.25 (s, 1H), 8.46 (t, 2H), 12.20 (br s, 1H).

This compound was prepared according to general procedure (F) with the following modification:

To a mixture of 3-(4-{2-(4-chlorophenyl)-2-[4-(4-trifluoromethoxyphenyl)thiazol-2-yl]ethyl}benzoylamino) propionic acid methyl ester (the product from step 5) (0.15 g, 0.255 mmol), N-bromosuccinimide (50 mg, 0.28 mmol) in tetrachloromethane (9 mL) was added a catalytic amount of dibenzoylperoxide and the resulting mixture was stirred at reflux for 4 hours. After cooling, the mixture was concentrated in vacuo and the residue was partitioned between ethyl acetate and water. The aqueous phase was extracted with ethyl acetate and the combined organic phases were washed with water (2×) and brine, dried over MgSO$_4$, treated with active carbon, filtered and concentrated in vacuo. The residue (157 mg) was dissolved in DMF (5 mL) and lithium carbonate (21 mg, 0.28 mmol) and lithium bromide (24 mg, 0.28 mmol) were added and the resulting mixture was refluxed for 3.5 hours. After cooling, the mixture was partitioned between water and ethyl acetate. The aqueous phase was extracted with ethyl acetate and the combined organic phases were washed with water (3×) treated with active carbon, dried (MgSO$_4$) and concentrated in vacuo. The residue (56 mg) was purified by HPLC to afford 14 mg of 3-(4-{2-(4-chlorophenyl)-2-[4-(4-trifluoromethoxyphenyl)-thiazol-2-yl]vinyl}benzoylamino) propionic acid methyl ester.

3-(4-{2-(4-Chlorophenyl)-2-[4-(4-trifluoromethoxyphenyl)thiazol-2-yl]vinyl}benzoylamino) propionic acid methyl ester (14 mg) was dissolved in methanol (5 mL) and 1 N sodium hydroxide (72 μL, 3 equivalents) and 5 drops THF were added and the resulting mixture was stirred at room temperature for 1 hour. More 1 N sodium hydroxide (72 μL, 3 equivalents) and 5 drops THF were added and the resulting mixture was stirred at room temperature for 1 hour and at 50° C. for 1 hour. The mixture was concentrated in vacuo and the residue was added water (5 mL) and 1 N hydrochloric acid was added to pH 2. The solid was filtered off, washed with water and dried in vacuo to afford 6 mg (4%) of the title compound.

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor.

Antagonism may be determined as the ability of the compounds to inhibit the amount of cAMP formed in the presence of 5 nM glucagon.

Glucagon Binding Assay (I)

Receptor binding is assayed using cloned human receptor (Lok et al., Gene 140, 203–209 (1994)). The receptor inserted in the pLJ6' expression vector using EcoRI/SSt1 restriction sites (Lok et al.) is expressed in a baby hamster kidney cell line (A3 BHK 57Q-25). Clones are selected in the presence of 0.5 mg/ml G-418 and are shown to be stable for more than 40 passages. The K$_d$ is shown to be 0.1 nM.

Plasma membranes are prepared by growing cells to confluence, detaching them from the surface and resuspending the cells in cold buffer (10 mM tris/HCl, pH 7.4 containing 30 mM NaCl, 1 mM dithiothreitol, 5 mg/l leupeptin (Sigma), 5 mg/l pepstatin (Sigma), 100 mg/l bacitracin (Sigma) and 15 mg/l recombinant aprotinin (Novo Nordisk A/S)), homogenization by two 10-s bursts using a Polytron PT 10–35 homogenizer (Kinematica), and centrifugation upon a layer of 41 w/v % sucrose at 95.000×g for 75 min. The white band located between the two layers is diluted in buffer and centrifuged at 40.000×g for 45 min. The precipitate containing the plasma membranes is suspended in buffer and stored at −80° C. until use.

Glucagon is iodinated according to the chloramine T method (Hunter and Greenwood, Nature 194, 495 (1962)) and purified using anion exchange chromatography (Jørgensen et al., Hormone and Metab. Res. 4, 223–224 (1972). The specific activity is 460 μCi/μg on the day of iodination. Tracer is stored at −18° C. in aliquots and used immediately after thawing.

Binding assays are carried out in triplicate in filter microtiter plates (MADV N65, Millipore). The buffer is 50 mM HEPES, 5 mM EGTA, 5 mM MgCl$_2$, 0.005% tween 20, pH 7.4. Glucagon is dissolved in 0.05 M HCl, added an equal amount (w/w) of human serum albumin. and freeze-dried. On the day of use, it is dissolved in water and diluted in buffer to the desired concentrations.

Test compounds are dissolved and diluted in DMSO. 140 μl buffer, 25 μl glucagon or buffer, and 10 μl DMSO or test compound are added to each well. Tracer (50.000 cpm) is diluted in buffer and 25 μl is added to each well. 1–4 μg freshly thawed plasma membrane protein diluted in buffer is then added in aliquots of 25 μl to each well. Plates are incubated at 30° C. for 2 hours. Non-specific binding is determined with 10$^{-6}$ M of glucagon. Bound tracer and unbound tracer are then separated by vacuum filtration (Millipore vacuum manifold). The plates are washed with 2×100 μl buffer/well. The plates are air dried for a couple of hours, whereupon the filters are separated from the plates using a Millipore Puncher. The filters are counted in a gamma counter.

Functional Assay (I)

The functional assay is carried out in 96 well microtiter plates (tissue culture plates, Nunc). The resulting buffer concentrations in the assay are 50 mM tris/HCl, 1 mM EGTA, 1.5 mM MgSO$_4$, 1.7 mM ATP, 20 μM GTP, 2 mM IBMX, 0.02% tween-20 and 0.1% human serum albumin. pH was 7.4. Glucagon and proposed antagonist are added in aliquots of 35 μl diluted in 50 mM tris/HCl, 1 mM EGTA, 1.85 mM MgSO$_4$, 0.0222% tween-20 and 0.111% human serum albumin, pH 7.4. 20 μl of 50 mM tris/HCl, 1 mM EGTA, 1.5 mM MgSO$_4$, 11.8 mM ATP, 0.14 mM GTP, 14 mM IBMX and 0.1% human serum albumin, pH 7.4 was added. GTP was dissolved immediately before the assay.

50 μl containing 5 μg of plasma membrane protein was added in a tris/HCl, EGTA, MgSO$_4$, human serum albumin buffer (the actual concentrations are dependent upon the concentration of protein in the stored plasma membranes).

The total assay volume is 140 µl. The plates are incubated for 2 hours at 37° C. with continuous shaking. Reaction is terminated by addition of 25 µl 0.5 N HCl. cAMP is measured by the use of a scintillation proximity kit (Amersham).

Glucagon Binding Assay (II)

BHK (baby hamster kidney cell line) cells are transfected with the human glucagon receptor and a membrane preparation of the cells is prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{125}$I-glucagon.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The glucagon binding assay is carried out in opti plates (Polystyrene Microplates, Packard). 50 µl assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 µl glucagon or test compound (in DMSO) are added to each well. 50 pi tracer ($^{125}$I-porcine glucagon, 50.000 cpm) and 50 µl membranes (7.5 µg) containing the human glucagon receptor are then added to the wells. Finally 50 µl WGA beads containing 1 mg beads are transferred to the well. The opti plates are incubated for 4 hours on a shaker and then settled for 8–48 hours. The opti plates are counted in a Topcounter. Non-specific binding is determined with 500 nM of glucagon.

Most of the tested compounds according to the examples showed IC$_{50}$ values below 1000 nM when tested in the glucagon binding assay (II).

GIP Binding Assay

BHK (baby hamster kidney cell line) cells are transfected with the human GIP receptor and a membrane preparation of the cells is prepared. Wheat Germ Agglutinin derivatized SPA beads containing a scintillant (WGA beads) (Amersham) bound the membranes. $^{125}$I-GIP bound to human GIP receptor in the membranes and excited the scintillant in the WGA beads to light emission. GIP or samples binding to the receptor competed with $^{125}$I-GIP.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The GIP binding assay is carried out in opti plates (Polystyrene Microplates, Packard). 50 µl assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 µl GIP or test compound (in DMSO) are added to each well. 50 µl tracer ($^{125}$I-porcine GIP, 50.000 cpm) and 50 pi membranes (20 µg) containing the human GIP receptor are then added to the wells. Finally 50 µl WGA beads containing 1 mg beads are transferred to the well. The opti plates are incubated for 3.5 hours on a shaker and then settled for 8–48 hours. The opti plates are counted in a Topcounter. Non-specific binding is determined with 500 nM of GIP.

Generally, the compounds show a higher affinity for the glucagon receptor compared to the GIP receptor.

What is claimed is:

1. A compound of the general formula (I):

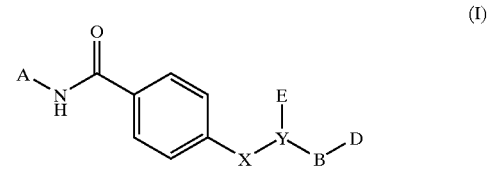

wherein

A is

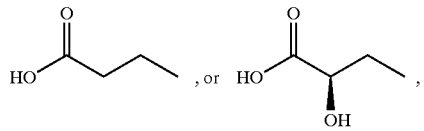

X is a valence bond, —CR$^1$R$^2$— or —NR$^1$—,

Y is >CR$^3$— or >N—,

R$^1$, R$^2$ and R$^3$ independently are hydrogen or C$_{1-6}$-alkyl, or R$^1$ and R$^3$ on adjacent atoms may be combined to form a double bond, E is C$_{1-10}$-alkyl or C$_{2-10}$-alkenyl, C$_{3-10}$-cycloalkyl, C$_{3-10}$-cycloalkenyl, C$_{7-10}$-bicycloalkyl, C$_{3-10}$-cycloalkyl-C$_{1-6}$-alkyl, C$_{3-10}$-cycloalkenyl-C$_{1-6}$-alkyl or C$_{7-10}$-bicycloalkyl-C$_{1-6}$-alkyl, wherein the rings may optionally be substituted with one or more substituents selected from halogen, C$_{1-6}$-alkyl, C$_{2-6}$-alkenyl, C$_{1-6}$-alkoxy, C$_{1-6}$-thioalkyl, —CF$_3$, —OCF$_3$, —SCF$_3$, —OCHF$_2$ and —SCHF$_2$, aryl, aryloxy, arylthio, aryl-C$_{1-6}$-alkyl, aryloxy-C$_{1-6}$-alkyl, arylthio-C$_{1-6}$-alkyl, diaryl-C$_{1-6}$-alkyl or (C$_{1-6}$-alkyl)(aryl)-C$_{1-7}$-alkyl, wherein the non-aromatic and aromatic rings may optionally be substituted with one or more substituents selected from halogen, $C_{1-6}$-alkyl, $C_{2-6}$-alkenyl, $C_{1-6}$-alkoxy, $C_{1-6}$-thioalkyl, —$CF_3$, —$OCF_3$, —$SCF_3$, —$OCHF_2$, —$SCHF_2$, $C_{3-10}$-cycloalkyl and $C_{3-10}$-cycloalkenyl, or with two substituents on adjacent positions which are combined to form a bridge $C_{1-6}$-alkylene, $C_{2-6}$-alkenylene or —O—$C_{1-6}$-alkylene-O—, B is

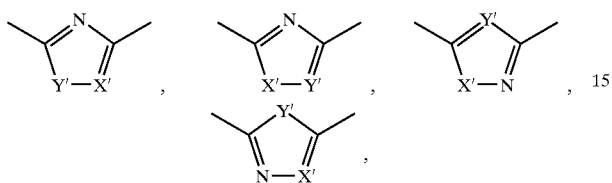

X' is —$CR^8$=,

Y' is —S—, $R^8$ is hydrogen, $C_{1-6}$-alkyl or aryl, wherein aryl is optionally substituted with one or two substituents selected from halogen, $C_{1-6}$-alkyl, $C_{1-6}$-alkoxy, $C_{1-6}$-thioalkyl, —$CF_3$, —$OCF_3$, —$SCF_3$, —$OCHF_2$, —$SCHF_2$, —$SO_2CF_3$ and —$SO_2$—$C_{1-6}$-alkyl;

$R^9$ is hydrogen or $C_{1-6}$-alkyl,

D is aryl, which may optionally be substituted with one or more substituents selected from
  halogen, —$CF_3$, —$OCF_3$, —$SCF_3$, —CN, —$NO_2$, $C_{1-10}$-alkyl, $C_{2-6}$-alkenyl, $C_{1-6}$-alkoxy, $C_{1-6}$-alkylthio, amino, $C_{1-6}$-alkylamino, di-$C_{1-6}$-alkylamino, —$SO_2CF_3$ and —$SO_2$—$C_{1-6}$-alkyl,
  $C_{3-8}$-cycloalkyl, $C_{3-8}$-cycloalkenyl, aryl and aryl-$C_{1-6}$-alkoxy,
    wherein the non-aromatic and aromatic rings optionally may be substituted with one to three substituents selected from halogen, —$CF_3$, —$OCF_3$, —$SCF_3$, —CN, —$NO_2$, $C_{1-10}$-alkyl, $C_{2-6}$-alkenyl, $C_{1-6}$-alkoxy and $C_{1-6}$-alkylthio, or with two substituents on adjacent positions which are combined to form a bridge —O—$(CH_2)_m$—O—$(CH_2)_p$— or —O—$(CF_2)_m$—O—$(CF_2)_p$—, wherein m is an integer of from 1 to 6, and p is 0 or 1,
  or with two substituents on adjacent positions which are combined to form a bridge —O—$(CH_2)_m$—O—$(CH_2)_p$— or —O—$(CF_2)_n$—O—$(CF_2)_p$—, wherein m is an integer of from 1 to 6, and p is 0 or 1, or a substituent on B may be combined with a substituent on D to form a —C(=O)— bridge, as well as any diastereomer or enantiomer or tautomeric form or mixtures thereof of these or a pharmaceutically acceptable salt thereof.

2. A compound according to claim 1, wherein

E is
  $C_{1-10}$-alkyl or $C_{2-10}$-alkenyl,
  $C_{3-10}$-cycloalkyl or $C_{3-10}$-cycloalkenyl, which may optionally be substituted with one or two substituents selected from halogen, $C_{1-6}$-alkyl, $C_{1-6}$-alkoxy, $C_{1-6}$-thioalkyl, —$CF_3$, —$OCF_3$, —$SCF_3$, —$OCHF_2$ and —$SCHF_2$,

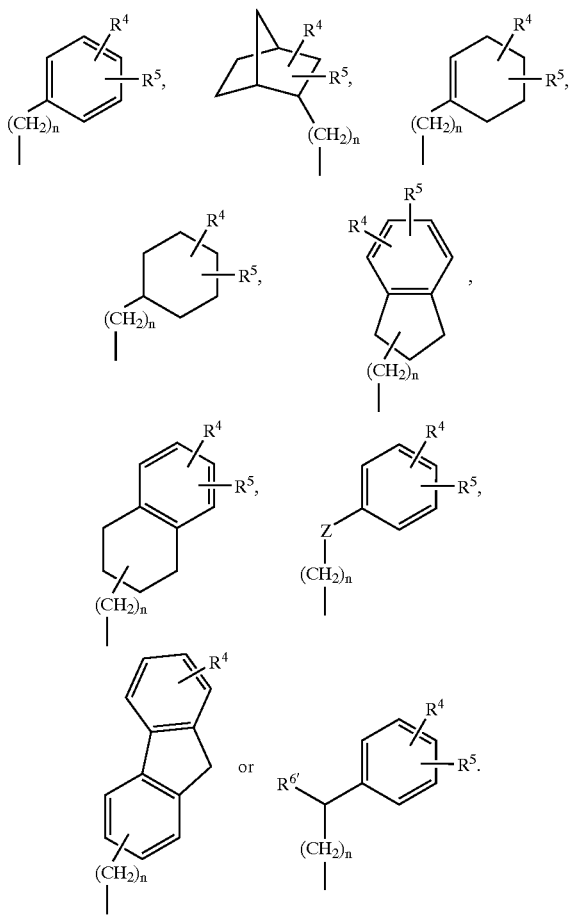

$R^4$ and $R^5$ independently are hydrogen, halogen, $C_{1-6}$-alkyl, $C_{2-6}$-alkenyl, $C_{1-6}$-alkoxy, $C_{16}$-thioalkyl, —$CF_3$, —$OCF_3$, —$SCF_3$, —$OCHF_2$, —$SCHF_2$, $C_{3-10}$-cycloalkyl or $C_{3-10}$-cycloalkenyl, or $R^4$ and $R^5$ on adjacent positions may be combined to form a bridge —O—$C_{1-6}$-alkylene-O—, $C_{1-8}$-alkylene or $C_{3-8}$-alkenylene, $R^6$ is $C_{1-6}$-alkyl or aryl, wherein aryl may optionally be substituted with one or two substituents selected from halogen, $C_{1-6}$-alkyl, $C_{2-6}$-alkenyl, $C_{1-6}$-alkoxy, $C_{1-6}$-thioalkyl, —$CF_3$, —$OCF_3$, —$SCF_3$, —$OCHF_2$ and —$SCHF_2$, n is an integer of from 0 to 6, Z is —O— or —S—, $R^7$ is hydrogen or $C_{1-6}$-alkyl, D is

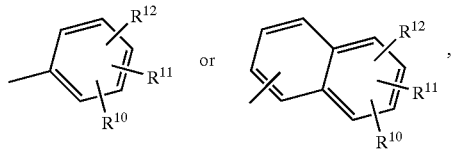

$R^{10}$, $R^{11}$ and $R^{12}$ independently are
  hydrogen, halogen, —$CF_3$, —$OCF_3$, —$SCF_3$, —CN, —$NO_2$, $C_{1-10}$-alkyl, $C_{2-6}$-alkenyl, $C_{1-6}$-alkoxy, $C_{1-6}$-alkylthio, amino, $C_{1-6}$-alkylamino, di-$C_{1-6}$-alkylamino, —$SO_2CF_3$ or —$SO_2$—$C_{1-6}$-alkyl,
  $C_{3-8}$-cycloalkyl, $C_{3-8}$-cycloalkenyl, aryl or aryl-$C_{1-6}$-alkoxy, wherein the non-aromatic and aromatic rings optionally may be substituted with one to three substituents selected from halogen, —$CF_3$, —$OCF_3$, —$SCF_3$, —CN, —$NO_2$, $C_{1-10}$-alkyl, $C_{2-6}$-alkenyl, $C_{1-6}$-alkoxy and $C_{1-6}$-alkylthio, or with two substituents on adjacent positions which are combined to form a bridge —O—$(CH_2)_m$—O—$(CH_2)_p$— or —O—$(CF_2)_m$—O—$(CF_2)_p$—, wherein m is an integer of from 1 to 6, and p is 0 or 1, or two of $R^{10}$, $R^{11}$ and $R^{12}$ on adjacent positions are combined to form a bridge —O—$(CH_2)_m$—O—$(CH_2)_p$— or —O—$(CF_2)_m$—O—$(CF_2)_p$—, wherein m is an integer of from 1 to 6, and p is 0 or 1, $R^{13}$ and $R^{15}$ independently are hydrogen, $C_{1-6}$-alkyl or aryl, wherein aryl is optionally substituted with one or two substituents selected from halogen, $C_{1-6}$-alkyl, $C_{1-6}$-alkoxy, $C_{1-6}$-thioalkyl, —$CF_3$, —$OCF_3$, —$SCF_3$, —$OCHF_2$ and —$SCHF_2$, $R^{14}$ is hydrogen or $C_{1-6}$-alkyl, $R^{16}$, $R^{17}$ and $R^{18}$ independently are hydrogen, halogen, —$CF_3$, —$OCF_3$, —$SCF_3$, —CN, —$NO_2$, $C_{1-10}$-alkyl, $C_{2-6}$-alkenyl, $C_{1-6}$-alkoxy and $C_{1-6}$-alkylthio, or with two substituents on adjacent positions which are combined to form a bridge —O—$(CH_2)_q$—O—$(CH_2)_r$— or —O—$(CF_2)_q$—O—$(CF_2)_r$—, wherein q is an integer of from 1 to 6, and r is 0 or 1, or when B is

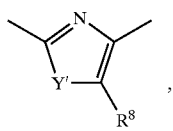

and D is

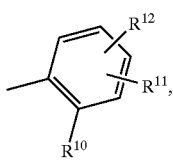

$R^8$ and $R^{10}$ may be combined to form a bridge —C(=O)—, as well as any diastereomer or enantiomer or tautomeric form thereof or mixtures thereof of these or a pharmaceutically acceptable salt thereof.

3. A compound according to claim 1, wherein A is

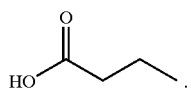

4. A compound according to claim 1, wherein X is —$CR^1R^2$—, wherein $R^1$ and $R^2$ are as defined in claim 1.

5. A compound according to claim 4, wherein X is —$CH_2$—.

6. A compound according to claim 1, wherein Y is >N—.

7. A compound according to claim 1, wherein Y is >CH—.

8. A compound according to claim 1, wherein B is

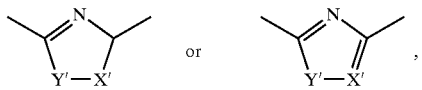

wherein X' and Y' are as defined in claim 1.

9. A compound according to claim 8, wherein B is

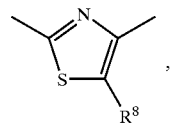

wherein $R^8$ is as defined in claim 1.

10. A compound according to claim 9, wherein $R^8$ is hydrogen, $C_{1-6}$-alkyl or phenyl, wherein phenyl is optionally substituted as defined in claim 1.

11. A compound according to claim 10, wherein $R^8$ is hydrogen, $C_{1-6}$-alkyl or phenyl.

12. A compound according to claim 11, wherein $R^8$ is hydrogen.

13. A compound according to claim 1, wherein E is $C_{1-10}$-alkyl, $C_{3-10}$-cycloalkyl, which may optionally be substituted as defined in claim 1,

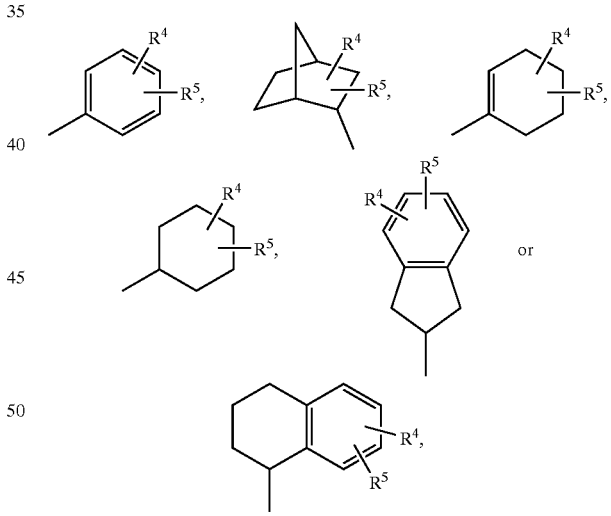

wherein $R^4$ and $R^5$ are as defined in claim 1.

14. A compound according to claim 13, wherein E is $C_{1-10}$-alkyl, $C_{3-10}$-cycloalkyl,

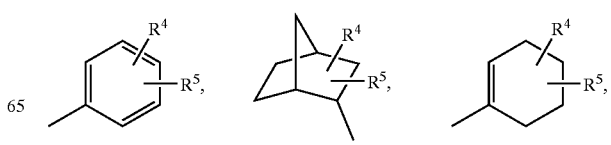

-continued

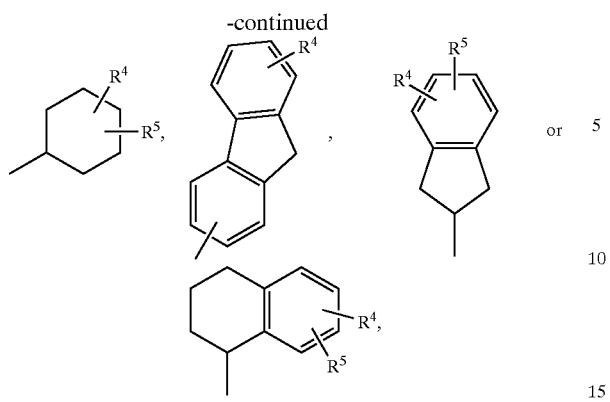

wherein $R^4$ and $R^5$ independently are hydrogen, halogen, $C_{1-6}$-alkyl, $C_{1-6}$-alkoxy, —$OCF_3$, —$CF_3$, —$SCF_3$, $C_{3-10}$-cycloalkyl or $C_{3-10}$-cycloalkenyl, or $R^4$ and $R^5$ on adjacent positions may be combined to form a bridge $C_{1-6}$-alkylene or $C_{2-6}$-alkenylene.

15. A compound according to claim 14, wherein E is

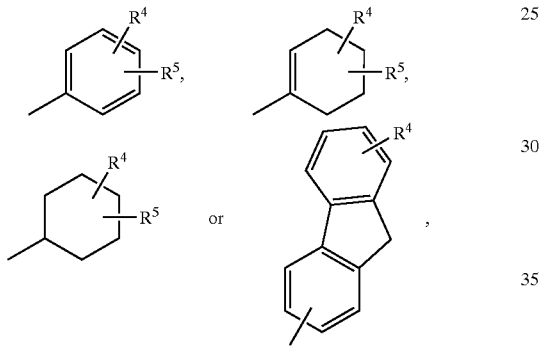

wherein $R^4$ and $R^5$ independently are hydrogen, halogen, $C_{1-6}$-alkyl, $C_{1-6}$-alkoxy, —$OCF_3$, —$CF_3$, —$SCF_3$, $C_{3-10}$-cycloalkyl or $C_{3-10}$-cycloalkenyl, or $R^4$ and $R^5$ on adjacent positions may be combined to form a bridge $C_{1-6}$-alkylene or $C_{2-6}$-alkenylene.

16. A compound according to claim 15 wherein E is

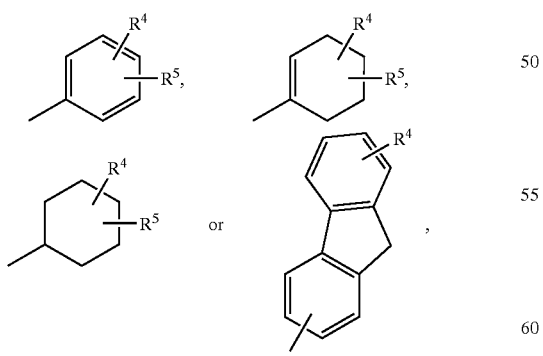

wherein $R^4$ and $R^5$ independently are hydrogen, halogen, $C_{1-6}$-alkyl, $C_{1-6}$-alkoxy, —$OCF_3$, —$CF_3$, —$SCF_3$, cyclohexyl or cyclohex-1-enyl, or $R^4$ and $R^5$ on adjacent positions may be combined to form a bridge $C_{1-6}$-alkylene.

17. A compound according to claim 16 wherein E is

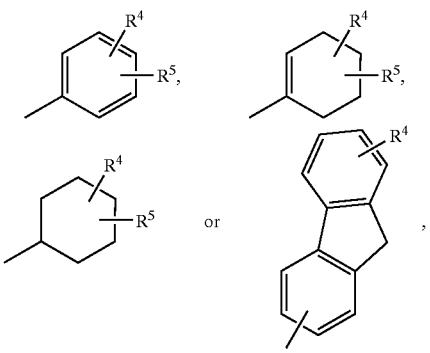

wherein $R^4$ is hydrogen and $R^5$ is $C_{1-6}$-alkyl, cyclohexyl, halogen, —$CF_3$ or cyclohex-1-enyl, or $R^4$ and $R^5$ on adjacent positions may be combined to form a bridge $C_{1-6}$-alkylene.

18. A compound according to claim 17 wherein E is

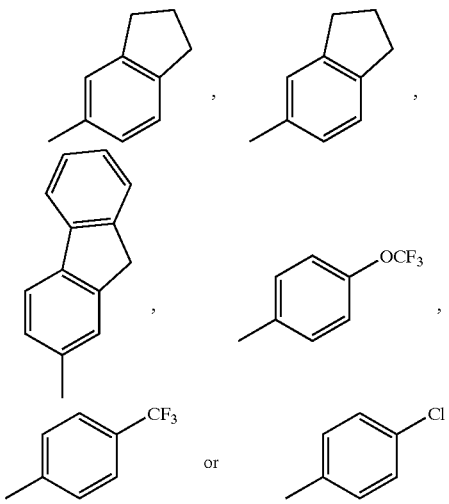

19. A compound according to claim 1, wherein E is

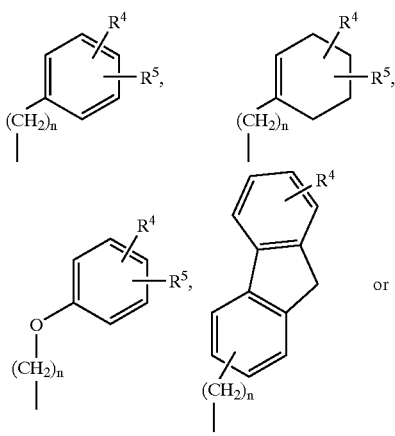

-continued

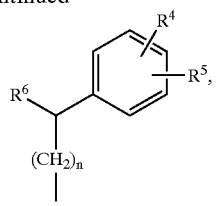

wherein n is 1, 2 or 3, and $R^4$, $R^5$ and $R^6$ are as defined in claim 1.

20. A compound according to claim 17, wherein $R^4$ and $R^5$ independently are hydrogen, halogen, —$OCF_3$, —$CF_3$, $C_{1-6}$-alkoxy or $C_{2-6}$-alkenyl, or $R^4$ and $R^5$ on adjacent atoms together form the bridge —O—$CH_2$—O—.

21. A compound according to claim 1, wherein D is

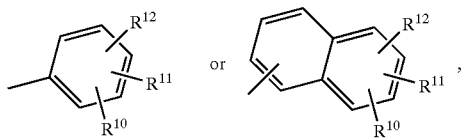

wherein $R^{10}$, $R^{11}$, $R^{12}$, $R^{15}$, $R^{16}$, $R^{17}$ and $R^{18}$ are as defined in claim 2.

22. A compound according to claim 1, wherein D is

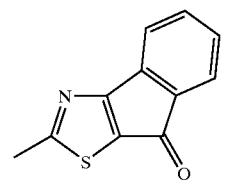

wherein $R^{10}$, $R^{11}$ and $R^{12}$ are as defined in claim 1.

23. A compound according to claim 21, wherein $R^{10}$, $R^{11}$ and $R^{12}$ independently are hydrogen, halogen, —$OCF_3$, —$CF_3$, —$NO_2$, di-$C_{1-6}$-alkylamino, $C_{1-10}$-alkyl, $C_{1-6}$-alkoxy or —CN, phenyl or phenyl-$C_{1-6}$-alkoxy, which may optionally be substituted with one or two substituents as defined in claim 1, or two of $R^{10}$, $R^{11}$ and $R^{12}$ in adjacent positions form a bridge —O—$CH_2$—O—, —O—$CH_2$—$CH_2$—O—, —O—$CH_2$—$CH_2$—$CH_2$—O—, —O—$CF_2$—O—, —O—$CF_2$—O—$CF_2$— or —O—$CF_2$—$CF_2$—O—.

24. A compound according to claim 21, wherein $R^{10}$, $R^{11}$ and $R^{12}$ independently are hydrogen, halogen, —$OCF_3$, —$CF_3$, —$NO_2$, di-$C_{1-6}$-alkylamino, $C_{1-10}$-alkyl, $C_{1-6}$-alkoxy or —CN, phenyl or phenyl-$C_{1-6}$-alkoxy, or two of $R^{10}$, $R^{11}$ and $R^{12}$ in adjacent positions form a bridge —O—$CH_2$—O—, —O—$CH_2$—$CH_2$—O— or —O—$CH_2$—$CH_2$—$CH_2$—O—.

25. A compound according to claim 21, wherein two of $R^{10}$ and $R^{11}$ are hydrogen, and $R^{12}$ is halogen, —$OCF_3$, —$CF_3$, —$NO_2$, di-$C_{1-6}$-alkylamino, $C_{1-10}$-alkyl, $C_{1-6}$-alkoxy or —CN.

26. A compound according to claim 1, wherein B and D together form wherein Y', is as defined in claim 1, and $R^{11}$ and $R^{12}$ are as defined in claim 2.

27. A compound according to claim 26, wherein B and D together form

28. A compound of the general formula ($I_1$):

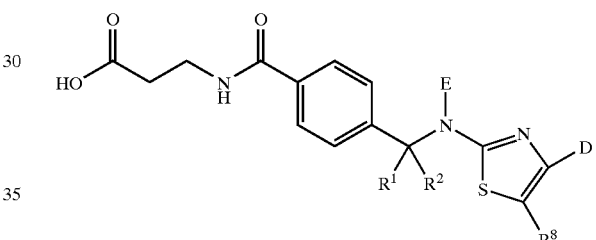

wherein $R^1$, $R^2$, $R^8$, E and D are as defined in claim 1, as well as any diastereomer or enantiomer or tautomeric form thereof or mixtures thereof of these or a pharmaceutically acceptable salt thereof.

29. A compound according to claim 1, which has an $IC_{50}$ value of no greater than 5 μM as determined by the Glucagon Binding Assay (I) or Glucagon Binding Assay (II).

30. A compound according to claim 29, which has an $IC_{50}$ value of less than 1 μM, preferably of less than 500 nM and even more preferred of less than 100 nM as determined by the Glucagon Binding Assay (I) or Glucagon Binding Assay (II).

31. A pharmaceutical composition comprising, as an active ingredient, at least one compound according to claim 1 together with one or more pharmaceutically acceptable carriers or excipients.

32. A pharmaceutical composition according to claim 31 in unit dosage form, comprising from about 0.05 mg to about 1000 mg, preferably from about 0.1 mg to about 500 mg and especially preferred from about 0.5 mg to about 200 mg of the compound.

* * * * *